US012735414B2

(12) United States Patent
Li et al.

(10) Patent No.: US 12,735,414 B2
(45) **Date of Patent: *Sep. 15, 2026**

(54) ROCK INHIBITOR AND PREPARATION METHOD THEREFOR AND USE THEREOF

(71) Applicant: WUHAN LL SCIENCE AND TECHNOLOGY DEVELOPMENT CO., LTD., Wuhan (CN)

(72) Inventors: Jinping Li, Wuhan (CN); Jun Lou, WUhan (CN); Xiaodan Guo, Wuhan (CN); Xian Zeng, Wuhan (CN); Yongkai Chen, Wuhan (CN); Yihan Zhang, Wuhan (CN); Wei Peng, Wuhan (CN); Chaodong Wang, Wuhan (CN)

(73) Assignee: WUHAN LL SCIENCE AND TECHNOLOGY DEVELOPMENT CO., LTD., Wuhan (CN)

( * ) Notice: Subject to any disclaimer, the term of this patent is extended or adjusted under 35 U.S.C. 154(b) by 1017 days.

This patent is subject to a terminal disclaimer.

(21) Appl. No.: 17/756,079

(22) PCT Filed: Nov. 12, 2020

(86) PCT No.: PCT/CN2020/128244

§ 371 (c)(1),
(2) Date: May 16, 2022

(87) PCT Pub. No.: WO2021/093795

PCT Pub. Date: May 20, 2021

(65) Prior Publication Data

US 2023/0050653 A1 Feb. 16, 2023

(30) Foreign Application Priority Data

Nov. 15, 2019 (CN) ........................ 201911121236.X

(51) Int. Cl.

| | |
|---|---|
| ***C07D 471/04*** | (2006.01) |
| ***C07D 401/04*** | (2006.01) |
| ***C07D 401/14*** | (2006.01) |
| ***C07D 403/04*** | (2006.01) |
| ***C07D 405/14*** | (2006.01) |
| ***C07D 413/04*** | (2006.01) |
| ***C07D 487/04*** | (2006.01) |
| ***C07D 513/04*** | (2006.01) |

(52) U.S. Cl.

CPC ......... *C07D 471/04* (2013.01); *C07D 401/04* (2013.01); *C07D 401/14* (2013.01); *C07D 403/04* (2013.01); *C07D 405/14* (2013.01); *C07D 413/04* (2013.01); *C07D 487/04* (2013.01); *C07D 513/04* (2013.01)

(58) Field of Classification Search

CPC .. C07D 471/04; C07D 401/04; C07D 401/14; C07D 403/04; C07D 405/14; C07D 413/04; C07D 487/04; C07D 513/04; C07D 403/14; A61P 11/00; A61P 3/10; A61P 9/00; A61P 25/00; A61P 27/02; A61K 31/4155; A61K 31/437; A61K 31/4725; A61K 31/519; A61K 31/538

See application file for complete search history.

(56) References Cited

U.S. PATENT DOCUMENTS

| | | | |
|---|---|---|---|
| 2009/0105231 | A1 | 4/2009 | Sawada et al. |
| 2018/0141959 | A1 | 5/2018 | Wang et al. |
| 2019/0284157 | A1 | 9/2019 | Wang et al. |
| 2020/0017520 | A1 | 1/2020 | Wang et al. |
| 2020/0255448 | A1 | 8/2020 | Wang et al. |

FOREIGN PATENT DOCUMENTS

| | | | |
|---|---|---|---|
| CN | 110382481 | A | 10/2019 |
| JP | 2009506979 | A | 2/2009 |
| JP | 2009286773 | A | 12/2009 |
| JP | 2011530511 | A | 12/2011 |
| JP | 2016525529 | A | 8/2016 |
| JP | 2018515623 | A | 6/2018 |

(Continued)

OTHER PUBLICATIONS

CAS Registry No. 2324638-08-4, which entered STN on Jun. 5, 2019 (Year: 2019).*

Chowdhury, Sarwat et al.; "Discovery and optimization of indole and 7-azaindoles as Rho kinase(ROCK) inhibitors(Part—I)"; Bioorganic & Medicinal Chemistry Letters; vol. 21; Year: 2011; pp. 7107-7112.

Sessions, E. Hampton et al.; "Discovery and optimization of indoles and 7-azaindoles as Rho kinase (ROCK) inhibitors (part—II)"; Bioorganic & Medicinal Chemistry Letters; vol. 21; Year: 2011; pp. 7113-7118.

(Continued)

*Primary Examiner* — Fereydoun G Sajjadi
*Assistant Examiner* — Anna Grace Kuckla
(74) *Attorney, Agent, or Firm* — NKL Law; Allen Xue

(57) ABSTRACT

The compound represented by formula (I), and racemates, stereoisomers, tautomers, isotopic markers, nitrogen oxides, solvates, polymorphs, metabolites, esters, pharmaceutically acceptable salts, or prodrugs thereof have ROCK inhibitory activity. The compound represented by formula (1) has good safety, good metabolic stability, and a low risk of potential hepatotoxicity. Further, the compound represented by formula (I) has a simple preparation method and is easy to purify, and therefore has good application prospects.

(I)

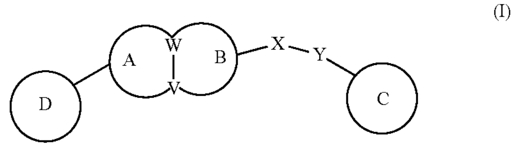

10 Claims, No Drawings

(56) References Cited

FOREIGN PATENT DOCUMENTS

| | | | | |
|---|---|---|---|---|
| WO | 2007026920 A2 | 3/2007 | | |
| WO | 2009022746 A1 | 2/2009 | | |
| WO | 2010024903 A1 | 3/2010 | | |
| WO | 2010056758 A1 | 5/2010 | | |
| WO | 2010108059 A1 | 9/2010 | | |
| WO | WO-2011050245 A1 * | 4/2011 | ......... | A61K 31/4025 |
| WO | WO-2012067965 A1 * | 5/2012 | ........... | A61K 31/437 |
| WO | 2012143796 A2 | 10/2012 | | |
| WO | 2016187324 A1 | 11/2016 | | |
| WO | 2018094362 A1 | 5/2018 | | |
| WO | 2019201296 A1 | 10/2019 | | |

OTHER PUBLICATIONS

Yan, Yin et al.; "Benzothiazoles as Rho-associated kinase(ROCK-II) inhibitors"; Bioorganic & Medicinal Chemistry Letters; vol. 19; Year: 2009; pp. 6686-6690.

Xiao, Yuanchun et al., "Study on Quantitative Structure-Activity Relationship of Indole Derivativesas rhokinase (ROCK) Inhibitors", Journal of Molecular Science, vol. 31, No. 4, Aug. 31, 2015, pp. 295-303.

Database Registry, Feb. 28, 2008 (Feb. 28, 2008), Anonymous: "Pyrazolo[1,5-a]pyrimidine-7-carboxamide, 2-(4-fluorophenyl)-N-[1-[4-(1-methylpropyl)phenyl]ethyl]-5-(1,3,5-trimethyl-1H-pyrazol-4-yl)-(CA Index Name)", XP055812206, retrieved from STN Database accession No. 1005577-39-8 *.

Database Registry, Feb. 28, 2008, Anonymous: "–/1-(C) File Registry RN-1005597-53-4 Registry ED-Entered STN: Feb. 28, 2008 CN-Pyrazolo[1,5-a]pyrimidine-7-carboxamide, 2-(4-fluorophenyl)-N-[1-[4-(1-methylethyl)phenyl]ethyl]-5-(1,3,5-trimethyl-1H-pyrazol-4-yl)-(CA Index Name)", XP055812211, retrieved from STN Database accession No. 1005597-53-4 *.

Database Registry May 9, 2003, "/1-(C) File Registry RN-512809-10-8 Registry Ed -Entered STN: May 9, 2003 CN-Pyrazolo[1,5-a]pyrimidine-2-carboxamide, 5-(1-ethyl-3-methyl-1H-pyrazol-4-yl)-N-[(4-fluorophenyl) methyl]-7-(trifluoromethyl)-(CA Index Name)", XP055812215, retrieved from STN Database accession No. 512809-10-8 *.

Canadian Intellectual Property Office, "Office Action", Aug. 23, 2023.

The State Intellectual Property Office of People's Republic of China, "The First Office Action", Jun. 29, 2023.

Eurasian Patent Office, "Office Action", Jul. 21, 2023.

European Patent Office, "Extended search report." Oct. 18, 2023.

Japan Patent Office, "Office Action", Sep. 20, 2024.

Intellectual Property Office of Singapore, "Written Opinion and Search Report", Mar. 10, 2025.

Yang, Xiaobao et al., "Structure-Activity Relationship Studies for Enhancer of Zeste Homologue 2 (EZH2) and Enhancer of Zeste Homologue 1 (EZH1) Inhibitors", Journal of Medicinal Chemistry, 2016, vol. 59, No. 16, pp. 7617-7633.

* cited by examiner

ROCK INHIBITOR AND PREPARATION METHOD THEREFOR AND USE THEREOF

CROSS-REFERENCE TO RELATED APPLICATIONS

This application is a U.S. national stage entry of PCT International Application No. PCT/CN2020/128244, filed on Nov. 12, 2020, which claims priority to Chinese Patent Application No. 201911121236.X filed with China National Intellectual Property Administration on Nov. 15, 2019 and entitled "ROCK INHIBITOR AND PREPARATION METHOD THEREFOR AND USE THEREOF", the content of which is incorporated herein by reference in its entirety.

TECHNICAL FIELD

The present disclosure relates to the field of medicines, and in particular to a compound capable of inhibiting ROCK activity and a preparation method therefor and use thereof.

BACKGROUND

Idiopathic interstitial pulmonary fibrosis (IPF) is a chronic and diffuse pulmonary interstitial disease with unknown cause and its pathological change is common interstitial pneumonia, and it mainly shows manifestation of common interstitial pneumonia according to histopathology and imageology examinations. The disease condition progresses irreversibly due to the complex pathogenesis of the disease, and early diagnosis is difficult; the survival rate of patients diagnosed with the disease is remarkably decreased over time, and the 3-year survival rate is 50%, and the 5-year survival rate is only 20%, which is lower than that of most cancers (such as leukemia, breast cancer, colon cancer, uterine tumor and renal cancer), and therefore the disease is called "non-cancerous cancer". At present, there is no definitely significantly effective therapeutic drug for IPF. According to the results of randomized control clinical trials in recent years and the actual clinical conditions in China, drugs such as pirfenidone and nintedanib can be used as appropriate. Only IPF patients with mild to moderate pulmonary dysfunction are recommended to be treated by nintedanib, while whether IPF patients with severe pulmonary dysfunction can benefit from treatment by nintedanib and the course of treatment still need to be further discussed.

Rho GTPase was discovered in 1985, and it belongs to the Ras superfamily and has 25% homology to Ras. At present, Rho GTPase members found in mammalian tissue cells are mainly Rho (A, B, C), Rac (1, 2, 3), Cdc42 (Cdc42Hs/G25K, TC10, Tcl), Rho D, Rho G, Chp (1, 2), Rnd (Rho E/Rnd3, Rnd1/Rho6, Rnd2/Rho7), Rho H/TTF, Rif, Wrch1 and Rho BTB (1, 2), where Rho (A, B, C) is one of the most important members of Rho GTPase. Rho-associated protein kinase (ROCK), also called Rho-associated kinase, belongs to serine/threonine protein kinase, and it has a molecular mass of about 160 kD and is a Rho downstream effector molecule which is studied most detailedly in terms of functional study at present. ROCK includes ROCK 1 (ROKβ, p160-ROCK) and ROCK 2 (ROKα) subtypes. The amino acid sequences of the two subtypes are 65% identical, with a high degree of similarity (92% identity) in the kinase domain. ROCK is distributed throughout the body, and in comparison, ROCK 1 is more highly expressed in non-neural tissues (blood, small intestine, thymus, etc.), while ROCK2 is more highly expressed in brain, heart and colon.

ROCK is involved in occurrence of various cardiovascular and cerebrovascular diseases, including hypertension, atherosclerosis, ischemic stroke, heart disease, diabetic nephropathy, ocular diseases, tumors, nerve injury diseases, radiation damage, autoimmune diseases and the like. For example, the Rho/ROCK signaling pathway is involved in NAD(P)H oxidase activation and induces oxidative stress, inducing cardiac microvascular damage and C-reactive protein-induced atherothrombosis; high glucose can activate Rho/ROCK pathway, induce the expression of visceral adipokine and type I procollagen in cardioblast, and cause the hyperproliferation of cardioblast and thus induce diabetic cardiomyopathy; activation of Rho/ROCK signaling pathway can regulate NF-kB signaling pathway, up-regulate inflammatory genes and induce the occurrence of diabetic nephropathy; Rho/ROCK signaling pathway changes biofilm permeability and affects metastasis of cancer cells; in the case of spinal cord injury, Rho is activated, inducing atrophy of growth cones and thereby causing axonal regeneration disorder and simultaneously inducing inhibition against neuron growth by chondroitin sulfate proteoglyca.

In addition, the Rho/ROCK signaling pathway is involved in the occurrence and progression of fibrosis diseases. Activation of Rho/ROCK signaling pathway can increase the level of ischemic myocardial fibrosis, and heart tissues of an acute myocardial fibrosis rat show significantly increased Rho and ROCK expression. Activation of Rho/ROCK signaling pathway can induce phosphorylation of actin, initiating cellular fibrosis. Both in vivo and in vitro experimental results demonstrate that cardiopulmonary physiological and pathological damage caused by exposure to radiation over a period of time is associated with fibrosis induced with the involvement of Rho/ROCK pathway. Formation of endothelial adhesion fibronectin and focal adhesion, decreased endothelial cell migration and endothelial dysfunction due to ionizing radiation are associated with actin scaffold reorganization and stress fiber formation induced by activation of Rho/ROCK signaling pathway.

With respect to lung injury by IPF, primarily alveolar epithelial cells (ACEs) are the targets, and the death of ACEs triggers wound healing responses including innate immune activation, vascular leakage and extravascular coagulation, fibroblast recruitment, proliferation and activation, synthesis and cross-linking of extracellular matrix, alveolar collapse and epithelial regeneration. ROCK signals can fundamentally regulate the activities of these cells involved in the healing response, particularly those of epithelial cells, endothelial cells, and fibroblasts. The key role of ROCK in these responses further suggests the potential of ROCK inhibitors for the treatment of pulmonary fibrosis.

Currently, no drugs that treat numerous disorders including fibrosis through inhibition of ROCK are available on the market. The development of new medicaments requires careful optimization of the chemical and biological properties of the lead compounds. Further, the compounds must have desired pharmacokinetic and pharmacodynamic characteristics. This laborious development process typically requires extensive experimentation. In many cases, the process of determining the optimal compound often requires the preparation of thousands of structurally similar compounds. Therefore, the development of a novel backbone compound having inhibitory effect on ROCK 1 and/or ROCK2 kinases by improving a ROCK kinase inhibitor is of positive significance for the treatment of the above-mentioned diseases.

SUMMARY

In order to solve the problems in the prior art, the present disclosure provides a compound of formula (I) or a racemate, a stereoisomer, a tautomer, an isotopically labeled compound, a nitrogen oxide, a solvate, a polymorph, a metabolite, an ester, a pharmaceutically acceptable salt or a prodrug thereof:

(I)

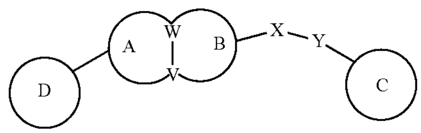

wherein,

W and V are each independently C or N;

X is —C(═O)$NR_x$— or —$NR_x$—C(═O)—;

Y is a chemical bond, or the following group unsubstituted or optionally substituted with one, two or more $R_y$: ($C_1$-$C_{20}$) aliphatic hydrocarbyl, or ($C_1$-$C_{20}$) aliphatic hydrocarbyl optionally comprising one, two or more heteroatoms;

ring A is the following group unsubstituted or optionally substituted with one, two or more $R_{ab}$: $C_{3-20}$ alicyclic hydrocarbyl, 3-20 membered heterocyclyl, $C_{6-20}$ aryl or 5-20 membered heteroaryl;

ring B is the following group unsubstituted or optionally substituted with one, two or more $R_{ab}$: $C_{3-20}$ alicyclic hydrocarbyl, 3-20 membered heterocyclyl, $C_{6-20}$ aryl or 5-20 membered heteroaryl;

ring C is the following group unsubstituted or optionally substituted with one, two or more $R_c$: $C_{3-20}$ alicyclic hydrocarbyl, 3-20 membered heterocyclyl, $C_{6-20}$ aryl or 5-20 membered heteroaryl;

ring D is the following group unsubstituted or optionally substituted with one, two or more $R_d$: $C_{3-20}$ alicyclic hydrocarbyl, 3-20 membered heterocyclyl, $C_{6-20}$ aryl or 5-20 membered heteroaryl;

each $R_y$, each $R_{ab}$, each $R_c$ and each $R_d$ are independently selected from H, halogen, nitro, nitroso, CN, OH, SH, ═O, —$NR_{11}R_{12}$, —C(O)$NR_{11}R_{12}$, —C(═S)$NR_{11}R_{12}$, —$S(O)_2NR_{11}R_{12}$, —C(═$NR_{13}$)$NR_{11}R_{12}$, —NHC(O)$NR_{11}R_{12}$, —$P(O)_2NR_{11}R_{12}$, —P(O)$R_{13}NR_{11}R_{12}$, —$NR_{11}S(O)_2R_{12}$, —$NR_{11}P(O)_2R_{12}$, —$NR_{11}P(O)R_{13}R_{12}$, —C(O)$R_{14}$, —NHC(O)$R_{14}$, —C(O)$OR_{15}$, —OC(O)$R_{15}$, and the following groups unsubstituted or optionally substituted with one, two or more R: ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl and 5-20 membered heteroaryl;

each $R_x$ is independently selected from H, halogen, CN, OH, SH, —$NR_{11}R_{12}$, —C(O)$NR_{11}R_{12}$, —C(═S)$NR_{11}R_{12}$, —$S(O)_2NR_{11}R_{12}$, —C(═$NR_{13}$)$NR_{11}R_{12}$, —NHC(O)$NR_{11}R_{12}$, —$P(O)_2NR_{11}R_{12}$, —P(O)$R_{13}NR_{11}R_{12}$, —$NR_{11}S(O)_2R_{12}$, —$NR_{11}P(O)_2R_{12}$, —$NR_{11}P(O)R_{11}R_{12}$, —C(O)$R_{14}$, —NHC(O)$R_{14}$, —C(O)$OR_{15}$, —OC(O)$R_{15}$, and the following groups unsubstituted or optionally substituted with one, two or more R: ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl and 5-20 membered heteroaryl;

$R_{11}$ and $R_{12}$ are each independently selected from H, and the following group unsubstituted or optionally substituted with one, two or more R: —$C(O)_{14}$, ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl or 5-20 membered heteroaryl; or, $R_{11}$ and $R_{12}$, together with a nitrogen atom attached thereto, form 3-20 membered heterocyclyl or 5-20 membered heteroaryl unsubstituted or optionally substituted with one, two or more R;

$R_{13}$ is selected from H, OH, CN, and the following groups unsubstituted or optionally substituted with one, two or more R: ($C_1$-$C_{20}$) aliphatic hydrocarbyl, and ($C_1$-$C_{20}$) aliphatic hydrocarbyl optionally comprising one, two or more heteroatoms;

$R_{14}$ is selected from H, OH, halogen, and the following groups unsubstituted or optionally substituted with one, two or more R: ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl and 5-20 membered heteroaryl;

$R_{15}$ is selected from H, and the following groups unsubstituted or optionally substituted with one, two or more R: ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl and 5-20 membered heteroaryl;

each R is independently selected from ═O, halogen, CN, OH, SH, $NH_2$, COOH, and the following groups unsubstituted or optionally substituted with one, two or more R': ($C_1$-$C_{20}$) aliphatic hydrocarbyl, ($C_1$-$C_{20}$) aliphatic hydrocarbyl optionally comprising one, two or more heteroatoms, $C_{3-20}$ alicyclic hydrocarbyl, 3-20 membered heterocyclyl, $C_{6-20}$ aryl and 5-20 membered heteroaryl;

each R' is independently selected from ═O, halogen, CN, OH, SH, $NH_2$, COOH, ($C_1$-$C_{20}$) aliphatic hydrocarbyl, and ($C_1$-$C_{20}$) aliphatic hydrocarbyl optionally comprising one, two or more heteroatoms.

In the "($C_1$-$C_{20}$) aliphatic hydrocarbyl optionally comprising one, two or more heteroatoms", the heteroatom may be selected from sulfur, nitrogen, oxygen, phosphorus and silicon; optionally, the heteroatom is optionally inserted into a C—C bond and a C—H bond in the aliphatic hydrocarbyl; for example, the "($C_1$-$C_{20}$) aliphatic hydrocarbyl optionally comprising one, two or more heteroatoms" may be selected from ($C_1$-$C_{20}$) aliphatic hydrocarbyloxy, ($C_1$-$C_{20}$) aliphatic hydrocarbylmercapto, ($C_1$-$C_{12}$) aliphatic hydrocarbyloxy, ($C_1$-$C_{12}$) aliphatic hydrocarbylmercapto, ($C_1$-$C_6$) aliphatic hydrocarbyloxy, ($C_1$-$C_6$) aliphatic hydrocarbylmercapto, ($C_1$-$C_6$) aliphatic hydrocarbyloxy($C_1$-$C_6$) aliphatic hydrocarbyl, ($C_1$-$C_6$) aliphatic hydrocarbylmercapto($C_1$-$C_6$) aliphatic hydrocarbyl, ($C_1$-$C_6$) aliphatic hydrocarbyloxy($C_1$-$C_6$) aliphatic hydrocarbyloxy, ($C_1$-$C_6$) aliphatic hydrocarbylmercapto($C_1$-$C_6$) aliphatic hydrocarbylmercapto, N—($C_1$-$C_3$) aliphatic hydrocarbylamino($C_1$-$C_6$) aliphatic hydrocarbyl, and N,N-di-($C_1$-$C_3$) aliphatic hydrocarbylamino($C_1$-$C_6$) aliphatic hydrocarbyl;

The ($C_1$-$C_{20}$) aliphatic hydrocarbyl may be selected from ($C_1$-$C_{20}$) alkyl, ($C_2$-$C_{20}$) alkenyl and ($C_2$-$C_{20}$) alkynyl, and it may be further selected from ($C_1$-$C_{12}$) alkyl, ($C_2$-$C_{12}$) alkenyl and ($C_2$-$C_{12}$) alkynyl; in some embodiments, it may be selected from ($C_1$-$C_6$) alkyl, ($C_2$-$C_6$) alkenyl and ($C_2$-$C_6$) alkynyl; for example, it is selected from methyl, ethyl, n-propyl, isopropyl, n-butyl, isobutyl, tert-butyl, n-pentyl, isopentyl, neopentyl, n-hexyl, vinyl, propenyl, butenyl, pentenyl, hexenyl, ethynyl, propynyl, butynyl, pentynyl and hexynyl, and further, it may be selected from methyl, ethyl, n-propyl, isopropyl, n-butyl, isobutyl, tert-butyl, n-pentyl, isopentyl, neopentyl, n-hexyl, vinyl, 1-propenyl, 2-propenyl, 1-methylvinyl, 1-butenyl, 1-ethylvinyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 2-butynyl, 1-isobutynyl, 1-isopentynyl, 2-isopentynyl, 1-methyl-2-propynyl, 3-butynyl, 1-pentynyl and 1-hexynyl;

the "halogen" is selected from F, Cl, Br and I.

According to an embodiment of the present disclosure, in the compound of formula (I), W and V are each independently C or N;

X is —C(═O)$NR_x$— or —$NR_x$—C(═O)—;

Y is a chemical bond, or the following group unsubstituted or optionally substituted with one, two or more $R_y$: ($C_1$-$C_{12}$) aliphatic hydrocarbyl, or ($C_1$-$C_{12}$) aliphatic hydrocarbyl optionally comprising one, two or more heteroatoms;

ring A is the following group unsubstituted or optionally substituted with one, two or more $R_{ab}$: $C_{3-12}$ alicyclic hydrocarbyl, 3-12 membered heterocyclyl, $C_{6-14}$ aryl or 5-14 membered heteroaryl;

ring B is the following group unsubstituted or optionally substituted with one, two or more $R_{ab}$: $C_{3-12}$ alicyclic hydrocarbyl, 3-12 membered heterocyclyl, 06-14 aryl or 5-14 membered heteroaryl;

ring C is the following group unsubstituted or optionally substituted with one, two or more $R_c$: $C_{3-12}$ alicyclic hydrocarbyl, 3-12 membered heterocyclyl, $C_{6-14}$ aryl or 5-14 membered heteroaryl;

ring D is the following group unsubstituted or optionally substituted with one, two or more $R_d$: $C_{3-12}$ alicyclic hydrocarbyl, 3-12 membered heterocyclyl, $C_{6-14}$ aryl or 5-14 membered heteroaryl;

each $R_y$, each $R_{ab}$, each $R_c$ and each $R_d$ are independently selected from H, halogen, nitro, nitroso, CN, OH, SH, ═O, —$NR_{11}R_{12}$, —C(O)$NR_{11}R_{12}$, —C(═S)$NR_{11}R_{12}$, —S(O)$_2NR_{11}R_{12}$, —C(═$NR_{13}$)$NR_{11}R_{12}$, —NHC(O)$NR_{11}R_{12}$, —P(O)$_2NR_{11}R_{12}$, —P(O)$R_{13}NR_{11}R_{12}$, —$NR_{11}$S(O)$_2R_{12}$, —$NR_{11}$P(O)$_2R_{12}$, —$NR_{11}$P(O)$R_{13}R_{12}$, —C(O)$R_{14}$, —NHC(O)$R_{14}$, —C(O)O$R_{15}$, —OC(O)$R_{15}$, and the following groups unsubstituted or optionally substituted with one, two or more R: ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl;

each $R_x$ is independently selected from H, halogen, CN, OH, SH, —$NR_{11}R_{12}$, —C(O)$NR_{11}R_{12}$, —C(═S)$NR_{11}R_{12}$, —S(O)$_2NR_{11}R_{12}$, —C(═$NR_{13}$)$NR_{11}R_{12}$, —NHC(O)$NR_{11}R_{12}$, —P(O)$_2NR_{11}R_{12}$, —P(O)$R_{13}NR_{11}R_{12}$, —$NR_{11}$S(O)$_2R_{12}$, —$NR_{11}$P(O)$_2R_{12}$, —$NR_{11}$P(O)$R_{13}R_{12}$, —C(O)$R_{14}$, —NHC(O)$R_{14}$, —C(O)O$R_{15}$, —OC(O)$R_{15}$, and the following groups unsubstituted or optionally substituted with one, two or more R: ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl;

$R_{11}$ and $R_{12}$ are each independently selected from H, and the following groups unsubstituted or optionally substituted with one, two or more R: —C(O)$R_{14}$, ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl; or, $R_{11}$ and $R_{12}$, together with a nitrogen atom attached thereto, form 3-12 membered heterocyclyl or 5-14 membered heteroaryl unsubstituted or optionally substituted with one, two or more R;

$R_{13}$ is selected from H, OH, CN, and the following groups unsubstituted or optionally substituted with one, two or more R: ($C_1$-$C_{12}$) aliphatic hydrocarbyl, and ($C_1$-$C_{12}$) aliphatic hydrocarbyl optionally comprising one, two or more heteroatoms;

$R_{14}$ is selected from H, OH, halogen, and the following groups unsubstituted or optionally substituted with one, two or more R: ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl;

$R_{15}$ is selected from H, and the following groups unsubstituted or optionally substituted with one, two or more R: ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl;

each R is independently selected from ═O, halogen, CN, OH, SH, $NH_2$, COOH, and the following groups unsubstituted or optionally substituted with one, two or more R': ($C_1$-$C_{12}$) aliphatic hydrocarbyl, ($C_1$-$C_{12}$) aliphatic hydrocarbyl optionally comprising one, two or more heteroatoms, $C_{3-12}$ alicyclic hydrocarbyl, 3-12 membered heterocyclyl, $C_{6-14}$ aryl and 5-14 membered heteroaryl;

each R' is independently selected from ═O, halogen, CN, OH, SH, $NH_2$, COOH, ($C_1$-$C_{12}$) aliphatic hydrocarbyl, and ($C_1$-$C_{12}$) aliphatic hydrocarbyl optionally comprising one, two or more heteroatoms.

In the "($C_1$-$C_{12}$) aliphatic hydrocarbyl optionally comprising one, two or more heteroatoms", the heteroatom may be selected from sulfur, nitrogen, oxygen, phosphorus and silicon; optionally, the heteroatom is optionally inserted into a C—C bond and a C—H bond in the aliphatic hydrocarbyl; for example, the "($C_1$-$C_{12}$) aliphatic hydrocarbyl optionally comprising one, two or more heteroatoms" may be selected from ($C_1$-$C_{12}$) aliphatic hydrocarbyloxy, ($C_1$-$C_{12}$) aliphatic hydrocarbylmercapto, ($C_1$-$C_6$) aliphatic hydrocarbyloxy, ($C_1$-$C_6$) aliphatic hydrocarbylmercapto, ($C_1$-$C_6$) aliphatic hydrocarbyloxy($C_1$-$C_6$) aliphatic hydrocarbyl, ($C_1$-$C_6$) aliphatic hydrocarbylmercapto($C_1$-$C_6$) aliphatic hydrocarbyl, ($C_1$-$C_6$) aliphatic hydrocarbyloxy($C_1$-$C_6$) aliphatic hydrocarbyloxy, ($C_1$-$C_6$) aliphatic hydrocarbylmercapto($C_1$-$C_6$) aliphatic hydrocarbylmercapto, N—($C_1$-$C_3$) aliphatic hydrocarbylamino($C_1$-$C_6$) aliphatic hydrocarbyl, and N,N-di-($C_1$-$C_3$) aliphatic hydrocarbylamino($C_1$-$C_6$) aliphatic hydrocarbyl;

the ($C_1$-$C_{12}$) aliphatic hydrocarbyl may be selected from ($C_1$-$C_{12}$) alkyl, ($C_2$-$C_{12}$) alkenyl and ($C_2$-$C_{12}$) alkynyl, and in some embodiments, it may be selected from ($C_1$-$C_6$)alkyl, ($C_2$-$C_6$)alkenyl and ($C_2$-$C_6$)alkynyl;

the "halogen" is selected from F, Cl, Br and I.

According to an embodiment of the present disclosure, in the compound of formula (I), W and V are each independently C or N;

X is —C(═O)$NR_x$— or —$NR_x$C(═O)—;

Y is a chemical bond, or the following group unsubstituted or optionally substituted with one, two or more $R_y$: ($C_1$-$C_6$) aliphatic hydrocarbyl, or ($C_1$-$C_6$) aliphatic hydrocarbyl optionally comprising one, two or more heteroatoms;

ring A is the following group unsubstituted or optionally substituted with one, two or more $R_{ab}$: $C_{3-7}$ alicyclic hydrocarbyl, 3-7 membered heterocyclyl, $C_{6-10}$ aryl or 5-10 membered heteroaryl;

ring B is the following group unsubstituted or optionally substituted with one, two or more $R_{ab}$: $C_{3-7}$ alicyclic hydrocarbyl, 3-7 membered heterocyclyl, $C_{6-10}$ aryl or 5-10 membered heteroaryl;

ring C is the following group unsubstituted or optionally substituted with one, two or more $R_c$: $C_{3-7}$ alicyclic hydrocarbyl, 3-7 membered heterocyclyl, $C_{6-10}$ aryl or 5-10 membered heteroaryl;

ring D is the following group unsubstituted or optionally substituted with one, two or more $R_d$: $C_{3-7}$ alicyclic hydrocarbyl, 3-7 membered heterocyclyl, $C_{6-10}$ aryl or 5-10 membered heteroaryl;

each $R_y$, each $R_{ab}$, each $R_c$ and each $R_d$ are independently selected from H, halogen, nitro, nitroso, CN, OH, SH, =O, $-NR_{11}R_{12}$, $-C(O)NR_{11}R_{12}$, $-C(=S)NR_{11}R_{12}$, $-S(O)_2NR_{11}R_{12}$, $-C(=NR_{13})NR_{11}R_{12}$, $-NHC(O)NR_{11}R_{12}$, $-P(O)_2NR_{11}R_{12}$, $-P(O)R_{13}NR_{11}R_{12}$, $-NR_{11}S(O)_2R_{12}$, $-NR_{11}P(O)_2NR_{11}R_{12}$, $-NR_{11}P(O)R_{13}R_{12}$, $-C(O)R_{14}$, $-NHC(O)R_{14}$, $-C(O)OR_{15}$, $-OC(O)R_{15}$, and the following groups unsubstituted or optionally substituted with one, two or more R: ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl;

each $R_x$ is independently selected from H, halogen, CN, OH, SH, $-NR_{11}R_{12}$, $-C(O)NR_{11}R_{12}$, $-C(=S)NR_{11}R_{12}$, $-S(O)_2NR_{11}R_{12}$, $-C(=NR_{13})NR_{11}R_{12}$, $-NHC(O)NR_{11}R_{12}$, $-P(O)_2NR_{11}R_{12}$, $-P(O)R_{13}NR_{11}R_{12}$, $-NR_{11}S(O)_2R_{12}$, $-NR_{11}P(O)_2R_{12}$, $-NR_{11}P(O)R_{13}R_{12}$, $-C(O)R_{14}$, $-NHC(O)R_{14}$, $-C(O)OR_{15}$, $-OC(O)R_{15}$, and the following groups unsubstituted or optionally substituted with one, two or more R: ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl;

$R_{11}$ and $R_{12}$ are each independently selected from H, and the following groups unsubstituted or optionally substituted with one, two or more R: $-C(O)R_{14}$, ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl; or, $R_{11}$ and $R_{12}$, together with a nitrogen atom attached thereto, form 3-7 membered heterocyclyl or 5-10 membered heteroaryl unsubstituted or optionally substituted with one, two or more R;

$R_{13}$ is selected from H, OH, CN, and the following groups unsubstituted or optionally substituted with one, two or more R: ($C_1$-$C_6$) aliphatic hydrocarbyl, and ($C_1$-$C_6$) aliphatic hydrocarbyl optionally comprising one, two or more heteroatoms;

$R_{14}$ is selected from H, OH, halogen, and the following groups unsubstituted or optionally substituted with one, two or more R: ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl;

$R_{15}$ is selected from H, and the following groups unsubstituted or optionally substituted with one, two or more R: ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl;

each R is independently selected from =O, halogen, CN, OH, SH, $NH_2$, COOH, and the following groups unsubstituted or optionally substituted with one, two or more R': ($C_1$-$C_6$) aliphatic hydrocarbyl, ($C_1$-$C_6$) aliphatic hydrocarbyl optionally comprising one, two or more heteroatoms, $C_{3-7}$ alicyclic hydrocarbyl, 3-7 membered heterocyclyl, $C_{6-10}$ aryl and 5-10 membered heteroaryl;

each R' is independently selected from =O, halogen, CN, OH, SH, $NH_2$, COOH, ($C_1$-$C_6$) aliphatic hydrocarbyl, and ($C_1$-$C_6$) aliphatic hydrocarbyl optionally comprising one, two or more heteroatoms.

According to an embodiment of the present disclosure, in the compound of formula (I), wherein, W and V are each independently C or N;

X is $-C(=O)NR_x-$ or $-NR_x-C(=O)-$;

Y can be selected from the following groups unsubstituted or optionally substituted with one, two or more $R_y$: methylene, ethylidene, propylidene, $-OCH_2-$, $-CH_2O-$, $-SCH_2-$ and $-CH_2S-$;

ring A is the following group unsubstituted or optionally substituted with one, two or more $R_{ab}$: $C_{3-7}$ alicyclic hydrocarbyl, 3-7 membered heterocyclyl, $C_{6-10}$ aryl or 5-10 membered heteroaryl;

ring B is the following group unsubstituted or optionally substituted with one, two or more $R_{ab}$: $C_{3-7}$ alicyclic hydrocarbyl, 3-7 membered heterocyclyl, $C_{6-10}$ aryl or 5-10 membered heteroaryl;

ring C is the following group unsubstituted or optionally substituted with one, two or more $R_c$: $C_{3-7}$ alicyclic hydrocarbyl, 3-7 membered heterocyclyl, $C_{6-10}$ aryl or 5-10 membered heteroaryl;

ring D is the following group unsubstituted or optionally substituted with one, two or more $R_d$: $C_{3-7}$ alicyclic hydrocarbyl, 3-7 membered heterocyclyl, $C_{6-10}$ aryl or 5-10 membered heteroaryl;

each $R_y$, each $R_{ab}$, each $R_c$ and each $R_d$ may be independently selected from H, halogen, nitro, nitroso, CN, OH, SH, COOH, =O, methyl, ethyl, propyl, butyl, pentyl, hexyl, vinyl, propenyl, butenyl, pentenyl, hexenyl, ethynyl, propynyl, butynyl, pentynyl, hexynyl, cyclopropyl, cyclobutyl, cyclopentyl, cyclohexyl, methoxy, ethoxy, propoxy, butoxy, pentyloxy, hexyloxy, $-O(CH_2)_nO(CH_2)_mCH_3$, $-S(CH_2)_nS(CH_2)_mCH_3$, $-CF_3$, $-CHF_2$, $-CH_2F$, $-CH_2CF_3$, $-CH_2CHF_2$, $-CH_2CH_2F$, $-NH_2(CH_2)_m-$, $(CH_3)_2N(CH_2)_m-$, $CH_3NH(CH_2)_m-$, $C_6H_5NH(CH_2)_m-$, $-(NH)_kC(O)NH_2$, $-(NH)_kC(O)NH(CH_2)_mCH_3$, $-(NH)_kC(O)N(CH_3)(CH_2)_mCH_3$, $-(NH)_kC(O)NHC_6H_5$, $(NH)_kC(O)(CH_2)_mCH_3$, $-(NH)_kC(O)(CH_2)_m C_6H_5$, $-OC(O)(CH_2)_mCH_3$, $-O(CH_2)_mC(=O)(CH_2)_m(NH)_kH$, $-C(O)O(CH_2)_mCH_3$, $-OC(O)(CH_2)_mC_6H_5$, $-C(O)O(CH_2)_mC_6H_5$, $-C(=S)NH_2$, $-C(=S)NHCH_3$, $-C(=S)N(CH_3)_2$, $-S(O)_2NH_2$, $-S(O)_2NHCH_3$, $-S(O)_2N(CH_3)_2$, $-NHS(O)_2NH_2$, $-NHS(O)_2CH_3$, $-NCH_3S(O)_2NHCH_3$, $-P(O)_2NH_2$, $-P(O)_2NHCH_3$, $-P(O)_2N(CH_3)_2$, $-NHP(O)_2CH_3$, $-N(CH_3)P(O)_2CH_3$, $-C(=NH)NH_2$, $-C(=NH)$ $NHCH_3$, $—C(=NH)N(CH_3)_2$, $—C(=NCH_3)NH_2$, $—C(=NCH_3)NHCH_3$, $—C(=NCH_3)N(CH_3)_2$, oxetanyl, azetidinyl, tetrahydropyranyl, tetrahydrofuranyl, morpholinyl, tetrahydrothienyl, dioxolyl, pyrrolidinyl, imidazolidinyl, pyrazolidinyl, pyrrolinyl, tetrahydropyranyl, piperidinyl, dithianyl, thiomorpholinyl, piperazinyl, trithianyl, diazepanyl, phenyl, benzyl,

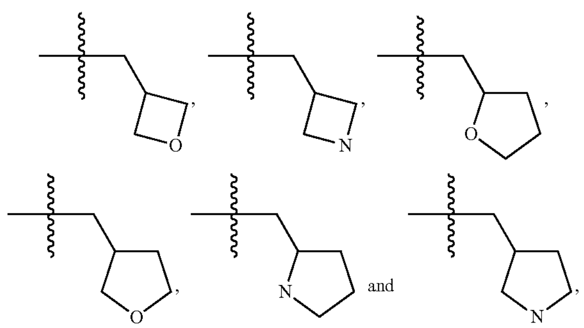

wherein n is selected from 1, 2 and 3; m is selected from 0, 1, 2 and 3; k is selected from 0 and 1; $R_x$, $R_y$, $R_{ab}$, $R_c$ and $R_d$ may be further substituted with one, two or more R; R is defined as in any of the embodiments above;

each $R_x$ may be independently selected from H, halogen, CN, OH, SH, COOH, methyl, ethyl, propyl, butyl, pentyl, hexyl, vinyl, propenyl, butenyl, pentenyl, hexenyl, ethynyl, propynyl, butynyl, pentynyl, hexynyl, cyclopropyl, cyclobutyl, cyclopentyl, cyclohexyl, methoxy, ethoxy, propoxy, butoxy, pentyloxy, hexyloxy, $—O(CH_2)_nO(CH_2)_mCH_3$, $—S(CH_2)_nS(CH_2)_mCH_3$, $—CF_3$, $—CHF_2$, $—CH_2F$, $—CH_2CF_3$, $—CH_2CHF_2$, $—CH_2CH_2F$, $NH_2(CH_2)_m—$, $(CH_3)_2N(CH_2)_m—$, $CH_3NH(CH_2)_m—$, $C_6H_5NH(CH_2)_m—$, $—(NH)_kC(O)NH_2$, $—(NH)_kC(O)NH(CH_2)_mCH_3$, $—(NH)_kC(O)N(CH_3)(CH_2)_mCH_3$, $—(NH)_kC(O)NHC_6H_5$, $—(NH)_kC(O)(CH_2)_mCH_3$, $—(NH)_kC(O)(CH_2)_mC_6H_5$, $—OC(O)(CH_2)_mCH_3$, $—C(O)O(CH_2)_mCH_3$, $—OC(O)(CH_2)_mC_6H_5$, $—C(O)O(CH_2)_mC_6H_5$, $—C(=S)NH_2$, $—C(=S)NHCH_3$, $—C(=S)N(CH_3)_2$, $—S(O)_2NH_2$, $—S(O)_2NHCH_3$, $—S(O)_2N(CH_3)_2$, $—NHS(O)_2NH_2$, $—NHS(O)_2CH_3$, $—NCH_3S(O)_2NHCH_3$, $—P(O)_2NH_2$, $—P(O)_2NHCH_3$, $—P(O)_2N(CH_3)_2$, $—NHP(O)_2CH_3$, $—N(CH_3)P(O)_2CH_3$, $—C(=NH)NH_2$, $—C(=NH)NHCH_3$, $—C(=NH)N(CH_3)_2$, $—C(=NCH_3)NH_2$, $—C(=NCH_3)NHCH_3$, $—C(=NCH_3)N(CH_3)_2$, oxetanyl, azetidinyl, tetrahydropyranyl, tetrahydrofuranyl, morpholinyl, tetrahydrothienyl, dioxolyl, pyrrolidinyl, imidazolidinyl, pyrazolidinyl, pyrrolinyl, tetrahydropyranyl, piperidinyl, dithianyl, thiomorpholinyl, piperazinyl, trithianyl, diazepanyl, phenyl, benzyl,

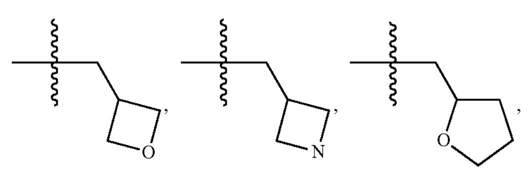

-continued

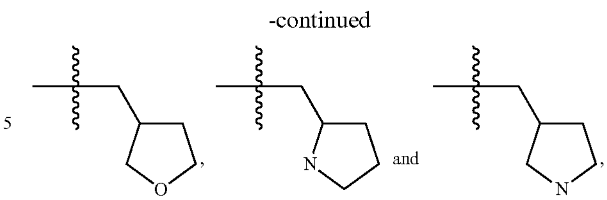

wherein n is selected from 1, 2 and 3; m is selected from 0, 1, 2 and 3; k is selected from 0 and 1; $R_x$ may be further substituted with one, two or more R; R is defined as in any of the embodiments above;

According to an embodiment of the present disclosure, $R_y$, $R_{ab}$, $R_c$ and $R_d$ may be independently selected from H, F, Cl, Br, I, nitro, nitroso, CN, OH, SH, COOH, =O, methyl, ethyl, n-propyl, isopropyl, n-butyl, isobutyl, Gerabutyl, n-pentyl, isopentyl, neopentyl, n-hexyl, vinyl, 1-propenyl, 2-propenyl, 1-methylvinyl, 1-butenyl, 1-ethylvinyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 2-butynyl, 1-isobutynyl, 1-isopentynyl, 2-isopentynyl, 1-methyl-2-propynyl, 3-butynyl, 1-pentynyl, 1-hexynyl, cyclopropyl, cyclobutyl, cyclopentyl, cyclohexyl, methoxy, ethoxy, propoxy, butoxy, hexyloxy, pentyloxy, $—OCH_2OCH_3$, $—OCH_2CH_2OCH_3$, $—OCH_2CH_2CH_2OCH_3$, $—OCH_2OCH_2CH_3$, $—OCH_2OCH_2CH_2CH_3$, $—OCH_2CH_2OCH_2CH_3$, $—OCH_2CH_2OCH_2CH_2CH_3$, $—SCH_2SCH_3$, $—SCH_2CH_2SCH_3$, $—SCH_2CH_2CH_2SCH_3$, $—SCH_2SCH_2CH_3$, $—SCH_2SCH_2CH_2CH_3$, $—SCH_2CH_2SCH_2CH_3$, $—SCH_2CH_2SCH_2CH_2CH_3$, $—CF_3$, $—CHF_2$, $—CH_2F$, $—CH_2CF_3$, $—CH_2CHF_2$, $—CH_2CH_2F$, $NH_2—$, $NH_2CH_2—$, $—NHCH_3$, $—N(CH_3)_2$, $(CH_3)_2NCH_2CH_2—$, $CH_3NHCH_2CH_2—$, $(CH_3)_2NCH_2—$, $(CH_3)_2NCH_2CH_2CH_2—$, $C_6H_5NH—$, $—C(O)NH_2$, $—NHC(O)NH_2$, $—C(O)NHCH_3$, $—C(O)N(CH_3)_2$, $—C(O)NHC_6H_5$, $—NHC(O)NHCH_3$, $—NHC(O)N(CH_2)_2$, $—NHC(O)NHC_6H_5$, $—NHC(O)CH_3$, $—NHC(O)CH_2CH_3$, $—NHC(O)CH_2C_6H_5$, $—C(O)CH_3$, $—C(O)CH_2CH_3$, $—C(O)C_6H_5$, $—OC(O)CH_3$, $—C(O)OCH_3$, $—OC(O)C_6H_5$, $—C(O)OC_6H_5$, $—OC(O)CH_2CH_3$, $—C(O)OCH_2CH_3$, $—OC(O)CH_2C_6H_5$, $—C(O)OCH_2C_6H_5$, $—C(=S)NH_2$, $—C(=S)NHCH_3$, $—C(=S)N(CH_3)_2$, $—S(O)_2NH_2$, $—S(O)_2NHCH_3$, $—S(O)_2N(CH_3)_2$, $—NHS(O)_2NH_2$, $—NHS(O)_2CH_3$, $—NCH_3S(O)_2NHCH_3$, $—P(O)_2NH_2$, $—P(O)_2NHCH_3$, $—P(O)_2N(CH_3)_2$, $—NHP(O)_2CH_3$, $—N(CH_3)P(O)_2CH_3$, $—C(=NH)NH_2$, $—C(=NH)NHCH_3$, $—C(=NH)N(CH_3)_2$, $—C(=NCH_3)NH_2$, $—C(=NCH_3)NHCH_3$, $—C(=NCH_3)N(CH_3)_2$, oxetanyl, azetidinyl, tetrahydropyranyl, tetrahydrofuranyl, morpholinyl, tetrahydrothienyl, dioxolyl, pyrrolidinyl, imidazolidinyl, pyrazolidinyl, pyrrolinyl, tetrahydropyranyl, piperidinyl, dithianyl, thiomorpholinyl, piperazinyl, trithianyl, diazepanyl, phenyl, benzyl, piperazinyl, trithianyl, diazepanyl, phenyl, benzyl,

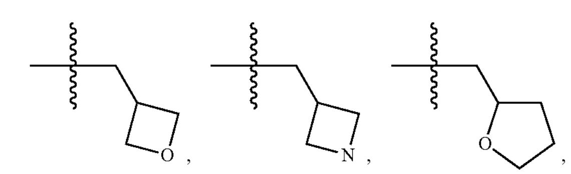

-continued

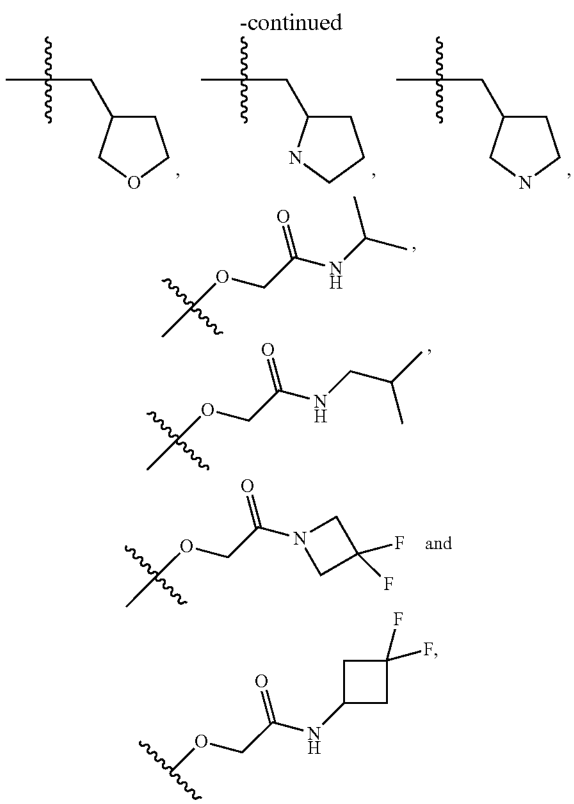

wherein $R_x$, $R_y$, $R_{ab}$, $R_c$ and $R_d$ may be further substituted with one, two or more R; R is defined as in any of the embodiments above;

$R_x$ may be independently selected from H, F, Cl, Br, I, CN, OH, SH, COOH, methyl, ethyl, n-propyl, isopropyl, n-butyl, isobutyl, tert-butyl, n-pentyl, isopentyl, neopentyl, n-hexyl, vinyl, 1-propenyl, 2-propenyl, 1-methylvinyl, 1-butenyl, 1-ethylvinyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 2-butynyl, 1-isobutynyl, 1-isopentynyl, 2-isopentynyl, 1-methyl-2-propynyl, 3-butynyl, 1-pentynyl, 1-hexynyl, cyclopropyl, cyclobutyl, cyclopentyl, cyclohexyl, methoxy, ethoxy, propoxy, butoxy, hexyloxy, pentyloxy, $-OCH_2OCH_3$, $-OCH_2CH_2OCH_3$, $-OCH_2CH_2CH_2OCH_3$, $-OCH_2OCH_2CH_3$, $-OCH_2OCH_2CH_2CH_3$, $-OCH_2CH_2OCH_2CH_3$, $-OCH_2CH_2OCH_2CH_2CH_3$, $-SCH_2SCH_3$, $-SCH_2CH_2SCH_3$, $-SCH_2CH_2CH_2SCH_3$, $-SCH_2SCH_2CH_3$, $-SCH_2SCH_2CH_2CH_3$, $-SCH_2CH_2SCH_2CH_3$, $-SCH_2CH_2SCH_2CH_2CH_3$, $-CF_3$, $-CHF_2$, $-CH_2F$, $-CH_2CF_3$, $-CH_2CHF_2$, $-CH_2CH_2F$, $NH_2-$, $NH_2CH_2-$, $-NHCH_3$, $-N(CH_3)_2$, $(CH_3)_2NCH_2CH_2-$, $CH_3NHCH_2CH_2-$, $(CH_3)_2NCH_2-$, $(CH_3)_2NCH_2CH_2CH_2-$, $C_6H_5NH-$, $-C(O)NH_2$, $-NHC(O)NH_2$, $-C(O)NHCH_3$, $-C(O)N(CH_3)_2$, $-C(O)NHC_6H_5$, $-NHC(O)NHCH_3$, $-NHC(O)N(CH_3)_2$, $-NHC(O)NHC_6H_5$, $-NHC(O)CH_3$, $-NHC(O)CH_2CH_3$, $-NHC(O)CH_2C_6H_5$, $-C(O)CH_3$, $-C(O)CH_2CH_3$, $-C(O)C_6H_5$, $-OC(O)CH_3$, $-C(O)OCH_3$, $-OC(O)C_6H_5$, $-C(O)OC_6H_5$, $-OC(O)CH_2CH_3$, $-C(O)OCH_2CH_3$, $-OC(O)CH_2C_6H_5$, $-C(O)OCH_2C_6H_5$, $-C(=S)NH_2$, $-C(=S)NHCH_3$, $-C(=S)N(CH_3)_2$, $-S(O)_2NH_2$, $-S(O)_2NHCH_3$, $-S(O)_2N(CH_3)_2$, $-NHS(O)_2NH_2$, $-NHS(O)_2CH_3$, $-NCH_3S(O)_2NHCH_3$, $-P(O)_2NH_2$, $-P(O)_2NHCH_3$, $-P(O)_2N(CH_3)_2$, $-NHP(O)_2CH_3$, $-N(CH_3)P(O)_2CH_3$, $-C(=NH)NH_2$, $-C(=NH)NHCH_3$, $-C(=NH)N(CH_3)_2$, $-C(=NCH_3)NH_2$, $-C(=NCH_3)NHCH_3$, $-C(=NCH_3)N(CH_3)_2$, oxetanyl, azetidinyl, tetrahydropyranyl, tetrahydrofuranyl, morpholinyl, tetrahydrothienyl, dioxolyl, pyrrolidinyl, imidazolidinyl, pyrazolidinyl, pyrrolinyl, tetrahydropyranyl, piperidinyl, dithianyl, thiomorpholinyl, piperazinyl, trithianyl, diazepanyl, phenyl, benzyl,

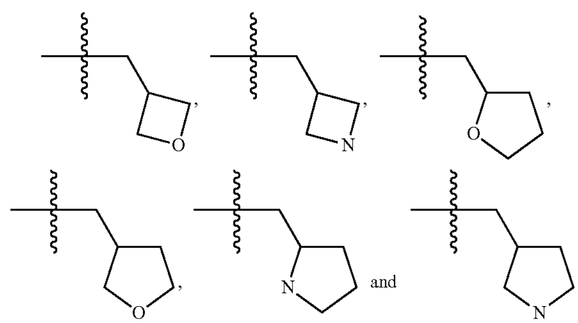

wherein $R_x$, $R_y$, $R_{ab}$, $R_c$ and $R_d$ may be further substituted with one, two or more R; R is defined as in any of the embodiments above;

According to an embodiment of the present disclosure, in some embodiments, W and V are not both N in the group

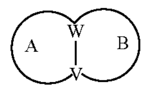;

in some embodiments, in the group

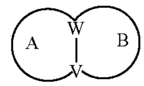, ring A and ring B are each independently selected from phenyl, $C_{5-6}$ alicyclic hydrocarbyl, 5-6 membered heterocyclyl and 5-6 membered heteroaryl; preferably, at least one of ring A and ring B is aryl or heteroaryl, or ring A and ring B are combined to form aryl or heteroaryl;

in some embodiments, in the group

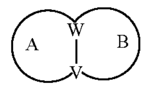, at least one of ring A and ring B is phenyl or 5-6 membered heteroaryl, and the other is selected from phenyl, $C_{5-6}$ alicyclic hydrocarbyl, 5-6 membered heterocyclyl and 5-6 membered heteroaryl; or ring A and ring B are combined to form aryl or heteroaryl;

In some embodiments, in the group

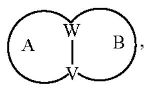

ring B is selected from a nitrogen-containing 5-6 membered heterocyclyl and 5-6 membered heteroaryl and is attached to the X group via an N atom present on the ring.

According to an embodiment of the present disclosure, in the compound of formula (I),

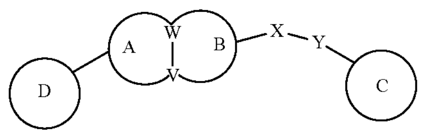

(I)

wherein, the group

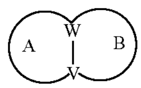

is selected from the following structures unsubstituted or optionally substituted with one, two or more $R_{ab}$:

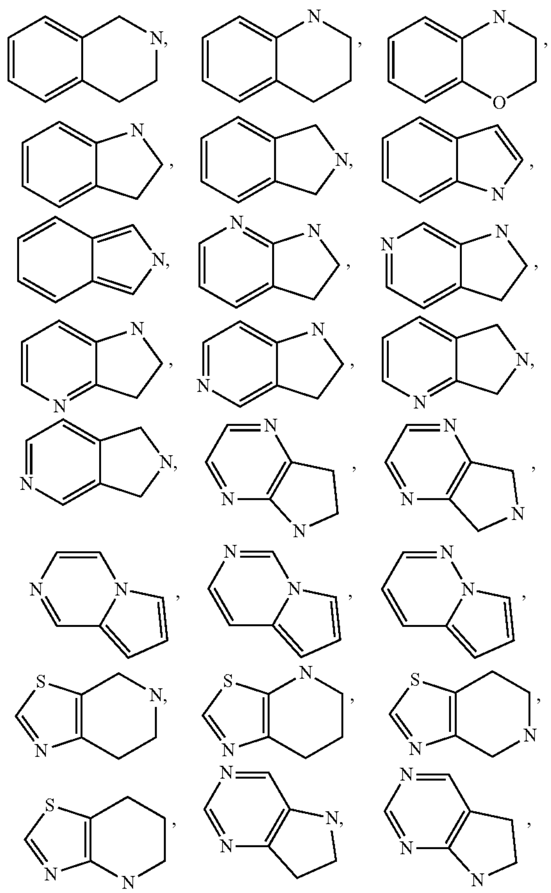

-continued

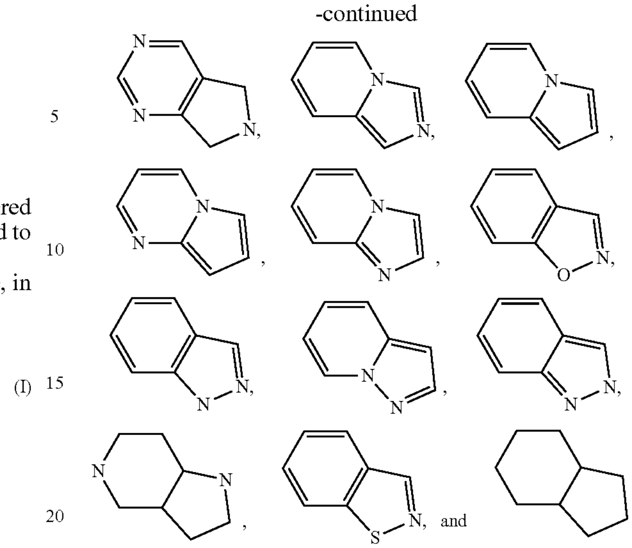

According to an embodiment of the present disclosure, the group

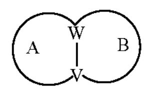

is selected from the following structures unsubstituted or optionally substituted with one, two or more $R_{ab}$:

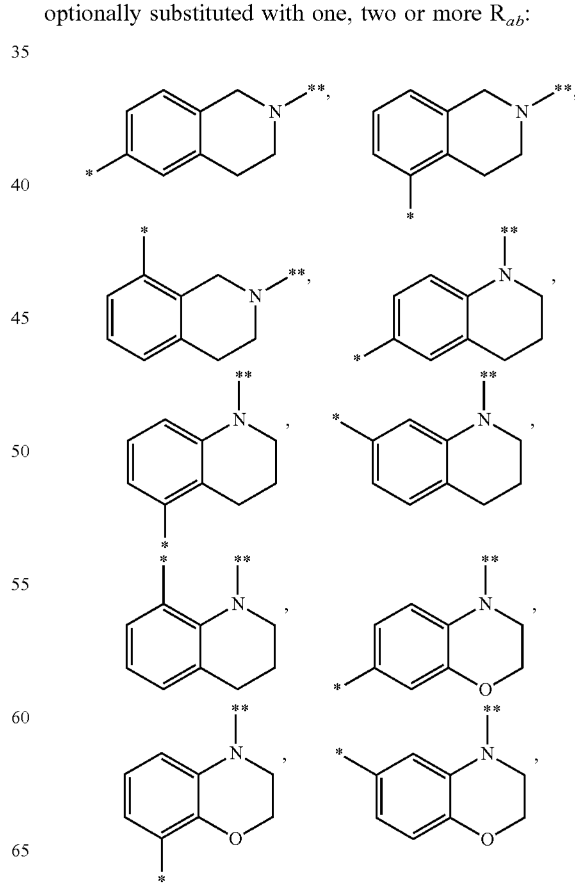

-continued
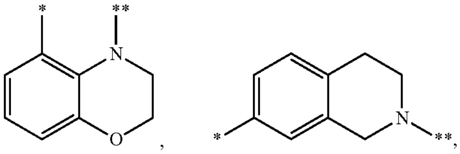
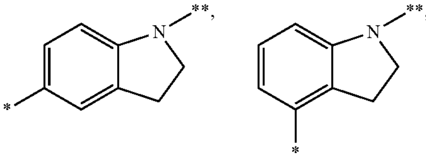
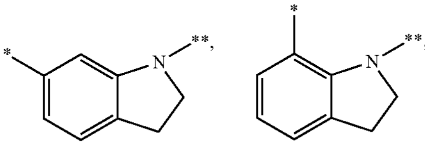
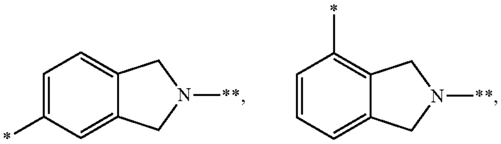
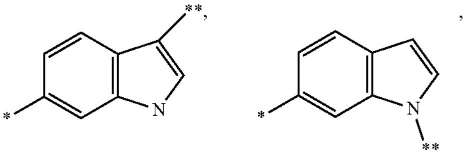
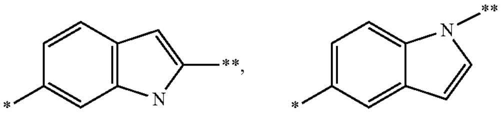
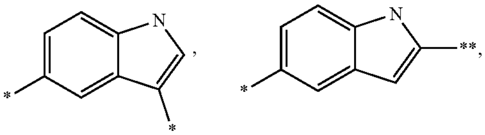
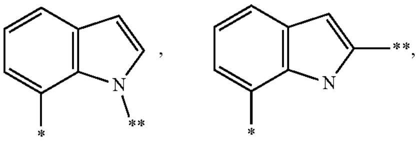
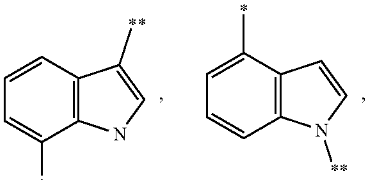
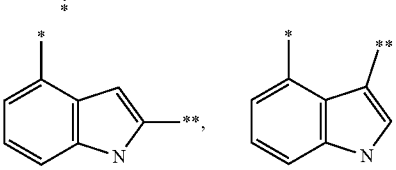
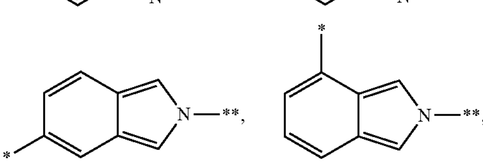
-continued
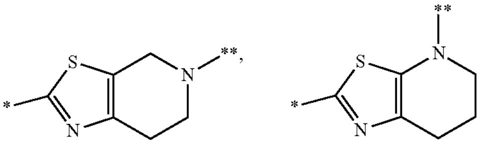
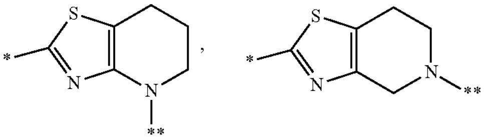
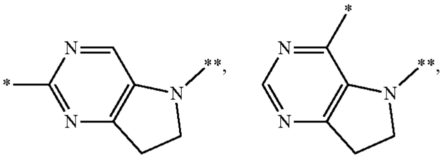
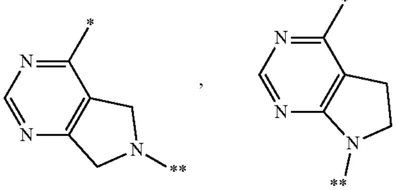
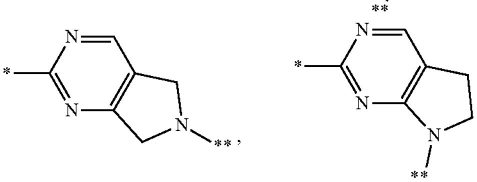
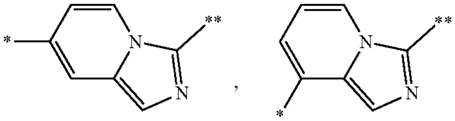
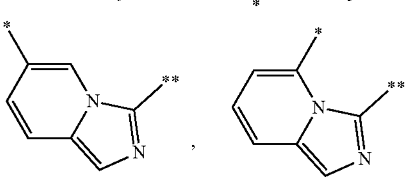
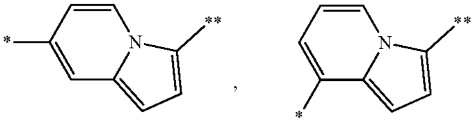
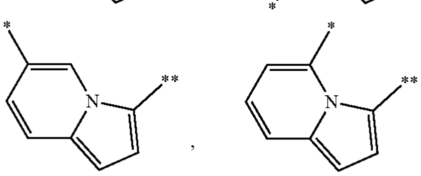
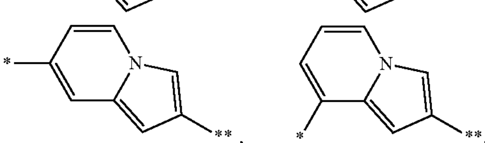
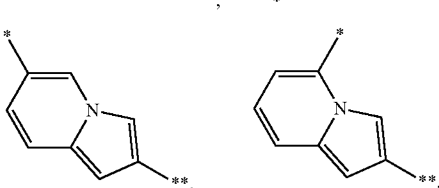

-continued
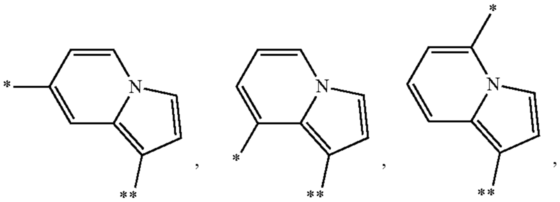
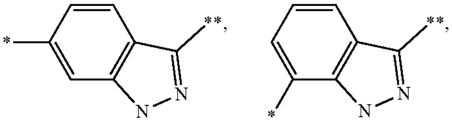
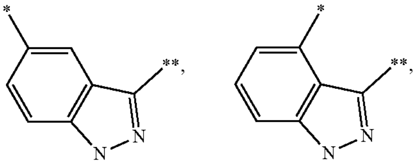
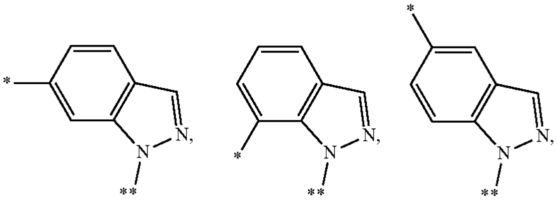
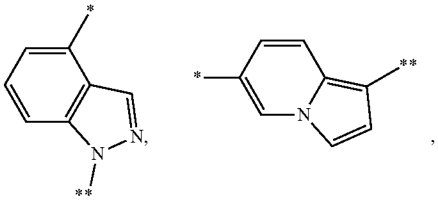
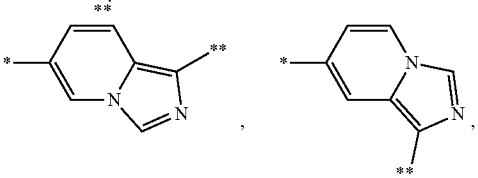
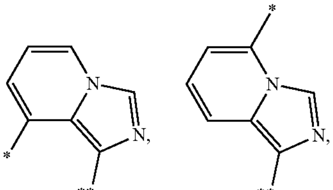
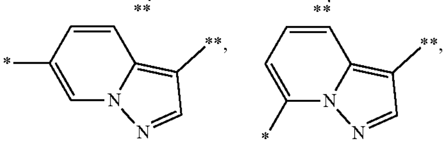
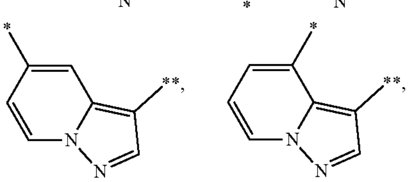
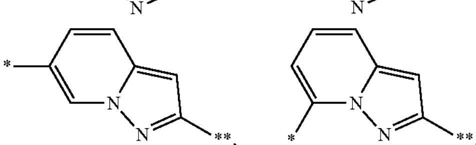
-continued
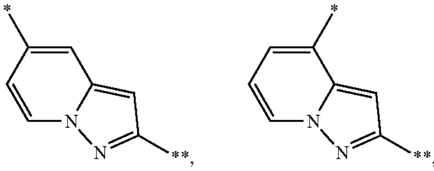
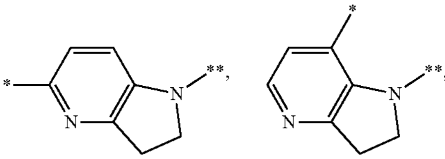
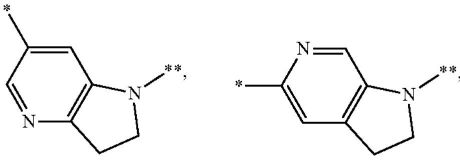
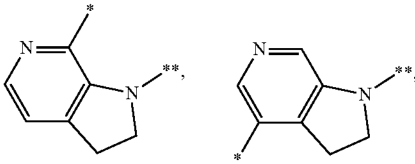
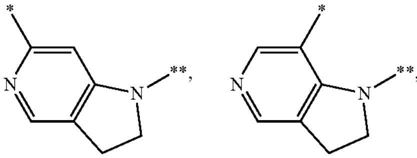
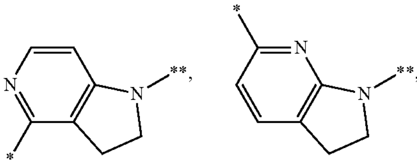
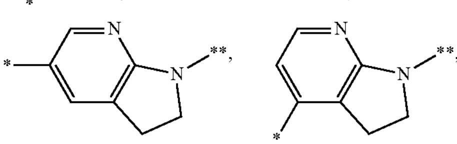
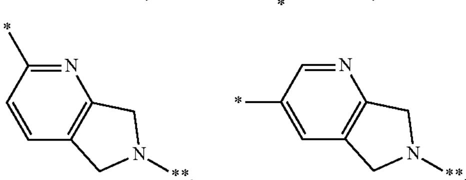
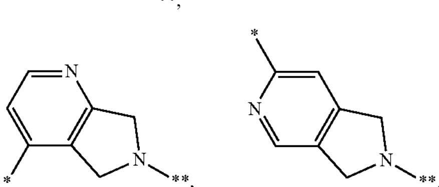
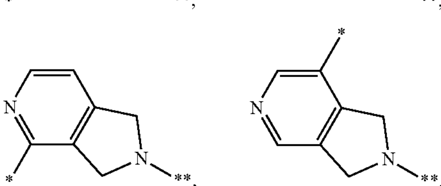

-continued

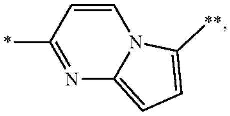 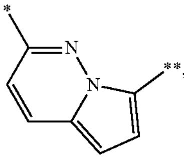

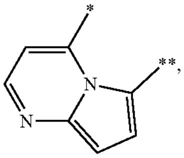 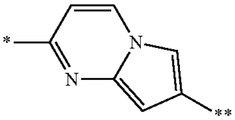,

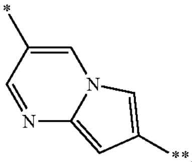 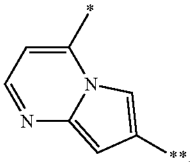

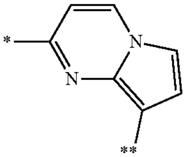, 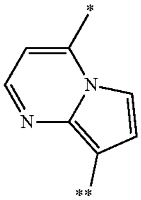,

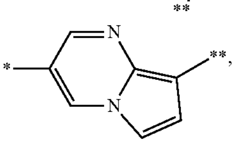 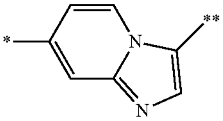,

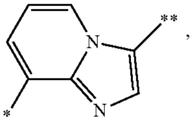 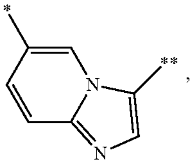

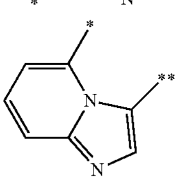, 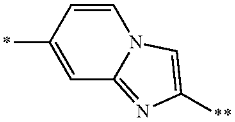,

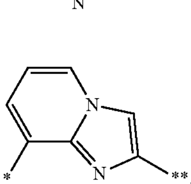 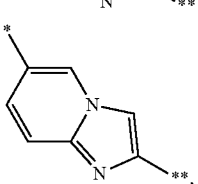

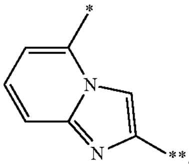 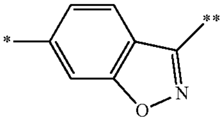,

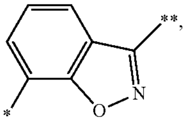 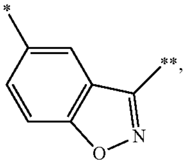 and

-continued

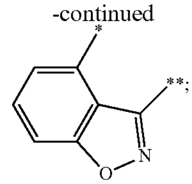

wherein, * and ** represent the positions where

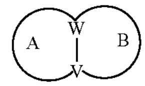

is attached to ring D and X, respectively; for example, if * represents the position where ring D is attached to, ** represents the position where X is attached to; if * represents the position where X is attached to, ** represents the position where ring D is attached to;

in some embodiments, the group

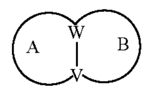

is selected from the following structures:

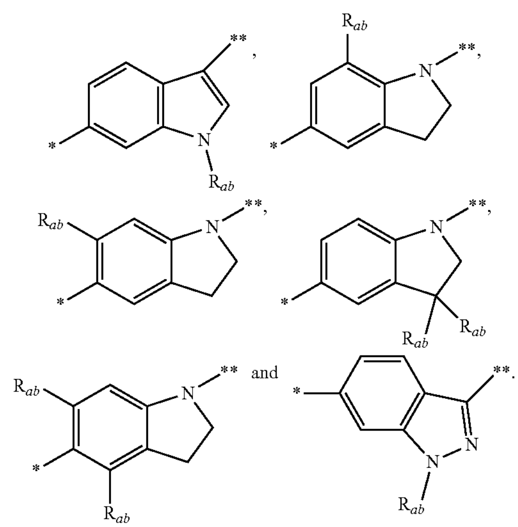

in some embodiments, ring C and ring D are each independently selected from the following groups unsubstituted or substituted with one, two or more $R_c/R_d$: phenyl, thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl, benzofuranyl, benzothienyl, benzoxazolyl, benzoisoxazolyl, benzimidazolyl, benzotriazolyl, indazolyl, indolyl, isoindolyl, pyridinyl, pyridazinyl, pyrimidinyl, pyrazinyl, triazinyl, quinolyl, quinazolinyl, isoquinolyl, azocinyl, indolizinyl, purinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl; $R_c$ and $R_d$ are defined as in any of the technical schemes of the general formula (I) above.

In some embodiments, ring C is independently selected from the following structures:

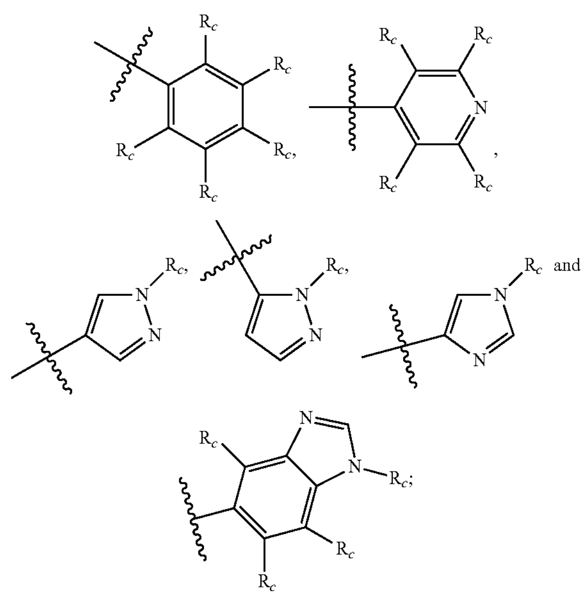

In some embodiments, ring D is independently selected from the following structures:

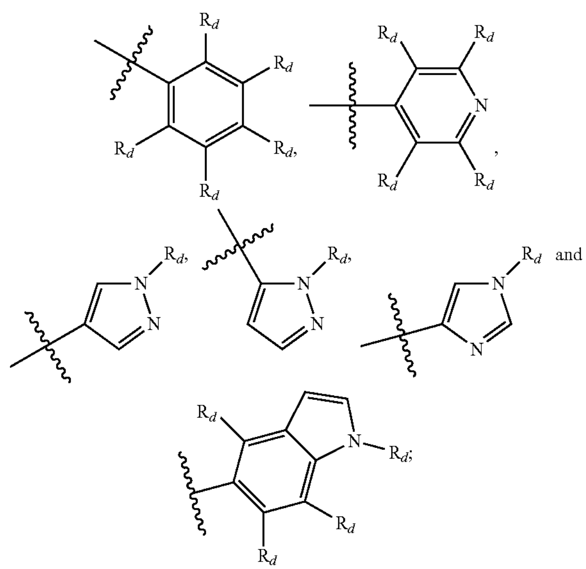

According to an embodiment of the present disclosure, in the compound of formula (I), (I)

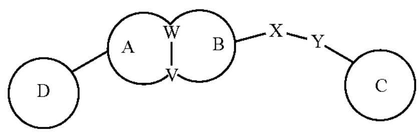

the group

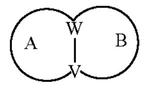

is of the following structure:

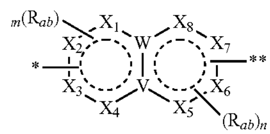

wherein W and V are each independently C or N, and W and V are not both N;

$X_1$, $X_2$, $X_3$, $X_4$, $X_5$, $X_6$, $X_7$ and $X_8$ are each independently a chemical bond, C, S, O or N; with the proviso that no more than one of $X_1$, $X_2$, $X_3$ and $X_4$ is a chemical bond, and no more than one of $X_5$, $X_6$, $X_7$ and $X_8$ is a chemical bond;

wherein, * and **represent the positions where the group is attached to ring D and X, respectively; for example, if * represents the position where ring D is attached to, ** represents the position where X is attached to; if * represents the position where X is attached to, ** represents the position where ring D is attached to;

the dashed rings shown in the structure represent that two atoms connected in a ring structure may have a single bond between them (i.e., the dashed portion corresponding to the connected ring atoms represents no bond) or a double bond between them (i.e., the dashed portion corresponding to the connected ring atoms is a single bond).

W, V, $R_{ab}$, X, Y, ring C and ring D are defined as in any of the embodiments of the general formula (I) above; m and n are selected from integers from 0 to 7, for example, selected from 0, 1, 2, 3 and 4.

According to an embodiment of the present disclosure, the compound of formula (I) is a compound of the following formula II (II)

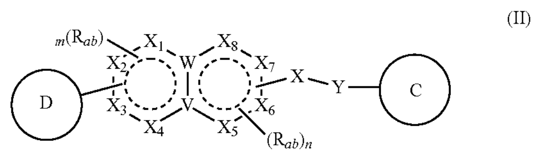

wherein, W and V are each independently C or N;

$X_1$, $X_2$, $X_3$, $X_4$, $X_5$, $X_6$, $X_7$ and $X_8$ are each independently a chemical bond, C, S, O or N;

with the proviso that no more than one of $X_1$, $X_2$, $X_3$ and $X_4$ is a chemical bond, and no more than one of $X_5$, $X_6$, $X_7$ and $X_8$ is a chemical bond;

W, V, $R_{ab}$, X, Y, ring C and ring D are defined as in any of the technical schemes of the general formula (I) above; m and n are selected from integers from 0 to 7, for example, selected from 0, 1, 2, 3 and 4.

Preferably, X and

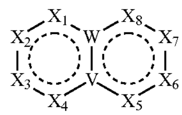

are connected via the N atom present on the ring.

According to an embodiment of the present disclosure, in the compound of formula (II),

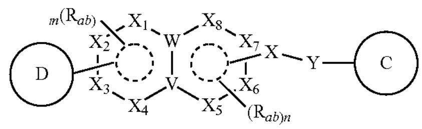

(II)

wherein, in the group

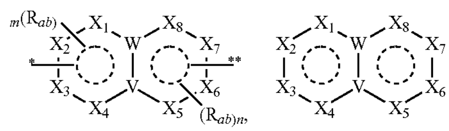

is selected from the following structures:

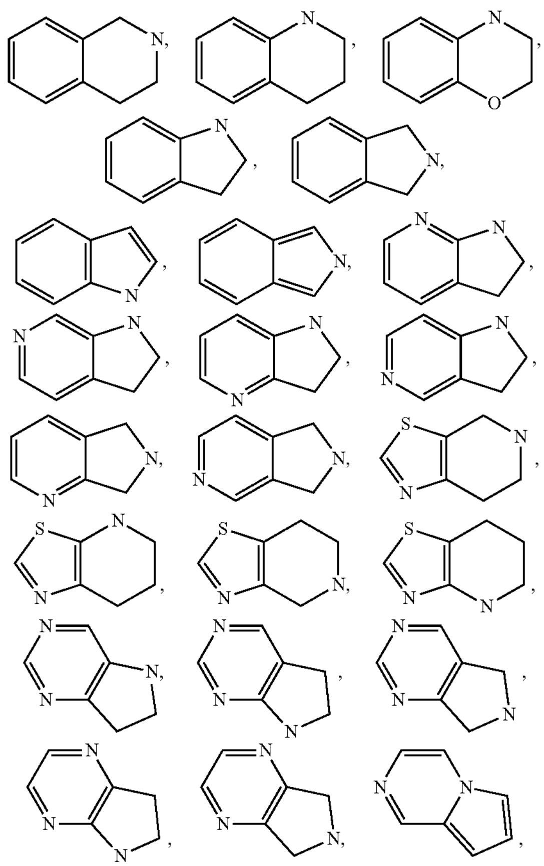

-continued

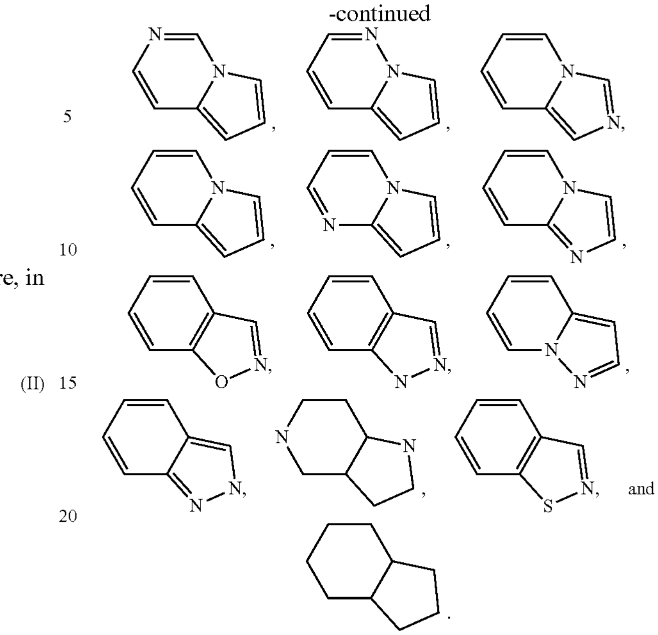

According to an embodiment of the present disclosure, in the compound of formula (II),

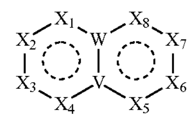

in the group

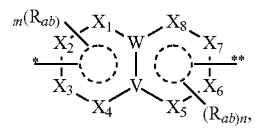

is selected from the following structures:

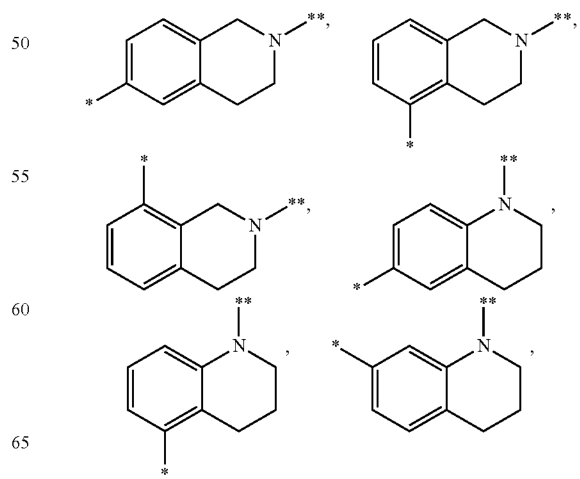

-continued
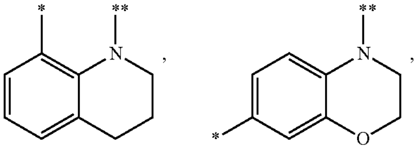
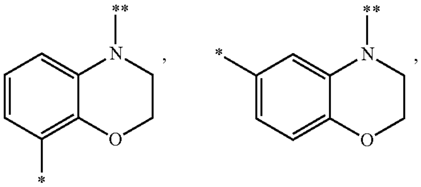
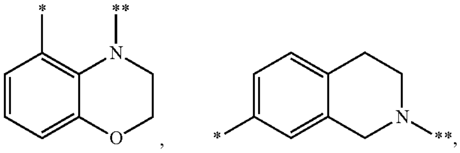
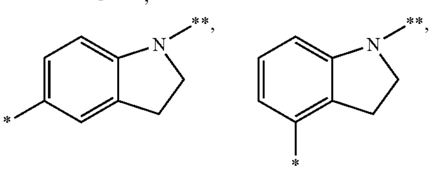
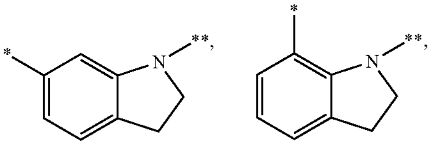
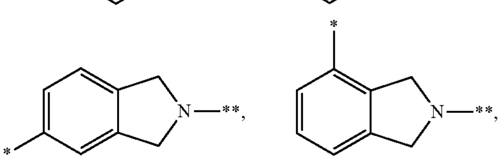
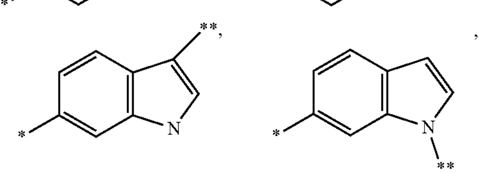
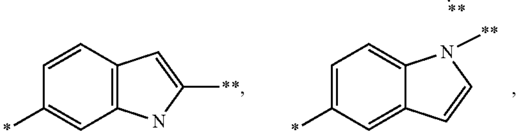
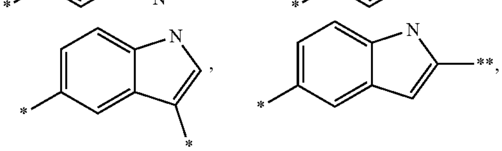
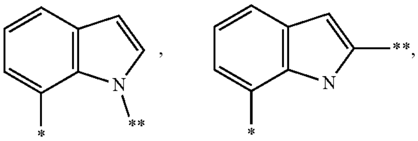
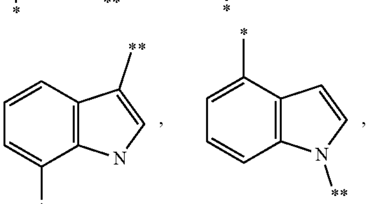
-continued
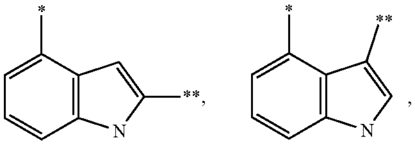
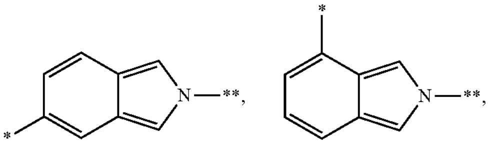
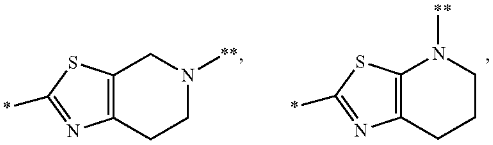
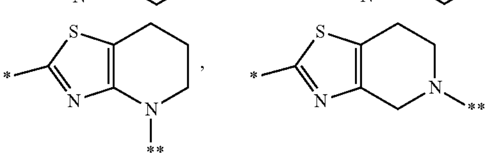
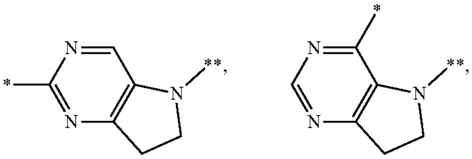
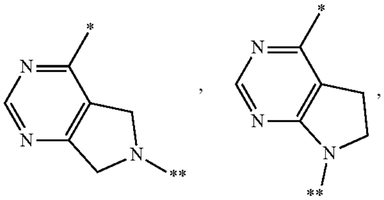
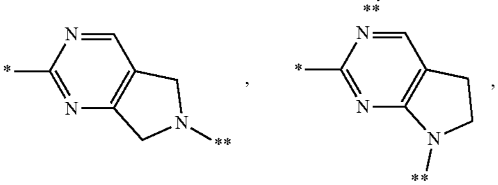
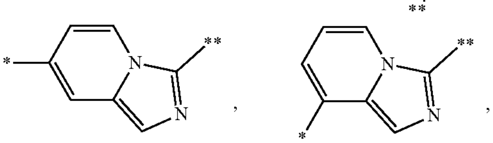
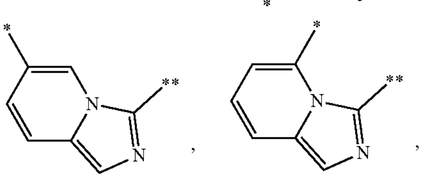
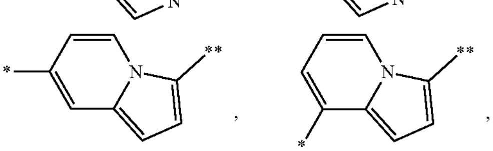
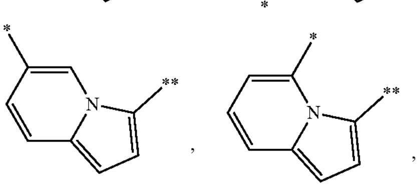

-continued
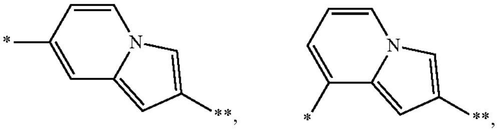
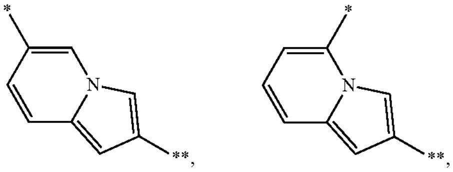
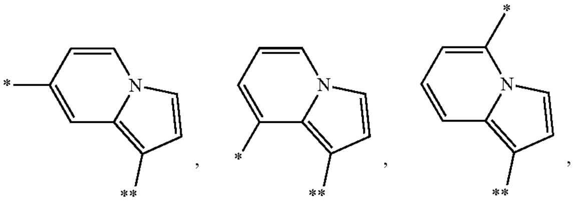
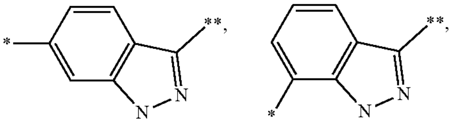
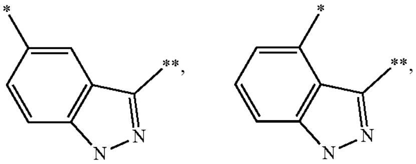
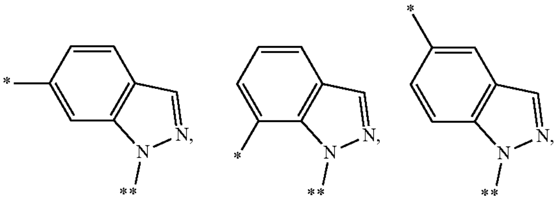
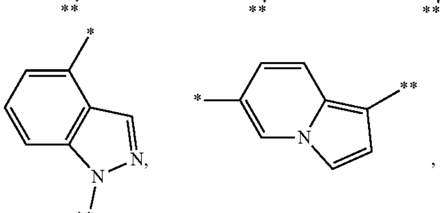
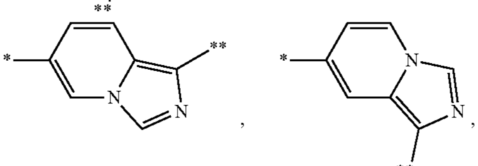
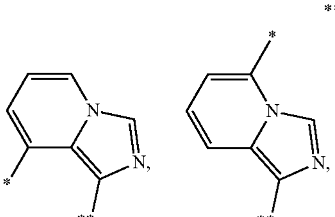
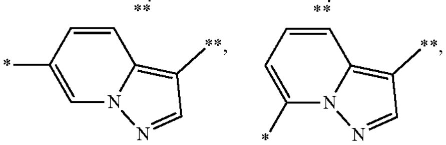
-continued
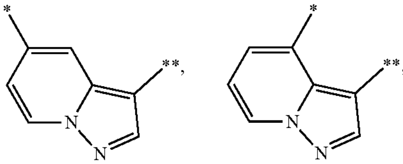
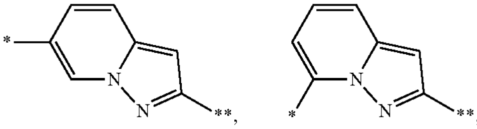
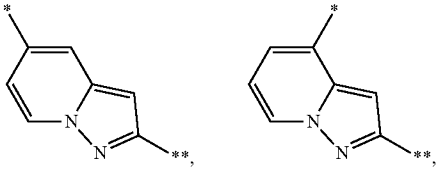
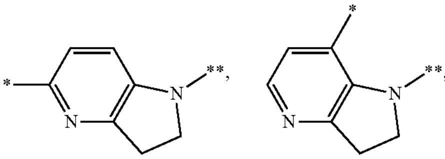
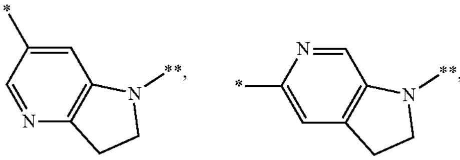
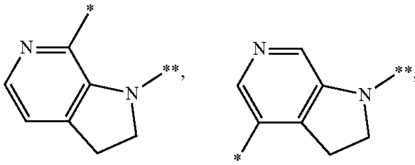
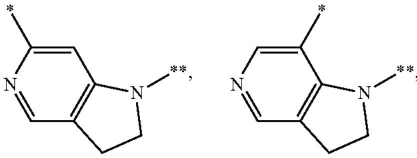
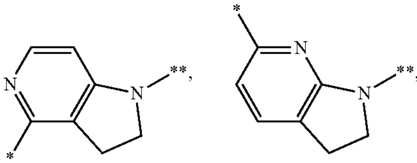
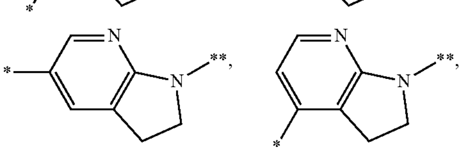
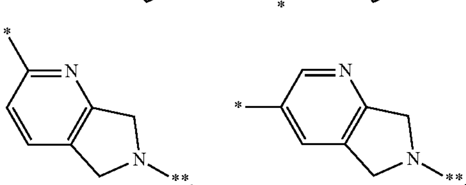

-continued

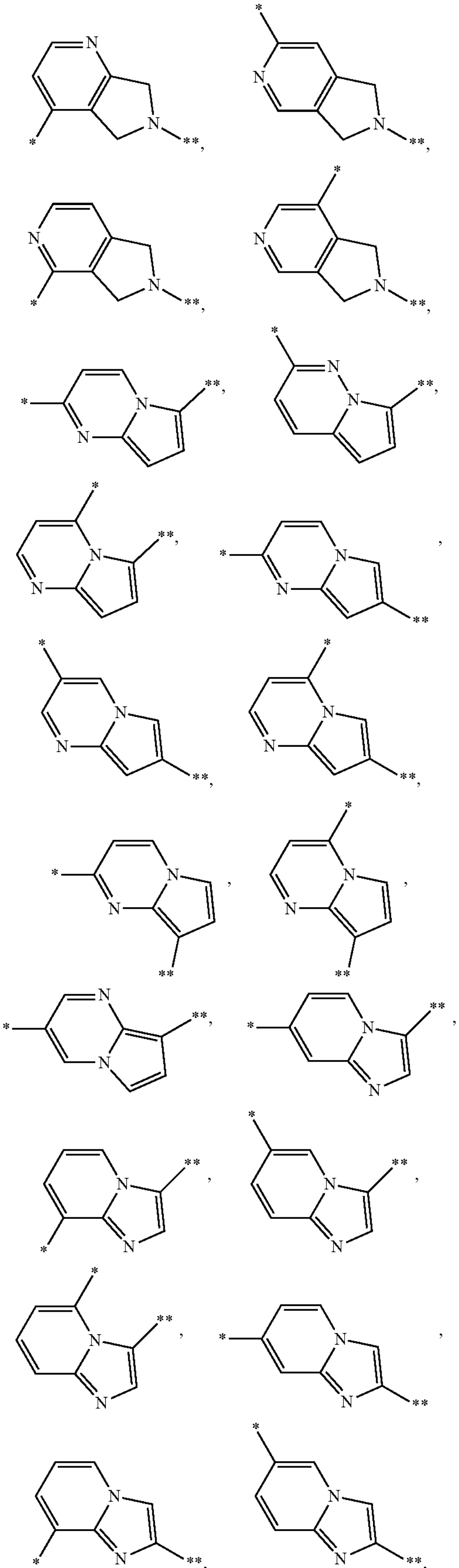

-continued

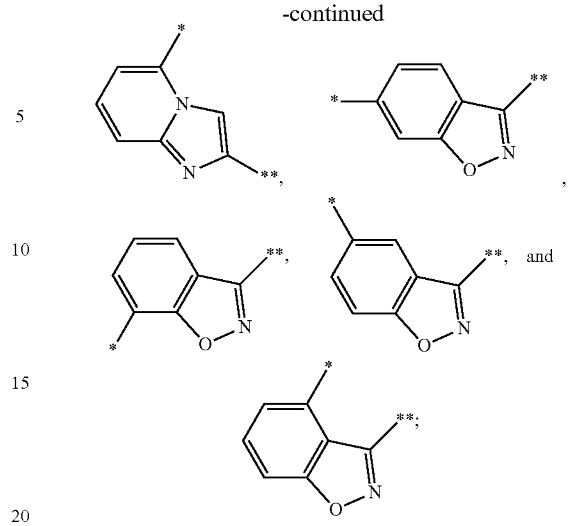

According to an embodiment of the present disclosure, in the group

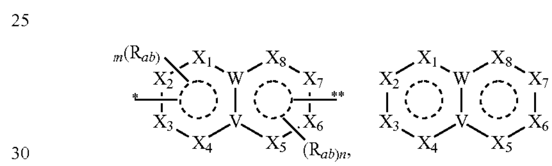

may be selected from the following structures:

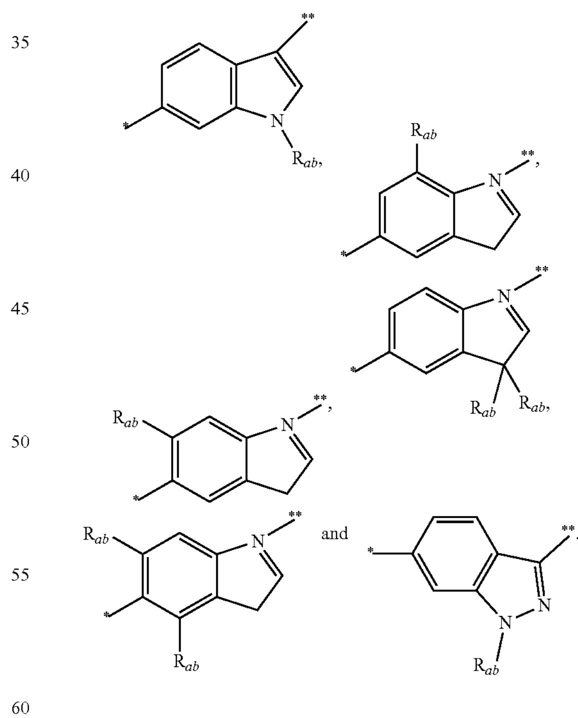

According to an embodiment of the present disclosure, in the compound of formula (I) or the racemate, the stereoisomer, the tautomer, the isotopically labeled compound, the nitrogen oxide, the solvate, the polymorph, the metabolite, the ester, the pharmaceutically acceptable salt or the prodrug thereof, the compound of formula (I) may be selected from the following structures:

| Compound No. | Structural formulas |
|---|---|
| T201 | 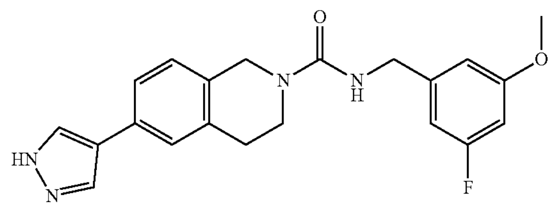 [SMILES: COc1cc(F)cc(CNC(=O)N2CCc3cc(-c4cn[nH]c4)ccc3C2)c1] |
| T202 | 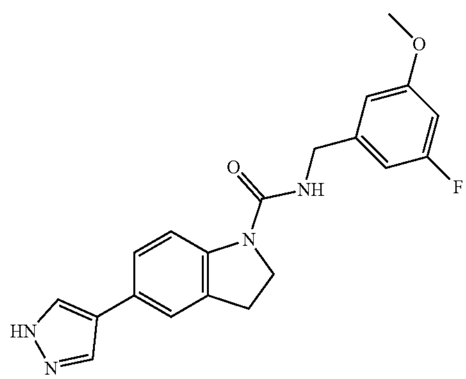 |
| T204 | 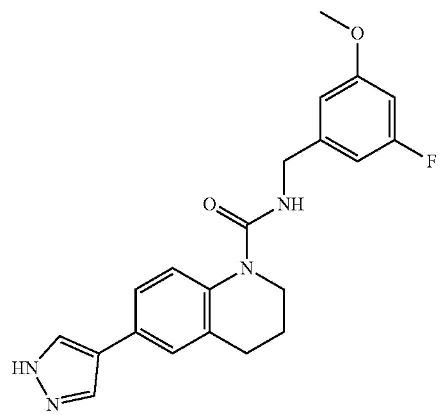 [SMILES: COc1cc(F)cc(CNC(=O)N2CCCc3cc(-c4cn[nH]c4)ccc32)c1] |
| T205 | 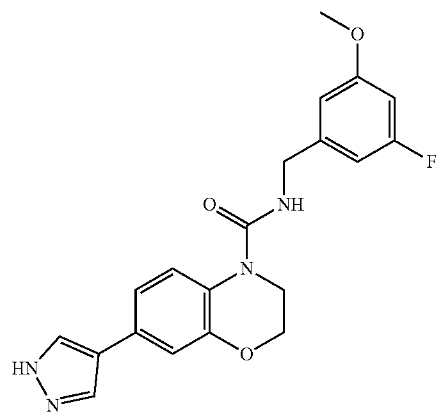 |

-continued
| Compound No. | Structural formulas |
|---|---|
| T206 | 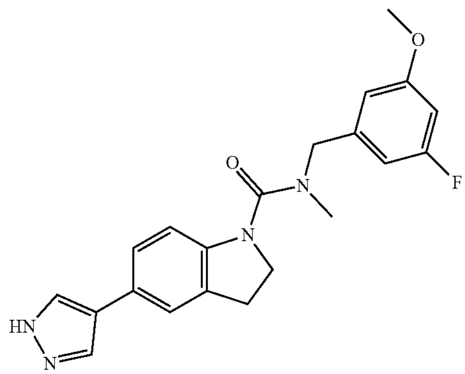 [SMILES: COc1cc(F)cc(CN(C)C(=O)N2CCc3cc(-c4cn[nH]c4)ccc32)c1] |
| T207 | 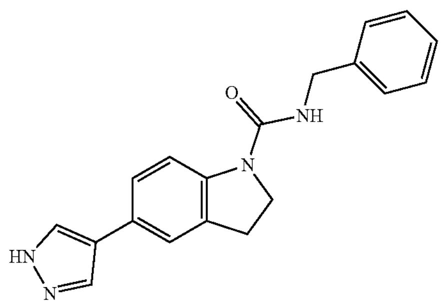 [SMILES: O=C(NCc1ccccc1)N1CCc2cc(-c3cn[nH]c3)ccc21] |
| T208 | 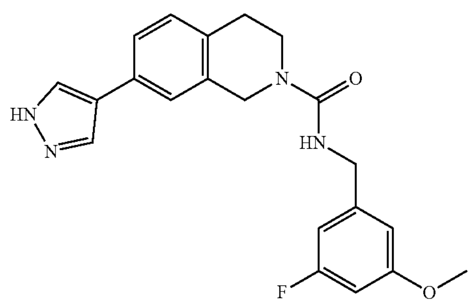 [SMILES: COc1cc(F)cc(CNC(=O)N2CCc3ccc(-c4cn[nH]c4)cc3C2)c1] |
| T209 | 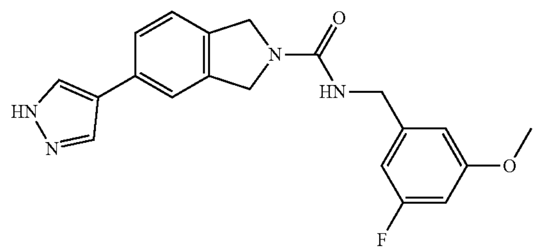 [SMILES: COc1cc(F)cc(CNC(=O)N2Cc3ccc(-c4cn[nH]c4)cc3C2)c1] |

-continued
| Compound No. | Structural formulas |
| --- | --- |
| T210 | 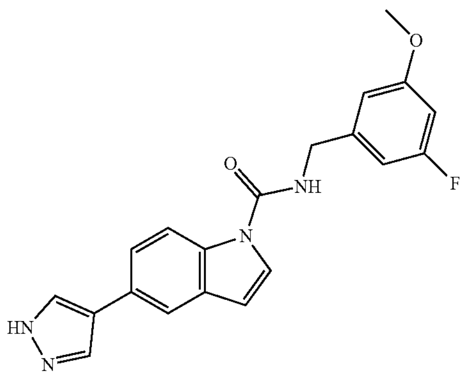 [SMILES: COc1cc(F)cc(CNC(=O)n2ccc3cc(-c4cn[nH]c4)ccc32)c1] |
| T211 | 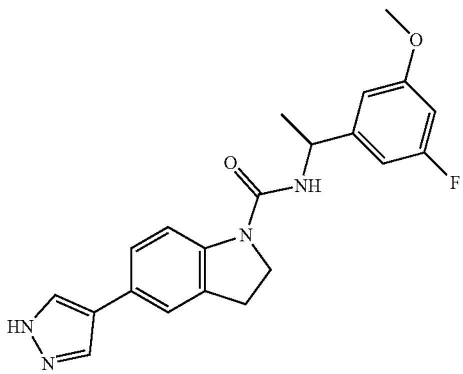 [SMILES: COc1cc(F)cc(C(C)NC(=O)N2CCc3cc(-c4cn[nH]c4)ccc32)c1] |
| T212 | 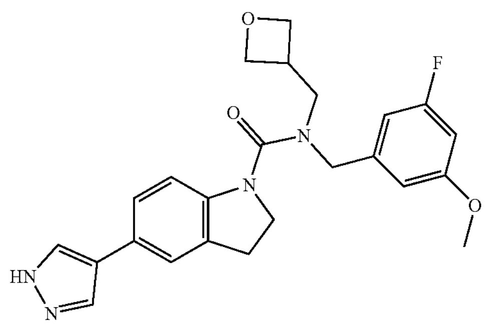 [SMILES: COc1cc(F)cc(CN(CC2COC2)C(=O)N2CCc3cc(-c4cn[nH]c4)ccc32)c1] |
| T213 | 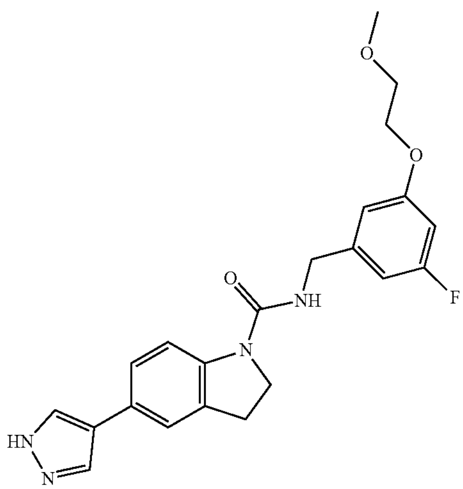 [SMILES: COCCOc1cc(F)cc(CNC(=O)N2CCc3cc(-c4cn[nH]c4)ccc32)c1] |

-continued
| Compound No. | Structural formulas |
|---|---|
| T214 | 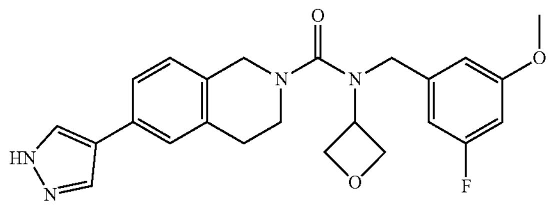 [SMILES: COc1cc(F)cc(CN(C(=O)N2CCc3cc(-c4cn[nH]c4)ccc3C2)C2COC2)c1] |
| T215 | 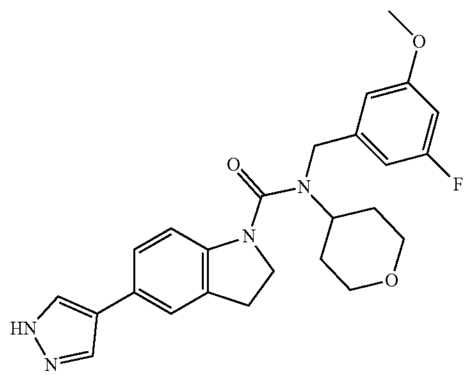 [SMILES: COc1cc(F)cc(CN(C(=O)N2CCc3cc(-c4cn[nH]c4)ccc32)C2CCOCC2)c1] |
| T216 | 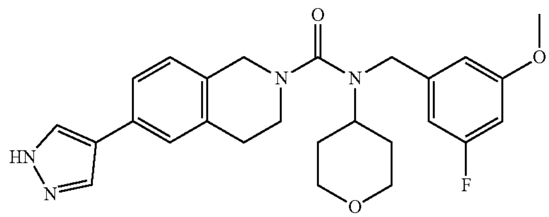 [SMILES: COc1cc(F)cc(CN(C(=O)N2CCc3cc(-c4cn[nH]c4)ccc3C2)C2CCOCC2)c1] |
| T217 | 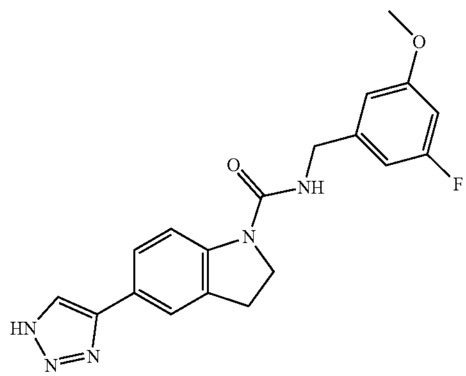 |
| T218 | 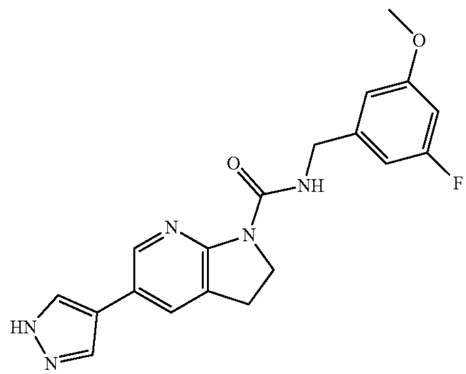 [SMILES: COc1cc(F)cc(CNC(=O)N2CCc3cc(-c4cn[nH]c4)cnc32)c1] |

-continued
| Compound No. | Structural formulas |
|---|---|
| T219 | 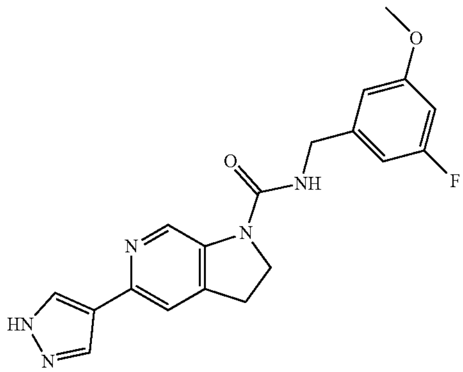 [SMILES: COc1cc(F)cc(CNC(=O)N2CCc3cc(-c4cn[nH]c4)ncc32)c1] |
| T220 | 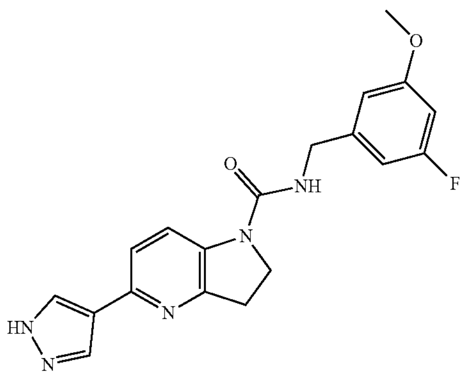 [SMILES: COc1cc(F)cc(CNC(=O)N2CCc3nc(-c4cn[nH]c4)ccc32)c1] |
| T221 | 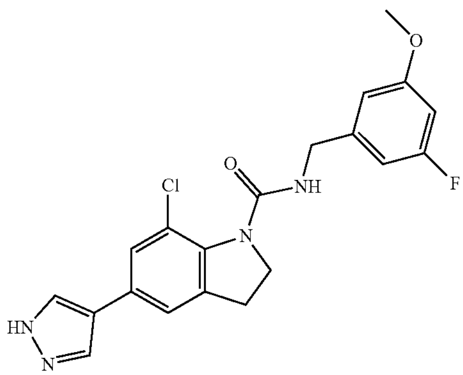 [SMILES: COc1cc(F)cc(CNC(=O)N2CCc3cc(-c4cn[nH]c4)cc(Cl)c32)c1] |
| T222 | 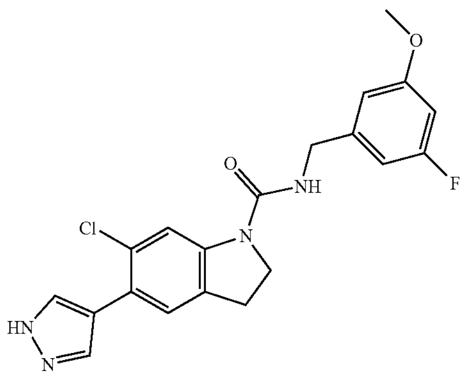 [SMILES: COc1cc(F)cc(CNC(=O)N2CCc3cc(-c4cn[nH]c4)c(Cl)cc32)c1] |

-continued
| Compound No. | Structural formulas |
|---|---|
| T223 | 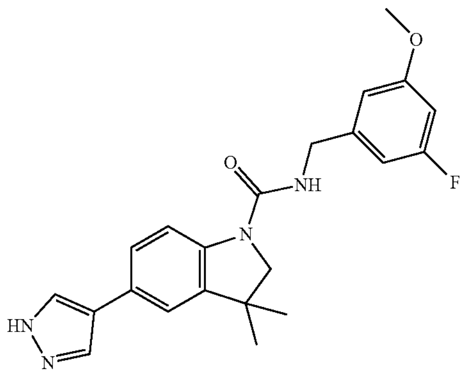 [SMILES: COc1cc(F)cc(CNC(=O)N2CC(C)(C)c3cc(-c4cn[nH]c4)ccc32)c1] |
| T224 | 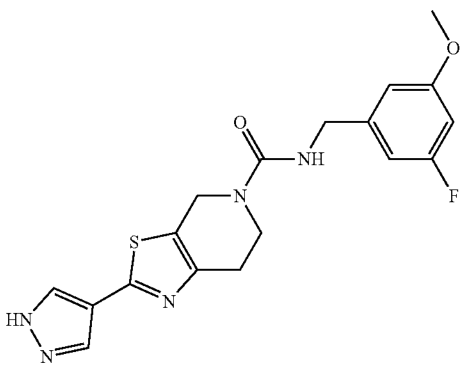 [SMILES: COc1cc(F)cc(CNC(=O)N2CCc3nc(-c4cn[nH]c4)sc3C2)c1] |
| T225 | 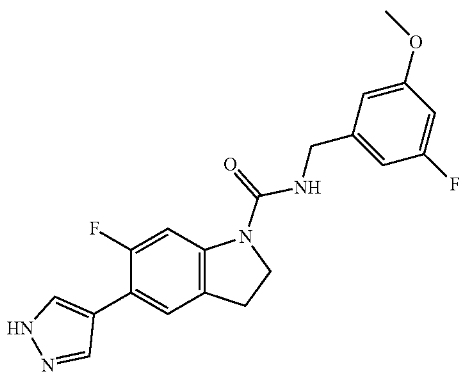 [SMILES: COc1cc(F)cc(CNC(=O)N2CCc3cc(-c4cn[nH]c4)c(F)cc32)c1] |
| T226 | 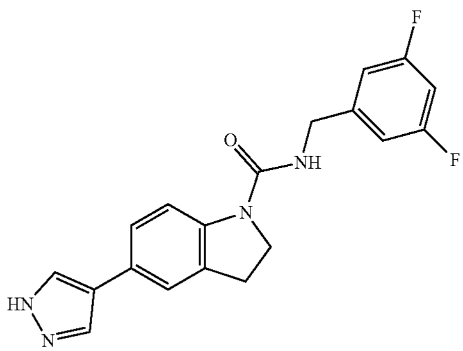 [SMILES: O=C(NCc1cc(F)cc(F)c1)N1CCc2cc(-c3cn[nH]c3)ccc21] |

-continued
| Compound No. | Structural formulas |
|---|---|
| T227 | 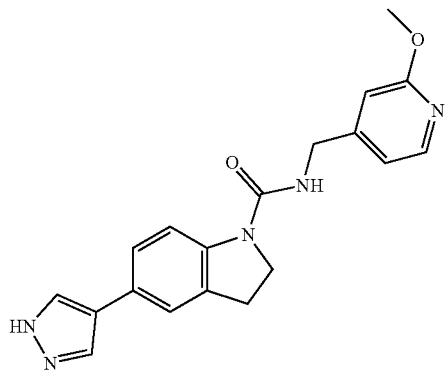 [SMILES: COc1cc(CNC(=O)N2CCc3cc(-c4cn[nH]c4)ccc32)ccn1] |
| T228 | 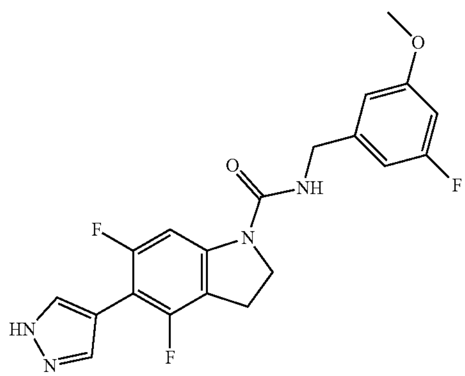 [SMILES: COc1cc(F)cc(CNC(=O)N2CCc3c2cc(F)c(-c2cn[nH]c2)c3F)c1] |
| T229 | 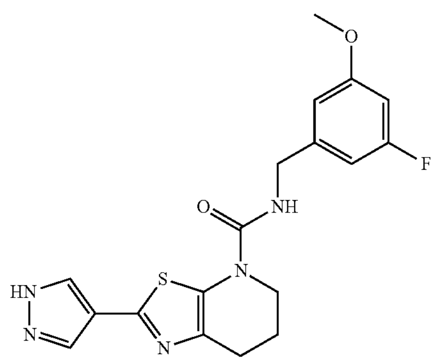 [SMILES: COc1cc(F)cc(CNC(=O)N2CCCc3nc(-c4cn[nH]c4)sc32)c1] |
| T230 | 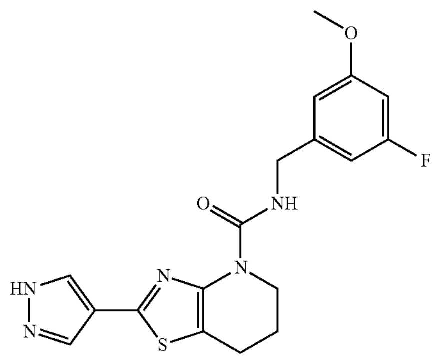 [SMILES: COc1cc(F)cc(CNC(=O)N2CCCc3sc(-c4cn[nH]c4)nc32)c1] |

-continued
| Compound No. | Structural formulas |
|---|---|
| T231 | 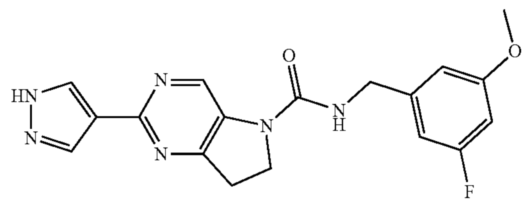 [SMILES: COc1cc(F)cc(CNC(=O)N2CCc3nc(-c4cn[nH]c4)ncc32)c1] |
| T232 | 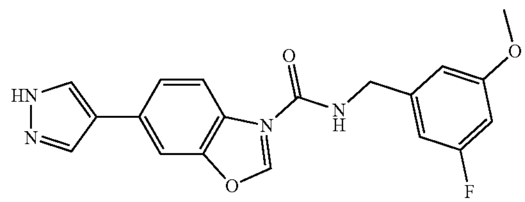 |
| T233 | 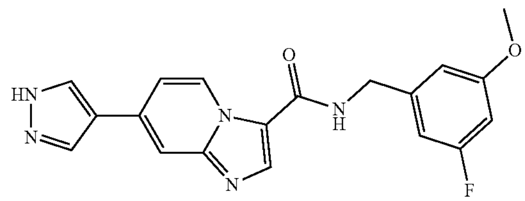 [SMILES: COc1cc(F)cc(CNC(=O)c2cnc3cc(-c4cn[nH]c4)ccn23)c1] |
| T234 | 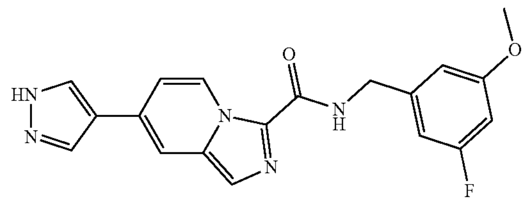 [SMILES: COc1cc(F)cc(CNC(=O)c2ncc3cc(-c4cn[nH]c4)ccn23)c1] |
| T235 | 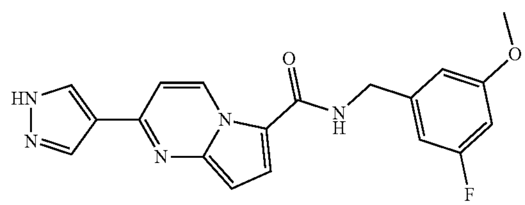 [SMILES: COc1cc(F)cc(CNC(=O)c2ccc3nc(-c4cn[nH]c4)ccn23)c1] |
| T236 | 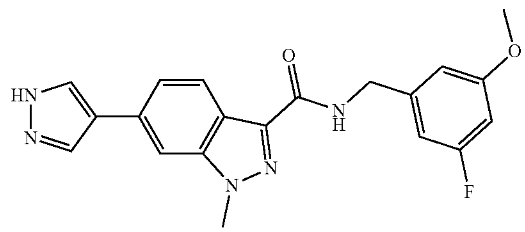 [SMILES: COc1cc(F)cc(CNC(=O)c2nn(C)c3cc(-c4cn[nH]c4)ccc23)c1] |
| T237 | 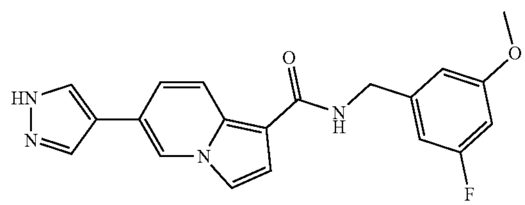 [SMILES: COc1cc(F)cc(CNC(=O)c2ccn3cc(-c4cn[nH]c4)ccc23)c1] |

-continued
| Compound No. | Structural formulas |
|---|---|
| T238 | 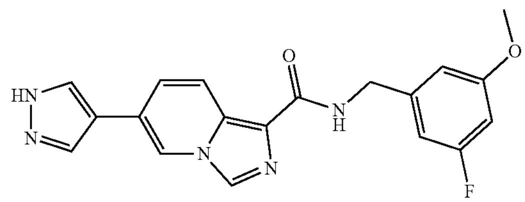 [SMILES: COc1cc(F)cc(CNC(=O)c2ncn3cc(-c4cn[nH]c4)ccc23)c1] |
| T239 | 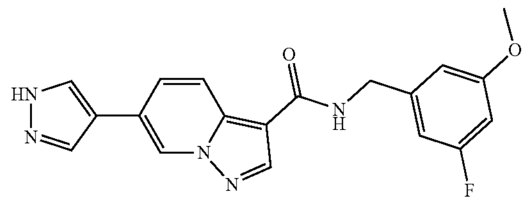 [SMILES: COc1cc(F)cc(CNC(=O)c2cnn3cc(-c4cn[nH]c4)ccc23)c1] |
| T240 | 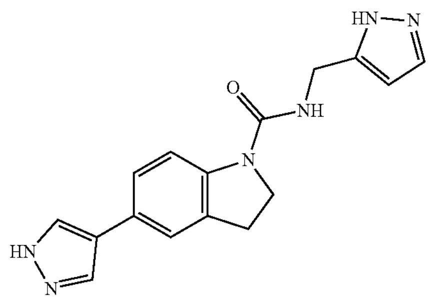 [SMILES: O=C(NCc1ccn[nH]1)N1CCc2cc(-c3cn[nH]c3)ccc21] |
| T241 | 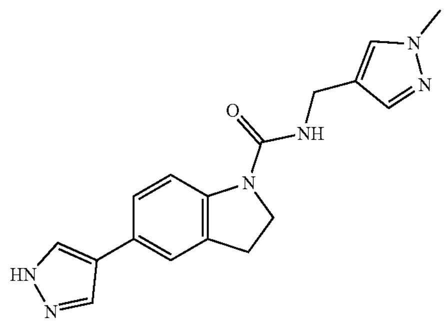 [SMILES: Cn1cc(CNC(=O)N2CCc3cc(-c4cn[nH]c4)ccc32)cn1] |
| T242 | 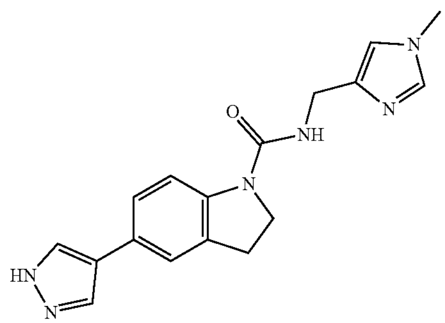 [SMILES: Cn1cnc(CNC(=O)N2CCc3cc(-c4cn[nH]c4)ccc32)c1] |

-continued
| Compound No. | Structural formulas |
|---|---|
| T243 | 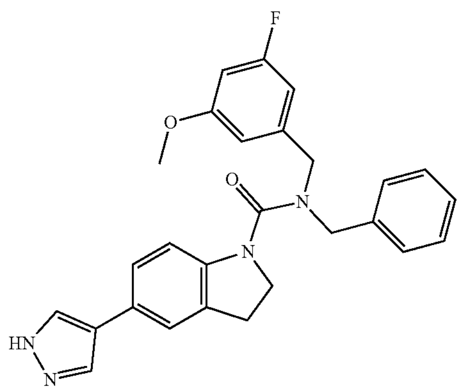 [SMILES: COc1cc(F)cc(CN(Cc2ccccc2)C(=O)N2CCc3cc(-c4cn[nH]c4)ccc32)c1] |
| T244 | 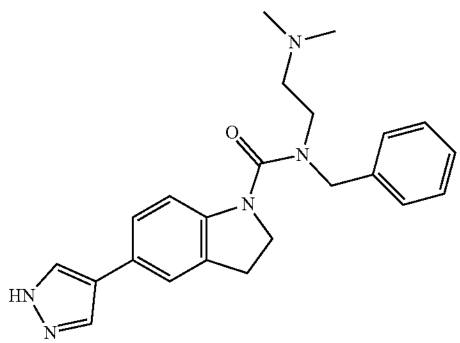 [SMILES: CN(C)CCN(Cc1ccccc1)C(=O)N1CCc2cc(-c3cn[nH]c3)ccc21] |
| T245 | 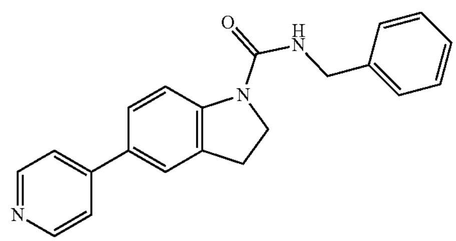 [SMILES: O=C(NCc1ccccc1)N1CCc2cc(-c3ccncc3)ccc21] |
| T246 | 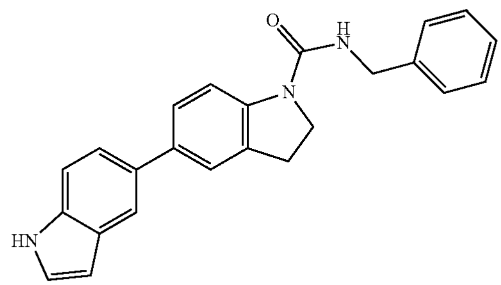 [SMILES: O=C(NCc1ccccc1)N1CCc2cc(-c3ccc4[nH]ccc4c3)ccc21] |
| T247 | 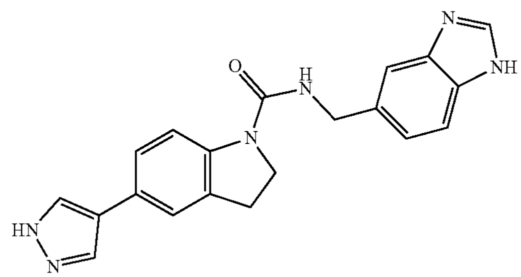 [SMILES: O=C(NCc1ccc2[nH]cnc2c1)N1CCc2cc(-c3cn[nH]c3)ccc21] |

-continued
| Compound No. | Structural formulas |
| --- | --- |
| T248 | 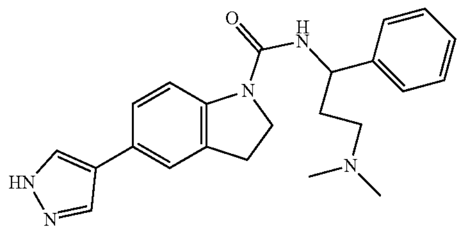 [SMILES: CN(C)CCC(NC(=O)N1CCc2cc(-c3cn[nH]c3)ccc21)c1ccccc1] |
| T249 | 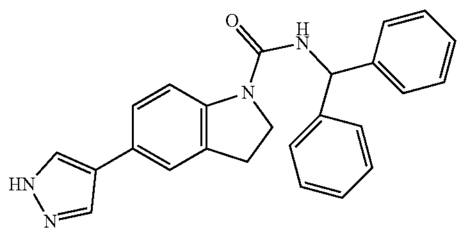 [SMILES: O=C(NC(c1ccccc1)c1ccccc1)N1CCc2cc(-c3cn[nH]c3)ccc21] |
| T340 | 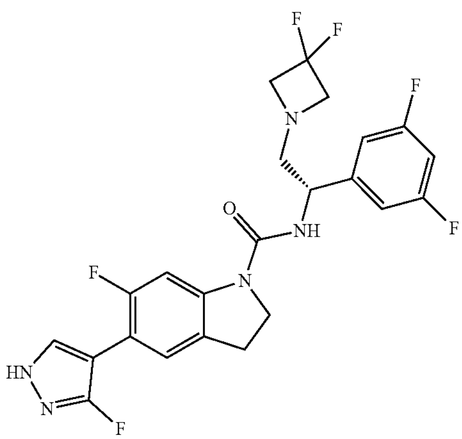 [SMILES: O=C(N[C@H](CN1CC(F)(F)C1)c1cc(F)cc(F)c1)N1CCc2cc(-c3c[nH]nc3F)c(F)cc21] |
| T341 | 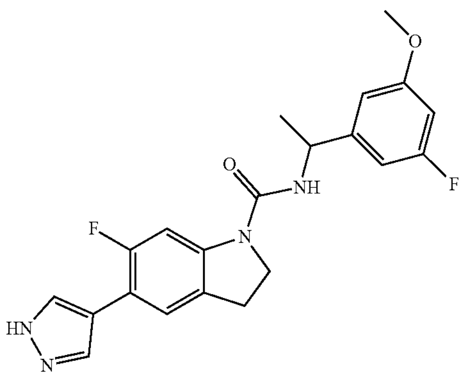 [SMILES: COc1cc(F)cc(C(C)NC(=O)N2CCc3cc(-c4cn[nH]c4)c(F)cc32)c1] |

-continued
| Compound No. | Structural formulas |
|---|---|
| T342 | 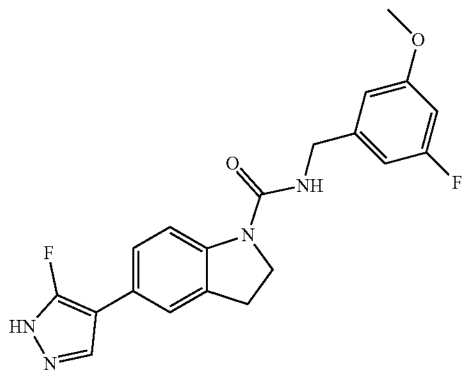 [SMILES: COc1cc(F)cc(CNC(=O)N2CCc3cc(-c4cn[nH]c4F)ccc32)c1] |
| T343 | 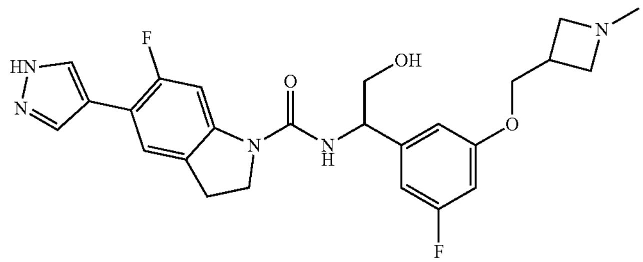 [SMILES: CN1CC(COc2cc(F)cc(C(CO)NC(=O)N3CCc4cc(-c5cn[nH]c5)c(F)cc43)c2)C1] |
| T344 | 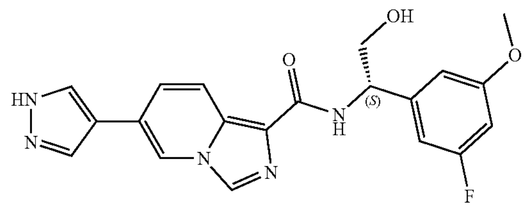 |
| T345 | 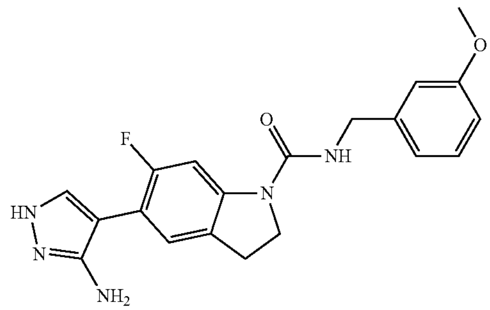 [SMILES: COc1cccc(CNC(=O)N2CCc3cc(-c4c[nH]nc4N)c(F)cc32)c1] |
| T346 | 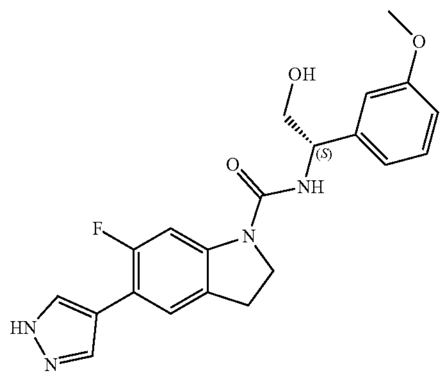 |

-continued
| Compound No. | Structural formulas |
|---|---|
| T347 | 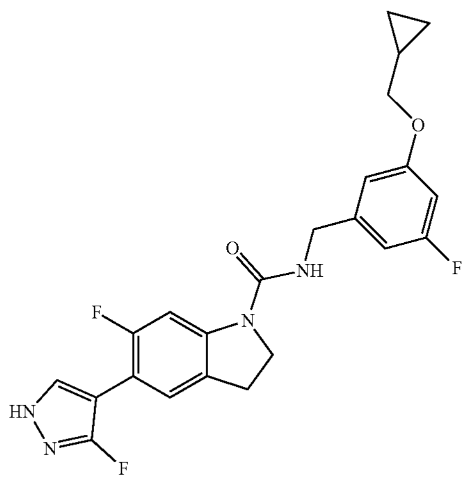 [SMILES: O=C(NCc1cc(F)cc(OCC2CC2)c1)N1CCc2cc(-c3c[nH]nc3F)c(F)cc21] |
| T348 | 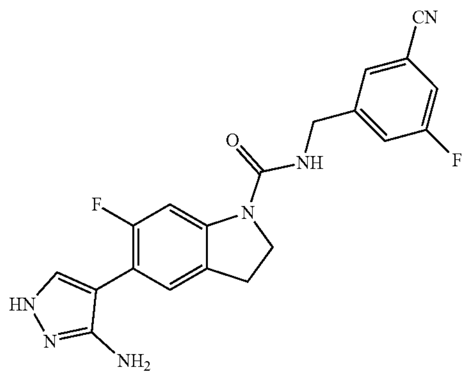 [SMILES: N#Cc1cc(F)cc(CNC(=O)N2CCc3cc(-c4c[nH]nc4N)c(F)cc32)c1] |
| T349 | 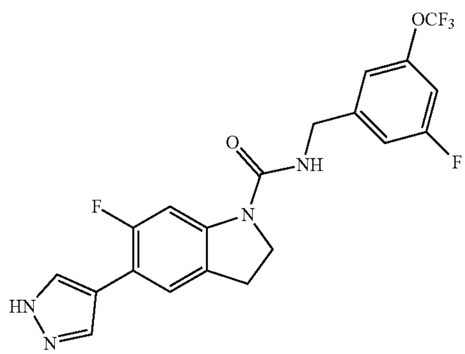 [SMILES: O=C(NCc1cc(F)cc(OC(F)(F)F)c1)N1CCc2cc(-c3cn[nH]c3)c(F)cc21] |
| T350 | 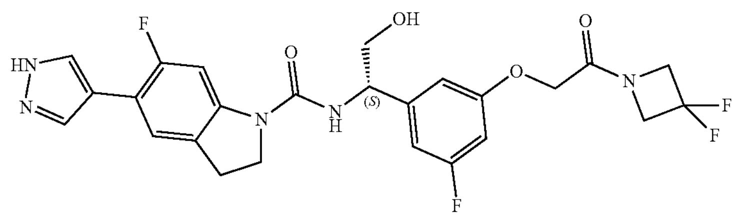 |

-continued
| Compound No. | Structural formulas |
|---|---|
| T351 | 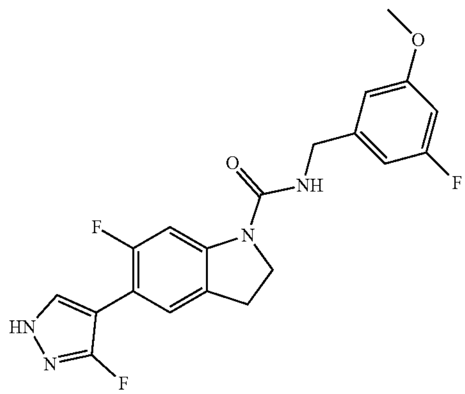 [SMILES: COc1cc(F)cc(CNC(=O)N2CCc3cc(-c4c[nH]nc4F)c(F)cc32)c1] |
| T352 | 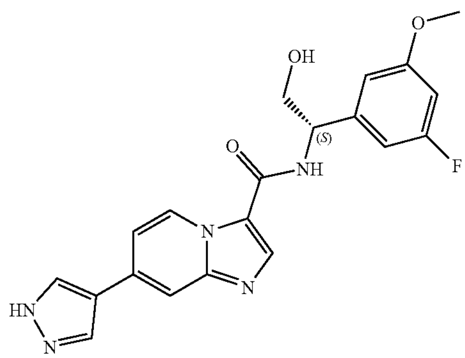 |
| T353 | 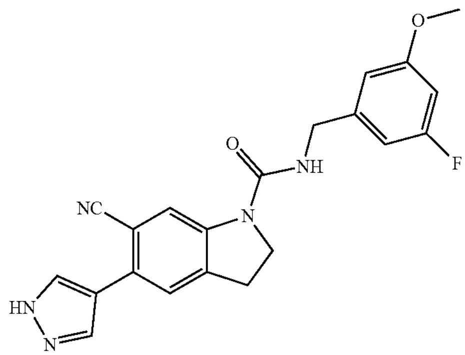 [SMILES: COc1cc(F)cc(CNC(=O)N2CCc3cc(-c4cn[nH]c4)c(C#N)cc32)c1] |
| T354 | 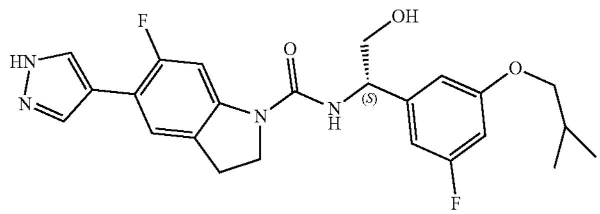 |
| T355 | 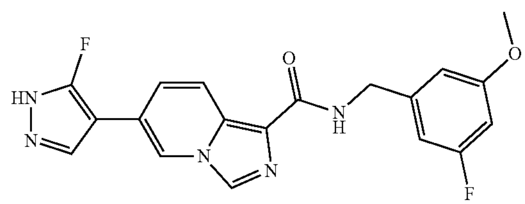 [SMILES: COc1cc(F)cc(CNC(=O)c2ncn3cc(-c4cn[nH]c4F)ccc23)c1] |

-continued
| Compound No. | Structural formulas |
|---|---|
| T356 | 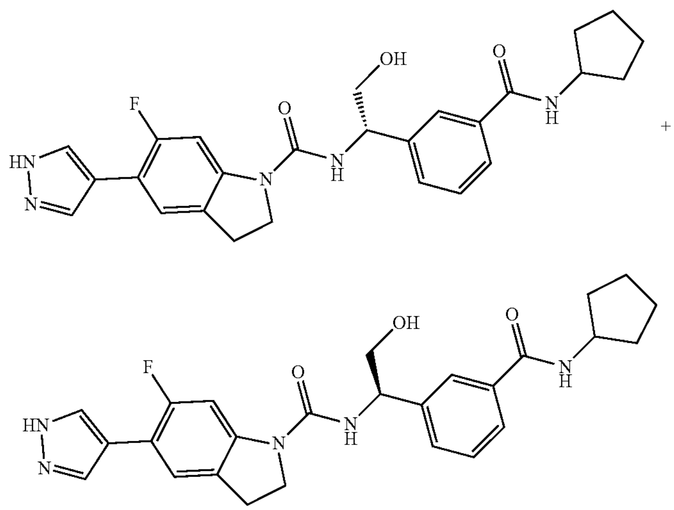 + |
| T357 | 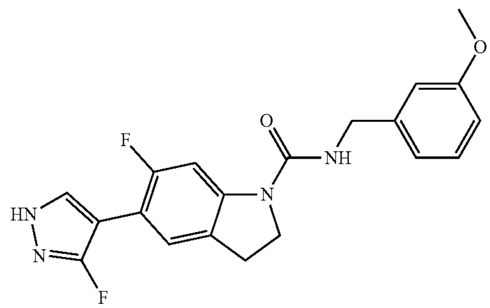 [SMILES: COc1cccc(CNC(=O)N2CCc3cc(-c4c[nH]nc4F)c(F)cc32)c1] |
| T358 | 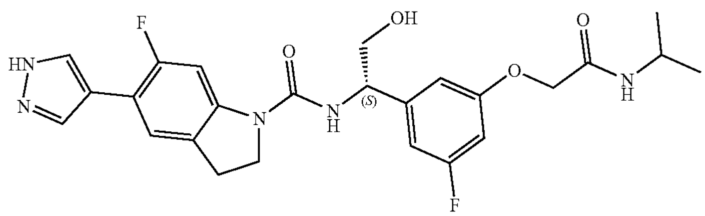 |
| T359 | 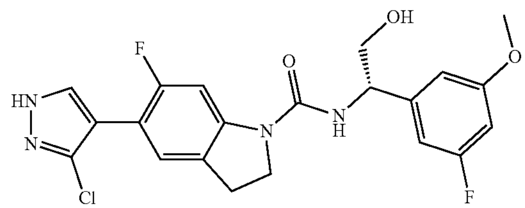 [SMILES: COc1cc(F)cc([C@@H](CO)NC(=O)N2CCc3cc(-c4c[nH]nc4Cl)c(F)cc32)c1] |
| T360 | 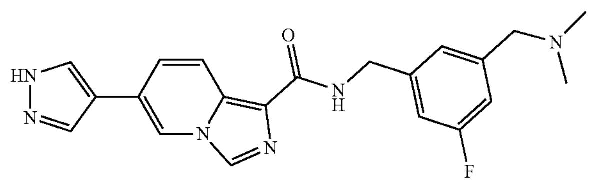 [SMILES: CN(C)Cc1cc(F)cc(CNC(=O)c2ncn3cc(-c4cn[nH]c4)ccc23)c1] |

-continued
| Compound No. | Structural formulas |
|---|---|
| T361 | 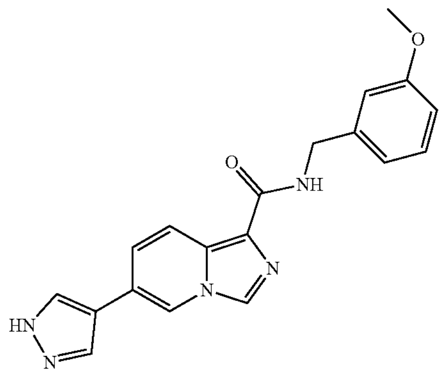 [SMILES: COc1cccc(CNC(=O)c2ncn3cc(-c4cn[nH]c4)ccc23)c1] |
| T362 | 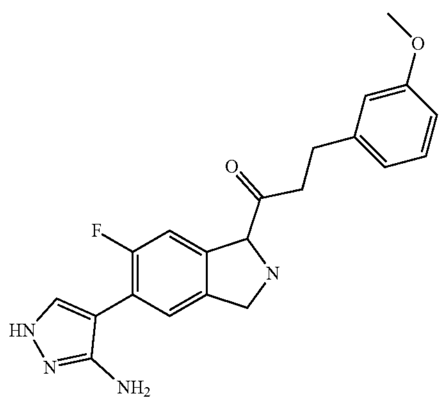 [SMILES: COc1cccc(CCC(=O)C2NCc3cc(-c4c[nH]nc4N)c(F)cc32)c1] |
| T363 | 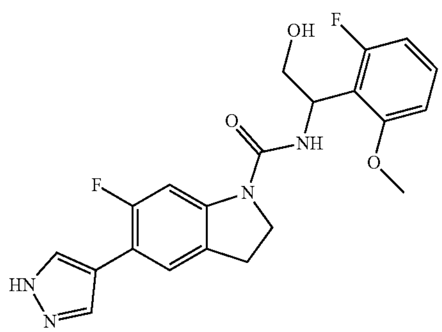 [SMILES: COc1cccc(F)c1C(CO)NC(=O)N1CCc2cc(-c3cn[nH]c3)c(F)cc21] |
| T364 | 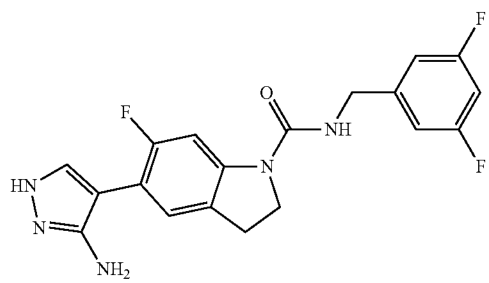 [SMILES: Nc1n[nH]cc1-c1cc2c(cc1F)N(C(=O)NCc1cc(F)cc(F)c1)CC2] |

-continued
| Compound No. | Structural formulas |
|---|---|
| T365 | 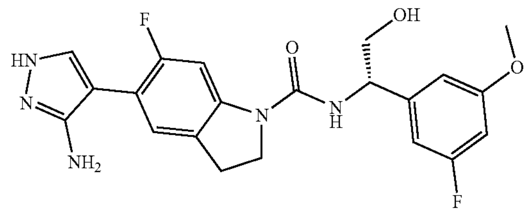 [SMILES: COc1cc(F)cc([C@@H](CO)NC(=O)N2CCc3cc(-c4c[nH]nc4N)c(F)cc32)c1] |
| T366 | 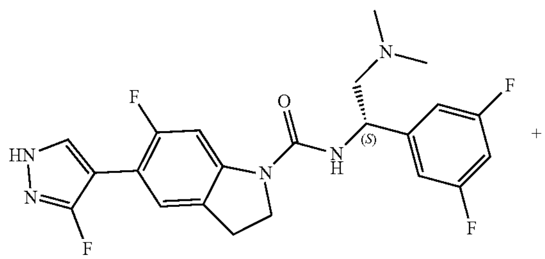 + 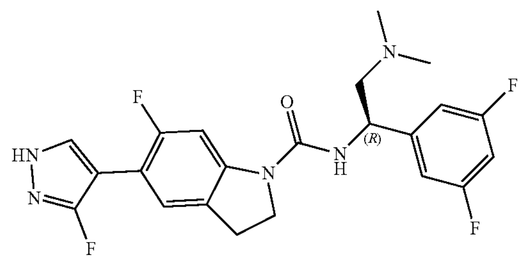 |
| T367 | 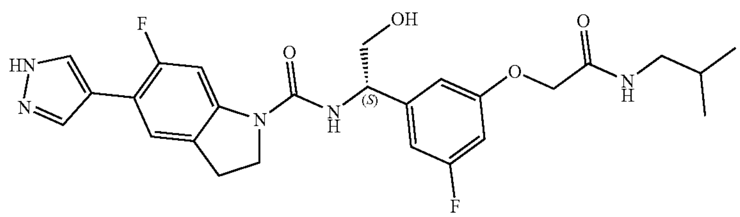 |
| T368 | 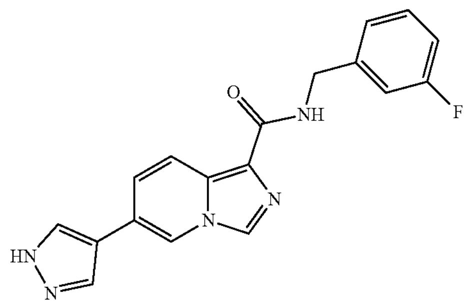 [SMILES: O=C(NCc1cccc(F)c1)c1ncn2cc(-c3cn[nH]c3)ccc12] |
| T369 | 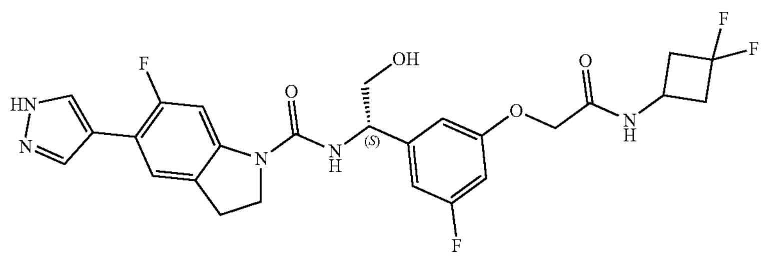 |

-continued
| Compound No. | Structural formulas |
|---|---|
| T370 | 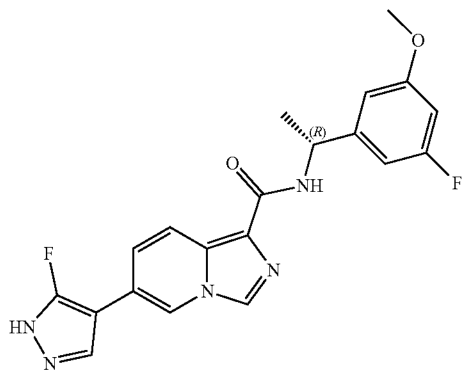 |
| T371 | 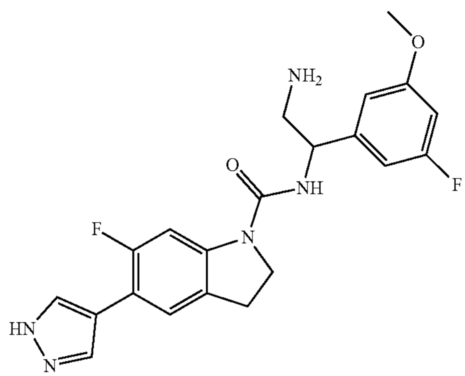 [SMILES: COc1cc(F)cc(C(CN)NC(=O)N2CCc3cc(-c4cn[nH]c4)c(F)cc32)c1] |
| T372 | 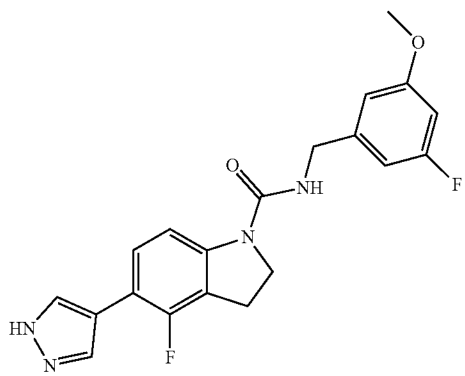 [SMILES: COc1cc(F)cc(CNC(=O)N2CCc3c2ccc(-c2cn[nH]c2)c3F)c1] |
| T373 | 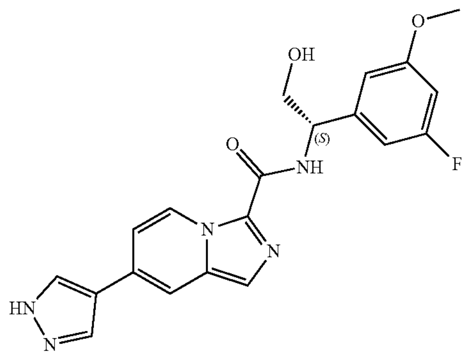 |

-continued
| Compound No. | Structural formulas |
|---|---|
| T374 | 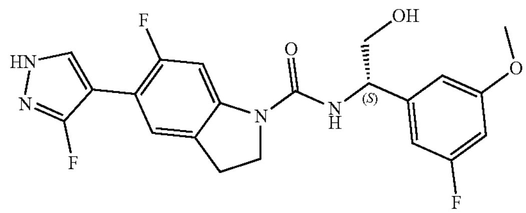 |
| T375 | 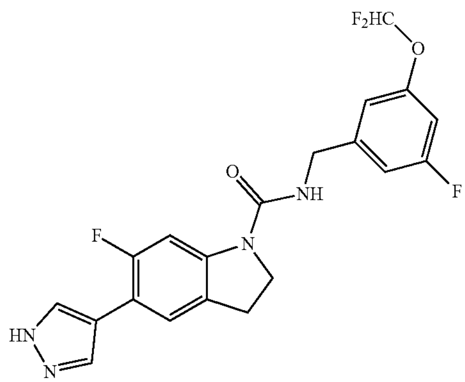 [SMILES: O=C(NCc1cc(F)cc(OC(F)F)c1)N1CCc2cc(-c3cn[nH]c3)c(F)cc21] |
| T376 | 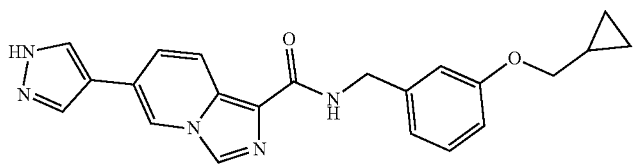 [SMILES: O=C(NCc1cccc(OCC2CC2)c1)c1ncn2cc(-c3cn[nH]c3)ccc12] |
| T377 | 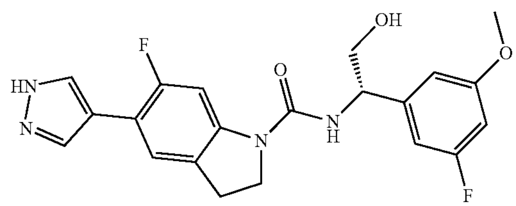 [SMILES: COc1cc(F)cc([C@@H](CO)NC(=O)N2CCc3cc(-c4cn[nH]c4)c(F)cc32)c1] |
| T378 | 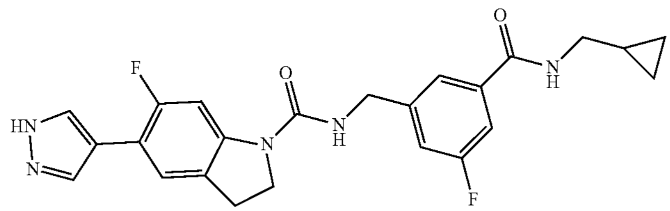 [SMILES: O=C(NCC1CC1)c1cc(F)cc(CNC(=O)N2CCc3cc(-c4cn[nH]c4)c(F)cc32)c1] |
| T379 | 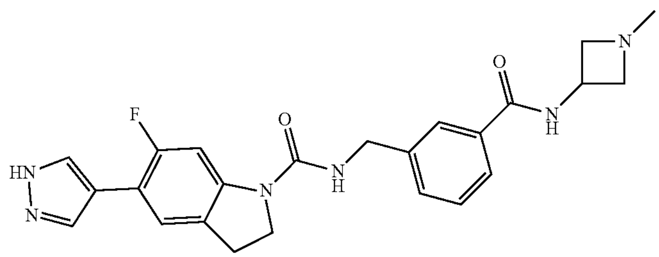 [SMILES: CN1CC(NC(=O)c2cccc(CNC(=O)N3CCc4cc(-c5cn[nH]c5)c(F)cc43)c2)C1] |

-continued
| Compound No. | Structural formulas |
|---|---|
| T380 | 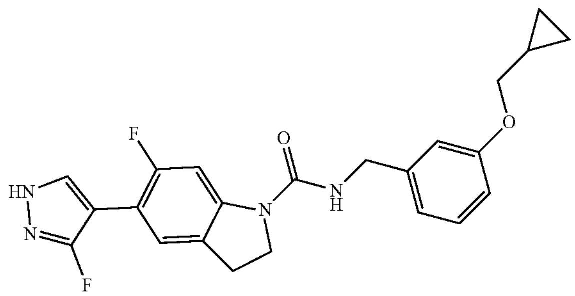 [SMILES: O=C(NCc1cccc(OCC2CC2)c1)N1CCc2cc(-c3c[nH]nc3F)c(F)cc21] |
| T381 | 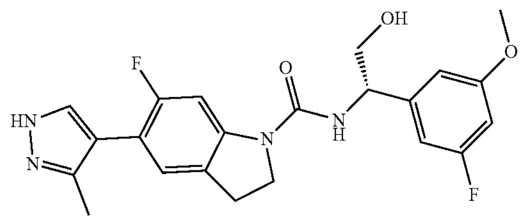 [SMILES: COc1cc(F)cc([C@@H](CO)NC(=O)N2CCc3cc(-c4c[nH]nc4C)c(F)cc32)c1] |
| T382 | 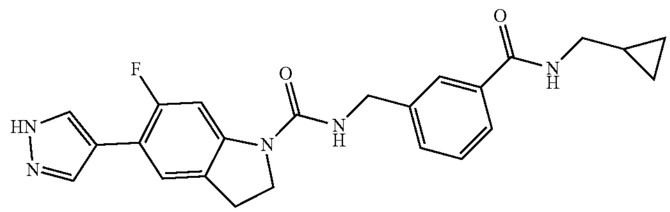 [SMILES: O=C(NCC1CC1)c1cccc(CNC(=O)N2CCc3cc(-c4cn[nH]c4)c(F)cc32)c1] |
| T383 | 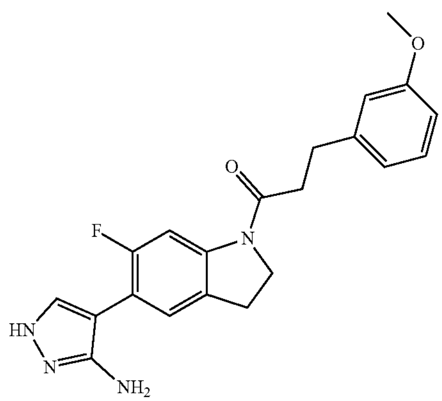 [SMILES: COc1cccc(CCC(=O)N2CCc3cc(-c4c[nH]nc4N)c(F)cc32)c1] |
| T384 | 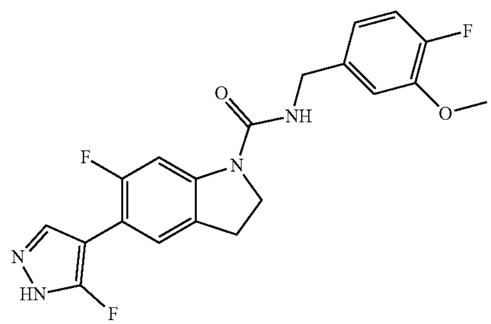 [SMILES: COc1cc(CNC(=O)N2CCc3cc(-c4cn[nH]c4F)c(F)cc32)ccc1F] |

-continued
| Compound No. | Structural formulas |
|---|---|
| T385 | 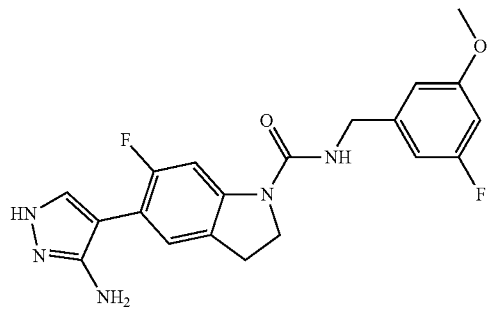 [SMILES: COc1cc(F)cc(CNC(=O)N2CCc3cc(-c4c[nH]nc4N)c(F)cc32)c1] |
| T386 | 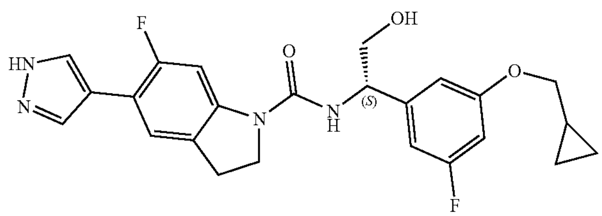 |
| T387 | 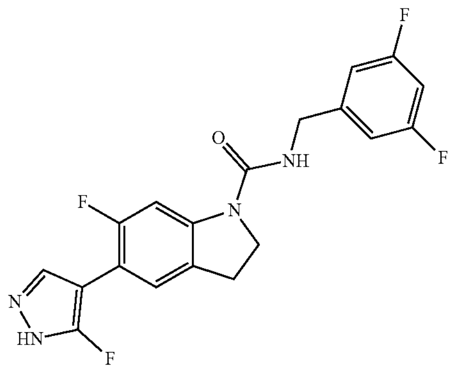 [SMILES: O=C(NCc1cc(F)cc(F)c1)N1CCc2cc(-c3cn[nH]c3F)c(F)cc21] |
| T388 | 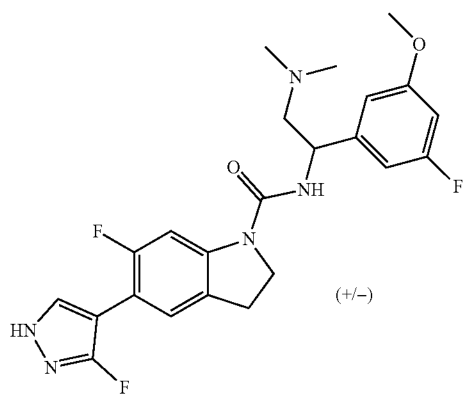 [SMILES: COc1cc(F)cc(C(CN(C)C)NC(=O)N2CCc3cc(-c4c[nH]nc4F)c(F)cc32)c1] |
| T389 | 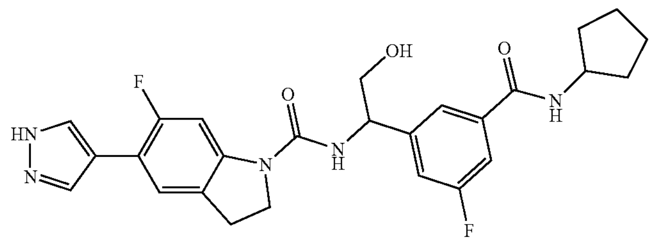 [SMILES: O=C(NC1CCCC1)c1cc(F)cc(C(CO)NC(=O)N2CCc3cc(-c4cn[nH]c4)c(F)cc32)c1] |

-continued

| Compound No. | Structural formulas |
|---|---|
| T390 | 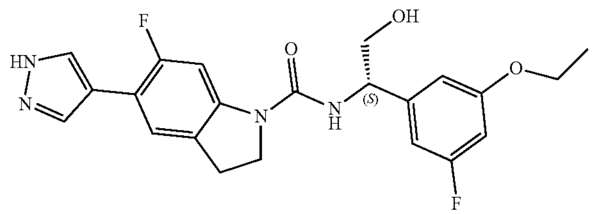 |
| T391 | 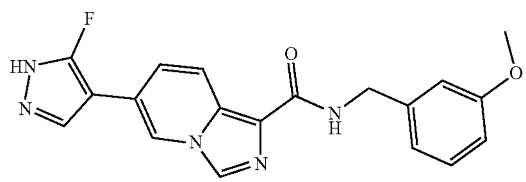 [SMILES: COc1cccc(CNC(=O)c2ncn3cc(-c4cn[nH]c4F)ccc23)c1] |

The present disclosure also provides a method for preparing the compound of formula (I) (including the compound of formula (II)), which comprises at least one of the following schemes:

scheme 1

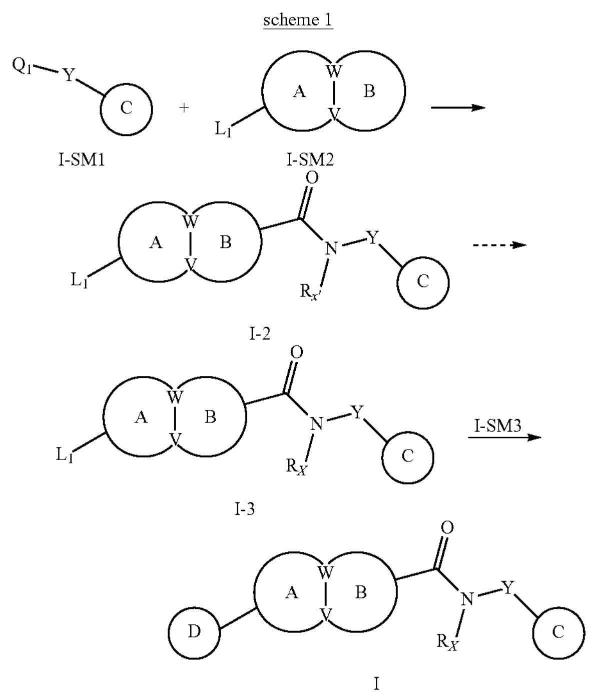

a1) reacting a compound I-SM1 with a compound I-SM2 under an alkaline condition to obtain a compound I-2;

a2) optionally, further subjecting the compound I-2 to derivatization treatment all; on amide nitrogen to obtain a compound I-3; and a3) subjecting the compound I-2 or I-3 and a compound I-SM3 to Suzuki coupling reaction to obtain a compound I;

wherein, A, B, C, D, W, V, Y and $R_x$ are defined as in the formula (I) above; $R_x$' is selected from $R_x$ and a group which may be converted to $R_x$ by derivatization step (a2); $L_1$ is selected from halogen, and the halogen may be selected from F, Cl, Br and I; the group Q1 is an isocyanate group or —N($R_x$')— active formate group; the compound I-SM3 is borate containing a ring D group;

scheme 2

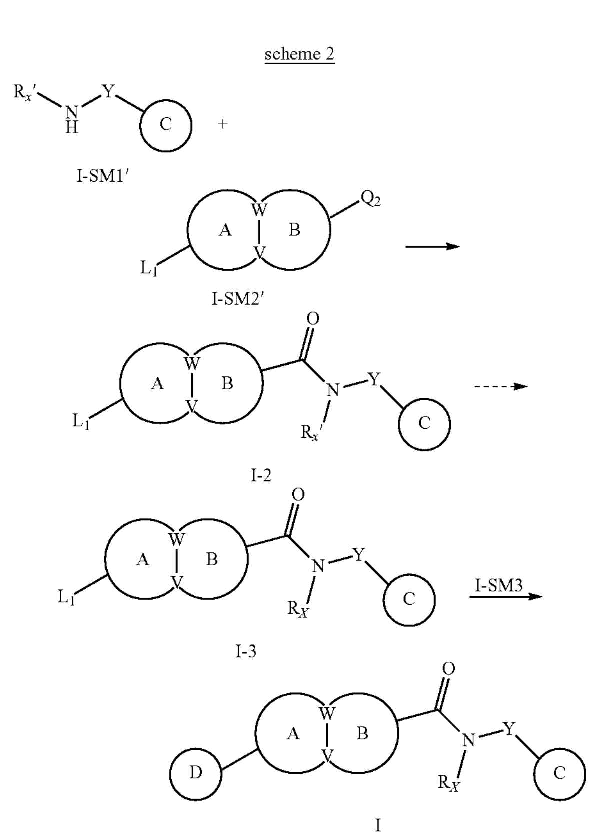

b1) reacting a compound I-SM1' with a compound I-SM2' under an alkaline condition to obtain a compound I-2;

b2) optionally, further subjecting the compound I-2 to derivatization treatment of $R_x$' on amide nitrogen to obtain a compound I-3; and b3) subjecting the compound I-2 or I-3 and a compound I-SM3 to Suzuki coupling reaction to obtain a compound I;

wherein, A, B, C, D, W, V, Y and $R_x$ are defined as in the formula (I) above; $R_x$' is selected from $R_x$ and a group which may be converted to $R_x$ by derivatization step (b2); $L_1$ is selected from halogen, and the halogen may be selected from F, Cl, Br and I; the group Q2 is an active formate group; the compound I-SM3 is borate containing a ring D group;

or scheme 3

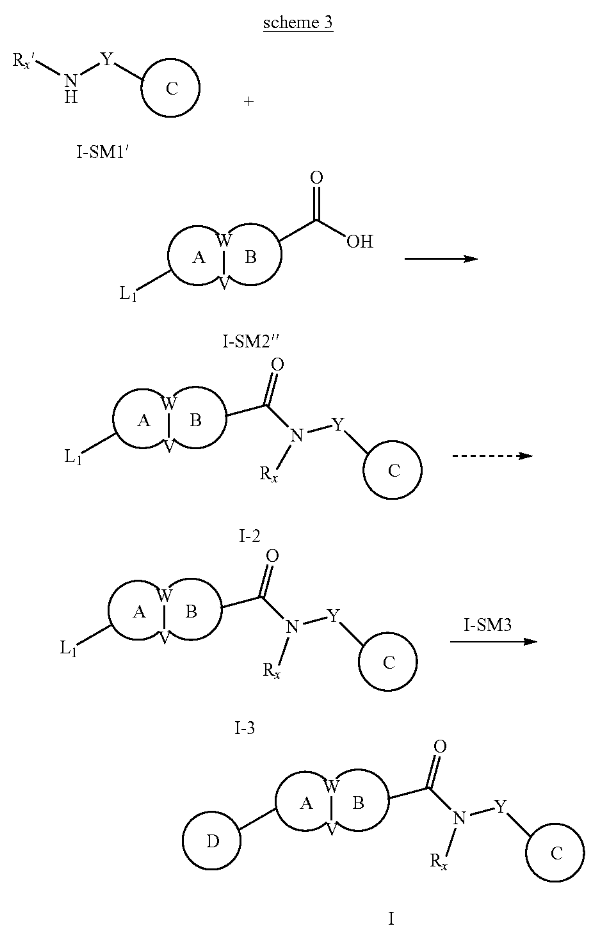

I-SM1'

I-SM2"

I-2

I-3

I c1) reacting a compound I-SM1' with a compound I-SM2" under an alkaline conditions to obtain a compound I-2;

c2) optionally, further subjecting the compound I-2 to derivatization treatment of $R_x$' on amide nitrogen to obtain a compound I-3; and c3) subjecting the compound I-2 or I-3 and a compound I-SM3 to Suzuki coupling reaction to obtain a compound I;

wherein, A, B, C, D, W, V, Y and $R_x$ are defined as in the formula (I) above; $R_x$' is selected from $R_x$ and a group which may be converted to $R_x$ by derivatization step (c2); $L_1$ is selected from halogen, and the halogen may be selected from F, Cl, Br and I; the compound I-SM3 is borate containing a ring D group.

Specific examples of scheme 1 may include scheme 1-1:

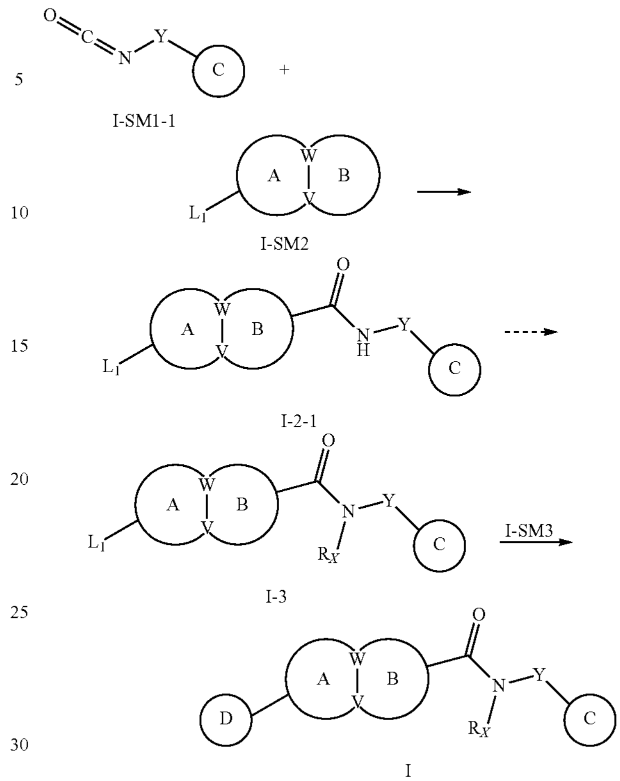

I-SM1-1

I-SM2

I-2-1

I-3

I a1') reacting a compound I-SM1-1 with a compound I-SM2 under an alkaline condition to obtain a compound I-2-1;

a2) optionally, further subjecting the compound I-2-1 to derivatization treatment of $R_x$' on amide nitrogen to obtain a compound I-3; and a3') subjecting the compound I-2-1 or I-3 and a compound I-SM3 to Suzuki coupling reaction to obtain a compound I;

wherein, A, B, C, D, W, V, Y and $R_x$ are defined as in the formula (I) above; $R_x$ is not H; $L_1$ is selected from halogen, and the halogen may be selected from F, Cl, Br and I; the compound I-SM3 is borate containing a ring D group;

or scheme 1-2

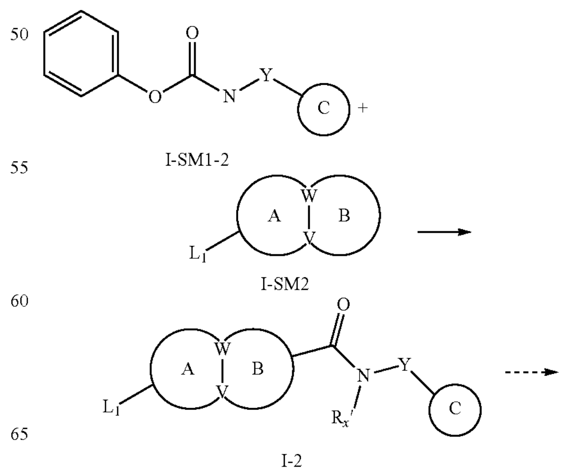

I-SM1-2

I-SM2

I-2

-continued

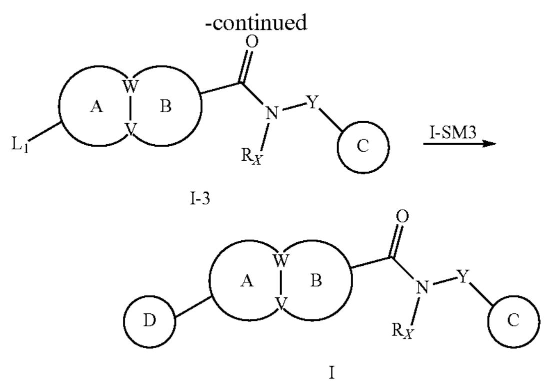

I-3

I a1") reacting a compound I-SM1-2 with a compound I-SM2 under an alkaline condition to obtain a compound I-2;

a2") optionally, further subjecting the compound I-2 to derivatization treatment of $R_x$' on amide nitrogen to obtain a compound I-3; and a3") subjecting the compound I-2 or I-3 and a compound I-SM3 to Suzuki coupling reaction to obtain a compound I;

wherein, ring A, ring B, ring C, ring D, W, V, Y and $R_x$ are selected from the definitions in the formula (I) above; $R_x$' is selected from $R_x$ and a group which may be converted to $R_x$ by derivatization step (a2"); $L_1$ is selected from halogen, and the halogen may be selected from F, Cl, Br and I; the compound I-SM3 is borate containing a ring D group;

A group protection or deprotection step may optionally be performed in the above schemes, and operations and conditions in the step may be conventional in the art. According to the preparation method of the present disclosure, leaving groups and amino protecting groups used may be groups commonly used in the art. For example, the leaving group may be selected from halogen (e.g., I or Cl),

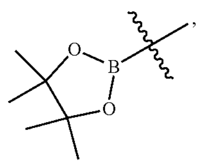 [SMILES: *B1OC(C)(C)C(C)(C)O1]

and the like. The "active formate group" described in the above schemes is a group conventionally selected by one skilled in the art to provide C═O in the reaction (phenol or alcohol fragment in the formate leaves), for example, the "active formate group" in "—N($R_x$')-active formate group", i.e. a group (in which the phenol or alcohol fragment is easy to leave) providing carbonyl of the amide structure —N($R_x$)—C(═O)— in the product, wherein the "active formate group" is preferably phenol formate (PhO(C═O)—) or a substituted phenol formate, e.g. p-nitrophenol formate (p-$NO_2$-PhO(C═O)—).

According to the preparation method of the present disclosure, operations and conditions in the steps may be conventional in the art. Operations and conditions in the step a1), a1'), a1"), b1) or c1) may be conventional in the art, and the base used is an inorganic base or an organic base, for example, at least one selected from triethylamine (TEA), potassium carbonate, isopropylamine, diisopropylethylamine (DIEA), pyridine, lithium carbonate, cesium carbonate, potassium tert-butoxide, sodium tert-butoxide, 1,8-diazabicycloundec-7-ene, sodium methoxide, sodium ethoxide, potassium phosphate, potassium hydrogen phosphate, potassium dihydrogen phosphate, sodium bicarbonate and potassium bicarbonate.

According to the preparation method of the present disclosure, for the step a1), a1'), a1"), b1) or c1), the reaction may preferably be performed in the presence of a solvent, preferably in an aprotic organic solvent, for example, one or more of tetrahydrofuran (THF), acetonitrile, DMF, dichloromethane, n-hexane, ethyl acetate, diethyl ether, methyl tert-butyl ether, toluene, chloroform, cyclohexane, dioxane and acetone.

According to the preparation method of the present disclosure, operations and conditions in the step a2), a2'), a2"), b2) or c2) may be conventional in the art. For example, such reactions as allylation and acylation may preferably be performed in the presence of a solvent, preferably an organic solvent, such as one or more of methanol, ethanol, isopropanol, tert-butanol, toluene, chloroform, cyclohexane, tetrahydrofuran (THF), dichloromethane, acetonitrile, DMF, n-hexane, ethyl acetate, diethyl ether, methyl tert-butyl ether, dioxane and acetone, preferably dichloromethane.

According to an embodiment of the present disclosure, for the coupling reaction in the step a3), a3'), a3"), b3) or c3), operations and conditions may be conventional in the art. The reaction may preferably be performed in the presence of a solvent, such as one or more of methanol, ethanol, isopropanol, tert-butanol, toluene, chloroform, cyclohexane, tetrahydrofuran (THF), acetonitrile, DMF, dichloromethane, n-hexane, ethyl acetate, diethyl ether, methyl tert-butyl ether, acetone, dioxane, DMF and water, preferably a mixed solution of dioxane or DMF and water.

According to an embodiment of the present disclosure, the coupling reaction in the step a3), a3'), a3"), b3) or c3) may be performed in the presence of a catalyst and a base, and the catalyst includes widely used Pd-containing catalysts, such as at least one of $Pd(OAc)_2$ and ligand XPhos, tetrakis(triphenylphosphine)palladium (i.e., $Pd(PPh_3)_4$), [1,1'-bis(diphenylphosphino)ferrocene]dichloropalladium (II) (i.e., $Pd(dppf)Cl_2$), and the like. For example, the reaction is performed in the presence of K3PO4, $Pd(OAc)_2$ and XPhos. The base is a conventional base in the art, and includes an inorganic base or an organic base, for example, at least one selected from triethylamine (TEA), potassium carbonate, isopropylamine, diisopropylethylamine (DIEA), pyridine, lithium carbonate, cesium carbonate, potassium tert-butoxide, sodium tert-butoxide, 1,8-diazabicycloundec-7-ene, sodium methoxide, sodium ethoxide, sodium fluoride, potassium fluoride, cesium fluoride, potassium phosphate, potassium hydrogen phosphate, potassium dihydrogen phosphate, sodium bicarbonate and potassium bicarbonate.

It will be understood by those skilled in the art that the compound of formula (I) or the racemate, the stereoisomer, the tautomer and the nitrogen oxide thereof can be used as a starting material or an intermediate to prepare the prodrug or the pharmaceutically acceptable salt of the compound of formula (I) or the racemate, the stereoisomer, the tautomer and the nitrogen oxide thereof. Therefore, the present disclosure also provides use of the compound of formula (I) or the racemate, the stereoisomer, the tautomer or the nitrogen oxide thereof in preparing the prodrug or the pharmaceutically acceptable salt of the compound of formula (I) or the racemate, the stereoisomer, the tautomer or the nitrogen oxide thereof.

The present disclosure also provides use of at least one of the compound of formula (I) and the racemate, the stereoisomer, the tautomer, the nitrogen oxide, the isotopically labeled compound, the solvate, the polymorph, the metabolite, the ester, the pharmaceutically acceptable salt and the prodrug thereof in preparing a medicament, wherein the medicament is an inhibitor of protein kinase.

In particular, the medicament has the function of regulating Rho-kinase. The medicament can be used for preventing or treating one or more diseases caused by high expression of ROCK or excessive activation of ROCK, such as cardiovascular and cerebrovascular diseases, neurological diseases, fibrosis diseases, ocular diseases, tumors, arterial thrombotic disorders, radiation damage, respiratory diseases, and autoimmune diseases, including atherosclerosis, acute coronary syndrome, hypertension, cerebral vasospasm, cerebral ischemia, ischemic stroke, restenosis, heart disease, heart failure, cardiac hypertrophy, myocardial ischemia-reperfusion injury, diabetes, diabetic nephropathy, cancer, neuronal degeneration (peripheral or central), nerve injury diseases, spinal cord injury, erectile dysfunction, platelet aggregation, leukocyte aggregation, glaucoma, ocular hypertension, asthma, osteoporosis, pulmonary fibrosis (such as idiopathic pulmonary fibrosis), hepatic fibrosis, renal fibrosis, COPD, kidney dialysis (epithelial stability), glomerulosclerosis, neuronal degeneration inflammation, and the like.

The present disclosure also provides a pharmaceutical composition comprising a therapeutically effective amount of at least one of the compound of formula (I) and the racemate, the stereoisomer, the tautomer, the nitrogen oxide, the isotopically labeled compound, the solvate, the polymorph, the metabolite, the ester, the pharmaceutically acceptable salt and the prodrug thereof.

Preferably, the pharmaceutical composition may optionally further comprise a pharmaceutically acceptable auxiliary material, such as a carrier or an excipient. As an example, the auxiliary material may be at least one selected from: a disintegrant, a glidant, a lubricant, a diluent, a filler, an adhesive and a colorant.

The pharmaceutical composition of the present disclosure has the function of regulating Rho-kinase. The pharmaceutical composition can be used for preventing or treating one or more diseases caused by high expression of ROCK or excessive activation of ROCK, such as cardiovascular and cerebrovascular diseases, neurological diseases, fibrosis diseases, ocular diseases, tumors, arterial thrombotic disorders, radiation damage, respiratory diseases, and autoimmune diseases, including atherosclerosis, acute coronary syndrome, hypertension, cerebral vasospasm, cerebral ischemia, ischemic stroke, restenosis, heart disease, heart failure, cardiac hypertrophy, myocardial ischemia-reperfusion injury, diabetes, diabetic nephropathy, cancer, neuronal degeneration (peripheral or central), nerve injury diseases, spinal cord injury, erectile dysfunction, platelet aggregation, leukocyte aggregation, glaucoma, ocular hypertension, asthma, osteoporosis, pulmonary fibrosis (such as idiopathic pulmonary fibrosis), hepatic fibrosis, renal fibrosis, COPD, kidney dialysis (epithelial stability), glomerulosclerosis, neuronal degeneration inflammation, and the like.

The present disclosure also provides a method for regulating Rho-kinase function, which comprises administering to an individual in need thereof an effective amount of the compound of formula (I) or the racemate, the stereoisomer, the tautomer, the nitrogen oxide, the isotopically labeled compound, the solvate, the polymorph, the metabolite, the ester, the pharmaceutically acceptable salt or the prodrug thereof or the pharmaceutical composition. The method can be used for preventing or treating one or more diseases caused by high expression of ROCK or excessive activation of ROCK.

The present disclosure also provides a method for preventing or treating one or more diseases caused by high expression of ROCK or excessive activation of ROCK, which comprises administering to an individual in need thereof an effective amount of the compound of formula (I) or the racemate, the stereoisomer, the tautomer, the nitrogen oxide, the isotopically labeled compound, the solvate, the polymorph, the metabolite, the ester, the pharmaceutically acceptable salt or the prodrug thereof or the pharmaceutical composition. The disease is, for example, cardiovascular and cerebrovascular diseases, neurological diseases, fibrosis diseases, ocular diseases, tumors, arterial thrombotic disorders, radiation damage, respiratory diseases, and autoimmune diseases, including atherosclerosis, acute coronary syndrome, hypertension, cerebral vasospasm, cerebral ischemia, ischemic stroke, restenosis, heart disease, heart failure, cardiac hypertrophy, myocardial ischemia-reperfusion injury, diabetes, diabetic nephropathy, cancer, neuronal degeneration (peripheral or central), nerve injury diseases, spinal cord injury, erectile dysfunction, platelet aggregation, leukocyte aggregation, glaucoma, ocular hypertension, asthma, osteoporosis, pulmonary fibrosis (such as idiopathic pulmonary fibrosis), hepatic fibrosis, renal fibrosis, COPD, kidney dialysis (epithelial stability), glomerulosclerosis, neuronal degeneration inflammation, and the like.

In another aspect, the present disclosure provides a compound of formula (I) for use in regulating Rho-kinase function, and the modulating comprises administering to an individual in need thereof an effective amount of one or more compounds disclosed herein or a pharmaceutical composition comprising the compound.

In yet another aspect, the present disclosure provides a compound of formula (I) for use in a method for preventing or treating one or more diseases caused by high expression of ROCK or excessive activation of ROCK, and the method comprises administering to an individual in need thereof an effective amount of the compound of formula (I) or the racemate, the stereoisomer, the tautomer, the nitrogen oxide, the isotopically labeled compound, the solvate, the polymorph, the metabolite, the ester, the pharmaceutically acceptable salt or the prodrug thereof or the pharmaceutical composition. The disease is, for example, cardiovascular and cerebrovascular diseases, neurological diseases, fibrosis diseases, ocular diseases, tumors, arterial thrombotic disorders, radiation damage, respiratory diseases, and autoimmune diseases, including atherosclerosis, acute coronary syndrome, hypertension, cerebral vasospasm, cerebral ischemia, ischemic stroke, restenosis, heart disease, heart failure, cardiac hypertrophy, myocardial ischemia-reperfusion injury, diabetes, diabetic nephropathy, cancer, neuronal degeneration (peripheral or central), nerve injury diseases, spinal cord injury, erectile dysfunction, platelet aggregation, leukocyte aggregation, glaucoma, ocular hypertension, asthma, osteoporosis, pulmonary fibrosis (such as idiopathic pulmonary fibrosis), hepatic fibrosis, renal fibrosis, COPD, kidney dialysis (epithelial stability), glomerulosclerosis, neuronal degeneration inflammation, and the like.

Definitions and Description

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification.

When a numerical range defined by "integer" is recited in the specification and claims of this application, it shall be construed as reciting both endpoints of the range and every integer within the range. For example, "an integer of 0 to 6" shall be construed to include every integer of 0, 1, 2, 3, 4, 5 and 6. The term "more" refers to three or more.

The term "halogen" refers to F, Cl, Br and I. In other words, F, Cl, Br and I may be described as "halogen" in the specification.

The term "aliphatic hydrocarbyl" includes saturated or unsaturated, linear or branched hydrocarbyl; the type of the aliphatic hydrocarbyl may be selected from alkyl, alkenyl, alkynyl and the like, and the number of carbon atoms of the aliphatic hydrocarbyl may be 1-20, may preferably be 1-12, may also be 1-10, and may further preferably be 1-6. For example, the ($C_1$-$C_{12}$) aliphatic hydrocarbyl may be selected from ($C_1$-$C_{12}$) alkyl, ($C_2$-$C_{12}$) alkenyl and ($C_2$-$C_{12}$) alkynyl, and in some embodiments, it may be selected from ($C_1$-$C_6$) alkyl, ($C_2$-$C_6$)alkenyl and ($C_2$-$C_6$)alkynyl. Specifically, it may include, but is not limited to: methyl, ethyl, n-propyl, isopropyl, n-butyl, isobutyl, tert-butyl, n-pentyl, isopentyl, neopentyl, n-hexyl, vinyl, propenyl, butenyl, pentenyl, hexenyl, ethynyl, propynyl, butynyl, pentynyl and hexynyl; further, it may be selected from methyl, ethyl, n-propyl, isopropyl, n-butyl, isobutyl, tert-butyl, n-pentyl, isopentyl, neopentyl, n-hexyl, vinyl, 1-propenyl, 2-propenyl, 1-methylvinyl, 1-butenyl, 1-ethylvinyl, 1-methyl-2-propenyl, 2-butenyl, 3-butenyl, 2-methyl-1-propenyl, 2-methyl-2-propenyl, 1-pentenyl, 1-hexenyl, ethynyl, 1-propynyl, 2-propynyl, 1-butynyl, 2-butynyl, 1-isobutynyl, 1-isopentynyl, 2-isopentynyl, 1-methyl-2-propynyl, 3-butynyl, 1-pentynyl and 1-hexynyl; the "aliphatic hydrocarbyl" may optionally comprise one, two or more heteroatoms (which may be construed as optional insertion of heteroatoms into any C—C bond and C—H bond of the aliphatic hydrocarbyl). Suitable heteroatoms will be apparent to those skilled in the art and include, for example, sulfur, nitrogen, oxygen, phosphorus and silicon. The aliphatic hydrocarbyl comprising heteroatoms may be selected from the following groups: ($C_1$-$C_{12}$) aliphatic hydrocarbyloxy, ($C_1$-$C_{12}$) aliphatic hydrocarbylmercapto, ($C_1$-$C_6$) aliphatic hydrocarbyloxy, ($C_1$-$C_6$) aliphatic hydrocarbylmercapto, ($C_1$-$C_6$) aliphatic hydrocarbyloxy($C_1$-$C_6$) aliphatic hydrocarbyl, ($C_1$-$C_6$) aliphatic hydrocarbylmercapto($C_1$-$C_6$) aliphatic hydrocarbyl, ($C_1$-$C_6$) aliphatic hydrocarbyloxy($C_1$-$C_6$) aliphatic hydrocarbyloxy, ($C_1$-$C_6$) aliphatic hydrocarbylmercapto($C_1$-$C_6$) aliphatic hydrocarbylmercapto, N—($C_1$—$C_3$) aliphatic hydrocarbylamino($C_1$-$C_6$) aliphatic hydrocarbyl, and N,N-di-($C_1$-$C_3$) aliphatic hydrocarbylamino($C_1$-$C_6$) aliphatic hydrocarbyl; for example, it may be methoxy, ethoxy, propoxy, butoxy, pentoxy, methoxymethyl, ethoxymethyl, propoxymethyl, methoxyethyl, ethoxyethyl, propoxyethyl, methoxypropyl, ethoxypropyl, propoxypropyl, N-methylaminomethyl, N-methylaminoethyl, N-ethylaminoethyl, N,N-dimethylaminomethyl, N,N-dimethylaminoethyl, or N,N-diethylaminoethyl; the "aliphatic hydrocarbyl" moieties contained in the other groups are defined as above.

The term "$C_{3-20}$ alicyclic hydrocarbyl" is to be understood as a cyclic hydrocarbyl that has aliphatic properties and contains closed carbocycle in the molecule. It may represent saturated or partially unsaturated monovalent monocyclic, bicyclic or polycyclic hydrocarbon rings, and also includes bridged or Spiro rings. For example, when the alicyclic hydrocarbyl contains two or more carbocycles, they may be linked in a variety of ways: two rings in the molecule may share one carbon atom, and the system is called spiro; two carbon atoms on the ring can be linked by a carbon bridge to form a bicyclic or polycyclic system, which is called a bridge ring; several rings may also be interconnected to form a cage-like structure. The alicyclic hydrocarbyl may have 3-20 carbon atoms and is preferably "$C_{3-12}$ alicyclic hydrocarbyl", and it may also be "$C_{3-7}$ alicyclic hydrocarbyl", which may have 3, 4, 5, 6, 7, 8, 9, 10, 11, 12, 13, 14, 15, 16, 17, 18, 19 or 20 carbon atoms. The alicyclic hydrocarbyl may be "cycloalkyl", "cycloalkenyl", "cycloalkynyl", etc. (the number of carbon atoms may be selected from any one of the above integers from 3 to 20), and the alicyclic hydrocarbyl may be monocyclic hydrocarbyl such as cyclopropyl, cyclobutyl, cyclopentyl, cyclohexyl, cycloheptyl, cyclooctyl, cyclononyl or cyclodecyl, or bicyclic hydrocarbyl such as decahydronaphthalene ring. For example, the term "$C_{3-7}$ cycloalkyl" refers to a saturated monovalent monocyclic or bicyclic hydrocarbon ring which may be a spiro or bridged ring, and it has 3, 4, 5, 6 or 7 carbon atoms. The $C_{3-7}$ cycloalkyl group may be, for example, cyclopropyl, cyclobutyl, cyclopentyl, cyclohexyl, bicyclo[1.1.0]butyl, spiropentyl, spiro[2.3]hexyl, bicyclo[1.1.1]pentyl, bicyclo[2.1.0]pentyl, bicyclo[2.1.1]hexyl or bicyclo[3.1.0]hexyl.

The term "3-20 membered heterocyclyl" refers to a saturated or partially unsaturated monovalent monocyclic, bicyclic or polycyclic hydrocarbon ring, and also includes bridged or spiro rings, and it comprises 1-5 heteroatoms independently selected from N, O, B, P, Si and S. The "3-20 membered heterocyclyl" may be, for example, "3-12 membered heterocyclyl", "3-7 membered heterocyclyl" or "5-6 membered heterocyclyl". The term "3-12 membered heterocyclyl" refers to a saturated monovalent monocyclic or bicyclic hydrocarbon ring comprising 1-5, preferably 1-3, heteroatoms selected from N, O, B, P, Si and S. The heterocyclyl may be connected to the rest of the molecule through any one of the carbon atoms or the nitrogen atom (if present). Each atom of the heterocyclyl is independently optionally substituted, e.g., with 1-5 substituents, 1-3 substituents or 1 substituent, regardless of whether the heterocyclyl is modified by "substituted" or not, and suitable substituents include, but are not limited to, OH, amino, oxo, halogen, CN, nitro, $C_{1-20}$ aliphatic hydrocarbyl, $C_{3-20}$ alicyclic hydrocarbyl, and the like. In particular, the heterocyclyl may include, but is not limited to: 3 membered rings, such as azirdinyl, oxiranyl and thiiranyl; 4 membered rings, such as azetidinyl, oxetanyl and thietanyl; 5 membered rings, such as dihydrofuranyl, tetrahydrofuranyl, dioxolyl, pyrrolidinyl, imidazolidinyl, pyrazolidinyl, pyrrolinyl, dihydrothienyl, tetrahydrothienyl, dihydropyrrolyl, dioxalanyl, oxasulfuranyl, disulfuranyl, oxazolidin-2-one, triazolinyl, oxadiazolinyl and thiadiazolinyl; or 6 membered rings such as dihydropyranyl, tetrahydropyranyl, piperidinyl, morpholinyl, dithianyl, thiomorpholinyl, dihydropyridinyl, thiacyclohexyl, dithiacyclohexyl, dioxanyl, piperazinyl or trithianyl; or 7 membered ring such as diazepanyl, azepanyl, oxepanyl and thiepanyl. Optionally, the heterocyclyl may be benzo-fused. The heterocyclyl may be bicyclic, such as but not limited to a 5,5-membered ring such as a hexahydrocyclopenta[c]pyrrol-2(1H)-yl ring, or a 5,6-membered bicyclic ring such as a hexahydropyrrolo[1,2-a]pyrazin-2(1H)-yl ring. The ring containing nitrogen atoms may be partially unsaturated, i.e., it may comprise one or more double bonds, such as but not limited to 2,5-dihydro-1H-pyrrolyl, 4H-[1,3,4]thiadiazinyl, 4,5-dihydrooxazolyl or 4H-[1,4]thiazinyl, or it may be benzo-fused, such as but not limited to dihydroisoquinolyl. According to the present disclosure, the heterocyclyl is non-aromatic.

The term "$C_{6-20}$ aryl" refers to an aromatic or partially aromatic monovalent monocyclic, bicyclic or tricyclic hydrocarbon ring having 6-20 carbon atoms, and is preferably "$C_{6-14}$ aryl" or "$C_{6-10}$ aryl".

The term "$C_{6-14}$ aryl" preferably refers to an aromatic or partially aromatic monovalent monocyclic, bicyclic or tricyclic hydrocarbon ring having 6, 7, 8, 9, 10, 11, 12, 13 or 14 carbon atoms ("$C_{6-14}$ aryl"), in particular a ring having 6 carbon atoms ("$C_6$ aryl"), such as phenyl; or a biphenyl, a ring having 9 carbon atoms ("$C_9$ aryl") such as indanyl or indenyl, a ring having 10 carbon atoms ("$C_{10}$ aryl") such as tetrahydronaphthyl, dihydronaphthyl or naphthyl, a ring having 13 carbon atoms ("$C_{13}$ aryl") such as fluorenyl, or a ring having 14 carbon atoms ("$C_{14}$ aryl") such as anthracenyl.

The term "5-20 membered heteroaryl" refers to an aromatic monovalent monocyclic, bicyclic or tricyclic ring which has 5-20 ring atoms and comprises 1-5 heteroatoms independently selected from N, O and S, such as "5-14 membered heteroaryl", "5-10 membered heteroaryl" or "5-6 membered heteroaryl". The term "5-14 membered heteroaryl" refers to a monovalent aromatic monocyclic, bicyclic or tricyclic ring which has 5, 6, 7, 8, 9, 10, 11, 12, 13 or 14 ring atoms, in particular 5, 6, 9 or 10 carbon atoms, comprises 1-5, preferably 1-3 heteroatoms independently selected from N, O and S, and may be benzo-fused in each case. The term "5-6 membered heteroaryl" refers to a monovalent monocyclic aromatic ring which has 5 or 6 ring atoms, comprises 1-3 heteroatoms independently selected from N, O and S, and may be benzo-fused in each case. In particular, the heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and the like and benzo derivatives thereof, such as benzofuranyl, benzothienyl, benzoxazolyl, benzoisoxazolyl, benzimidazolyl, benzotriazolyl, indazolyl, indolyl, and isoindolyl; or pyridinyl, pyridazinyl, pyrimidinyl, pyrazinyl, triazinyl and the like and benzo derivatives thereof, such as quinolyl, quinazolinyl, and isoquinolyl; or azocinyl, indolizinyl, purinyl and the like and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, and the like.

Unless otherwise stated, the heterocyclyl, heteroaryl or heteroarylene includes all possible isomeric forms thereof, e.g., positional isomers thereof. Accordingly, for some illustrative non-limiting examples, pyridinyl or pyridinylene includes pyridin-2-yl, pyridinylene-2-yl, pyridin-3-yl, pyridinylene-3-yl, pyridin-4-yl, and pyridinylene-4-yl; thienyl or thienylene includes thien-2-yl, thien-2-ylene, thien-3-yl, and thien-3-ylene.

Unless otherwise indicated, the term "leaving group", as used herein, shall refer to a charged or uncharged atom or group that is liberated during a substitution or replacement reaction. Suitable examples include, but are not limited to, H, F, Br, Cl, I, mesylate group, tosylate group, and the like.

In any method for preparing the compound disclosed herein, it may be necessary and/or desirable to protect sensitive or reactive groups on any molecule concerned. This can be achieved by conventional protective groups, as described in textbooks or in reference books in the art. The protective group may be removed at a convenient subsequent stage using methods known in the art. Those skilled in the art will recognize that, other reagents, including but not limited to Pd/C, $Pd(OH)_2$, $PdCl_2$, $Pd(OAc)_2/Et_3SiH$, Raney nickel, an appropriately selected acid, an appropriately selected base, fluoride, and the like, may be used in this deprotection step depending on the particular protective group.

The target compound may be isolated according to known methods, for example by extraction, filtration or column chromatography.

According to the molecular structure, the compounds disclosed herein may be chiral and may therefore exist in various enantiomeric forms. These compounds may therefore exist in racemic or optically active form. The compounds disclosed herein or intermediates thereof may be separated into enantiomers by chemical or physical methods well known to those skilled in the art, or used in this form for synthesis. In the case of racemic amines, diastereoisomers are prepared from mixtures by reaction with optically active resolving agents. Examples of suitable resolving agents are optically active acids such as R- or S-tartaric acid, diacetyltartaric acid, dibenzoyltartaric acid, mandelic acid, malic acid, lactic acid, suitable N-protected amino acids (e.g., N-benzoylproline or N-benzenesulfonylproline) or various optically active camphorsulfonic acids. Enantiomeric resolution by chromatography can be advantageously performed with the aid of optically active resolving agents, such as dinitrobenzoylphenylglycine, cellulose triacetate or other carbohydrate derivatives or chirally derivatized methacrylate polymers immobilized on silica gel. Suitable eluents for this purpose are mixtures of solvent containing water or alcohol, for example, hexane/isopropanol/acetonitrile.

Those skilled in the art will appreciate that not all nitrogen-containing heterocycles can form N-oxides, as nitrogen needs to have available lone pairs of electrons used for oxidation to oxides; those skilled in the art will identify nitrogen-containing heterocycles capable of forming N-oxides. Those skilled in the art will also recognize that tertiary amines are capable of forming N-oxides. Synthetic methods for preparing N-oxides of heterocycles and tertiary amines are well known to those skilled in the art and include oxidation by peroxy acids such as peroxyacetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for preparing N-oxides have been widely described and reviewed in the literature.

A pharmaceutically acceptable salt may be, for example, acid addition salts of the compounds disclosed herein having a nitrogen atom in the chain or ring with sufficient basicity, for example, acid addition salts formed with the following inorganic acids: hydrochloric acid, hydrofluoric acid, hydrobromic acid, hydroiodic acid, sulfuric acid, pyrosulfuric acid, phosphoric acid or nitric acid; hydrosulfates; or acid addition salts with the following organic acids: formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, peroxosulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptoic acid, glycerophosphoric acid, aspartic acid, sulfosalicylic acid, hemi sulfuric acid, or thiocyanic acid.

In addition, another suitable pharmaceutically acceptable salt of the compounds disclosed herein having sufficient acidity is an alkali metal salt (e.g., sodium salt or potassium salt), an alkaline earth metal salt (e.g., calcium salt or magnesium salt), an ammonium salt, or a salt formed with an organic base which provides a physiologically acceptable cation, for example, a salt formed with: a sodium ion, a potassium ion, N-methylglucamine, dimethylglucamine, ethylglucamine, lysine, dicyclohexylamine, 1,6-hexanediamine, ethanolamine, glucosamine, meglumine, sarcosine, serinol, trihydroxymethylaminomethane, aminopropanediol, or 1-amino-2,3,4-butanetriol. As an example, the pharmaceutically acceptable salts include salts formed from the group —COOH with the following: a sodium ion, a potassium ion, a calcium ion, a magnesium ion, N-methylglucamine, dimethylglucamine, ethylglucamine, lysine, dicyclohexylamine, 1,6-hexanediamine, ethanolamine, glucosamine, meglumine, sarcosine, serinol, trishydroxymethylaminomethane, aminopropanediol, or 1-amino-2,3,4-butanetriol.

In addition, the basic nitrogen-containing groups may be quaternized with the following agents: lower alkyl halides such as methyl, ethyl, propyl and butyl chlorides, bromides and iodides; dialkyl sulfates such as dimethyl sulfate, diethyl sulfate, dibutyl sulfate, and dipentyl sulfate; long chain halides such as decyl, lauryl, myristyl and stearyl chlorides, bromides and iodides; and aralkyl halides such as benzyl and phenethyl bromides. As an example, pharmaceutically acceptable salts include hydrochloride, sulfate, nitrate, bisulfate, hydrobromide, acetate, oxalate, citrate, mesylate, formate, meglumine, and the like.

Since the compounds disclosed herein may have a plurality of salt-forming sites, the "pharmaceutically acceptable salt" includes not only a salt formed at 1 salt-forming site of the compounds disclosed herein but also salts formed at 2, 3 or all of the salt-forming sites thereof. For this purpose, the molar ratio of the compound of formula I to a radical ion (anion) of an acid or a cation of a base required for salt formation may vary within a wide range, and may be, for example, 4:1 to 1:4, such as 3:1, 2:1, 1:1, 1:2, and 1:3.

According to the present disclosure, the pharmaceutically acceptable anions include anions selected from those generated by the ionization of inorganic or organic acids. The "inorganic acid" includes, but is not limited to, hydrochloric acid, hydrofluoric acid, hydrobromic acid, hydroiodic acid, sulfuric acid, pyrosulfuric acid, phosphoric acid, or nitric acid. The "organic acid" includes, but is not limited to, formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentanepropionic acid, digluconic acid, 3-hydroxy-2-naphthoic acid, nicotinic acid, pamoic acid, pectinic acid, peroxosulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptoic acid, glycerophosphoric acid, aspartic acid, sulfosalicylic acid, hemisulfuric acid, or thiocyanic acid.

The term "tautomer" refers to functional isomers resulting from the rapid movement of an atom in a molecule between two positions. The compounds disclosed herein may exhibit the tautomerism. Tautomeric compounds may exist in two or more interconvertible forms. Prototropic tautomers result from the migration of a covalently bonded hydrogen atom between two atoms. Tautomers generally exist in an equilibrium form. Trying to separate a single tautomer usually lead to a mixture, the physicochemical properties of which are consistent with the mixture of the compound. The position of the equilibrium depends on the chemical properties of the molecule. For example, in many aliphatic aldehydes and ketones such as acetaldehyde, the keto form predominates; whereas in phenols, the enol form predominates. The present disclosure comprises all tautomeric forms of the compound.

The term "effective amount" or "therapeutically effective amount" refers to an amount of the compounds disclosed herein sufficient to effect the intended use, including but not limited to the treatment of a disease as defined below. The therapeutically effective amount may vary depending on the following factors: the intended use (in vitro or in vivo), or the subject and diseases or conditions being treated, such as weight and age of the subject, severity of the diseases or conditions and mode of administration, which can be readily determined by one of ordinary skill in the art. The specific dosage will vary depending on the following factors: the selected particular compound, the dosage regimen to be followed, whether to administer in combination with other compounds, the schedule of administration, the tissue to be administered and the physical delivery system carried.

The term "auxiliary material" refers to a pharmaceutically acceptable inert ingredient. Examples of types of excipients include, without limitation, adhesives, disintegrants, lubricants, glidants, stabilizers, fillers, diluents, and the like. Excipients are capable of enhancing the handling characteristics of the pharmaceutical formulation, i.e., making the formulation more amenable to direct compression by increasing flowability and/or adhesiveness. Examples of typical pharmaceutically acceptable carriers suitable for use in the above formulations include: saccharides, such as lactose, sucrose, mannitol, and sorbitol; starches, such as corn starch, tapioca starch and potato starch; cellulose and its derivatives, such as sodium carboxymethylcellulose, ethyl cellulose and methyl cellulose; calcium phosphates, such as dicalcium phosphate and tricalcium phosphate; sodium sulfate; calcium sulfate; polyvinylpyrrolidone; polyvinyl alcohol; stearic acid; alkaline earth metal stearate, such as magnesium stearate and calcium stearate; vegetable oils such as peanut oil, cottonseed oil, sesame oil, olive oil and corn oil; nonionic, cationic and anionic surfactants; a glycol polymer; fatty alcohols; and grain hydrolysis solids and other nontoxic compatible auxiliary materials commonly available in pharmaceutical formulations, such as fillers, adhesives, disintegrants, buffers, preservatives, antioxidants, lubricants, and colorants.

Part of the abbreviations in the text are defined as follows: HATU: 2-(7-benzotriazole oxide)-N,N,N',N'-tetramethyluronium hexafluorophosphate; Pd(dppf)$Cl_2$: [1,1'-bis(diphenylphosphino)ferrocene]dichloropalladium(II); EA: ethyl acetate; Boc: tert-butoxycarbonyl.

Beneficial Effects of the Present Disclosure

The compound provided herein has excellent ROCK inhibitory activity. In addition, the compound of the present disclosure has good safety and metabolic stability and high bioavailability. Further, the compound of the present disclosure has a low risk of potential hepatotoxicity. Finally, the compound of the present disclosure is simple in preparation and easy to purify, and therefore has good application prospects.

DETAILED DESCRIPTION

The compounds of the general formulas disclosed herein and the preparation method and use thereof will be described in detail with reference to the following examples. The following examples are merely exemplary illustration and explanation of the present disclosure, and should not be construed as limiting the protection scope of the present disclosure. All techniques implemented based on the aforementioned content of the present disclosure are encompassed within the protection scope of the present disclosure.

Unless otherwise stated, the starting materials and reagents used in the following examples are all commercially available products or can be prepared by known methods.

Preparation Examples

Example 1: Preparation of Compound N-(3-fluoro-5-methoxybenzyl)-6-(1H-pyrazol-4-yl)-3,4-dihydroisoquinoline-2(1H)-carboxamide (T201)

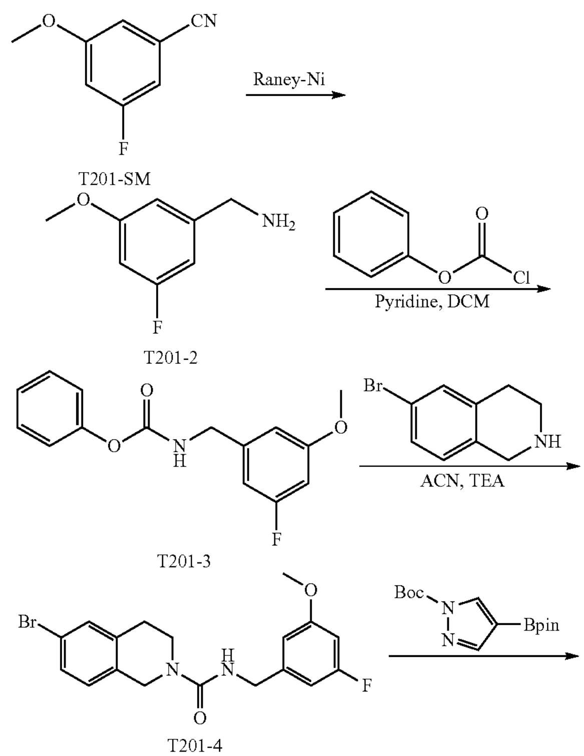

T201-SM

T201-2

T201-3

T201-4

-continued

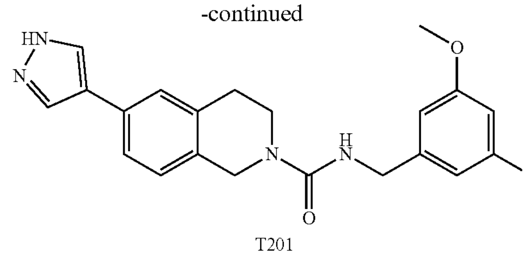

T201

1.1 Preparation of Compound (3-fluoro-5-methoxyphenyl)methanamine (T201-2)

Ranney Ni (100 mg) and aqueous ammonia (0.2 mL) were added to a solution of compound T201-SM (500 mg) in methanol, and the mixture was stirred overnight at room temperature under hydrogen atmosphere. The reaction solution was filtered and concentrated under reduced pressure, and the residue was purified by column chromatography to give the title product (300 mg).

LCMS: $[M+H]^+$=156.3.

1.2 Preparation of Compound phenyl-3-fluoro-5-methoxybenzyl carbamate (T201-3)

Compound T201-2 (50 mg) and pyridine (76 mg) were dissolved in dichloromethane (5 mL), and phenyl chloroformate (75 mg) was added dropwise at 0° C. After the addition was completed, the mixture was stirred at room temperature for 4 h. The reaction solution was extracted with water and dichloromethane, and the organic phase was washed with saturated brine and dried over anhydrous sodium sulfate. The organic phase was then concentrated under reduced pressure to give the title product.

LCMS: $[M+H]^+$=276.1.

1.3 Preparation of Compound 6-bromo-N-(3-fluoro-5-methoxybenzyl)-3,4-dihydroisoquinoline-2(1H)-carboxamide (T201-4)

Compound T201-3 (30 mg), 6-bromo-1,2,3,4-tetrahydroisoquinoline (CAS: 226942-29-6, 23 mg), and triethylamine (22 mg) were dissolved in acetonitrile (3 mL). The mixture was stirred overnight at 80° C., and then the reaction was completed. The reaction solution was concentrated under reduced pressure and the residue was purified by column chromatography to give the title product (30 mg).

LCMS: $[M+H]^+$=395.0.

1.4 Preparation of Compound N-(3-fluoro-5-methoxybenzyl)-6-(1H-pyrazol-4-yl)-3,4-dihydroisoquinoline-2(1H)-carboxamide (T201)

Compound T201-4 (30 mg), 1-Boc-pyrazole-4-boronic acid pinacol ester (CAS: 552846-17-0; 24 mg), sodium carbonate (16.2 mg), potassium acetate (15 mg) and $Pd(PPh_3)_4$ (8.8 mg) were dissolved in dioxane/$H_2O$ (10 mL/2 mL). the mixture was stirred overnight at 90° C. under nitrogen atmosphere, and then the reaction was completed. The reaction solution was filtered and concentrated, and the residue was purified by preparative high performance liquid chromatography, and lyophilized to give the target product (5 mg).

$^1$H NMR (400 MHz, DMSO-d6) δ=12.90 (s, 1H), 8.14 (s, 1H), 7.90 (s, 1H), 7.42-7.41 (m, 2H), 7.19-7.16 (m, 1H), 7.12-7.10 (m, 1H), 6.68-6.64 (m, 3H), 4.51 (s, 2H), 4.24 (d, J=5.6 Hz, 2H), 3.72 (s, 3H), 3.60 (t, J=6.0 Hz, 2H), 2.81 (t, J=5.6 Hz, 2H); LCMS: $[M+H]^+$=381.1.

Example 2: Preparation of Compound N-(3-fluoro-5-methoxybenzyl)-5-(1H-pyrazol-4-yl) indoline-1-carboxamide (T202)

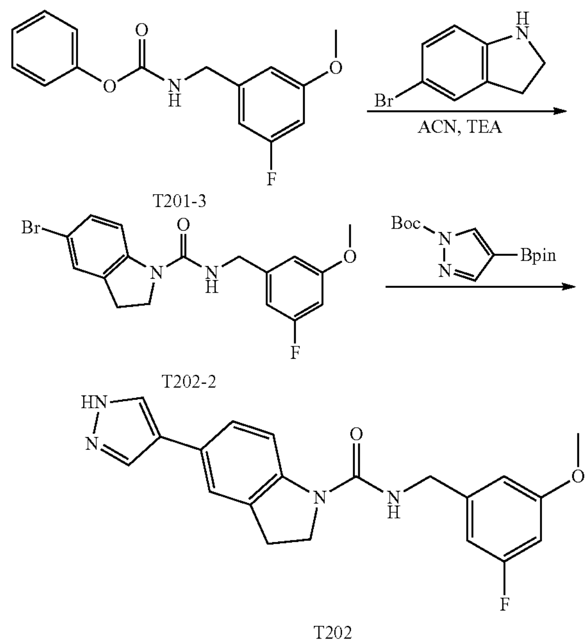

T201-3

T202-2

T202

2.1 Preparation of Compound 5-bromo-N-(3-fluoro-5-methoxybenzyl)-2,3-indoline-1-carboxamide (T202-2)

Compound T201-3 (300 mg), 5-bromoindoline (CAS: 22190-33-6, 215 mg) and triethylamine (219 mg) were dissolved in acetonitrile (10 mL). The mixture was stirred overnight at 80° C., and then the reaction was completed. The reaction solution was concentrated under reduced pressure and the residue was purified by column chromatography to give the title compound (549 mg).

LCMS: $[M+H]^+$=381.3.

2.2 Preparation of Compound N-(3-fluoro-5-methoxybenzyl)-5-(1H-pyrazol-4-yl)indoline-1-carboxamide (T202)

Compound T202-2 (200 mg), 1-Boc-pyrazole-4-boronic acid pinacol ester (171 mg), sodium carbonate (112 mg), potassium acetate (103 mg) and $Pd(PPh_3)_4$ (61 mg) were dissolved in dioxane/$H_2O$ (10 mL/2 mL). The mixture was stirred overnight at 90° C. under nitrogen atmosphere, and then the reaction was completed. The reaction solution was filtered and concentrated, and the residue was purified by preparative high performance liquid chromatography, and lyophilized to give the target product (100 mg).

$^1$H NMR (400 MHz, DMSO-d6) δ=12.80 (s, 1H), 8.05 (s, 1H), 7.82-7.77 (m, 2H), 7.40 (s, 1H), 7.32-7.30 (m, 1H), 7.25-7.22 (m, 1H), 6.75-6.66 (m, 3H), 4.30 (d, J=6.0 Hz, 2H), 3.97 (d, J=8.8 Hz, 2H), 3.76 (s, 3H), 3.16 (t, J=8.4 Hz, 2H). LCMS: $[M+H]^+$=367.1.

Example 3: Preparation of Compound 1-methyl-6-(1H-pyrazol-4-yl)-1H-indole-3-carboxylic acid-3-fluoro-5-methoxy-benzoylamide (T203)

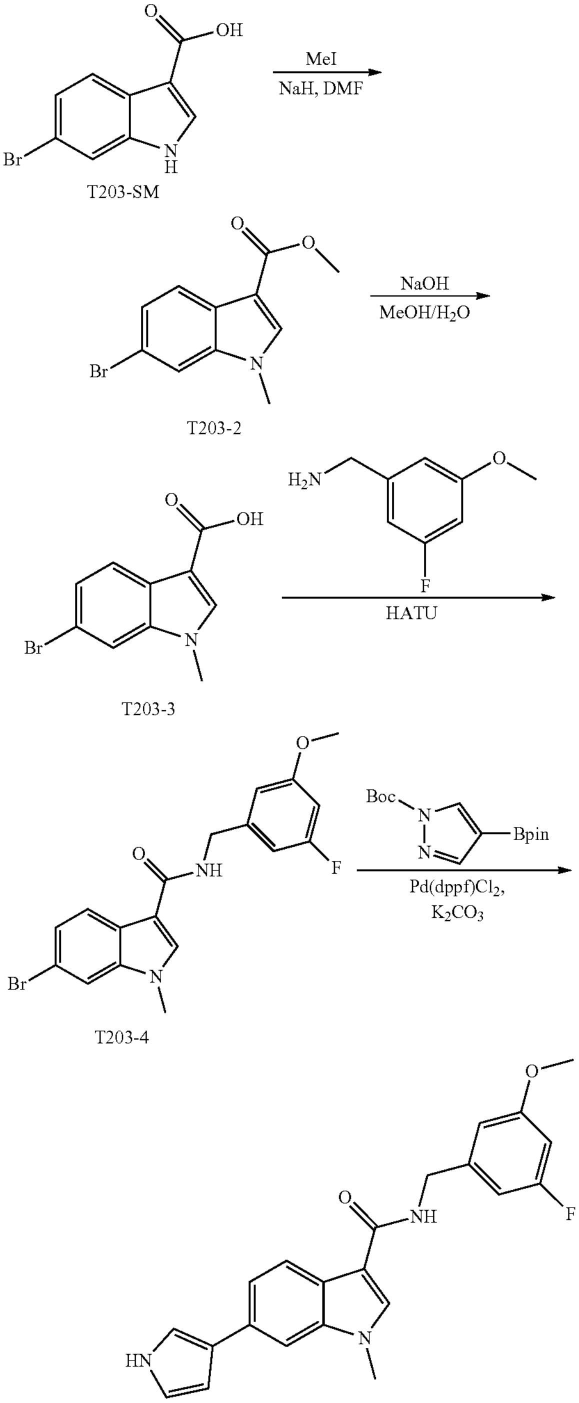

T203-SM

T203-2

T203-3

T203-4

T203

3.1 Preparation of Compound methyl 6-bromo-1-methyl-1H-indole-3-carboxylate (T203-2)

Sodium hydride (100 mg) was added to a solution of compound 6-bromoindole-3-carboxylic acid (CAS: 101774-27-0, 300 mg) in DMF (10 mL) at 0° C. under nitrogen atmosphere. After the addition was completed, the mixture was reacted at 0° C. for 20 min. Iodomethane (0.23 mL) was added to the system above in one portion, and the resulting mixture was then stirred at room temperature for 12 h. Ammonium chloride solution was added to quench the reaction, and ethyl acetate was added for extraction. The organic phases were combined and washed with saturated brine, and the organic phase was dried and concentrated to give a crude product (350 mg), which was directly used in the next step.

3.2 Preparation of Compound 6-bromo-1-methyl-1H-indole-3-carboxylic acid (T203-3)

A mixture of compound T203-2 (300 mg) and sodium hydroxide (150 mg) in methanol (20 mL) and water (5 mL) was heated to 50° C. and reacted for 16 h. The reaction solution was concentrated to remove methanol, and then the pH value was adjusted to 1-2 with diluted hydrochloric acid. The reaction solution was then extracted with water and ethyl acetate, and the organic phase was dried and concentrated to give the title compound (210 mg).

3.3 Preparation of Compound 6-bromo-1-methyl-1H-indole-3-carboxylic acid 3-fluoro-5-methoxy-benzamide (T203-4)

Compound T203-3 (210 mg), compound T201-2 (146 mg) and DIEA (0.4 mL) were dissolved in DMF (15 mL), and then HATU (328 mg) was added in portions. After the addition was completed, the mixture was stirred overnight at room temperature. The reaction solution was diluted with water (30 mL) and extracted with ethyl acetate. The organic phases were combined, washed with diluted hydrochloric acid, sodium bicarbonate solution and brine, dried and concentrated to give a crude product (310 mg). LCMS: $[M+H]^+$=393.0.

3.4 Preparation of Compound 1-methyl-6-(1H-pyrazol-4-yl)-1H-indole-3-carboxylic acid-3-fluoro-5-methoxy-benzoylamide (T203)

Compound T203-4 (220 mg), 1-Boc-pyrazole-4-boronic acid pinacol ester (142 mg), Pd(dppf)$Cl_2$ (36 mg) and potassium carbonate (234 mg) were added to dioxane (20 mL) and water (4 mL), and the mixture was heated to 100° C. and reacted for 16 h under nitrogen atmosphere. The reaction solution was concentrated under reduced pressure, and the residue was purified by preparative high performance liquid chromatography and lyophilized to give the target product (8 mg).

$^1$H NMR (400 MHz, DMSO-d6): δ 12.84 (s, 1H), 8.43 (d, J=6.0 Hz, 1H), 8.20-8.19 (m, 1H), 8.08 (d, J=8.4 Hz, 1H), 7.98 (s, 2H), 7.72 (s, 1H), 7.44-7.42 (m, 1H), 6.76 (s, 1H), 6.73-6.67 (m, 2H), 4.43 (d, J=6.4 Hz, 2H), 3.85 (s, 3H), 3.75 (s, 3H). LCMS: $[M+H]^+$=379.1.

Example 4: Preparation of Compound N-(3-fluoro-5-methoxybenzyl)-6-(1H-pyrazol-4-yl)-3,4-dihydroquinoline-1(2H)-carboxamide (T204)

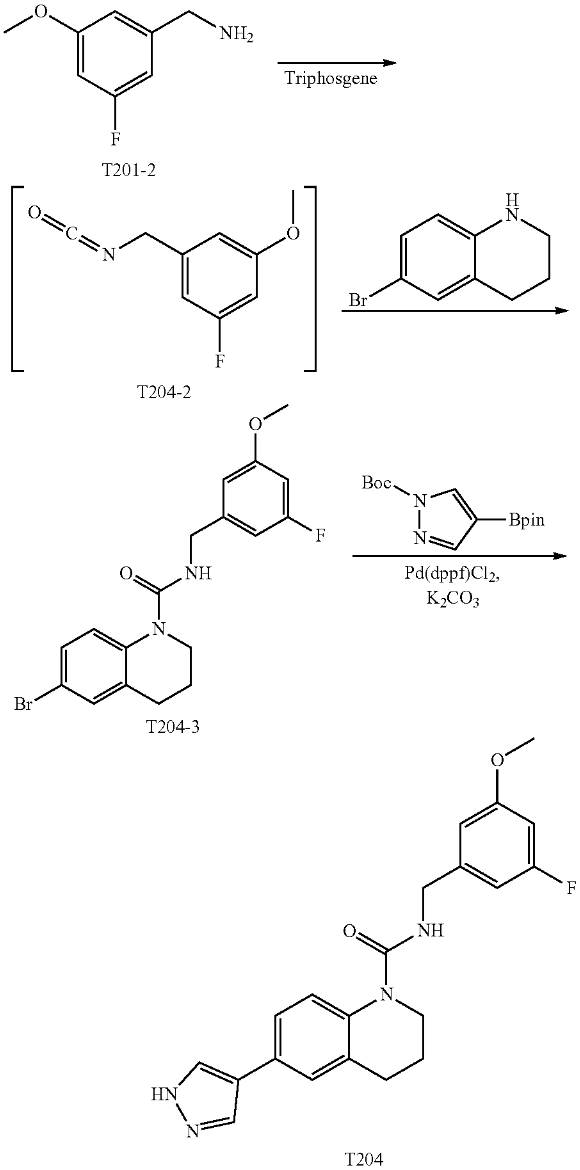

T201-2

T204-2

T204-3

T204

4.1 Preparation of Compound 6-bromo-N-(3-fluoro-5-methoxybenzyl)-3,4-dihydroquinoline-1(2H)-carboxamide (T204-3)

Compound T201-2 (200 mg) was dissolved in dichloromethane (10 mL) with stirring in an ice bath, and triethylamine (260 mg) and triphosgene (126 mg) were added. After the mixture was stirred at room temperature for 2 h, compound 6-bromo-1,2,3,4-tetrahydroquinoline (CAS: 22190-35-8, 270 mg) was added, and then the resulting mixture was stirred overnight at room temperature. After the reaction was completed, water and dichloromethane were added for extraction. The organic phase was concentrated under reduced pressure, and the residue was purified by column chromatography to give the product (80 mg). LCMS: $[M+H]^+$=393.2.

Example 4.2: Preparation of Compound N-(3-fluoro-5-methoxybenzyl)-6-(1H-pyrazol-4-yl)-3,4-dihydroquinoline-1(2H)-carboxamide (T204)

Compound T204-3 (130 mg), 1-Boc-pyrazole-4-boronic acid pinacol ester (146 mg), potassium carbonate (91.5 mg) and Pd(dppf)$Cl_2$ (24 mg) were dispersed in dioxane (10 mL) and water (2 mL). The mixture was heated to 100° C. and stirred overnight under reflux under nitrogen atmosphere. After the reaction was completed, the reaction solution was cooled to room temperature, purified by preparative high performance liquid chromatography, and lyophilized to give the target product (13.5 mg).

$^1$H NMR (400 MHz, DMSO-d6) δ 12.16 (br, 1H), 7.23 (s, 2H), 7.40-7.34 (m, 4H), 6.71-6.69 (m, 3H), 4.26 (d, J=6.0 Hz, 2H), 3.76 (s, 3H), 3.63-3.62 (m, 2H), 2.72-2.71 (m, 2H), 1.86-1.85 (m, 2H); LCMS: $[M+H]^+$=381.1.

Example 5: Preparation of Compound N-(3-fluoro-5-methoxybenzyl)-7-(1H-pyrazol-4-yl)-2H-benzo[b][1,4]oxazine-4(3H)-carboxamide (T205)

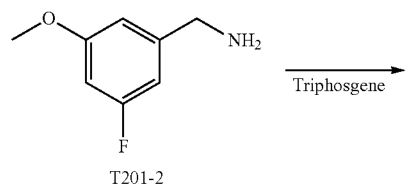

T201-2

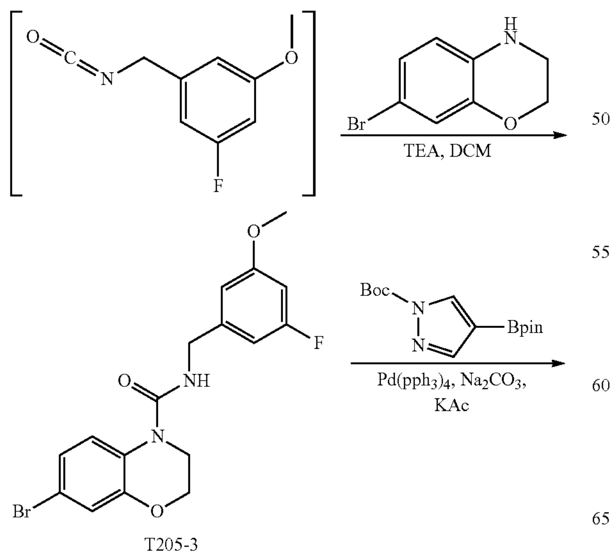

T205-3

-continued

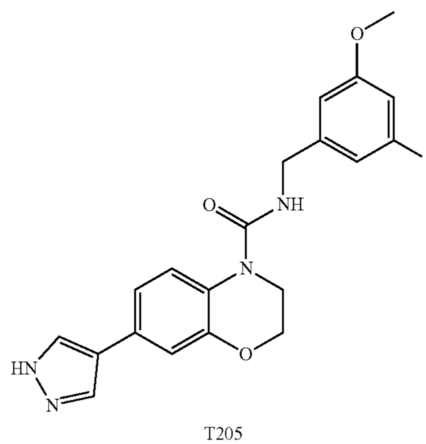

T205

5.1 Preparation of Compound 7-bromo-N-(3-fluoro-5-methoxybenzyl)-2,3-dihydro-4H-benzo [b][1,4]oxazine-4-formamide (T205-3)

Triphosgene (254.6 mg) was added dropwise to a solution of compound T201-2 (400 mg) and triethylamine (521 mg) in dichloromethane (15 mL) at 0° C. under nitrogen atmosphere. After the addition was completed, the mixture was stirred at 0° C. for 3 h, followed by addition of compound 7-bromo-3,4-dihydro-2H-benzo[b][1,4]oxazine (CAS: 105679-22-9, 400 mg). The resulting mixture was stirred overnight at room temperature, and then the reaction was completed. The reaction solution was concentrated under reduced pressure and the residue was purified by column chromatography to give the product (160 mg). LCMS: $[M+H]^+$=395.0.

5.2 Preparation of Compound N-(3-fluoro-5-methoxybenzyl)-7-(1H-pyrazol-4-yl)-2H-benzo[b][1,4]oxazine-4(3H)-carboxamide (T205)

Compound T205-3 (160 mg), 1-Boc-pyrazole-4-boronic acid pinacol ester (143 mg), sodium carbonate (86 mg), potassium acetate (79.5 mg) and $Pd(PPh_3)_4$ (46.9 mg) were dissolved in dioxane/$H_2O$ (10 mL/2 mL). The mixture was stirred overnight at 90° C. under nitrogen atmosphere, and then the reaction was completed. The reaction solution was filtered and concentrated, and the residue was purified by preparative high performance liquid chromatography, and lyophilized to give the target product (31 mg).

$^1$H NMR (400 MHz, DMSO-d6) δ=12.85 (s, 1H), 7.98 (s, 2H), 7.56-7.54 (m, 1H), 7.48-7.45 (m, 1H), 7.11-7.09 (m, 2H), 6.72-6.66 (m, 3H), 4.28 (d, J=5.6 Hz, 2H), 4.21-4.19 (m, 2H), 3.77-3.76 (m, 5H).

LCMS: $[M+H]^+$=383.1.

Example 6: Preparation of Compound N-(3-fluoro-5-methoxybenzyl)-N-methyl-5-(1H-pyrazol-4-yl)indoline-1-carboxamide (T206)

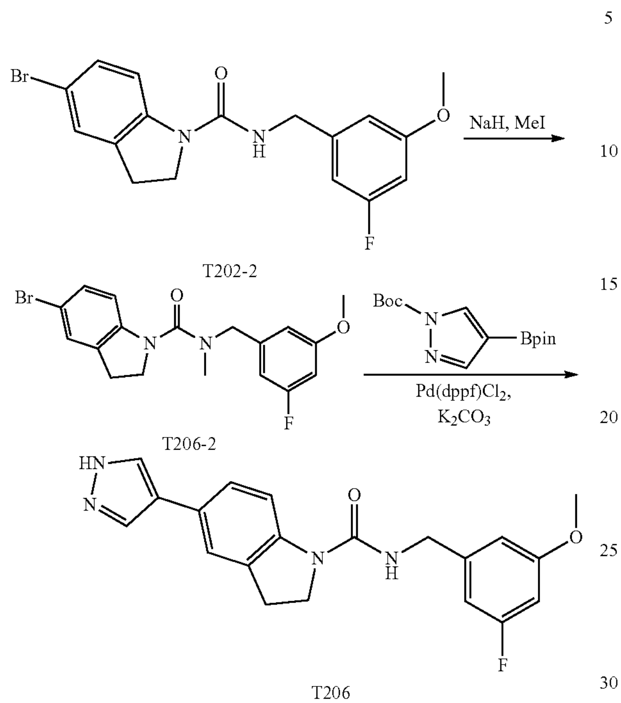

T202-2

T206-2

T206

6.1 Preparation of Compound 5-bromo-N-(3-fluoro-5-methoxybenzyl)-N-methylindoline-1-carboxamide (T206-2)

Sodium hydride (60%, 24 mg) was added to a solution of compound T202-2 (150 mg) in DMF in an ice bath. After the addition was completed, the mixture was reacted at 0° C. for 1 h. Iodomethane (56 mg) was then added to the reaction system, and after the addition was competed, the resulting mixture was stirred overnight at room temperature. After the reaction was completed as monitored by liquid chromatography, aqueous ammonium chloride solution was added to quench the reaction. The reaction solution was concentrated under reduced pressure, and the residue was purified by column chromatography to give the product (155 mg). LCMS: $[M+H]^+$=395.1.

6.2 Preparation of Compound N-(3-fluoro-5-methoxybenzyl)-5-(1H-pyrazol-4-yl)indoline-1-carboxamide (T206)

Compound T206-2 (160 mg), 1-Boc-pyrazole-4-boronic acid pinacol ester (143 mg), potassium carbonate (112 mg) and $Pd(dppf)Cl_2$ (30 mg) were dissolved in dioxane/$H_2O$ (10 mL/2 mL). The mixture was stirred overnight at 110° C. under nitrogen atmosphere, and then the reaction was completed. The reaction solution was filtered and concentrated, and the residue was purified by preparative high performance liquid chromatography to give the target product (41 mg).

$^1$H NMR (400 MHz, DMSO-d6) δ=12.82 (s, 1H), 8.06 (s, 1H), 7.84 (s, 1H), 7.45 (s, 1H), 7.37-7.35 (m, 1H), 7.00 (d, J=8.4 Hz, 1H), 6.77-6.72 (m, 3H), 4.43 (s, 2H), 3.89 (d, J=8.4 Hz, 2H), 3.78 (s, 3H), 3.05 (t, J=8.4 Hz, 2H), 2.80 (s, 3H). LCMS: $[M+H]^+$=381.1.

Example 7: Preparation of Compound N-benzyl-5-(1H-pyrazol-4-yl)indoline-1-carboxamide (T207)

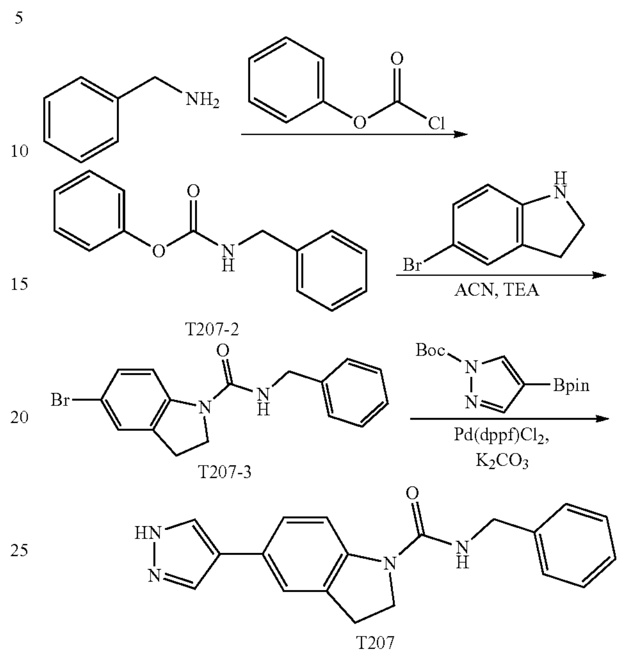

T207-2

T207-3

T207

7.1 Preparation of Compound phenyl benzylcarbamate (T207-2)

Benzylamine (300 mg) and pyridine (663.6 mg) were dissolved in dichloromethane (5 mL), and phenyl chloroformate (658 mg) was added dropwise at 0° C. After the dropwise addition was completed, the mixture was stirred overnight at room temperature, and then the reaction was completed. The reaction solution was extracted with water and dichloromethane, and the organic phase was washed with saturated brine and dried over anhydrous sodium sulfate. The organic phase was then concentrated under reduced pressure to give the product (400 mg).

LCMS: $[M+H]^+$=228.1.

7.2 Preparation of Compound N-benzyl-5-bromoindoline-1-carboxamide (T207-3)

Compound T207-2 (400 mg), 5-bromoindoline (348 mg) and triethylamine (343.4 mg) were dissolved in acetonitrile (5 mL). The mixture was stirred overnight at 80° C., and then the reaction was completed. The reaction solution was concentrated under reduced pressure and the residue was purified by column chromatography to give the title compound (233 mg).

$^1$H NMR (400 MHz, DMSO-d6) δ=7.76 (d, J=8.4 Hz, 1H), 7.32-7.27 (m, 6H), 7.24-7.21 (m, 2H), 4.32 (d, J=6.0 Hz, 1H), 3.96 (t, J=8.4 Hz, 1H), 3.14 (t, J=8.8 Hz, 1H); LCMS: $[M+H]^+$=331.0.

7.3 Preparation of Compound N-benzyl-5-(1H-pyrazol-4-yl)indoline-1-carboxamide (T207)

Compound T207-3 (221 mg), 1-Boc-pyrazole-4-boronic acid pinacol ester (235 mg), sodium carbonate (142 mg) and $Pd(dppf)Cl_2$ (97 mg) were dissolved in dioxane/$H_2O$ (10 mL/2 mL). The mixture was stirred overnight at 80° C. under nitrogen atmosphere, and then the reaction was completed. The reaction solution was filtered and concentrated, and the residue was purified by preparative high performance liquid chromatography to give the target product (8.8 mg).

$^1$H NMR (400 MHz, DMSO-d6) δ=12.76 (br, 1H), 7.89 (br, 2H), 7.80 (d, J=8.8 Hz, 1H), 7.39 (s, 1H), 7.33-7.30 (m, 5H), 7.24-7.20 (m, 2H), 4.34 (d, J=5.6 Hz, 2H), 3.96 (t, J=8.4 Hz, 1H), 3.15 (t, J=8.4 Hz, 1H). LCMS: $[M+H]^+$=319.1.

Example 8. Preparation of Compound N-(3-fluoro-5-methoxybenzyl)-7-(1H-pyrazol-4-yl)-3,4-dihydroisoquinoline-2(1H)-carboxamide (T208)

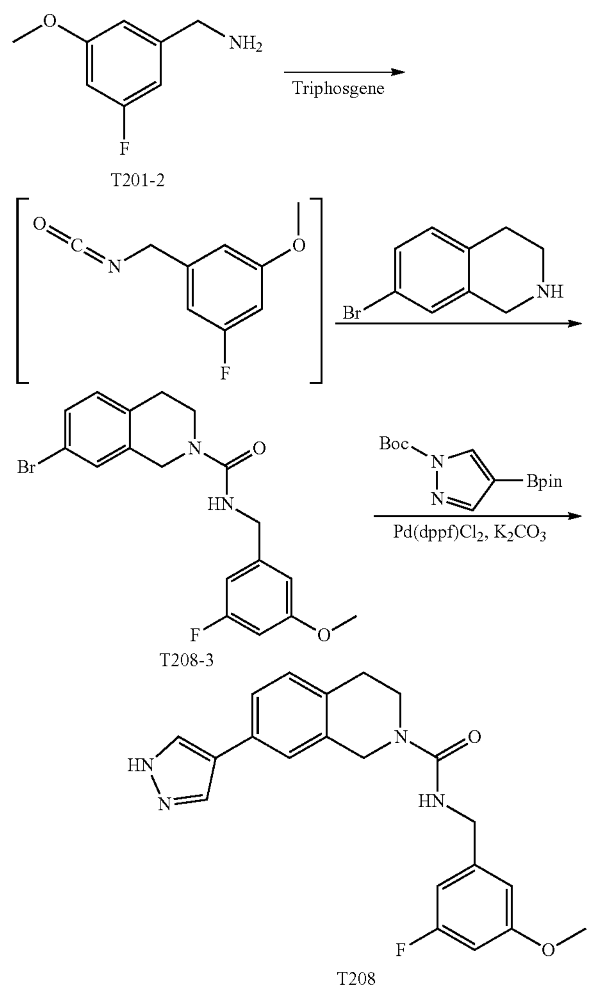

T201-2

T208-3

T208

8.1 Preparation of Compound 7-bromo-N-(3-fluoro-5-methoxybenzyl-3,4-dihydroisoquinoline-2(1H)-formamide (T208-3)

Compound T201-2 (200 mg) was dissolved in dichloromethane (10 mL) with stirring in an ice bath, and triethylamine (260 mg) and triphosgene (126 mg) were added. After the mixture was stirred at room temperature for 2 h, compound 7-bromo-1,2,3,4-tetrahydroquinoline (CAS: 17680-55-6, 270 mg) was added, and then the resulting mixture was stirred overnight at room temperature. After the reaction was completed, water and dichloromethane were added for extraction. The organic phase was concentrated under reduced pressure, and the residue was purified by column chromatography to give the title compound (70 mg).

LCMS: $[M+H]^+$=393.4.

8.2 Preparation of Compound N-(3-fluoro-5-methoxybenzyl)-7-(1H-pyrazol-4-yl)-3,4-dihydroisoquinoline-2(1H)-carboxamide (T208)

Compound T208-3 (70 mg), 1-Boc-pyrazole-4-boronic acid pinacol ester (78 mg), potassium carbonate (49 mg) and Pd(dppf)$Cl_2$ (26 mg) were dispersed in dioxane (10 mL) and water (2 mL). The mixture was heated to 100° C. and stirred overnight under reflux under nitrogen atmosphere. After the reaction was completed, the reaction solution was cooled to room temperature and purified by preparative high performance liquid chromatography to give the target product (16.1 mg).

$^1$H NMR (400 MHz, DMSO-d6) δ 12.88 (s, 1H), 8.13 (br, 1H), 7.95 (br, 1H), 7.40-7.36 (m, 2H), 7.19-7.12 (m, 2H), 6.67-6.63 (m, 3H), 4.54 (s, 2H), 4.24 (d, J=6.0 Hz, 1H), 3.71 (s, 3H), 3.61-3.58 (m, 2H), 3.78-3.73 (m, 2H); LCMS: $[M+H]^+$=380.9.

Example 9: Preparation of Compound N-(3-fluoro-5-methoxybenzyl)-5-(1H-pyrazol-4-yl)isoindoline-2-carboxamide (T209)

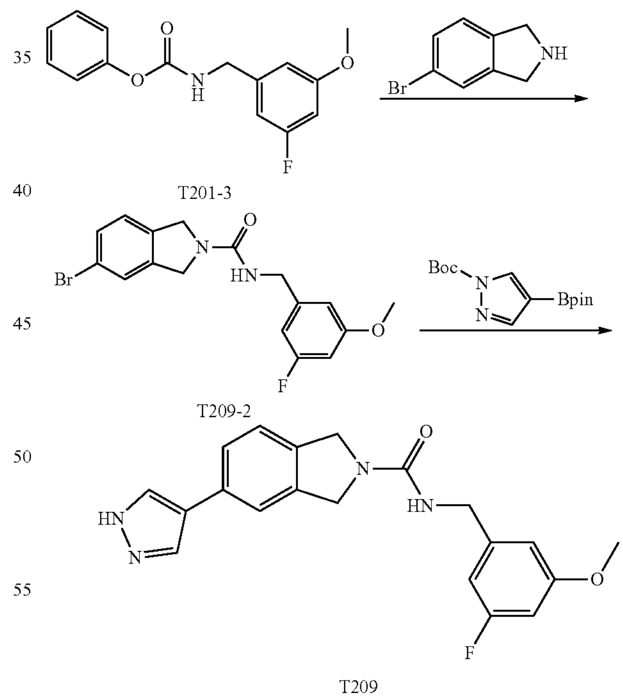

T201-3

T209-2

T209

9.1 Preparation of Compound 5-bromo-N-(3-fluoro-5-methoxybenzyl)isoindoline-2-carboxamide (T209-2)

Compound T201-3 (300 mg) was dissolved in acetonitrile (10 mL), and then triethylamine (220 mg) and compound 5-bromoisoindoline (CAS: 127168-84-7, 170 mg) were added. The mixture was stirred overnight at 80° C. After the reaction was completed, the reaction solution was concentrated under reduced pressure and the residue was purified by column chromatography to give the product (100 mg). LCMS: $[M+H]^+$=379.3.

9.2 Preparation of Compound N-(3-fluoro-5-methoxybenzyl)-5-(1H-pyrazol-4-yl)isoindoline-2-carboxamide (T209)

Compound T209-2 (130 mg), 1-Boc-pyrazole-4-boronic acid pinacol ester (151.7 mg), potassium carbonate (94.9 mg) and $Pd(dppf)Cl_2$ (25 mg) were dispersed in dioxane (10 mL) and water (2 mL). The mixture was heated to 110° C. and refluxed for 16 h under nitrogen atmosphere. After the reaction was completed, the reaction solution was cooled to room temperature and purified by preparative high performance liquid chromatography to give the target product (14.8 mg).

$^1H$ NMR (400 MHz, DMSO-d6) δ 12.92 (s, 1H), 8.11 (br, 2H), 7.56-7.53 (m, 2H), 7.30 (d, J=8.0 Hz, 1H), 7.00-6.97 (m, 1H), 6.74-6.64 (m, 3H), 4.64-4.62 (m, 4H), 4.27 (d, J=6.0 Hz, 2H), 3.75 (s, 3H).

LCMS: $[M+H]^+$=367.1.

Example 10

Reference was made to the preparation methods of the Examples 1-2 and 4-9 above to obtain the following compounds:

| Compound No. | LC-MS: $[M + H]^+$ |
|---|---|
| T210 | 365.1 |
| T211 | 382.1 |
| T212 | 437.2 |
| T213 | 411.3 |
| T214 | 437.4 |
| T215 | 451.0 |
| T216 | 465.2 |

Example 11: Preparation of Compound N-(3-fluoro-5-methoxybenzyl)-5-(1H-1,2,3-triazol-4-yl)indoline-1-carboxamide (T217)

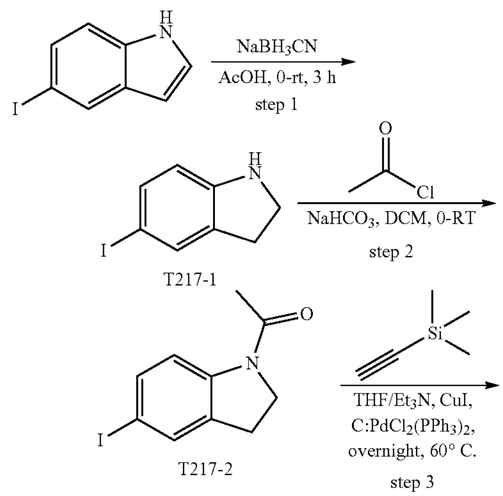

T217-1

T217-2

-continued

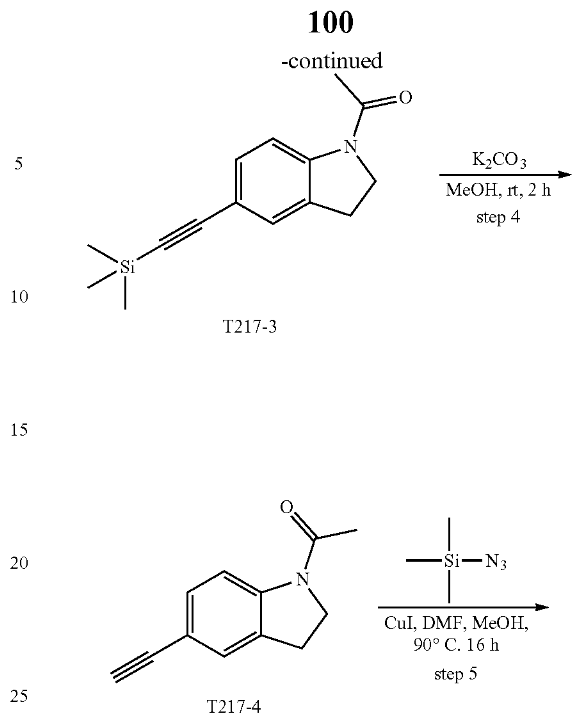

T217-3

T217-4

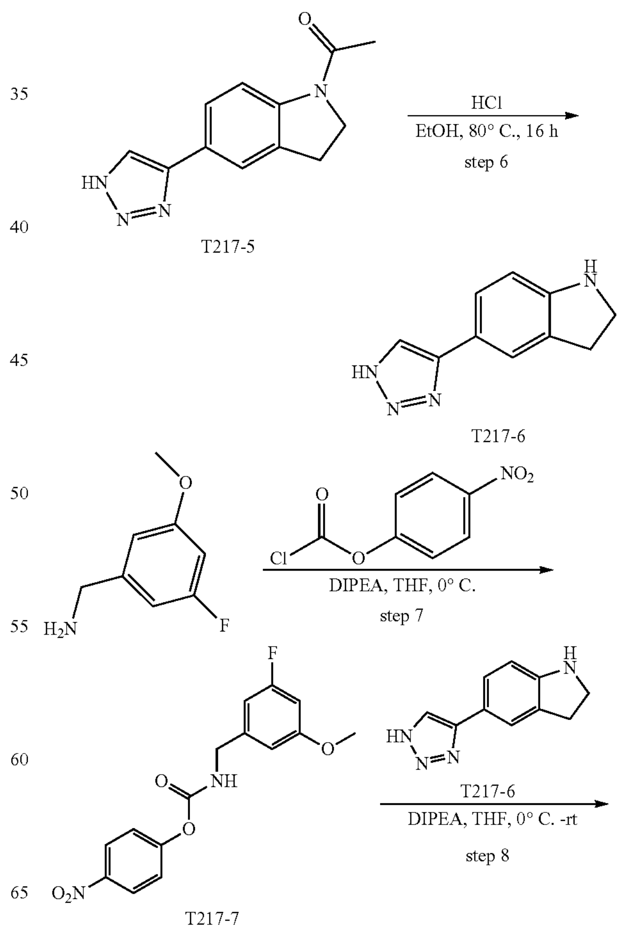

T217-5

T217-6

T217-7

-continued

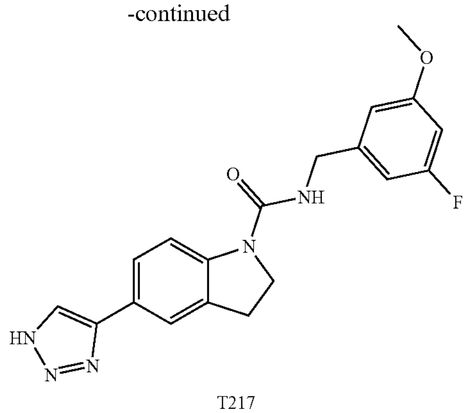

T217

1 Preparation of Compound 5-iodoindoline (T217-1)

5-iodo-1H-indole (4.50 g) was dissolved in acetic acid (40 mL), and sodium cyanoborohydride (1.75 g) was added in portions at 0° C. The mixture was reacted at room temperature for 3 h. The reaction solution was poured into water (50 mL), and sodium hydroxide 50% in aqueous solution was added to adjust the pH to 10. The mixture was extracted with ethyl acetate (50 mL×2). The organic phase was washed with saturated brine (20 mL×2), dried over anhydrous sodium sulfate, filtered and concentrated to give a crude product in the form of a white solid (4.53 g). LC-MS $[M+H]^+$: 245.9.

2 Preparation of Compound 1-(5-iodoindolin-1-yl)ethan-1-one (T217-2)

Compound T217-1 (4.53 g) was dissolved in dichloromethane (80 mL), and sodium bicarbonate (7.77 g) was added, followed by addition of acetyl chloride (2.90 g) at 0° C. The mixture was stirred overnight at room temperature. The reaction solution was filtered, and the filtrate was concentrated under reduced pressure to give a crude product in the form of a white solid (5.00 g). LC-MS $[M+H]^+$: 287.9.

3 Preparation of Compound 1-(5-((trimethylsilyl)ethynyl)indolin-1-yl)ethan-1-one (T217-3)

Compound T217-2 (5.30 g) was dissolved in anhydrous tetrahydrofuran (60 mL) and triethylamine (30 mL), and bis(triphenylphosphine)palladium(II) dichloride (1.04 g), copper(I) iodide (0.28 g) and trimethylsilylacetylene (2.72 g) were added. The mixture was reacted overnight at 60° C. under nitrogen atmosphere. The reaction solution was filtered, and the filtrate was concentrated. The resulting crude product was separated by silica gel column chromatography (petroleum ether/ethyl acetate=20:1-5:1) to give a pale yellow solid (4.18 g, 86% yield). LC-MS $[M+H]^+$: 258.1.

4 Preparation of Compound 1-(5-ethynylindolin-1-yl)ethan-1-one (T217-4)

Compound T217-3 (4.18 g) was dissolved in methanol (80 mL), and potassium carbonate (12.36 g) was added. The mixture was reacted at 25° C. for 2 h. The reaction solution was poured into water (100 mL), and ethyl acetate (100 mL×2) was added for extraction. The organic phase was washed with saturated brine (50 mL×2), dried over anhydrous sodium sulfate, filtered and concentrated to give a crude product in the form of a pale yellow solid (2.80 g, 84% yield). LC-MS $[M+H]^+$: 186.1.

5 Preparation of Compound 1-(5-(1H-1,2,3-triazol-4-yl)indolin-1-yl)ethan-1-one (T217-5)

Compound 1217-4 (2.80 g) was dissolved in N,N-dimethylformamide (30 mL), and copper(I) iodide (0.29 g) and trimethylsilyl azide (2.62 g) were added. The mixture was reacted at 90° C. for 16 h under nitrogen atmosphere. The reaction solution was filtered, and the filtrate was extracted with ethyl acetate (60 mL×2). The organic phase was washed with saturated brine (30 mL) (a large amount of product was present in water), dried over anhydrous sodium sulfate, filtered and concentrated. The resulting crude product was separated by silica gel column chromatography (dichloromethane/methanol=10:1) to give a pale yellow solid (0.98 g, 28% yield). LC-MS $[M+H]^+$: 228.9.

6 Preparation of Compound 5-(1H-1,2,3-triazol-4-yl)indoline hydrochloride (T217-6)

Compound T217-5 (0.91 g) was dissolved in ethanol (20 mL), and hydrochloric acid (6 N, 2.50 mL) was added. The mixture was reacted at 80° C. for 16 h. The reaction solution was concentrated under reduced pressure to give a crude product in the form of a black solid (0.96 g), LC-MS $[M+H]^+$: 187.0.

7 Preparation of Compound 4-nitrophenyl(3-fluoro-5-methoxybenzyl)carbamate (T217-7)

p-nitrophenyl chloroformate (0.54 g) was dissolved in anhydrous tetrahydrofuran (5 mL), and a solution of (3-fluoro-5-methoxyphenyl)methylamine (0.30 g) and N,N-di isopropylethyl amine (1.00 g) in tetrahydrofuran (5 mL) was added dropwise at 0° C. The mixture was reacted at 0° C. for 2 h. The reaction solution was directly used in the next step without purification. MS $[M+H]^+$=213.9 (solvent: methanol).

8 Preparation of Compound N-(3-fluoro-5-methoxybenzyl)-5-(1H-1,2,3-triazol-4-yl)indoline-1-carboxamide (T217)

Compound T217-6 (0.22 g) and N,N-diisopropylethylamine (0.52 g) were dissolved in anhydrous tetrahydrofuran (5 mL), and compound T217-7 (0.42 g) was added at 0° C. The mixture was reacted at 0° C. for 2 h. Methanol (5 mL) was added to quench the reaction, and the reaction solution was concentrated under reduced pressure. The resulting crude product was separated by preparative chromatography to give a white solid (22.4 mg, 6.1% yield). LC-MS $[M+H]^+$: 367.8.

$^1$H NMR (400 MHz, DMSO) δ 8.19 (s, 1H), 7.88 (d, J=8.4 Hz, 1H), 7.65 (s, 1H), 7.59 (d, J=8.3 Hz, 1H), 7.33 (t, J=5.9 Hz, 1H), 6.77-6.71 (m, 2H), 6.71-6.66 (m, 1H), 4.31 (d, J=5.7 Hz, 2H), 4.00 (t, J=8.7 Hz, 2H), 3.76 (s, 3H), 3.20 (q, J=8.6 Hz, 2H).

Example 12: Preparation of Compound N-(3-fluoro-5-methoxybenzyl)-5-(1H-pyrazol-4-yl)-2,3-dihydro-1H-pyrrolo(2,3-b)pyridine-1-carboxamide (T218)

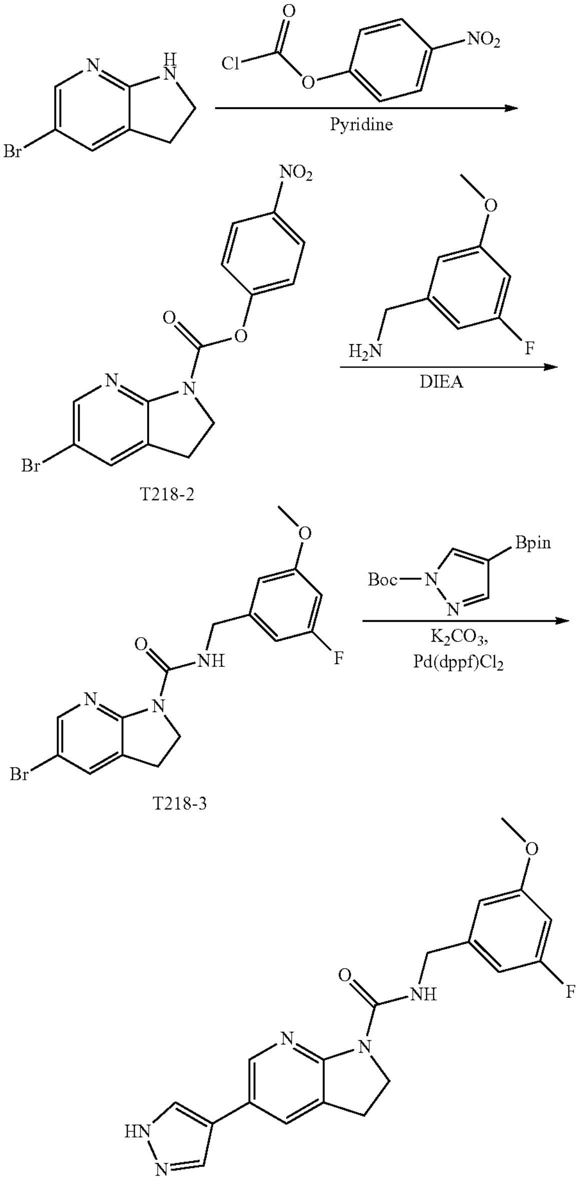

T218-2

T218-3

T218

1 Preparation of Compound 4-nitrophenyl5-bromo-2,3-dihydro-1H-pyrrolo(2,3-b)pyridine-1-carboxylic acid (T218-2)

4-nitrophenyl chloroformate (1.22 g) was dissolved in THF (8 mL), and then a solution of 5-bromo-2,3-dihydro-7-azaindole (CAS: 115170-40-6, 1.00 g) and pyridine (1.19 g) in THF (2 mL) was added dropwise under nitrogen atmosphere. The mixture was stirred overnight at room temperature. After the reaction was complete as detected by LCMS, the reaction solution was directly used in the next step. MS: $[M+H]^+$=364.0.

2 Preparation of Compound 5-bromo-N-(3-fluoro-5-methoxybenzyl)-2,3-dihydro-1H-pyrrolo(2,3-b)pyridine-1-carboxamide (T218-3)

Diisopropylethylamine (3.19 g) and (3-fluoro-5-methoxyphenyl)methylamine (1.38 g) were added to the reaction solution obtained in the previous step, and the mixture was stirred overnight at room temperature. The reaction solution was concentrated under reduced pressure and the residue was purified by column chromatography to give the product (1.97 g). MS: $[M+H]^+$=380.0.

3 Preparation of Compound N-(3-fluoro-5-methoxybenzyl)-S-(1H-pyrazol-4-yl)-2,3-dihydro-1H-pyrrolo(2,3-b)pyridine-1-carboxamide (1218)

Compound T218-3 (500 mg), 1-Boc-pyrazole-4-boronic acid pinacol ester (779 mg), potassium carbonate (729 mg) and Pd(dppf)$Cl_2$ (96 mg) were dissolved in DMF (5 mL) and water (1 mL), and the mixture was stirred at 90° C. for 3 h under nitrogen atmosphere. The reaction solution was cooled to room temperature, and then water (30 mL) was added and ethyl acetate was added for extraction. The organic phases were combined, washed with saturated brine, dried over anhydrous sodium sulfate, filtered and concentrated, and the crude product was purified by column chromatography to give the target product (380 mg).

$^1$H NMR (400 MHz, DMSO) δ 12.98 (brs, 1H), 9.35 (t, J=6.0 Hz, 1H), 8.30 (s, 1H), 8.18 (brs, 1H), 7.95 (brs, 1H), 7.86 (s, 1H), 6.78-6.68 (m, 3H), 4.47 (d, J=6.0 Hz, 2H), 4.00 (t, J=8.6 Hz, 2H), 3.76 (s, 3H), 3.09 (t, J=8.4 Hz, 2H); MS: (M+H)_368.2.

Example 13

Reference was made to the preparation method of the Example 12 above to obtain the compound T219; MS: $(M+H)^-$=368.2.

Example 14: Preparation of Compound N-(3-fluoro-5-methoxybenzyl)-5-(1H-pyrazol-4-yl)-2,3-dihydro-1H-pyrrolo(3,2-b)pyridine-1-carboxamide (T220)

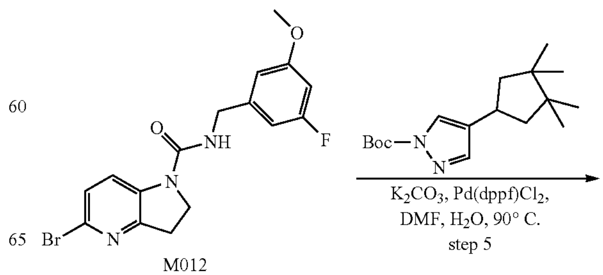

M012

-continued

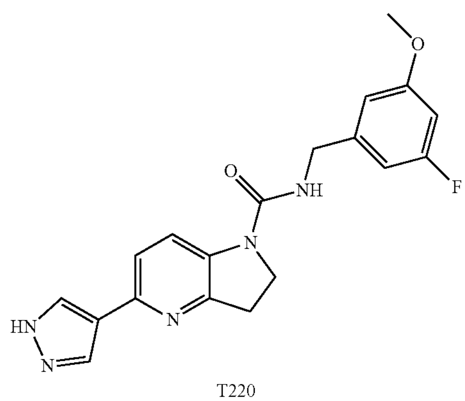

T220

Compound M012 (500 mg), tert-butyl 4-(4,4,5,5-tetramethyl-1,3,2-dioxaborolan-2-yl)-1H-pyrazole-1-carboxylate (779 mg), potassium carbonate (729 mg) and [1,1'-bis(diphenylphosphino)ferrocene]dichloropalladium(II) (96 mg) were dissolved in DMF (5 mL) and water (1 mL). The mixture was stirred at 90° C. for 3 h under nitrogen atmosphere. The reaction solution was cooled to room temperature, water (30 mL) was added, and ethyl acetate (20 mL×3) was added for extraction. The organic phases were combined, washed with saturated brine (20 mL), dried over anhydrous sodium sulfate, filtered and concentrated, and the resulting crude product was purified by silica gel column chromatography (DCM:MeOH=95:5) to give a white solid (360 mg, 73% yield). MS $(M+H)^+$=367.8.

$^1$H NMR (400 MHz, DMSO) δ 12.92 (brs, 1H), 8.05 (brs, 2H), 7.97 (d, J=8.4 Hz, 1H), 7.42 (t, J=5.9 Hz, 1H), 7.39 (d, J=8.4 Hz, 1H), 6.81-6.64 (m, 3H), 4.32 (d, J=5.8 Hz, 2H), 4.01 (t, J=8.8 Hz, 2H), 3.76 (s, 3H), 3.25 (t, J=8.7 Hz, 2H).

Example 15: Preparation of Compound 7-chloro-N-(3-fluoro-5-methoxybenzyl)-5-(1H-pyrazol-4-yl) indoline-1-carboxamide (T221)

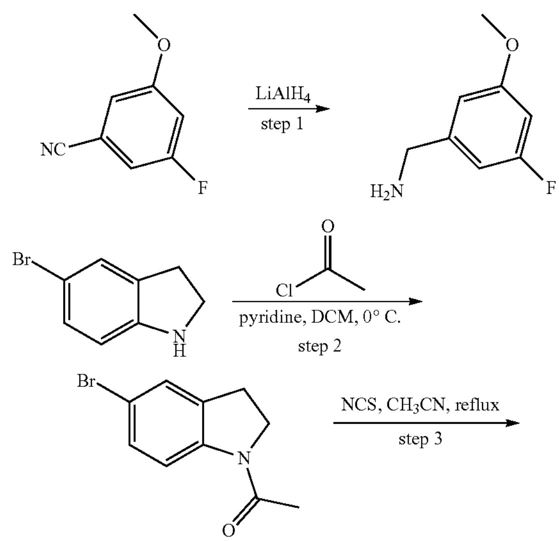

-continued

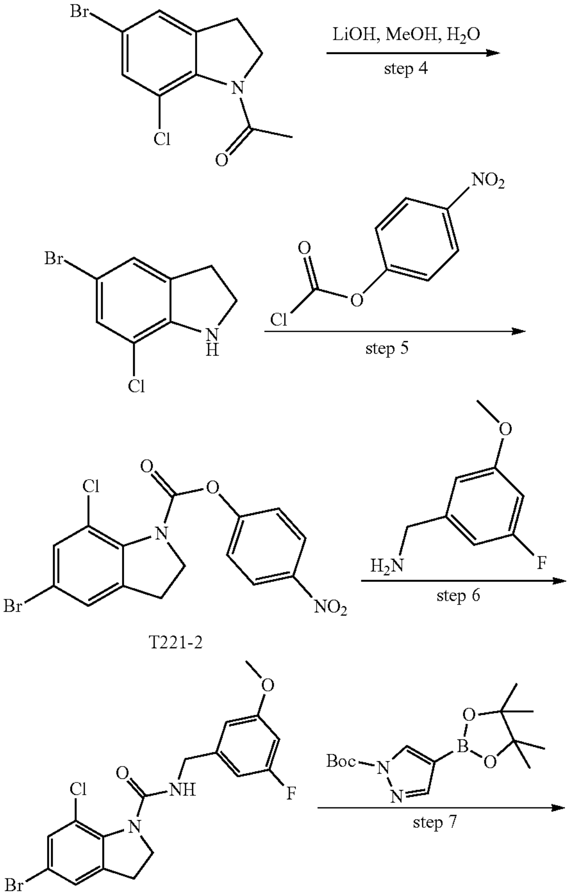

T221-2

T221-3

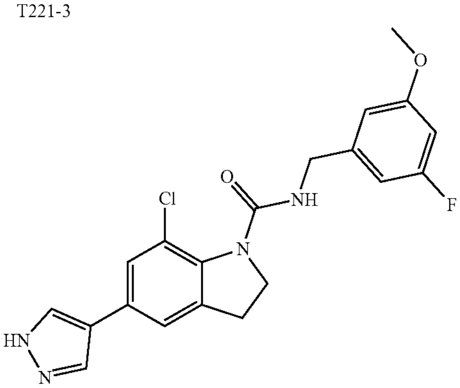

T221

1. Preparation of Compound 3-fluoro-5-methoxybenzylamine

Lithium aluminum hydride (10.0 g) was dissolved in tetrahydrofuran (100 mL), and in an ice water bath, a solution of 3-fluoro-5-methoxybenzonitrile (8.0 g) in tetrahydrofuran (20 mL) was slowly added dropwise at 0° C. under nitrogen atmosphere. After the dropwise addition was completed, the mixture was warmed to room temperature and stirred for 3 h. After the reaction was completed, the reaction solution was placed in the ice bath, and saturated sodium sulfate solution was slowly added dropwise until all the gas was released. The reaction solution was concentrated under reduced pressure, and the organic solvent was removed by rotary evaporation. The residue was diluted with water (30 mL) and extracted with ethyl acetate (60 mL×3). The organic phases were combined, dried over anhydrous sodium sulfate and filtered, and the filtrate was concentrated by rotary evaporation to give a yellow oil (6.1 g, 74% yield). LC-MS $[M+H]^+$: 156.0.

2 Preparation of Compound 1-(5-bromoindoline-1-yl)ethan-1-one 5-bromoindoline (4.0 g) and pyridine (2.4 g) were dissolved in tetrahydrofuran (50 mL), and in an ice water bath, acetyl chloride (1.9 g) was slowly added dropwise at 0° C. The mixture was warmed to room temperature and stirred overnight. Water (20 mL) was added to quench the reaction, and the mixture was extracted with ethyl acetate (30 mL×3). The organic phases were combined, washed with saturated brine (30 mL), dried over anhydrous sodium sulfate and filtered, and the filtrate was concentrated by rotary evaporation. The resulting crude product was purified by silica gel column chromatography (petroleum ether:ethyl acetate=10:1) to give a white solid (4.0 g, 82%). LC-MS $[M+H]^+$: 239.8.

3 Preparation of Compound 1-(5-bromo-7-chloroindoline-1-yl)ethan-1-one

Compound 1-(5-bromodihydroindol-1-yl)ethan-1-one (3.0 g) and NCS (1.8 g) were dissolved in acetonitrile (50 mL), and the mixture was stirred overnight under reflux. The reaction solution was cooled to room temperature and concentrated by rotary evaporation. The resulting crude product was purified by silica gel column chromatography (petroleum ether:ethyl acetate=3:1) to give a white solid (1.2 g, 35% yield). LC-MS $[M+H]^+$: 273.8.

4. Preparation of Compound 5-bromo-7-chloroindoline

Compound 1-(5-bromo-7-chloroindoline-1-yl)ethan-1-one (1.2 g) and lithium hydroxide monohydrate (1.84 g) were dissolved in methanol/water (1/1, 30 mL), and the mixture was stirred overnight at 70° C. Water (30 mL) was added for dilution, and ethyl acetate (30 mL 3) was added for extraction. The organic phases were combined, dried over anhydrous sodium sulfate, filtered and concentrated, and the resulting crude product was purified by silica gel column chromatography (petroleum ether:ethyl acetate=2:1) to give the product in the form of a white solid (0.9 g, 88% yield). LC-MS $[M+H]^+$: 231.8.

5 Preparation of Compound p-nitrophenyl 5-bromo-7-chloroindoline-1-carboxylate (T221-2)

Compound 5-bromo-7-chloroindoline (800 mg) and pyridine (816 mg) were dissolved in tetrahydrofuran (20 mL), and p-nitrophenyl chloroformate (832 mg) was added. The mixture was stirred at room temperature for 4 h, and the reaction solution was directly used in the next step without treatment. LC-MS $[M+Na]^+$: 418.5.

6 Preparation of Compound 5-bromo-7-chloro-N-(3-fluoro-5-methoxybenzyl)-indoline-1-carboxamide (T221-3)

(3-fluoro-5-methoxyphenyl)methylamine (1333 mg) was added directly to the reaction solution obtained in the previous step, and the mixture was stirred overnight under reflux. The reaction solution was concentrated by rotary evaporation, and the residue was purified by silica gel column chromatography (petroleum ether/ethyl acetate=2:1) to give a pale yellow oily liquid (700 mg, 85% purity, 68% yield). LC-MS $[M+H]^+$: 412.6.

7 Preparation of Compound 7-chloro-N-(3-fluoro-5-methoxybenzyl)-5-(1H-pyrazol-4-yl)indoline-1-carboxamide (T221)

Compound T221-3 (500 mg), 1-Boc-pyrazole-4-boronic acid pinacol ester (714 mg), potassium carbonate (500 mg) and [1,1'-bis(di phenyl phosphino)ferrocene]dichloropalladium(II) (89 mg) were dissolved in anhydrous dioxane (15 mL) and water (3 mL) under nitrogen atmosphere, and the mixture was reacted at 90° C. for 12 h. The reaction solution was cooled to room temperature, diluted with water (20 mL) and extracted with ethyl acetate (15 mL×2). The organic phases were combined, washed with saturated brine (15 mL), dried over anhydrous sodium sulfate, filtered and concentrated, and the resulting crude product was purified by silica gel column chromatography (petroleum ether/ethyl acetate=0-100%) and then purified by preparative chromatography to give a white solid (40 mg, 8.7% yield). LC-MS $[M+H]^+$: 400.9.

$^1$H NMR (400 MHz, DMSO) δ 12.91 (brs, 1H), 8.05 (brs, 2H), 7.66 (t, J=6.0 Hz, 1H), 7.46 (s, 1H), 7.44 (s, 1H), 6.78-6.67 (m, 3H), 4.30 (d, J=5.8 Hz, 2H), 4.03 (t, J=7.9 Hz, 2H), 3.77 (s, 3H), 3.09 (t, J=7.9 Hz, 2H).

Example 16: Preparation of 6-chloro-N-(3-fluoro-5-methoxybenzyl)-5-(1H-pyrazol-4-yl)indoline-1-carboxamide (T222)

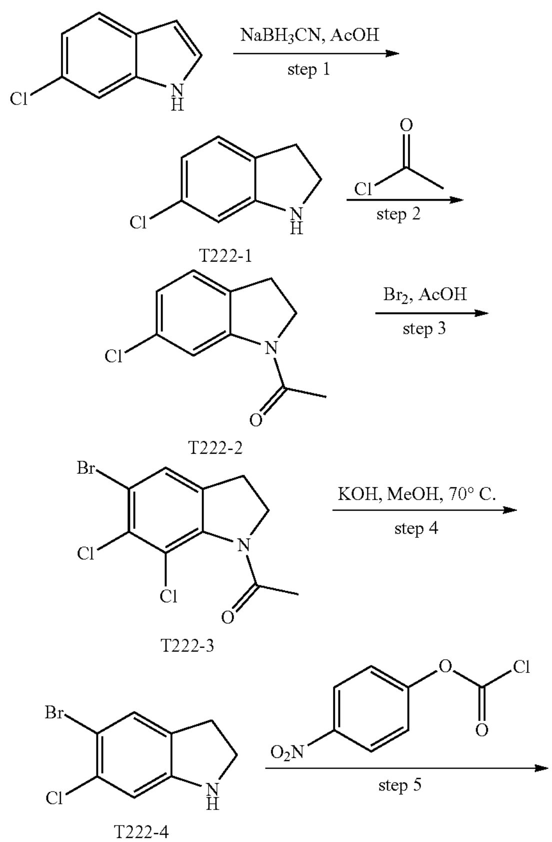

T222-1

T222-2

T222-3

T222-4

-continued

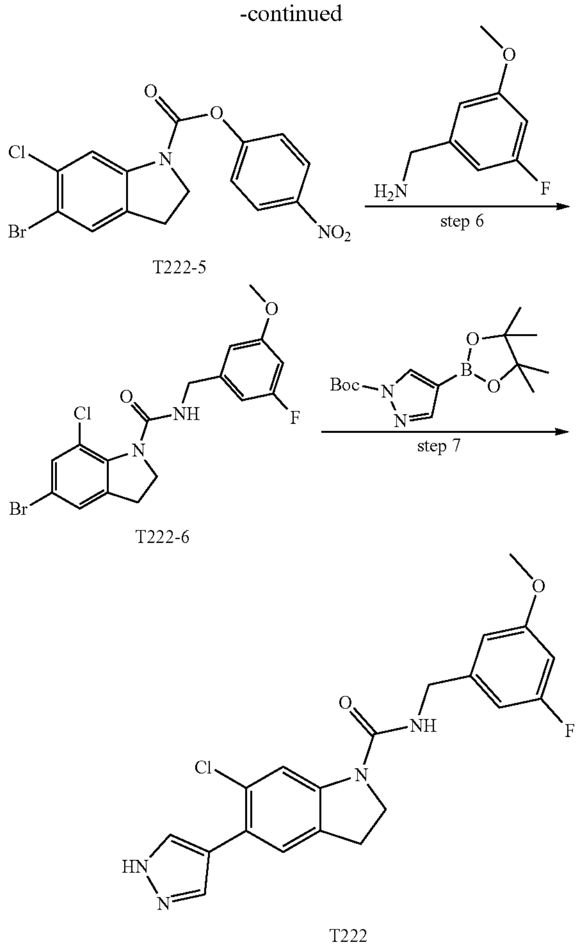

T222-5

T222-6

T222

1. Preparation of Compound 6-chloroindoline (T222-1)

6-chloroindole (2.0 g) was dissolved in acetic acid (20 mL), and in an ice water bath, sodium cyanoborocyanide (1.0 g) was slowly added at 0° C. After the addition was completed, the mixture was warmed to room temperature and stirred for 12 h. After the reaction was completed, the reaction solution was placed in an ice bath, the pH was adjusted to be alkaline with NaOH solution (1 N), and dichloromethane was added for extraction. The organic phase was dried over anhydrous sodium sulfate and concentrated by rotary evaporation to give a crude product in the form of a white solid (2.2 g). LC-MS $[M+H]^+$: 153.9.

2 Preparation of Compound 1-(6-chloroindoline-1-yl)ethan-1-one (T222-2)

Compound T222-1 (2.2 g) and pyridine (1.3 g) were dissolved in tetrahydrofuran (50 mL), and in an ice water bath, acetyl chloride (1.1 g) was slowly added dropwise at 0° C. The mixture was warmed to room temperature and stirred overnight. Water (50 mL) was added to quench the reaction, and ethyl acetate (60 mL×3) was added for extraction. The organic phases were combined, washed with saturated brine (40 mL×2), dried over anhydrous sodium sulfate, filtered and concentrated by rotary evaporation. The resulting crude product was purified by silica gel column chromatography (petroleum ether:ethyl acetate=10:1) to give a white solid (2.5 g, 97% two-step yield). LC-MS $[M+H]^+$: 239.8.

3 Preparation of Compound 1-(5-bromo-6-chloroindoline-1-yl)ethan-1-one (T222-3)

Compound T222-2 (2.3 g) was dissolved in acetic acid (30 mL), and in an ice water bath, bromine (2.1 g) was slowly added dropwise. The mixture was warmed to room temperature and reacted for 4 h. Solid was precipitated out during the reaction, and after the reaction was completed, the mixture was filtered under vacuum. The filter cake was washed once with ethyl acetate to give a white solid (2.5 g, 77% yield). LC-MS $[M+H]^+$: 273.8.

4. Preparation of Compound 5-bromo-6-chloroindoline (T222-4)

Compound T222-3 (2.5 g) and KOH (5.1 g) were dissolved in methanol/water (1:1, 30 mL), and the mixture was warmed to 70° C. and stirred overnight. The reaction solution was then cooled to room temperature and concentrated by rotary evaporation to give a crude product, which was purified by silica gel column chromatography (petroleum ether:ethyl acetate=2:1) to give the product in the form of a white solid (1.6 g, 75.6% yield). LC-MS $[M+H]^+$: 231.8.

5 Preparation of Compound p-nitrophenyl 5-bromo-6-chloroindoline-1-carboxylate (T222-5)

Compound T222-4 (1.6 g) and pyridine (1.6 g) were dissolved in tetrahydrofuran (30 mL), and p-nitrophenyl chloroformate (1.7 g) was added. The mixture was stirred for 4 h. After the reaction was completed, the reaction solution was concentrated under reduced pressure, and the residue was purified by silica gel column chromatography (petroleum ether/ethyl acetate=2/1) to give a crude product in the form of a yellow solid (2 g). LC-MS $[M+Na]^+$: 418.5.

6 Preparation of Compound 5-bromo-6-chloro-N-(3-fluoro-5-methoxybenzyl) indoline-1-carboxamide (T222-6)

Compound T222-5 (2 g, crude product) was dissolved in DMF (20 mL), and (3-fluoro-5-methoxyphenyl)carboxamide (3.2 g) and triethylamine (2.08 g) were added. The mixture was warmed to 130° C. and stirred overnight. The reaction solution was diluted with water and extracted with ethyl acetate (50 mL×3). The organic phases were combined, washed with saturated brine (50 mL), dried over anhydrous sodium sulfate, filtered and concentrated by rotary evaporation, and the residue was purified by silica gel column chromatography (petroleum ether/ethyl acetate=2:1) to give a yellow solid (2 g, 70.3% two-step yield). LC-MS $[M+H]^+$: 412.6.

7 Preparation of Compound 6-chloro-N-(3-fluoro-5-methoxybenzyl)-5-(1H-pyrazol-4-yl)indoline-1-carboxamide (T222)

Under nitrogen atmosphere, compound T222-6 (400 mg), 1-tert-butoxycarbonylpyrazole-4-boronic acid pinacol ester (570 mg), potassium carbonate (400 mg) and [1,1'-bis(diphenylphosphino)ferrocene]dichloropalladium(II) (71 mg) were dissolved in anhydrous dioxane (30 mL) and water (3 mL), and the mixture was reacted at 90° C. for 12 h. The reaction solution was cooled to room temperature, diluted with water (20 mL) and extracted with ethyl acetate (15 mL×2), and the organic phases were combined, washed with saturated brine (15 mL), dried over anhydrous sodium sulfate, filtered and concentrated. The residue was purified by silica gel column chromatography (petroleum ether/ethyl acetate=0-100%) and then purified by preparative chromatography to give a white solid (102.6 mg, 26.3% yield). LC-MS $[M+H]^+$: 400.9.

$^1H$ NMR (400 MHz, DMSO) δ 12.97 (s, 1H), 8.06 (s, 1H), 7.90 (s, 1H), 7.81 (s, 1H), 7.42-7.34 (m, 2H), 6.76-6.67 (m, 3H), 4.31 (d, J=5.8 Hz, 2H), 4.01 (t, J=8.7 Hz, 2H), 3.76 (s, 3H), 3.16 (t, J=8.6 Hz, 2H).

Example 17: Preparation of Compound N-(3-fluoro-5-methoxybenzyl)-2-(1H-pyrazol-4-yl)-6,7-dihydrothiazolo[5,4-c]pyridine-5(4H)-carboxamide (T224)

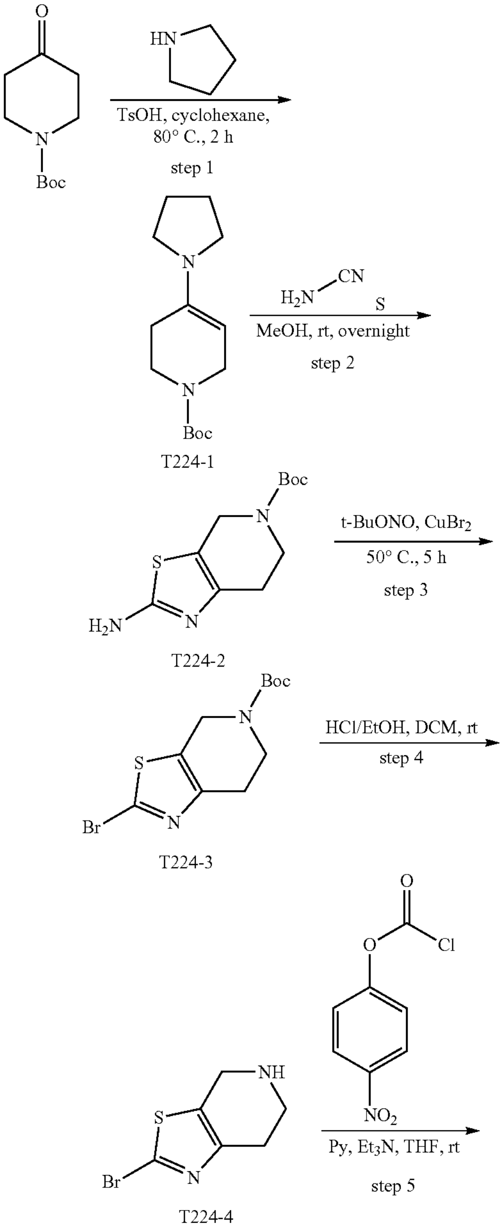

T224-1

T224-2

T224-3

T224-4

-continued

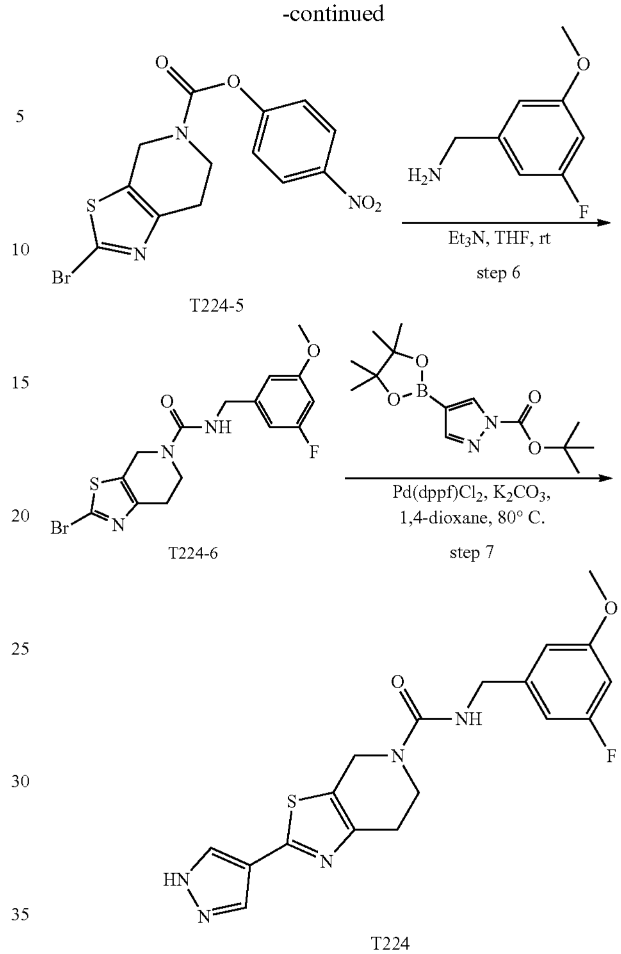

T224-5

T224-6

T224

1 Preparation of Compound tert-butyl 4-(pyrrolidin-1-yl)-3,6-dihydropyridine-1(2H)-carboxylate (T224-1)

Tert-butyl 4-carbonylpiperidine-1-carboxylate (2.00 g), tetrahydropyrrole (0.75 g) and p-toluenesulfonic acid monohydrate (10 mg) were dissolved in cyclohexane (20 mL), and the mixture was reacted at 80° C. for 2 h in a reaction apparatus provided with a reflux water separator. The reaction solution was cooled to room temperature and filtered, and the filtrate was concentrated by rotary evaporation to give a crude product in the form of a yellow solid (2.37 g), which was directly used in the next step.

2 Preparation of Compound tert-butyl 2-amino-6,7-dihydrothiazolo[5,4-c]pyridine-5(4H)-carboxylate (T224-2)

Compound T224-1 (2.00 g) and elemental sulfur powder (0.25 g) were dissolved in methanol (15 mL). The mixture was cooled to 0° C., and a solution of cyanamide (0.34 g) in methanol (5 mL) was added dropwise. After the addition was completed, the mixture was stirred overnight at room temperature. After the reaction was completed, the reaction solution was filtered, and the filter cake was washed with ethyl acetate (30 mL). The filter cake was collected and dried to give a crude product in the form of a pale yellow solid (2.20 g). LC-MS $[M+H]^+$: 255.8.

3 Preparation of Compound tert-butyl 2-bromo-6,7-dihydrothiazolo[5,4-c]pyridine-5(4H)-carboxylate (T224-3)

Compound T224-2 (2.00 g), tert-butyl nitrite (1.22 g) and cuprous bromide (2.13 g) were dissolved in N,N-dimethylformamide (50 mL), and the mixture was reacted at 50° C. for 5 h under nitrogen atmosphere. The reaction solution was cooled to room temperature, and water (50 mL) was added to quench the reaction. The reaction solution was filtered, and the filtrate was extracted with ethyl acetate (40 mL×3). The organic phases were combined, washed with saturated brine (50 mL 3), dried over anhydrous sodium sulfate, filtered and concentrated, and the resulting crude product was purified by silica gel column chromatography (petroleum ether:ethyl acetate=4:1) to give the product in the form of a white solid (300 mg, 10% yield). LC-MS $[M+H]^+$: 318.7.

4 Preparation of Compound 2-bromo-4,5,6,7-tetrahydrothiazolo[5,4-c]pyridine (T224-4)

Compound T224-3 (300 mg) was dissolved in dichloromethane (2 mL), and a solution of hydrogen chloride in ethanol (33%, 1 mL) was added. The mixture was stirred overnight at room temperature. After the reaction was completed, the reaction solution was concentrated by rotary evaporation, and dichloromethane (30 mL) was added. The mixture was washed with saturated sodium bicarbonate solution (20 mL) and saturated brine (20 mL), dried over anhydrous sodium sulfate, filtered and concentrated, and the resulting crude product was purified by silica gel column chromatography (dichloromethane:ethyl acetate=10:1) to give a white solid (250 mg, 91%). LC-MS $[M+H]^+$: 218.7.

5 Preparation of Compound p-nitrophenyl 2-bromo-6,7-dihydrothiazolo[5,4-c]pyridine-5(4H)-carboxylate (T224-5)

Compound T224-4 (150 mg) was dissolved in tetrahydrofuran (4 mL), and p-nitrophenyl chloroformate (215 mg), pyridine (170 mg) and triethylamine (358 mg) were added. The mixture was stirred overnight at room temperature under nitrogen atmosphere. After the reaction was completed, the reaction solution was directly used in the next step. LC-MS $[M+H]^+$: 383.5.

6 Preparation of Compound 2-bromo-N-(3-fluoro-5-methoxybenzyl)-6,7-dihydrothiazolo[5,4-c]pyridine-5(4H)-carboxamide (T224-6)

(3-fluoro-5-methoxyphenyl)methylamine (400 mg) and triethylamine (303 mg) were added to the reaction solution obtained in the previous step, and the mixture was stirred at room temperature for 4 h. Water (20 mL) was added to quench the reaction, and ethyl acetate (15 mL×3) was added for extraction. The organic phases were combined, washed with a saturated saline brine (20 mL), dried over anhydrous sodium sulfate and filtered, and the filtrate was concentrated by rotary evaporation. The resulting crude product was purified by silica gel column chromatography (4 g, petroleum ether:ethyl acetate=10:1) to give a white solid (120 mg, 41.88%). LC-MS $[M+H]^+$: 399.6.

7 Preparation of Compound N-(3-fluoro-5-methoxybenzyl)-2-(1H-pyrazol-4-yl)-6,7-dihydrothiazolo [5,4-c]pyridine-5(4H)-carboxamide (T224)

Compound T224-6 (100 mg), tart-butyl 4-(4,4,5,5-tetramethyl-1,3,2-dioxaborolan-2-yl)-1H-pyrazole-1-carboxylate (106 mg), [1,1'-bis(diphenylphosphino)ferrocene]dichloropalladium(II) (35 mg) and potassium carbonate (99 mg) were dissolved in a mixed solution of 1,4-dioxane (8 mL) and water (2 mL), and the mixture was stirred overnight at 80° C. The reaction solution was filtered, and the filtrate was concentrated by rotary evaporation. The residue was purified by silica gel column chromatography (4 g, dichloromethane: ethyl acetate=5:1), purified by preparative chromatography (chromatographic column: -Gemini-C18, 150×21.2 mm, Sum; mobile phase: ACN-$H_2O$ (0.05% $NH_3$); gradient: 25-40) and then lyophilized to give a white solid (14.3 mg). LC-MS $[M+H]^+$: 388.2.

$^1$H NMR (400 MHz, DMSO) δ 13.26 (brs, 1H), 8.31 (s, 1H), 7.92 (s, 1H), 7.37 (t, J=5.8 Hz, 1H), 6.69-6.62 (m, 3H), 4.62 (s, 2H), 4.24 (d, J=5.6 Hz, 2H), 3.75-3.70 (m, 5H), 2.81-2.75 (m, 2H).

Example 18: Preparation of Compound 6-fluoro-N-(3-fluoro-5-methoxybenzyl)-5-(1H-pyrazol-4-yl) indoline-1-carboxamide (T225)

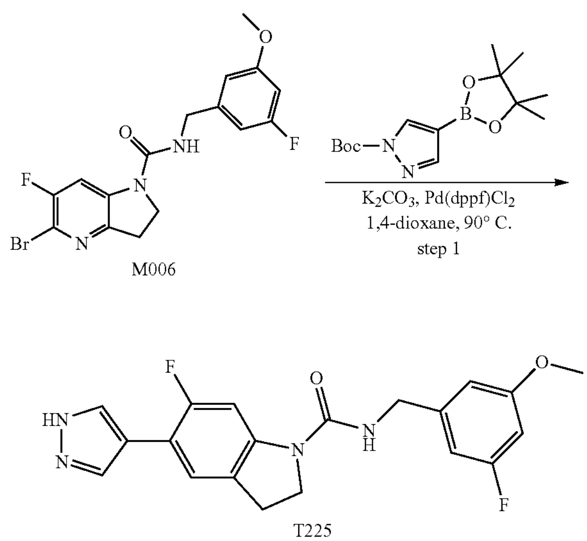

M006

T225

Compound M006 (2.90 g) was dissolved in 1,4-dioxane (20 mL) and water (5 mL), and tert-butyl 4 (4,4,5,5-tetramethyl-1,3,2-dioxaborolan-2-yl)-1H-pyrazole-1-carboxylate (2.58 g), potassium carbonate (4.09 g) and [1,1'-bis(diphenylphosphino)ferrocene]dichloropalladium(II) (534 mg) were added under nitrogen atmosphere. The mixture was reacted at 90° C. for 3 h, and then the reaction solution was cooled to room temperature. Water (20 mL) was added, and ethyl acetate (50 mL×3) was added for extraction. The organic phases were combined, washed with saturated brine (50 mL), dried over anhydrous sodium sulfate, filtered and concentrated by rotary evaporation. The resulting crude product was purified by high pressure liquid chromatography to give compound T225 in the form of a white solid (1.1 g, 28.9% yield). MS $[M+H]^+$=385.0.

$^1$H NMR (300 MHz, CD3OD) δ 7.91 (s, 2H), 7.63 (d, J=12.9 Hz, 1H), 7.43 (d, J=7.7 Hz, 1H), 6.74 (s, 1H), 6.67 (d, J=8.9 Hz, 1H), 6.57-6.53 (m, 1H), 4.40 (s, 2H), 4.03 (t, J=8.6 Hz, 2H), 3.79 (s, 3H), 3.21 (t, J=8.7 Hz, 2H).

Example 19: Preparation of Compound 4,6-difluoro-N-(3-fluoro-5-methoxybenzyl)-5-(1H-pyrazol-4-yl)indoline-1-carboxamide (T228)

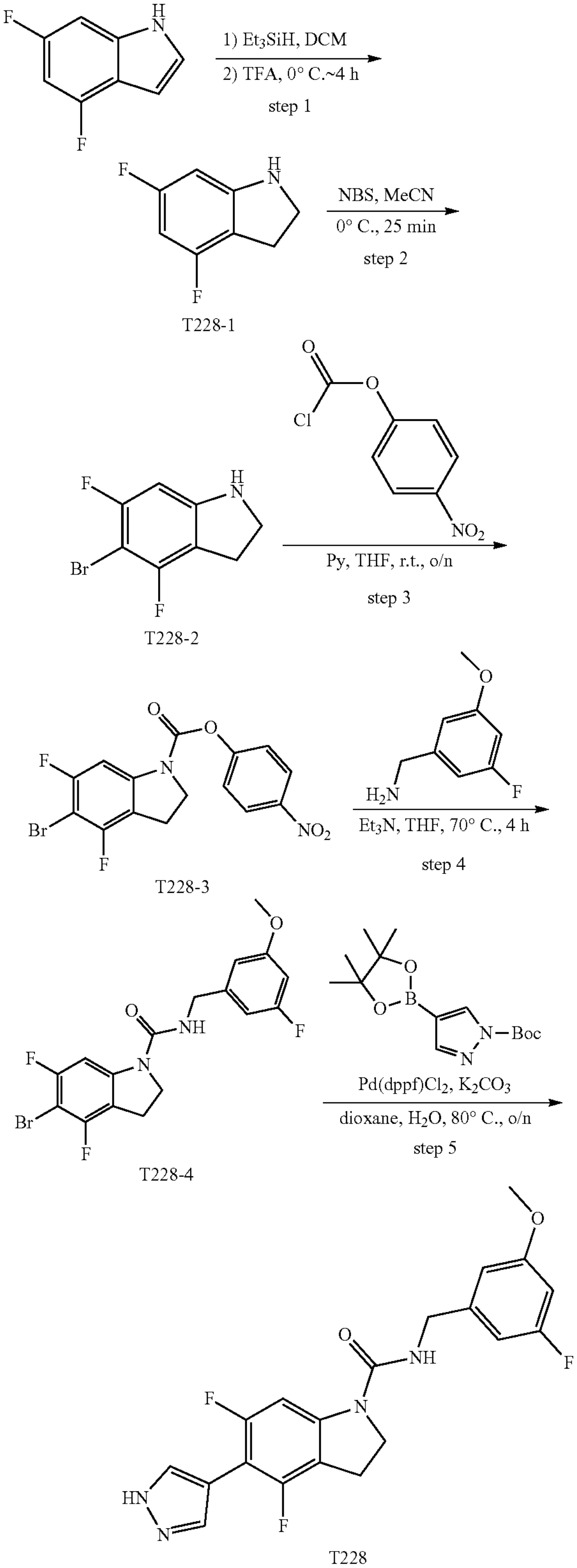

1 Preparation of Compound 4,6-difluoroindoline (T228-1)

4,6-difluoro-1H-indole (1.68 g) was dissolved in anhydrous dichloromethane (36 mL), and triethylsilane (3.55 g, 30.56) was added. The mixture was cooled to 0° C., and trifluoroacetic acid (18 mL) was added dropwise. After the dropwise addition was completed, the resulting mixture was warmed to room temperature and reacted for 4 h. After the reaction was completed, saturated aqueous sodium carbonate solution was added to adjust the pH to 10, and dichloromethane (30 mL×3) was added for extraction. The organic phases were combined, washed with saturated brine (30 mL), dried over anhydrous sodium sulfate, filtered and concentrated by rotary evaporation, and the resulting crude product was purified by silica gel column chromatography (12 g, petroleum ether:ethyl acetate=10:1) to give the product T228-1 (900 mg, 52.6% yield). LC-MS $[M+H]^+$: 156.0.

2 Preparation of Compound 5-bromo-4,6-difluoroindoline (T228-2)

Compound T228-1 (800 mg) was dissolved in anhydrous acetonitrile (8 mL), and the mixture was cooled to 0° C. and a solution of N-bromosuccinimide (551 mg) in anhydrous acetonitrile (5 mL) was added dropwise. After the dropwise addition was completed, the mixture was controlled to be 0° C. and reacted for 25 min. After the reaction was completed, saturated sodium bicarbonate solution (20 mL) was added to quench the reaction, and ethyl acetate (20 mL×3) was added for extraction. The organic phases were combined, washed with saturated brine (30 mL), dried over anhydrous sodium sulfate, filtered and concentrated by rotary evaporation, and the residue was purified by silica gel column chromatography (4 g, petroleum ether:ethyl acetate=15:1) to give compound T228-2 (400 mg, 29.8% yield). LC-MS $[M+H]^+$: 233.9.

3 Preparation of Compound p-nitrophenyl 5-bromo-4,6-difluoroindoline-1-carboxylate (T228-3)

p-nitrophenyl chloroformate (388 mg) was dissolved in anhydrous tetrahydrofuran (5 mL) under nitrogen atmosphere, and a solution of compound T228-2 (300 mg) and pyridine (304 mg) in tetrahydrofuran (5 mL) was added dropwise. The mixture was stirred overnight at room temperature. The reaction solution was directly used in the next step without treatment. LC-MS $[M+H]^+$: 398.9.

4 Preparation of Compound 5-bromo-4,6-difluoro-N-(3-fluoro-5-methoxybenzyl)indoline-1-carboxamide (T228-4)

(3-fluoro-5-methoxyphenyl)methylamine (398 mg) and triethylamine (388 mg) were added to the reaction solution obtained in the previous step, and the mixture was heated under reflux for 4 h. After the reaction was completed, water (30 mL) was added to quench the reaction, and ethyl acetate (20 mL×3) was added for extraction. The organic phases were combined, washed with saturated brine (30 mL), dried over sodium sulfate, filtered and concentrated by rotary evaporation, and the residue was purified by silica gel column chromatography (4 g, dichloromethane:ethyl acetate=5:1) to give the product T228-4 (210 mg, 35.5%). LC-MS $[M+H]^+$: 414.8.

5 Preparation of Compound 4,6-difluoro-N-(3-fluoro-5-methoxybenzyl)-5-(1H-pyrazol-4-yl)indoline-1-carboxamide (T228)

Compound T228-4 (210 mg), tart-butyl 4-(4,4,5,5-tetramethyl-1,3,2-dioxaborolan-2-yl)-1H-pyrazole-1-carboxylate (223 mg), [1,1'-bis(diphenylphosphino)ferrocene]dichloropalladium (II) (75 mg) and potassium carbonate (211 mg) were dissolved in a mixed solution of 1,4-dioxane (5 mL) and water (1 mL) under nitrogen atmosphere, and the mixture was stirred overnight at 80° C. The reaction solution was filtered, and the filtrate was concentrated by rotary evaporation. The residue was purified by silica gel column chromatography (4 g, dichloromethane:ethyl acetate=1:1), purified by preparative chromatography (chromatographic column: -Gemini-C18, 150×21.2 mm, Sum; mobile phase: ACN-$H_2O$ (0.05% $NH_3$); gradient: 20-70) and then lyophilized to give the pure product (21.2 mg, 7.3% yield). LC-MS $[M+H]^+$: 403.1.

$^1H$ NMR (301 MHz, CDCl3) δ 8.07 (s, 2H), 7.67 (d, J=12.4 Hz, 1H), 6.69 (s, 1H), 6.67 (d, J=11.0 Hz, 1H), 6.55 (d, J=10.5 Hz, 1H), 4.91 (t, J=4.5 Hz, 1H), 4.49 (d, J=5.4 Hz, 2H), 4.03 (t, J=8.6 Hz, 2H), 3.81 (s, 3H), 3.26 (t, J=8.5 Hz, 1H).

For example 20, reference was made to the preparation method of Example 19 above to obtain the following compounds:

| Compound No. | LC-MS: $[M + H]^+$ |
|---|---|
| T223 | 395.2 |
| T226 | 355.2 |
| T227 | 350.2 |
| T229 | 388.2 |
| T230 | 388.2 |
| T231 | 369.1 |
| T240 | 309.2 |
| T241 | 323.1 |
| T242 | 323.2 |
| T243 | 457.2 |
| T244 | 390.2 |
| T245 | 330.3 |
| T246 | 368.1 |
| T247 | 359.2 |
| T248 | 390.2 |
| T249 | 395.1 |

Reference was made to the preparation method of the Example 3 above to obtain the following

| Compound No. | LC-MS: $[M + H]^+$ |
|---|---|
| T232 | 367.1 |
| T233 | 366.2 |
| T234 | 366.2 |
| T235 | 366.2 |
| T236 | 380.2 |
| T237 | 365.2 |
| T239 | 366.2 |

Example 21: Preparation of N-(3-fluoro-5-methoxybenzyl)-6-(1H-pyrazol-4-yl)imidazo[1,5-a]pyridine-1-carboxamide (T238)

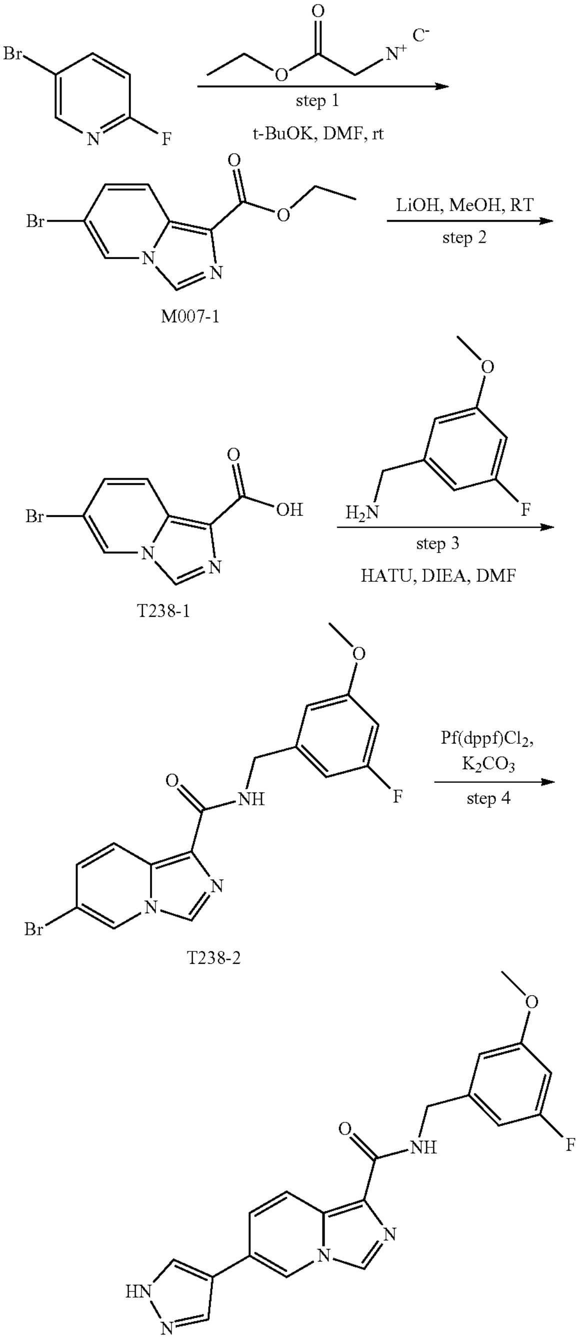

M007-1

T238-1

T238-2

T238

1 Preparation of ethyl-6-bromoimidazo[1,5-a]pyridine-1-carboxylate (M007-1)

5-bromo-2-fluoropyridine (15.0 g) was dissolved in DMF (150 mL) under nitrogen atmosphere, ethyl-2-isocyanoacetate (28.9 g) was added, and then potassium tert-butoxide (28.7 g) was added in portions. The mixture was reacted at room temperature for 2 h. Water (200 mL) was added to quench the reaction, and ethyl acetate (150 mL×3) was added for extraction. The organic phases were combined, washed with saturated brine (150 mL×2), dried over anhydrous sodium sulfate, filtered and concentrated. The crude product was separated by silica gel column chromatography (petroleum ether/ethyl acetate=5/1) to give a yellow oil (8.0 g, 34.9% yield). LC-MS $[M+H]^+$: 268.9/270.9.

2 Preparation of 6-bromoimidazo[1,5-a]pyridine-1-carboxylic acid (T238-1)

Ethyl-6-bromoimidazo[1,5-a]pyridine-1-carboxylate (M007-1, 7.5 g) was dissolved in methanol/water/tetrahydrofuran (1/1/3, 75 mL), and lithium hydroxide (5.8 g) was added. The mixture was reacted at room temperature for 3 h. The pH was adjusted to 5-6 with diluted hydrochloric acid (1 N), and a large amount of solid was precipitated out. The mixture was filtered and washed with water. The filter cake was collected and dried to give a white solid (6.5 g, 96.6% yield). LC-MS $[M+H]^+$: 240.9/242.9.

3 Preparation of 6-bromo-N-(3-fluoro-5-methoxybenzyl) imidazo[1,5-u]pyridine-1-carboxamide (T238-2)

6-bromoimidazo[1,5-a]pyridine-1-carboxylic acid (6.5 g) was dissolved in DMF (65 mL) under nitrogen atmosphere, and HATU (15.4 g) and DIEA (10.4 g) were added. After the mixture was stirred at room temperature for 30 min, (3-fluoro-5-methoxyphenyl)methylamine (6.3 g) was added, and the resulting mixture was stirred at room temperature for 1 h. Water (100 mL) was added to quench the reaction, and ethyl acetate (80 mL×3) was added for extraction. The organic phases were combined, washed with saturated brine (100 mL×2), dried over anhydrous sodium sulfate, filtered and concentrated to 30 mL, and a large amount of solid was precipitated out. The mixture was filtered, and the filter cake was washed with a small amount of ethyl acetate. The solid was collected and dried to give the product (4.0 g). The filtrate was concentrated under reduced pressure, and the resulting crude product was separated by silica gel column chromatography (petroleum ether/ethyl acetate=2/1) to give the product (2.0 g). The products were combined and a yellow solid (6.0 g, 58.8% yield) was obtained. LC-MS $[M+H]^+$: 378.0/380.0.

4 Preparation of N-(3-fluoro-5-methoxybenzyl)-6-(1H-pyrazol-4-yl)imidazo[1,5-a]pyridine-1-carboxamide (T238)

6-bromo-N-(3-fluoro-5-methoxybenzyl)imidazo[1,5-a] pyridine-1-carboxamide (4.0 g) was dissolved in 1,4-dioxane (40 mL) and water (10 mL), and tert-butyl-4-(4,4,5,5-tetramethyl-1,3,2-dioxaborolan-2-yl)-1H-pyrazole-1-carboxylate (4.7 g), Pd(dppf)$Cl_2$ (774 mg) and potassium carbonate (4.4 g) were added. The mixture was reacted at 90° C. for 12 h under nitrogen atmosphere. The reaction solution was diluted with water (50 mL) and extracted with ethyl acetate (50 mL×3). The organic phases were combined, washed with saturated brine (50 mL), dried over anhydrous sodium sulfate, filtered and concentrated, and the resulting crude product was separated by silica gel column chromatography (dichloromethane/methanol=30/1) to give a light black solid (2.5 g, 85% purity), which was further separated by preparative chromatography (chromatographic column: -Gemini-C18, 150×21.2 mm, 5 urn; mobile phase: ACN-$H_2O$ (0.1% FA); gradient: 30-50) to give an off-white solid (1.5 g, 38.7% yield). MS $[M+H]^+$=366.1.

$^1$H NMR (400 MHz, DMSO) δ 13.07 (s, 1H), 8.77 (s, 1H), 8.69 (t, J=6.4 Hz, 1H), 8.38 (s, 1H), 8.27 (brs, 1H), 8.07 (d, J=9.4 Hz, 1H), 7.98 (brs, 1H), 7.46 (dd, J=9.4, 1.4 Hz, 1H), 6.78-6.64 (m, 3H), 4.43 (d, J=6.4 Hz, 2H), 3.74 (s, 3H).

Example 22: Preparation of Intermediate 1, Compound 4-nitrophenyl 5-bromo-6-fluoroindoline-1-carboxylate (M001)

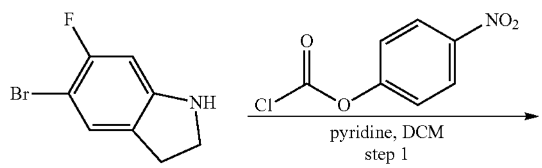

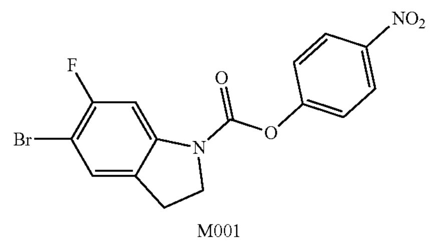

M001

4-nitrophenyl chloroformate (6.21 g) was dissolved in dichloromethane (40 mL), and a solution of 5-bromo-6-fluoroindoline (6.00 g) and pyridine (8.86 g) in dichloromethane (50 mL) was added dropwise at 0° C. The mixture was stirred overnight at room temperature. Dichloromethane (100 mL) was added, and the mixture was washed with saturated brine (50 mL×2), dried over anhydrous sodium sulfate, filtered and concentrated. The resulting crude product was separated by silica gel column chromatography (petroleum ether/dichloromethane=3:1) to give a grey solid (7.20 g, 68% yield). MS $[M+H]^+$=380.9/382.9.

Example 23: Preparation of Intermediate 2, Compound (S)-5-bromo-6-fluoro-N-(1-(3-fluoro-5-methoxyphenyl)-2-hydroxyethyl)indoline-1-carboxamide (M002)

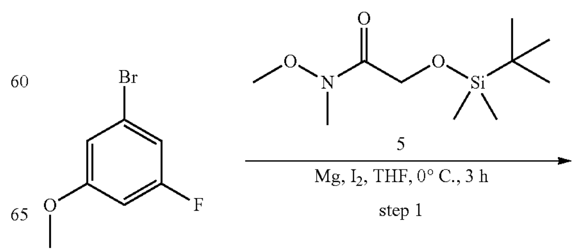

-continued

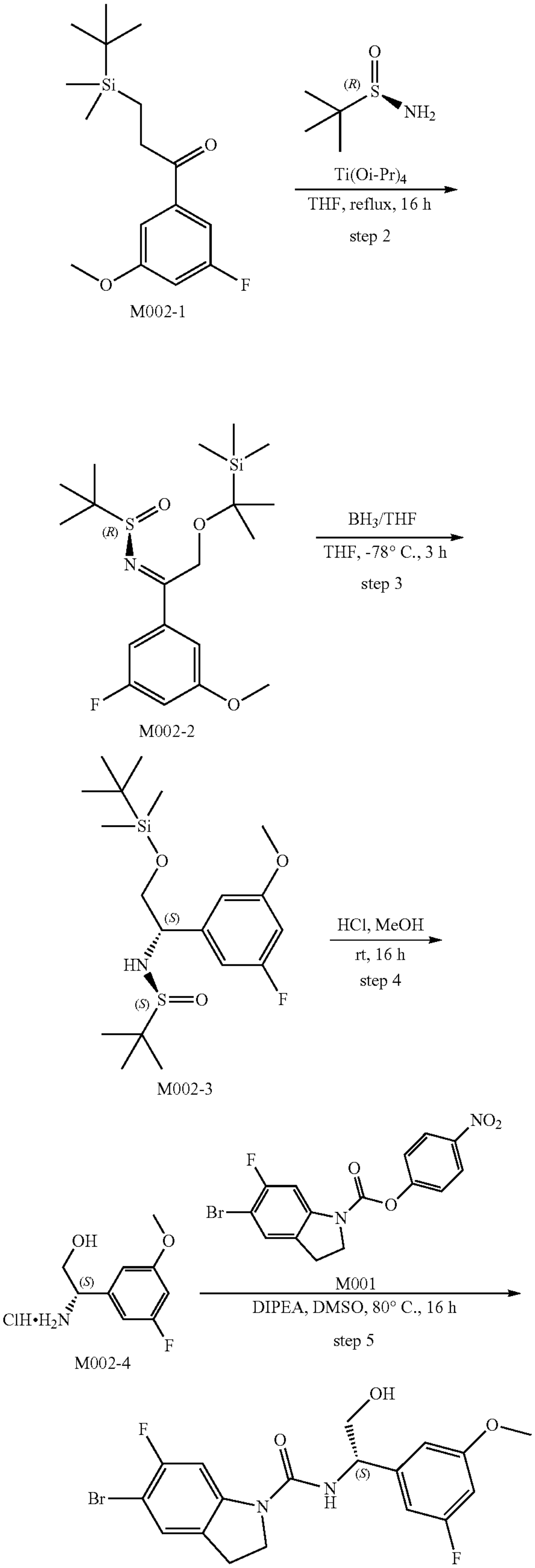

M002-1

M002-2

M002-3

M002-4

M002

(1) Preparation of Compound 2-((tert-butyldimethylsilyl)oxy)-1-(3-fluoro-5-methoxyphenyl)ethan-1-one (M002-1)

Magnesium chips (1.05 g) and two iodine granules were added to anhydrous tetrahydrofuran (5 mL), and a solution of 3-bromo-5-fluoroanisole (7.50 g) in tetrahydrofuran (35 mL) was added dropwise within 0.5 h under nitrogen atmosphere. The prepared Grignard reagent was added dropwise to a solution of 2-((tert-butyl dimethylsilyl)oxy)-N-methoxy-N-methylacetamide (9.39 g) in tetrahydrofuran (40 mL) at 0° C., and the mixture was reacted at room temperature for 3 h. Saturated aqueous ammonium chloride solution (30 mL) was added to quench the reaction, and ethyl acetate (100 mL×2) was added for extraction. The organic phase was washed with saturated brine (50 mL) and concentrated under reduced pressure to give a crude product, which was purified by silica gel column chromatography (petroleum ether:ethyl acetate=(100:1 to 20:1)) to give a pale yellow liquid (9.10 g, 72% yield). MS $[M+H]^+$=299.1.

(2) Preparation of Compound (R,Z)—N-(2-((tert-butyldimethylsilyl)oxy)-1-(3-fluoro-5-methoxyphenyl)ethylene)-2-methylpropane-2-sulfinamide (M002-2)

Compound M002-1 (9.10 g) and (R)-(+)-tert-butylsulfinamide (4.43 g) were dissolved in dioxane (90 mL), and tetraisopropyl titanate (21.68 g) was added. The mixture was refluxed for 16 h under nitrogen atmosphere. The reaction solution was cooled down and poured into ethyl acetate (200 mL), and then saturated brine (20 mL) was added. The mixture was rapidly stirred and filtered, and the filter cake was washed with ethyl acetate (50 mL). The organic phase was washed with saturated brine (50 mL), dried over anhydrous sodium sulfate and filtered, and the filtrate was concentrated. The residue was purified by silica gel column chromatography (petroleum ether:ethyl acetate=5:1) to give a pale yellow liquid (7.10 g, 58% yield). MS $[M+H]^+$=402.1.

(3) Preparation of Compound (S)—N—((S)-2-((tert-butyldimethylsilyl)oxy)-1-(3-fluoro-5-methoxyphenyl)ethyl)-2-methylpropane-2-sulfinamide (M002-3)

Compound M002-2 (7.80 g) was dissolved in anhydrous tetrahydrofuran (70 mL), and a solution of borane in tetrahydrofuran (1 mol/L, 58 mL) was added at −70° C. under nitrogen atmosphere. The mixture was reacted at −78° C. for 3 h. Water (50 mL) was added slowly to quench the reaction, and ethyl acetate (100 mL×2) was added for extraction. The organic phase was washed with saturated brine (80 mL), dried over anhydrous sodium sulfate, filtered and concentrated, and the resulting crude product was separated by silica gel column chromatography (petroleum ether:ethyl acetate=10:1-5:1) to give a yellow liquid (4.40 g, 56% yield). MS $[M+H]^+$=404.1.

(4) Preparation of Compound (S)-2-amino-2-(3-fluoro-5-methoxyphenyl)ethane-1-ol hydrochloride (M002-4)

Compound M002-3 (2.00 g) was dissolved in methanol (20 mL), and methanolic hydrochloric acid (4 N, 4 mL) was added. The mixture was stirred overnight at room temperature. The reaction solution was then concentrated under reduced pressure to give a white solid (1.00 g, 91% yield). MS $[M+H]^+$=186.0.

(5) Preparation of Compound (S)-5-bromo-6-fluoro-N-(1-(3-fluoro-5-methoxyphenyl)-2-hydroxyethyl) indoline-1-carboxamide (M002)

Compound M002-4 (1.16 g) and N,N-diisopropylethylamine (2.71 g) were dissolved in dimethyl sulfoxide (16 mL), and compound M001 (2.00 g) was added. The mixture was reacted at 80° C. for 16 h under nitrogen atmosphere. The reaction solution was poured into water (40 mL), and ethyl acetate (60 mL×2) was added for extraction. The organic phase was washed with saturated brine (20 mL×3), dried over anhydrous sodium sulfate, filtered and concentrated. The resulting crude product was separated by silica gel column chromatography (dichloromethane:ethyl acetate=50:1-10:1) to give a pale yellow solid (1.70 g, 76% yield). MS [M+H]=426.9/428.9.

Example 24: Preparation of Intermediate 3, Compound 5-bromo-6-fluoro-N-(1-(3-fluoro-5-methoxyphenyl)-ethyl)indoline-1-carboxamide (M003)

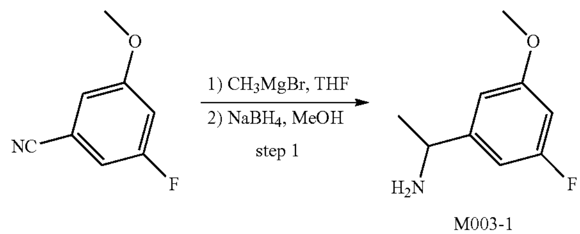

M003-1

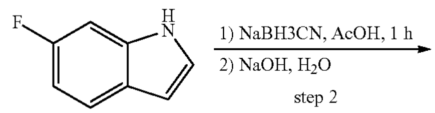

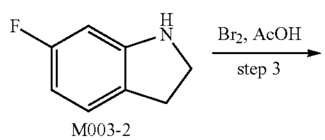

M003-2

-continued

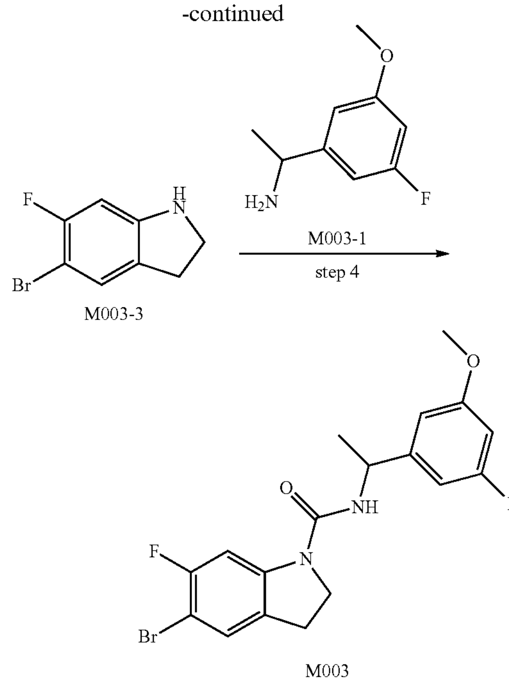

M003-3

M003

(1) Preparation of Compound 1-(3-fluoro-5-methoxyphenyl)ethylamine (M003-1)

A solution of methylmagnesium bromide in tetrahydrofuran (20 mL, 2 N) was cooled to 0° C. under nitrogen atmosphere, and 3-fluoro-5-methoxybenzonitrile (2.0 g) was slowly added dropwise. After the addition was completed, the mixture was reacted at 0° C. for 4 h, and then methanol (20 mL) was added, followed by addition of sodium borohydride (1.0 g) in portions. The mixture was stirred overnight at room temperature. The reaction solution was concentrated by rotary evaporation under reduced pressure, and the resulting solid was dissolved in dichloromethane (40 mL), and the pH was adjusted to 1 with diluted hydrochloric acid. After extraction, the aqueous phase was extracted with dichloromethane (20 mL 2), and the aqueous phase was retained. The aqueous phase was adjusted to pH 8-9 with sodium carbonate solution and extracted with dichloromethane (20 mL×3). The organic phases were combined, washed with saturated brine (30 mL), dried over anhydrous sodium sulfate, filtered and concentrated to give a yellow oil (800 mg). LC-MS $[M+H]^+$: 170.1.

(2) Preparation of Compound 6-fluoroindoline (M003-2)

6-fluoro-1H-indole (1.0 g) was dissolved in glacial acetic acid (10 mL), and sodium cyanoborohydride (536 mg) was added in portions. The mixture was reacted at room temperature for 30 min. The reaction solution was poured into sodium hydroxide solution (50 mL, 1 N), and ethyl acetate (50 mL×3) was added for extraction. The organic phases were combined, washed with saturated brine (50 mL), dried over anhydrous sodium sulfate, filtered and concentrated, and the resulting crude product was separated by silica gel column chromatography (PE/EA=5/1) to give a purple oily liquid (800 mg, 78.4% yield). LC-MS $[M+H]^+$: 138.1.

(3) Preparation of Compound 5-bromo-6-fluoroindoline (M003-3)

Compound M003-2 (700 mg) was dissolved in glacial acetic acid (10 mL), and then the mixture was cooled to 0° C. and bromine (896 mg) was added dropwise. After the dropwise addition was completed, the mixture was stirring at room temperature for 30 min. Water (50 mL) was added to quench the reaction, the pH was adjusted to 8-9 with sodium bicarbonate, and ethyl acetate (30 mL×3) was added for extraction. The organic phases were combined, washed with saturated brine (50 mL), dried over anhydrous sodium sulfate, filtered and concentrated, and the resulting crude product was separated by silica gel column chromatography (PE/EA=5/1) to give a brown oily liquid (350 mg, 31.9% yield). LC-MS $[M+H]^-$: 215.9.

(4) Preparation of Compound 5-bromo-6-fluoro-N-(1-(3-fluoro-5-methoxyphenyl)ethyl)indoline-1-carboxamide (M003)

Compound M003-3 (300 mg) was dissolved in tetrahydrofuran (10 mL), and 4-nitrophenyl chlorate (420 mg) and pyridine (220 mg) were added. The mixture was reacted overnight at room temperature. The reaction solution was concentrated under reduced pressure, and the resulting solid was dissolved in DMF (10 mL), followed by addition of compound M003-1 (705 mg) and pyridine (220 mg). The mixture was reacted at 100° C. for 12 h. Water (30 mL) was added to quench the reaction, and ethyl acetate (30 mL×3) was added for extraction. The organic phases were combined, washed with saturated brine (30 mL), dried over anhydrous sodium sulfate, filtered and concentrated, and the resulting crude product was separated by silica gel column chromatography (PE/EA=5/1) to give a yellow solid (300 mg, 52.5% yield). LC-MS $[M+H]^+$: 410.9.

Example 25: Preparation of Intermediate 4, Compound (S)-5-bromo-6-fluoro-N-(1-(3-fluoro-5-hydroxyphenyl)-2-hydroxyethyl)indoline-1-carboxamide (M004)

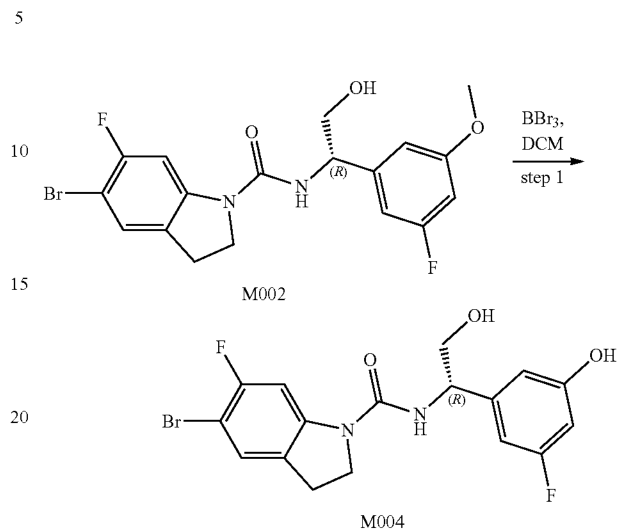

M002

M004

Compound M002 (600 mg) was dissolved in dichloromethane (10 mL) under nitrogen atmosphere, and the mixture was cooled to −78° C., and then boron tribromide (2 N, 3 mL) was added slowly. The mixture was then stirred at room temperature for 4 h. After the reaction was completed as detected, the reaction solution was concentrated under reduced pressure to give compound M004 in the form of a greyish-white solid (crude product, 720 mg). MS $(M+H)^+$= 413 1.

Example 26: Preparation of Intermediate 5, Compound (S)-2-(3-fluoro-5-(1-(6-fluoro-5-(1N-pyrazol-4-yl)indoline-1-carboxamido)-2-hydroxyethyl)phenoxy)acetic acid (M005)

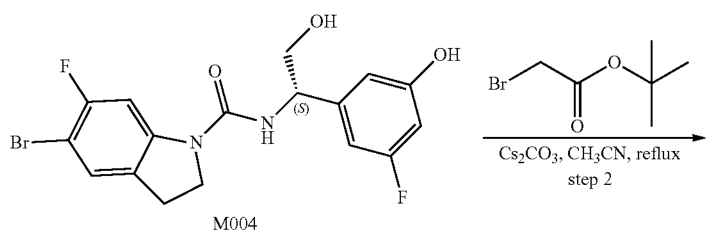

M004

-continued

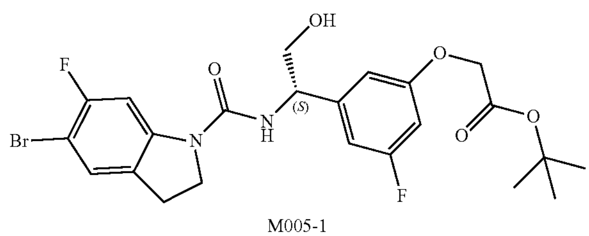

M005-1

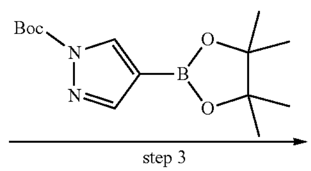

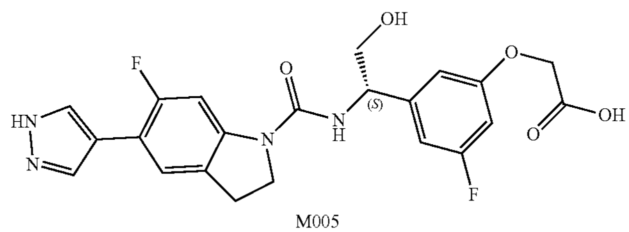

M005

(1) Preparation of Compound (S)-tert-butyl 2-(3-(1-(5-bromo-6-fluoroindoline-1-carboxamido)-2-hydroxyethyl)-5-fluorophenoxy)acetate (M005-1)

Compound M004 (450 mg) was dissolved in acetonitrile (15 mL), and cesium carbonate (532 mg) was added. The mixture was mixed well by stirring, and a solution of tert-butyl bromoacetate (223 mg) in acetonitrile (2 mL) was added. The mixture was stirred overnight at 70° C. The reaction solution was filtered through celite under vacuum, and the filter cake was washed with acetonitrile. The filtrate was combined and concentrated under reduced pressure. The resulting crude product was purified by column chromatography (petroleum ether:ethyl acetate=3:2) to give compound M005-1 in the form of a greyish-white solid (350 mg, 60.28% yield). MS (M+H)+=527.1.

(2) Preparation of Compound (S)-2-(3-fluoro-5-(1-(6-fluoro-5-(1H-pyrazol-4-yl)indoline-1-carboxamido)-2-hydroxyethyl)phenoxy)acetic acid (M005)

Compound M005-1 (300 mg), tert-butyl (4-(4,4,5,5-tetramethyl-1,3,2-dioxaborolan-2-yl)pyrazol-1-yl)carboxylate (336 mg) and potassium carbonate (315 mg) were dissolved in dioxane/water (4:1, 5 mL) under nitrogen atmosphere. The mixture was mixed well by stirring, and [1,1'-bis (diphenylphosphino)ferrocene]dichloropalladium(II) (41 mg) was added. The mixture was stirred at 90° C. for 5 h. The reaction solution was concentrated under reduced pressure to give a crude product (about 500 mg). MS $(M+H)^+$= 458.7.

Example 27: Preparation of Intermediate 6, Compound 5-bromo-6-fluoro-N-(3-fluoro-5-methoxybenzyl)indoline-1-carboxamide (M006)

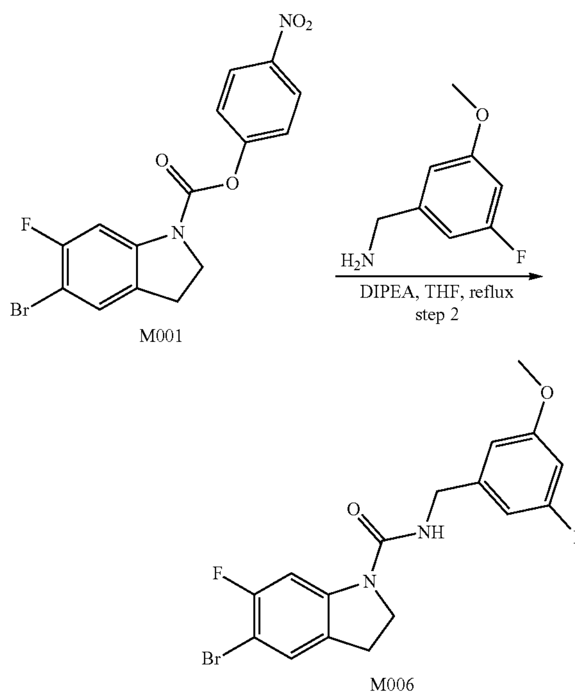

M001

M006

(1) Preparation of Compound 5-bromo-6-fluoro-N-(3-fluoro-5-methoxybenzyl)indoline-1-carboxamide (M006)

Compound M001 (450 mg) was dissolved in anhydrous tetrahydrofuran (5 mL), and (3-fluoro-5-methoxyphenyl) methylamine (205 mg) and N,N-diisopropylethylamine (426 mg) were added under nitrogen atmosphere. The mixture was heated under reflux for 16 h. After the reaction was completed, water (20 mL) was added to quench the reaction, and ethyl acetate (20 mL 3) was added for extraction. The organic phases were combined, washed with saturated brine (30 mL×2), dried over anhydrous sodium sulfate, filtered and concentrated by rotary evaporation, and the resulting crude product was purified by silica gel column chromatography (eluent: petroleum ether:ethyl acetate=10:1) to give compound M006 in the form of a yellow oil (350 mg, 80% yield). MS $[M+H]^+$=398.1.

Example 28: Preparation of Intermediate 7, Compound 6-(1H-pyrazol-4-yl)imidazo[1,5-a]pyridine-1-carboxylic acid (M007)

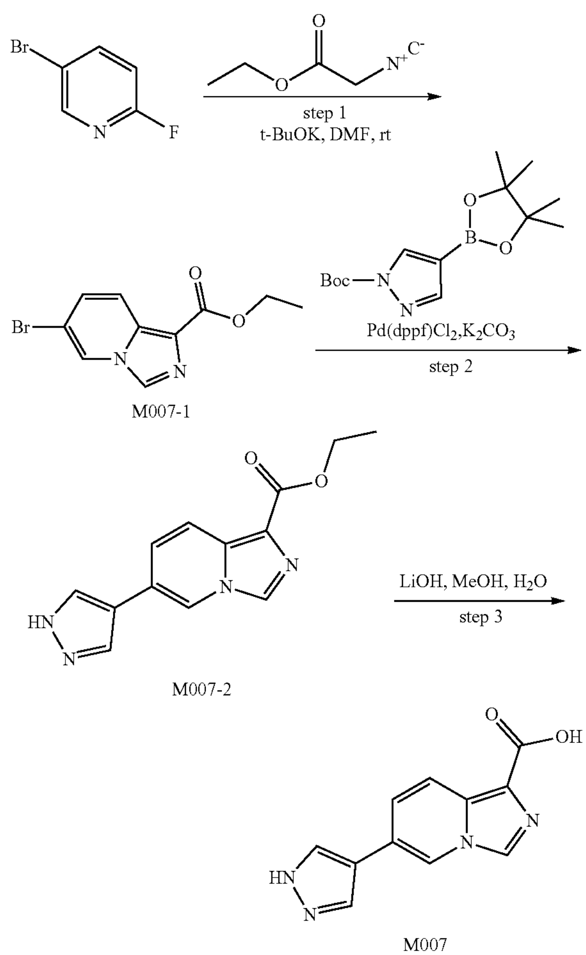

M007-1

M007-2

M007

(1) Preparation of compound ethyl 6-bromoimidazo[1,5-a]pyridine-1-carboxylate (M007-1)

5-bromo-2-fluoropyridine (10 g) was dissolved in DMF (100 mL) under nitrogen atmosphere, and the mixture was cooled to 0° C., and at this temperature, ethyl 2-isocyanoacetate (19.3 g) was added and potassium tert-butoxide (19 g) was added slowly in portions. The mixture was warmed to room temperature and reacted at room temperature for 2 h. Water (200 mL) was added to quench the reaction, and ethyl acetate (200 mL×3) was added for extraction. The organic phase was washed with saturated brine (200 mL), dried over anhydrous sodium sulfate and concentrated, and the residue was purified by silica gel column chromatography (PE/EA=5/1) to give a yellow oily liquid (4 g, 26.1% yield). LC-MS $[M+H]^+$: 269.0.

(2) Preparation of Compound ethyl 6-(1H-pyrazol-4-yl)imidazo[1,5-a]pyridine-1-carboxylate (M007-2)

Compound M007-1 (3 g) was dissolved in 1,4-dioxane/water (4/1, 30 mL) under nitrogen atmosphere, and Teributyl 4-(4,4,5,5-tetramethyl-1,3,2-dioxaborolan-2-yl)-1H-pyrazole-1-carboxylate (4.9 g, 16.7 mmol), $Pd(dppf)Cl_2$ (812 mg) and potassium carbonate (4.6 g) were added. The mixture was reacted at 80° C. for 4 h. Water (30 mL) was added to quench the reaction, and ethyl acetate (30 mL×3) was added for extraction. The organic phase was washed with saturated brine (30 mL), dried over anhydrous sodium sulfate and concentrated under reduced pressure, and the residue was purified by silica gel column chromatography (DCM/MeOH=15/1) to give a brown solid (1.5 g, 52.6% yield).

LC-MS $[M+H]^+$: 257.1.

(3) Preparation of Compound 6-(1H-pyrazol-4-yl) imidazo[1,5-a]pyridine-1-carboxylic acid (M007)

Compound M007-2 (1.5 g) was dissolved in tetrahydrofuran/water/methanol (3/1/1, 15 mL) under nitrogen atmosphere, and lithium hydroxide (1.2 g) was added. The mixture was reacted overnight at room temperature and then concentrated under reduced pressure. The pH was adjusted to 5-6 with diluted hydrochloric acid (1 N), and the mixture was concentrated under reduced pressure to give a crude product (3.0 g). LC-MS $[M+H]^+$: 229.1.

Example 29: Preparation of Intermediate 8, Compound 6-fluoro-N-(3-fluoro-5-methoxybenzyl)-5-(4,4,5,5-tetramethyl-1,3,2-dioxaborolan-2-yl)indoline-1-carboxamide (M008)

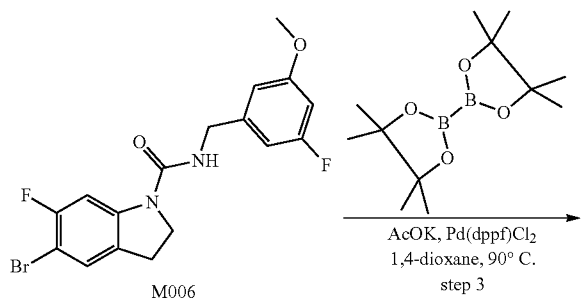

M006

-continued

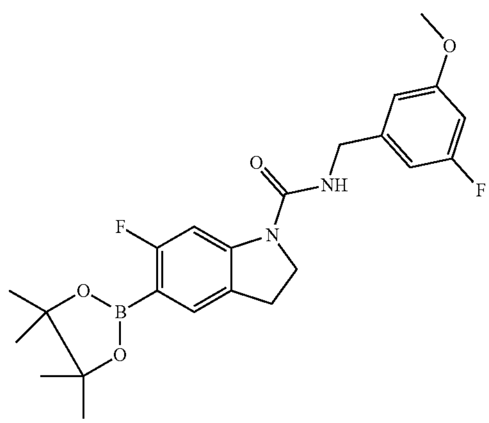

M008

Compound M006 (350 mg) was dissolved in anhydrous 1,4-dioxane (5 mL), and 4,4,4',4',5,5,5',5'-octamethyl-2,2'-bi(1,3,2-dioxaborolane) (280 mg), potassium acetate (173 mg) and [1,1'-bis(diphenylphosphino)ferrocene]dichloropalladium(II) (32 mg) were added under nitrogen atmosphere. The mixture was reacted at 90° C. for 3 h, and after the reaction was completed, the reaction solution was cooled to room temperature, filtered and concentrated by rotary evaporation to give compound M008 in the form of a brown oil (400 mg, crude product). MS $[M+H]^+$=445.1.

Example 30: Preparation of Intermediate 9, Compound 6-fluoro-N-(3-methoxybenzyl)-5-(4,4,5,5-tetramethyl-1,3,2-dioxaborolan-2-yl)indoline-1-carboxamide (M009)

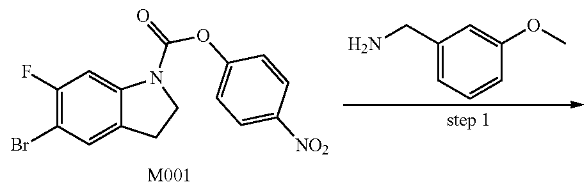

M001

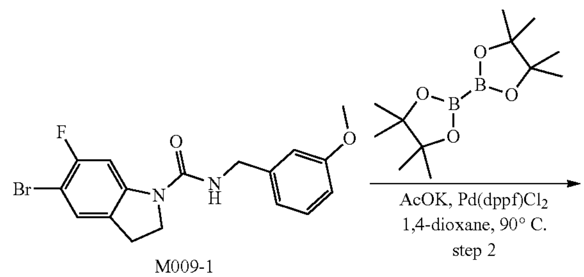

M009-1

-continued

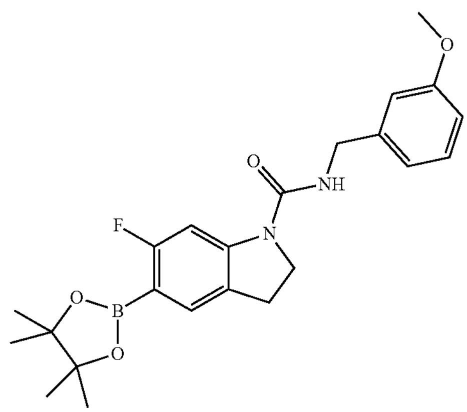

M009

(1) Preparation of Compound 5-bromo-6-fluoro-N-(3-methoxybenzyl)indoline-1-carboxamide (M009-1)

Compound M001 (1600 mg) and 3-methoxybenzylamine (1150 mg) were added to THE (20 mL), and then N,N-diisopropylethylamine (2714 mg) was added with stirring at room temperature. The mixture was stirred at 75° C. for 15 h in an oil bath. After the reaction was completed, the reaction solution was concentrated under reduced pressure, and the resulting crude product was purified by column chromatography (petroleum ether:ethyl acetate=3:1) to give a yellow solid (1500 mg, 94.2% yield), MS (M+H)+=381.1.

(2) Preparation of Compound 6-fluoro-N-(3-methoxybenzyl)-5-(4,4,5,5-tetramethyl-1,3,2-dioxaborolan-2-yl)indoline-1-carboxamide (M009)

Compound M009-1 (1500 mg), 4,4,5,5-tetramethyl-2-(4,4,5,5-tetramethyl-1,3,2-dioxaborolan-2-yl)-1,3,2-dioxaborolane (2010 mg), potassium acetate (1940 mg) and [1,1'-bis(diphenylphosphino)ferrocene]dichloropalladium (II) (579 mg) were added to 1,4-dioxane (20 mL) under nitrogen atmosphere, and the mixture was stirred at 90° C. for 5 h in an oil bath. After the reaction was completed, the reaction solution was concentrated, and the residue was purified by silica gel column chromatography (dichloromethane:methanol=50:1) to give a yellow oil (800 mg, 47.4% yield), MS $(M+H)^+$=427.1.

Example 31: Preparation of Intermediate 10, Compound (S)-6-fluoro-N-(1-(3-fluoro-5-methoxyphenyl)-2-hydroxyethyl)-5-(4,4,5,5-tetramethyl-1,3,2-dioxaborolan-2-yl)indoline-1-carboxamide (M010)

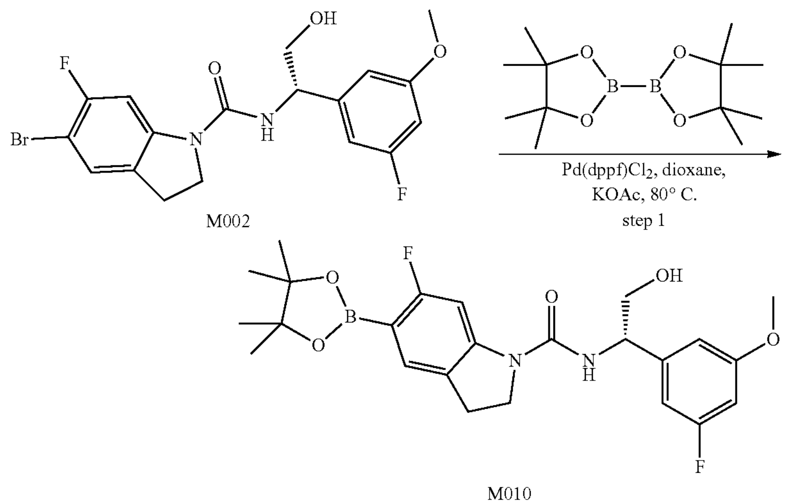

M002

M010

A solution of compound M002 (200 mg), 4,4,5,5-tetramethyl-2-(4,4,5,5-tetramethyl-1,3,2-dioxaborolan-2-yl)-1,3,2-dioxaborolane (238 mg) and potassium acetate (138 mg) were dissolved in dioxane (4 mL) under nitrogen atmosphere, and [1,1'-bis(diphenylphosphino)ferrocene]dichloropalladium(II) (34 mg) was added. The mixture was reacted at 80° C. for 6 h. The reaction solution was concentrated under reduced pressure to give the compound (crude product), MS $(M+H)^-$=475.3.

Example 32: Preparation of Intermediate 11, Compound 3-((6-fluoro-5-(1H-pyrazol-4-yl)indoline-1-carboxamido<oxalylamino>)methyl)benzoic acid (M011)

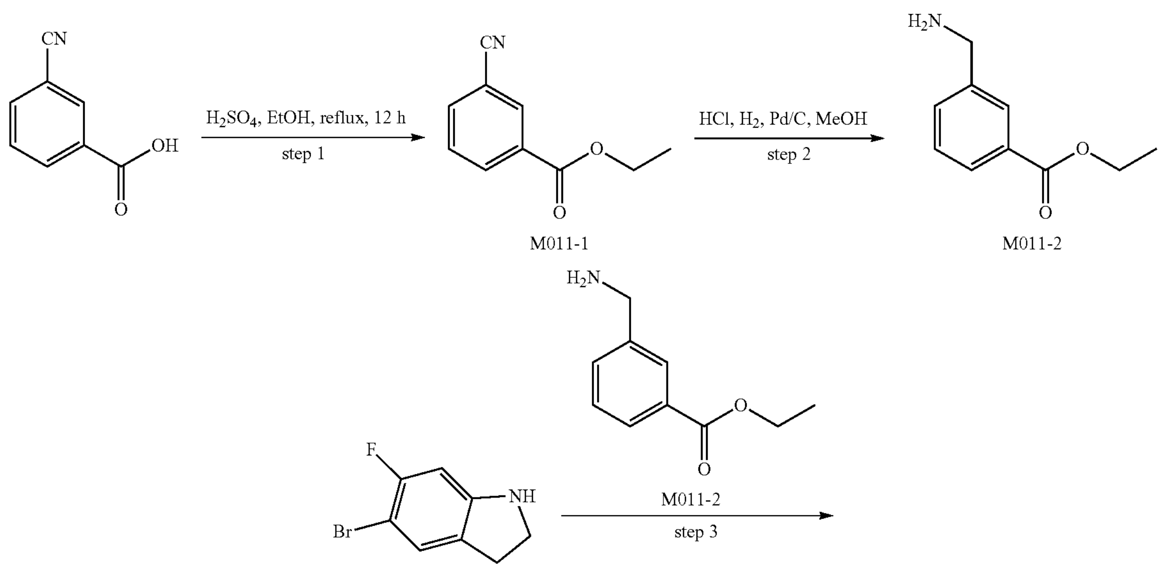

M011-1

M011-2

M011-2

-continued

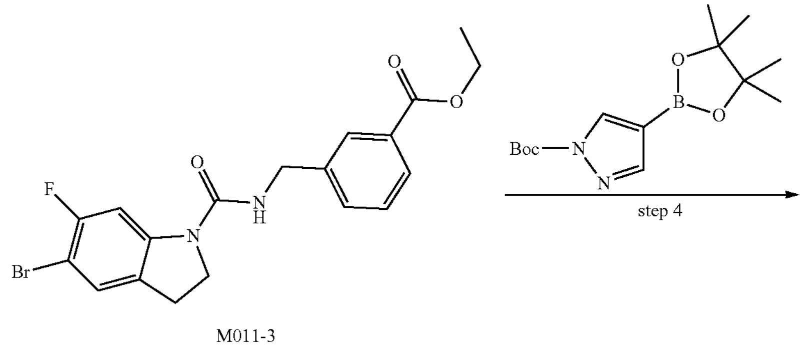

M011-3

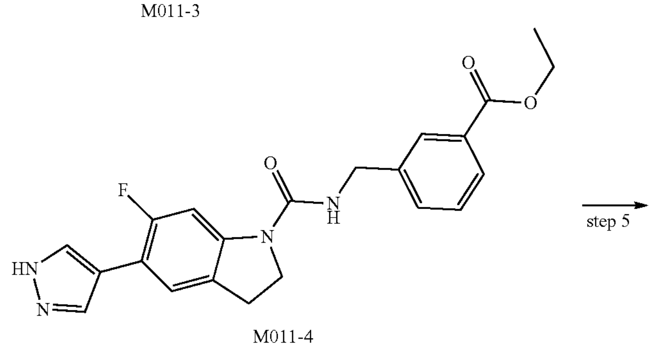

M011-4

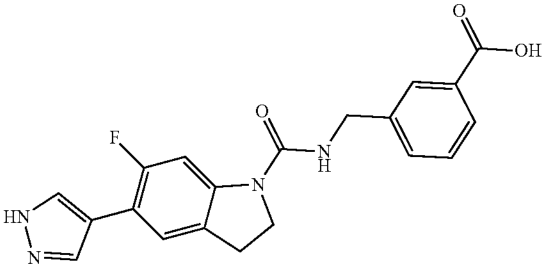

M011

(1) Preparation of Compound ethyl 3-cyanobenzoate (M011-1)

3-cyanobenzoic acid (3.0 g) was dissolved in ethanol (30 mL), and concentrated sulfuric acid (3 mL) was added. The mixture was stirred under reflux for 12 h. The reaction solution was concentrated under reduced pressure, diluted with water (50 mL) and extracted with ethyl acetate (30 mL×2). The organic phases were combined, washed with saturated brine (30 mL), dried over anhydrous sodium sulfate, filtered and concentrated, and the residue was purified by silica gel column chromatography (PE/EA=10/1) to give a yellow oily liquid (2.0 g, 57% yield). LC-MS $[M+H]^+$: 176.0.

(2) Preparation of Compound ethyl 3-(aminomethyl)benzoate (M011-2)

Compound M011-1 (2.0 g) was dissolved in methanol (20 mL), and 5% Pd/C (500 mg) and concentrated hydrochloric acid (1 mL) were added. The mixture was stirred overnight at room temperature under hydrogen atmosphere. The reaction solution was filtered and concentrated by rotary evaporation, and the resulting solid was dissolved in dichloromethane (50 mL), followed by addition of sodium carbonate solution (20 mL, 2 N). The mixture was stirred at room temperature for 30 min, washed with water (20 mL×3), dried over anhydrous sodium sulfate and concentrated to give a yellow oily liquid (2.0 g, crude product). LC-MS $[M+H]^+$: 180.0.

(3) Preparation of Compound ethyl 3-((5-bromo-6-fluoroindoline-1-carboxamido<oxalylamino>) methyl)benzoate (M011-3)

5-bromo-6-fluoroindoline (1000 mg) was dissolved in tetrahydrofuran (15 mL), and 4-nitrophenyl chlorate (1400 mg) and pyridine (1098 mg) were added. The mixture was reacted overnight at room temperature. Compound M011-2 (1244 mg) and DIEA (1791 mg) were added to the reaction solution, and the resulting mixture was reacted at 70° C. for 12 h. Water (30 mL) was added to quench the reaction, and ethyl acetate (30 mL×3) was added for extraction. The organic phases were combined, washed with saturated brine (30 mL), dried over anhydrous sodium sulfate, filtered and concentrated, and the residue was separated by silica gel column chromatography (PE/EA=3/1) to give a yellow solid (800 mg, 41% yield). LC-MS $[M+H]^+$: 422.9.

(4) Preparation of Compound ethyl 3-((6-fluoro-5-(1H-pyrazol-4-yl)indoline-1-carboxamido<oxalylamino>)methyl)benzoate (M011-4)

Compound M011-3 (800 mg) was dissolved in 1,4-dioxane (10 mL) and water (2 mL) under nitrogen atmosphere, and sera-butyl 4-(4,4,5,5-tetramethyl-1,3,2-dioxaborolan-2-yl)-1 N-pyrazole-1-carboxylate (840 mg), Pd(dppf)$Cl_2$ (118 mg) and potassium carbonate (788 mg) were added. The mixture was reacted overnight at 90° C. The reaction solution was diluted with water (25 mL) and extracted with ethyl acetate (30 mL×3). The organic phases were combined, washed with saturated brine (30 mL), dried over anhydrous sodium sulfate, filtered and concentrated, and the residue was separated by column chromatography (PE/EA=3/1) to give a white solid (500 mg, 64% yield), MS [M/2+H]=408.8.

(5) Preparation of Compound 3-((6-fluoro-5-(1H-pyrazol-4-yl)indoline-1-carboxamido<oxalylamino>)methyl)benzoic acid (M011)

Compound M011-4 (500 mg) was dissolved in tetrahydrofuran/methanol (1/1=8 mL), and sodium hydroxide solution (2 N, 3 mL) was added. The mixture was stirred overnight at room temperature. The pH was adjusted to 5-6 with concentrated hydrochloric acid, and the reaction solution was directly concentrated under reduced pressure to give a white liquid (650 mg, crude product). LC-MS $[M+H]^+$: 481.0.

Example 33: Preparation of Intermediate 12, Compound 5-bromo-N-(3-fluoro-5-methoxybenzyl)-2,3-dihydro-1H-pyrrolo(3,2-h)pyridine-1-carboxamide (M012)

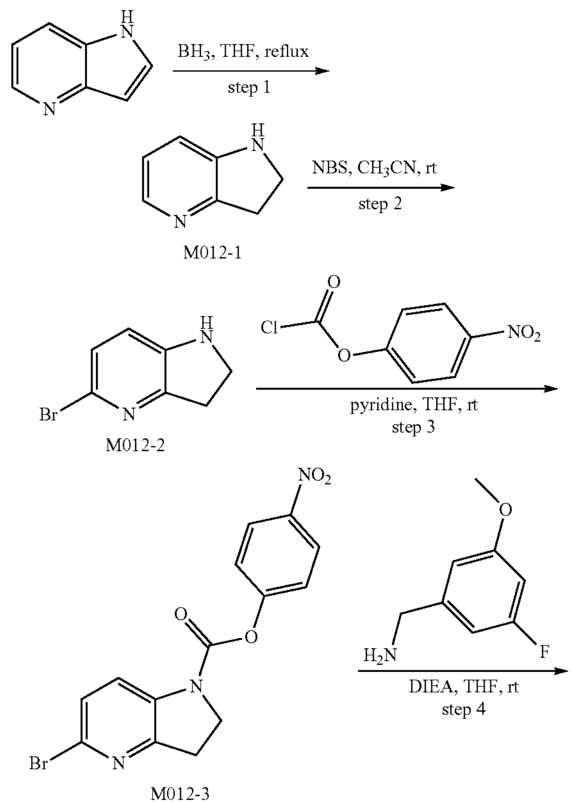

M012-1
M012-2
M012-3

-continued

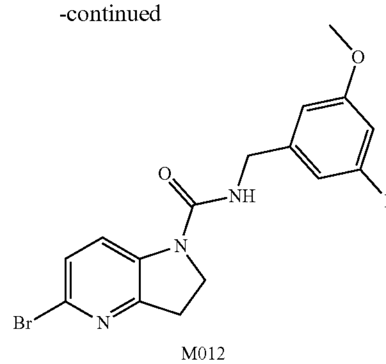

M012

(1) Preparation of Compound 2,3-dihydro-1H-pyrrolo(3,2-b)pyridine (M012-1)

1H-pyrrolo (3,2-b)pyridine (2.00 g) was dissolved in anhydrous tetrahydrofuran (50 mL), and a solution of borane in tetrahydrofuran (51 mL, 1 M) was added under nitrogen atmosphere. The mixture was heated under reflux and stirred for 4 h. The reaction solution was cooled to room temperature, and in an ice water bath, methanol was slowly added dropwise to quench the reaction. Then the reaction solution was concentrated under reduced pressure. The residue was dissolved in methanol (50 mL), and the mixture was refluxed overnight. The reaction solution was concentrated under reduced pressure, and the residue was purified by silica gel column chromatography (DCM:MeOH=20:1) to give a yellow solid (1.00 g, 49% yield). MS $(M+H)^+$=121.1.

(2) Preparation of Compound 5-bromo-2,3-dihydro-1H-pyrrolo(3,2-b)pyridine (M012-2)

Compound M012-1 (1.00 g) was dissolved in anhydrous acetonitrile (30 mL), and a solution of N-bromosuccinimide (1.63 g) in acetonitrile (10 mL) was slowly added dropwise. The mixture was stirred at room temperature for 3 h. Water (30 mL) was added, and ethyl acetate (20 mL×3) was added for extraction. The organic phases were combined, washed with saturated brine (20 mL), dried over anhydrous sodium sulfate, filtered and concentrated, and the resulting crude product was purified by silica gel column chromatography (PE:EA=2:1) to give a greyish-green solid (0.81 g, 48% yield). MS $(M+H)^+$=199.1.

(3) Preparation of Compound 4-nitrophenyl-5-bromo-2,3-dihydro-111-pyrrolo(3,2-b)pyridine-1-carboxylic acid (M012-3)

4-nitrophenyl chloroformate (607 mg) was dissolved in THF (8 mL), and then a solution of compound M012-2 (500 mg) and pyridine (596 mg) in THF (2 mL) was added dropwise under nitrogen atmosphere. The mixture was stirred overnight at room temperature. After the reaction was complete as detected by LCMS, the reaction solution was directly used in the next step without treatment. MS $(M+H)^-$= 364.0.

(4) Preparation of Compound 5-bromo-N-(3-fluoro-5-methoxybenzyl)-2,3-dihydro-1H-pyrrolo(3,2-b)pyridine-1-carboxamide (M012)

N,N-diisopropylethylamine (1616 mg) and (3-fluoro-5-methoxyphenyl)methylamine (621 mg) were added to the reaction solution obtained in the previous step, and the mixture was stirred overnight at room temperature. The reaction solution was concentrated under reduced pressure, and the residue was purified by silica gel column chromatography (PE:EA=3:1) to give a yellow solid (950 mg, 98% two-step yield). MS $(M+H)^-$=380.0.

Example 34: Preparation of Intermediate 13, Compound N-(3,5-difluorobenzyl)-6-fluoro-5-(4,4,5,5-tetramethyl-1,3,2-dioxaborolan-2-yl)indoline-1-carboxamide (M013)

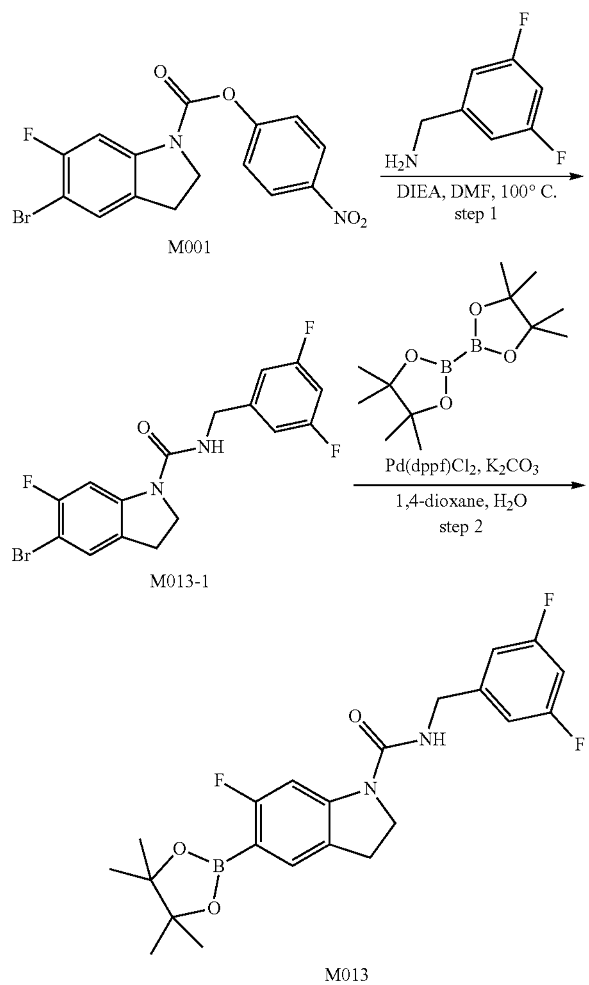

(1) Preparation of Compound 5-bromo-N-(3,5-difluorobenzyl)-6-fluoroindoline-1-carboxamide (M013-1)

Compound M001 (1000 mg) and (3,5-difluorophenyl) methylamine (450 mg) were dissolved in dimethylformamide (10 mL), and the mixture was mixed well by stirring, followed by addition of diisopropylethylamine (1693 mg). The resulting mixture was stirred at 100° C. for 1 h. The reaction solution was diluted with water (50 mL) and extracted with ethyl acetate (20 mL×3). The organic phases were combined, washed with saturated brine (20 mL), dried over anhydrous sodium sulfate and concentrated under reduced pressure, and the resulting crude product was purified by column chromatography (petroleum ether:ethyl acetate=5:1) to give compound M013-1 in the form of a white solid (860 mg, 80.96% yield). MS $(M+H)^+$=382.2.

(2) Preparation of Compound N-(3,5-difluorobenzyl)-6-fluoro-5-(4,4,5,5-tetramethyl-1,3,2-dioxaborolan-2-yl)indoline-1-carboxamide (M013)

Compound M013-1 (860 mg) was dissolved in anhydrous 1,4-dioxane (15 mL) under nitrogen atmosphere, and 4,4,4',4',5,5,5',5'-octamethyl-2,2'-bi(1,3,2-dioxaborolane) (1698.85 mg), potassium acetate (875.409 mg) and [1,1'-bis (diphenylphosphino)ferrocene]dichloropalladium(II) (244.754 mg) were added. The mixture was reacted at 90° C. for 4 h. After the reaction was completed, the reaction solution was filtered and concentrated by rotary evaporation, and the resulting crude product was purified by column chromatography (petroleum ether:dichloromethane=15:1) to give compound M013 in the form of a brown oil (350 mg, 34.49% yield). MS $(M+H)^-$=433.3.

Example 35: Preparation of Compound 5-(3-amino-1H-pyrazol-4-yl)-6-fluoro-N-(3-methoxybenzyl) indoline-1-carboxamide (T345)

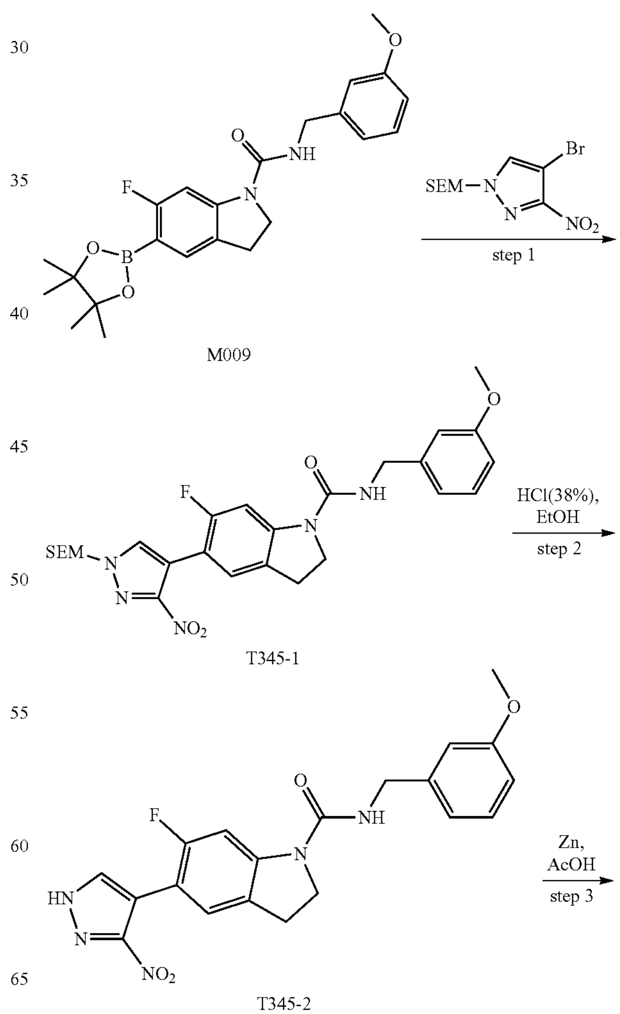

-continued

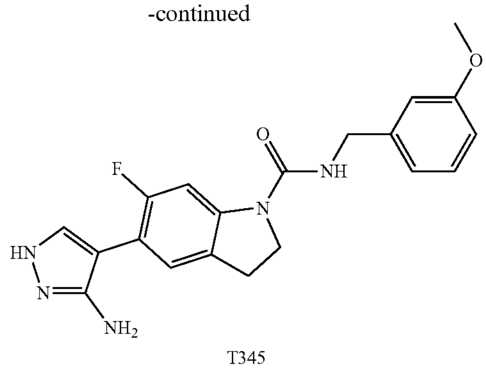

T345

1 Preparation of Compound 6-fluoro-N-(3-methoxybenzyl)-5-(3-nitro-1-(((2-(trimethylsilyl)ethoxy)methyl)-1H-pyrazol-4-yl)indoline-1-carboxamide (T345-1)

Compound M009 (800 mg), 4-bromo-3-nitro-1-(((2-(trimethylsilyl)ethoxy)methyl)-1H-pyrazole (544 mg), anhydrous potassium carbonate (1040 mg) and [1,1'-bis(diphenylphosphino)ferrocene]dichloropalladium(II) (137 mg) were added to 1,4-dioxane/water (20:1, 10 mL) under nitrogen atmosphere. The mixture was stirred at 80° C. for 2 h in an oil bath. After the reaction was completed, the reaction solution was diluted with water (50 mL) and extracted with ethyl acetate (30 mL×3). The organic phases were combined, washed with saturated brine (20 mL), dried over anhydrous sodium sulfate, filtered and concentrated, and the residue was purified by silica gel column chromatography (petroleum ether:ethyl acetate=20:1) to give a yellow oil (650 mg, 63.9% yield), MS $(M+H)^+$=542.1.

2 Preparation of Compound 6-fluoro-N-(3-methoxybenzyl)-5-(3-nitro-1H-pyrazol-4-yl)indoline-1-carboxamide (T345-2)

Compound 1345-1 (650 mg) was dissolved in ethanol (10 mL), and concentrated hydrochloric acid (1 mL) was added. The mixture was stirred under reflux in an oil bath for 5 h, and after the reaction was completed as detected by liquid mass spectrometry, the reaction solution was directly used in the next step without treatment. MS $(M+H)^+$=412.1.

3 Preparation of Compound 5-(3-amino-1H-pyrazol-4-yl)-6-fluoro-N-(3-methoxybenzyl)indoline-1-carboxamide (T345)

Activated zinc powder (798 mg) was added to the reaction solution obtained in the previous step in an ice bath, and then acetic acid (3 mL) was added. The mixture was warmed to room temperature and stirred for 2 h. The reaction solution was concentrated under reduced pressure, and then saturated sodium bicarbonate (10 mL) was added and ethyl acetate (5 mL×3) was added for extraction. The organic phases were combined, dried over anhydrous sodium sulfate, filtered and concentrated, and the resulting crude product was purified by silica gel column chromatography (dichloromethane:methanol=20:1) to give a white solid (98 mg, 21.4% two-step yield), MS (M+H)+=382.2.

$^1$H NMR (400 MHz, DMSO) δ 11.69 (s, 1H), 7.61 (d, J=12.9 Hz, 1H), 7.46 (s, 1H), 7.31 (dd, J=11.5, 6.1 Hz, 2H), 7.24 (t, J=8.0 Hz, 1H), 6.93-6.87 (m, 2H), 6.80 (dd, J=7.3, 1.9 Hz, 1H), 4.59 (s, 2H), 4.31 (d, J=5.8 Hz, 2H), 3.99 (t, J=8.7 Hz, 2H), 3.74 (s, 3H), 3.12 (t, J=8.5 Hz, 2H).

Example 36: Preparation of Compound 6-fluoro-N-(1-(3-fluoro-5-methoxyphenyl)ethyl)-5-(1H-pyrazol-4-yl)indoline-1-carboxamide (T341)

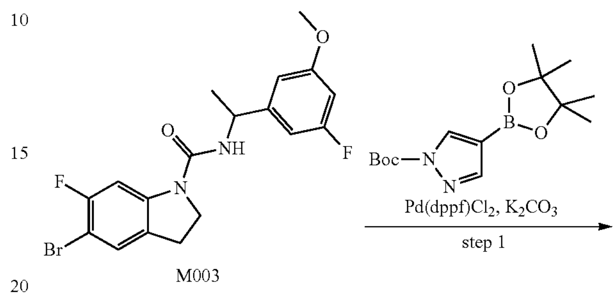

M003

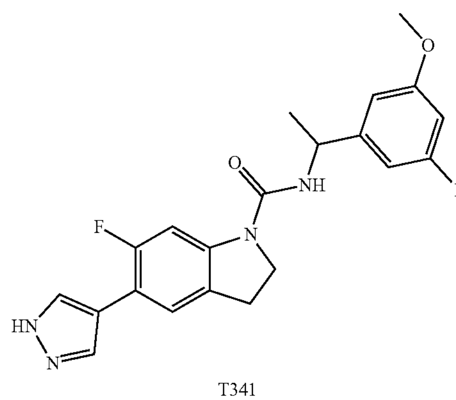

T341

Compound M003 (200 mg) was dissolved in 1,4-dioxane (10 mL) and water (2 mL), and tert-butyl 4-(4,4,5,5-tetramethyl-1,3,2-dioxaborolan-2-yl)-1H-pyrazole-1-carboxylate (288 mg), Pd(dppf)$Cl_2$ (72 mg) and potassium carbonate (203 mg) were added under nitrogen atmosphere. The mixture was reacted at 90° C. for 12 h. The reaction solution was cooled to room temperature, diluted with water (25 mL) and extracted with ethyl acetate (30 mL×3). The organic phases were combined, washed with saturated brine (30 mL), dried over anhydrous sodium sulfate, filtered and concentrated, and the residue was separated by preparative chromatography to give a white solid (47.8 mg). MS [M/2+H]+=399.1.

$^1$H NMR (400 MHz, MeOD) δ 7.97 (s, 2H), 7.61 (d, J=13.1 Hz, 1H), 7.45 (d, J=7.7 Hz, 1H), 6.80 (s, 1H), 6.77-6.71 (m, 1H), 6.57 (dt, J=10.7, 2.3 Hz, 1H), 4.99 (d, J=7.1 Hz, 1H), 4.12-4.04 (m, 2H), 3.81 (s, 3H), 3.22 (t, J=8.7 Hz, 2H), 1.53 (d, J=7.1 Hz, 3H).

Example 37: Preparation of Compound (S)-5-(3-amino-1H-pyrazol-4-yl)-6-fluoro-h-(1-(3-fluoro-5-methoxyphenyl)-2-hydroxyethyl)indoline-1-carboxamide (T365)

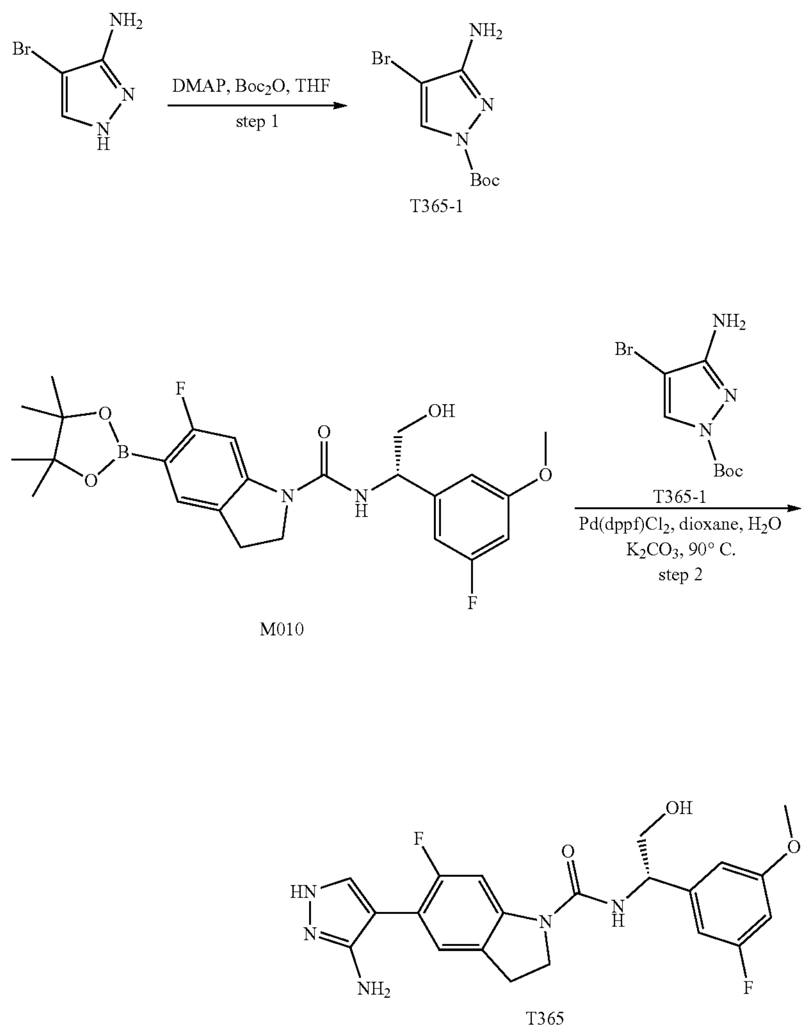

T365-1

M010

T365

1 Preparation of Compound tert-butyl 3-amino-4-bromo-1H-pyrazole-1-carboxylate (T365-1)

4-bromo-1H-pyrazol-3-amine (2.00 g) and 4-dimethyl-aminopyridine (150 mg) were dissolved in tetrahydrofuran (20 mL), and di-tert-butyl dicarbonate (2.80 g) was added in portions. The mixture was stirred overnight at room temperature. The reaction solution was concentrated under reduced pressure, and the resulting crude product was purified by silica gel column chromatography (petroleum ether: ethyl acetate=3:1) to give a greyish-white solid (2.1 g, 65.2% yield). MS $(M+H)^+$=547.1.

2 Preparation of Compound (S)-5-(3-amino-1H-pyrazol-4-yl)-6-fluoro-N-(1-(3-fluoro-5-methoxyphenyl)-2-hydroxyethyl)indoline-1-carboxamide (T365)

Compound M010 (500 mg, crude product) obtained in the previous step, compound T365-1 (233 mg) and potassium carbonate (122 mg) were dissolved in NA-dimethylformamide/water (3:1, 4 mL) under nitrogen atmosphere, and tetrakis(triphenylphosphine)palladium(0) (32 mg) was added. The mixture was reacted at 90° C. for 4 h. The reaction solution was diluted with water (30 mL) and extracted with ethyl acetate (20 mL×3). The organic phases were combined, dried over anhydrous sodium sulfate, filtered and concentrated. The resulting crude product was purified by silica gel column chromatography (dichloromethane:methanol=20:1) to give a sample (20 mg), which was purified by preparative chromatography and lyophilized to give a white solid (3.4 mg). MS $(M+H)^+$=430.0.

$^1H$ NMR (400 MHz, DMSO) δ 11.67 (s, 1H), 7.55 (d, J=12.8 Hz, 1H), 7.46 (s, 1H), 7.31 (d, J=8.0 Hz, 1H), 6.86-6.79 (m, 3H), 6.72-6.67 (m, 1H), 4.94 (s, 1H), 4.82 (dd, J=13.6, 7.5 Hz, 1H), 4.58 (s, 2H), 4.14-4.02 (m, 2H), 3.77 (s, 3H), 3.67-3.59 (m, 2H), 3.14 (t, J=8.9 Hz, 2H).

Example 38: Preparation of Compound (S)-5-(3-chloro-1H-pyrazol-4-yl)-6-fluoro-N-(1-(3-fluoro-5-methoxyphenyl)-2-hydroxyethyl)indoline-1-carboxamide (T359)
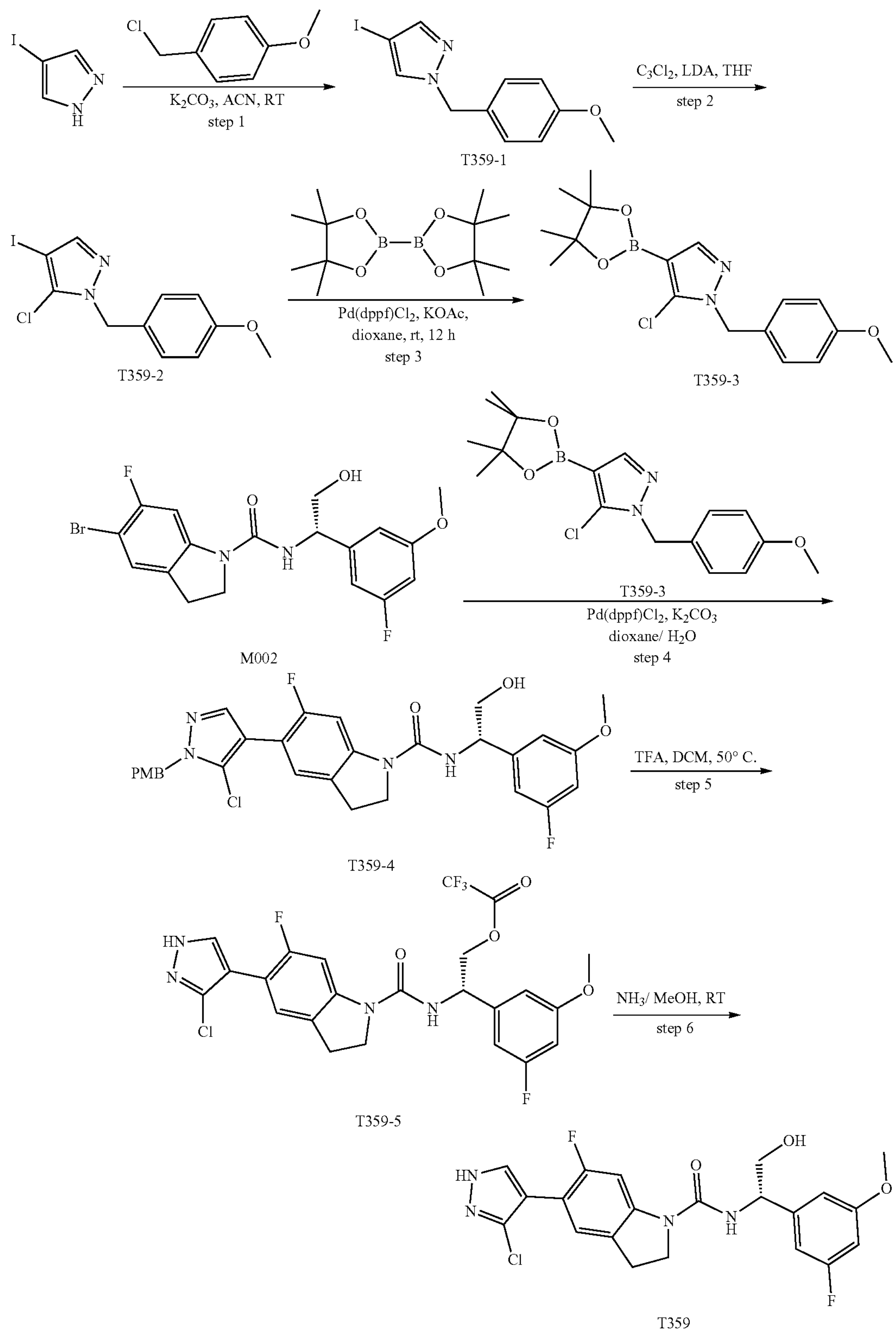
T359-1
T359-2
T359-3
M002
T359-4
T359-5
T359

1 Preparation of Compound 4-iodo-1-(4-methoxybenzyl)-1H-pyrazole (T359-1)

4-iodo-1H-pyrazole (5.00 g) was dissolved in acetonitrile (45 mL), and potassium carbonate (10.60 g) was added. The mixture was stirred at room temperature, and then a solution of 1-(chloromethyl)-4-methoxybenzene (4.80 g) in acetonitrile (5 mL) was added dropwise. The resulting mixture was stirred overnight at room temperature. After the reaction was completed as detected, the reaction solution was filtered through celite under vacuum, and ethyl acetate was used for washing. The filtrate was concentrated under reduced pressure. The resulting crude product was purified by silica gel column chromatography (petroleum ether:ethyl acetate=10:1) to give a white solid (5.9 g, 72.9% yield). MS $(M+H)^+$=315.0.

2 Preparation of Compound 5-chloro-4-iodo-1-(4-methoxybenzyl)-1H-pyrazole (T359-2)

Compound T359-1 (5.00 g) was dissolved in tetrahydrofuran (20 mL) under nitrogen atmosphere, and then the mixture was cooled to −78° C., and LDA (2.4 M, 7.96 mL) was added dropwise. The resulting mixture was stirred for 30 min, followed by addition of a solution of hexachloroethane (4.5 g) in tetrahydrofuran (5 mL). The mixture was stirred at −78° C. for 2 h. After the reaction was completed as detected, saturated ammonium chloride (20 mL) was added to quench the reaction, and ethyl acetate (20 mL×3) was added for extraction. The organic phases were combined, washed with saturated brine, dried over anhydrous sodium sulfate, filtered and concentrated. The resulting crude product was purified by silica gel column chromatography (petroleum ether:ethyl acetate=3:1) to give a white solid (5.00 g, 90.2% yield).

$^1$H NMR (301 MHz, CDCl3) δ 7.54 (s, 1H), 7.21 (d, J=8.5 Hz, 2H), 6.86 (d, J=8.6 Hz, 2H), 5.31 (s, 2H), 3.78 (s, 3H).

3 Preparation of Compound 5-chloro-1-(4-methoxybenzyl)-4-(4,4,5,5-tetramethyl-1,3,2-dioxaborolan-2-yl)-1H-pyrazole (T359-3)

Compound T359-2 (2000 mg), 4,4,5,5-tetramethyl-2-(4,4,5,5-tetramethyl-1,3,2-dioxaborolan-2-yl)-1,3,2-dioxaborolane (1603 mg) and potassium acetate (1126 mg) were dissolved in dioxane (10 mL) under nitrogen atmosphere, and [1,1'-bis(diphenylphosphino)ferrocene]dichloropalladium(II) (419 mg) was added. The mixture was stirred overnight at room temperature. After the reaction was complete as detected, the reaction solution was concentrated under reduced pressure and then directly used in the next step. MS $(M+H)^+$=475.3.

4 Preparation of Compound (S)-5-(5-chloro-1-(4-methoxybenzyl)-1H-pyrazol-4-yl)-6-fluoro-N-(1-(3-fluoro-5-methoxyphenyl)-2-hydroxyethylindoline-1-carboxamide (T359-4)

A solution of compound M002 (160 mg), compound T359-3 (155 mg) and potassium carbonate (153 mg) were dissolved in dioxane/water (3:1, 5 mL) under nitrogen atmosphere, and [1,1'-bis(diphenylphosphino)ferrocene]dichloropalladium(II) (27 mg) was added. The mixture was stirred at 90° C. for 4 h in an oil bath. The reaction solution was concentrated under reduced pressure, and the residue was purified by silica gel column chromatography (dichloromethane:ethyl acetate=2:1) to give a brown oil (120 mg, 56.9% yield). MS (M+H)=569.1.

5 Preparation of Compound (S)-2-(5-(3-chloro-1H-pyrazol-4-yl)-6-fluoroindoline-1-carboxamido)-2-(3-fluoro-5-methoxyphenyl)ethyl 2,2,2-trifluoroacetate (T359-5)

Compound T359-4 (120 mg) was dissolved in dichloromethane (10 mL), and trifluoroacetic acid (3 mL) was added. The mixture was stirred at 50° C. for 1.5 h. The reaction solution was concentrated under reduced pressure to give a brown oil (100 mg), and the crude product was directly used in the next step, MS $(M+H)^+$=545.0.

6 Preparation of Compound (S)-5-(3-chloro-1H-pyrazol-4-yl)-6-fluoro-N-(1-(3-fluoro-5-methoxyphenyl)-2-hydroxyethyl)indoline-1-carboxamide (T359)

Compound T359-5 (100 mg, crude product) was placed in a round-bottomed flask, and a solution of ammonia (7 N, 3 mL) in methanol was added. The mixture was stirred at room temperature for 1 h. The reaction solution was concentrated under reduced pressure, and the residue was purified by silica gel preparative plate (dichloromethane:methanol=20:1) to give compound T359 in the form of a white solid (30 mg, 33.4% yield). MS $(M+H)^+$=449.0.

$^1$H NMR (400 MHz, DMSO) δ 13.22 (s, 1H), 7.96 (s, 1H), 7.61 (d, J=12.4 Hz, 1H), 7.29 (d, J=7.7 Hz, 1H), 6.90 (d, J=7.9 Hz, 1H), 6.84-6.79 (m, 2H), 6.69 (dt, J=11.0, 2.2 Hz, 1H), 4.94 (t, J=5.9 Hz, 1H), 4.83 (dd, J=13.5, 7.4 Hz, 1H), 4.18-4.04 (m, 2H), 3.77 (s, 3H), 3.71-3.58 (m, 2H), 3.17 (t, J=8.6 Hz, 2H).

Example 39: Preparation of Compound (S)-6-fluoro-5-(3-fluoro-1H-pyrazol-4-yl)-N-(1-(3-fluoro-5-methoxyphenyl)-2-hydroxyethyl)indoline-1-carboxamide (T374)

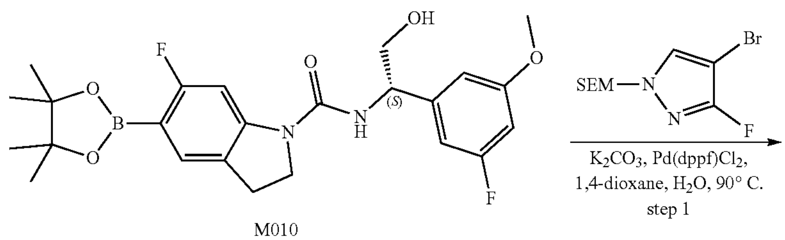

M010

-continued

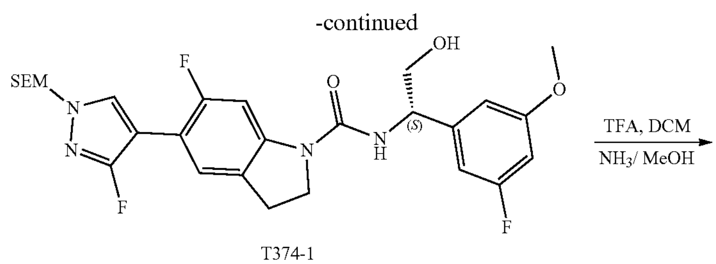

T374-1

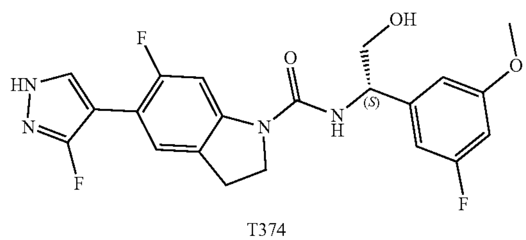

T374

1 Preparation of Compound (S)-6-fluoro-5-(3-fluoro-1-((2-(trimethylsilyl)ethoxy)methyl)-1H-pyrazol-4-yl)-N-(1-(3-fluoro-5-methoxyphenyl)-2-hydroxyethyl)indoline-1-carboxamide (T374-1)

4-bromo-3-fluoro-1-((2-(trimethylsilyl)ethoxy)methyl)-1H-pyrazole (M010) (100 mg) was dissolved in 1,4-dioxane (3 mL) and water (0.5 mL), and compound M010 (200 mg, crude product), potassium carbonate (94 mg) and [1,1'-bis (diphenylphosphino)ferrocene]dichloropalladium (II) (25 mg) were added under nitrogen atmosphere. The mixture was reacted at 90° C. for 3 h. The reaction solution was cooled to room temperature, and then water (10 mL) was added and ethyl acetate (20 mL 3) was added for extraction. The organic phases were combined, washed with saturated brine (20 mL 2), dried over anhydrous sodium sulfate, filtered and concentrated. The resulting crude product was purified by silica gel column chromatography (eluent: petroleum ether:ethyl acetate=2:1) to give compound T374-1 in the form of a yellow oil (16.9% yield). MS $[M+H]^+$=563.1.

2 Preparation of Compound (S)-6-fluoro-5-(3-fluoro-1H-pyrazol-4-yl)N-(1-(3-fluoro-5-methoxyphenyl)-2-hydroxyethyl)indoline-1-carboxamide (T374)

Compound T374-1 (40 mg) was dissolved in dichloromethane (1 mL), and trifluoroacetic acid (0.3 mL) was added. The mixture was reacted at room temperature for 2 h. After the reaction was completed, the reaction solution was concentrated under reduced pressure, and then a solution of ammonia in methanol (7 N, 1 mL) was added. The resulting mixture was stirred at room temperature for 1 h. The reaction solution was concentrated under reduced pressure, and the resulting crude product was purified by preparative chromatography to give compound T374 in the form of a white solid (5.1 mg, 15.7% yield). MS $[M+H]^+$=433.0.

$^1$H NMR (400 MHz, MeOD) δ7.80 (t, J=2.5 Hz, 1H), 7.64 (d, J=12.9 Hz, 1H), 7.41 (d, J=7.5 Hz, 1H), 6.83 (s, 1H), 6.80-6.75 (m, 1H), 6.61 (dt, J=10.8, 2.3 Hz, 1H), 5.00-4.93 (m, 1H), 4.18-4.13 (m, 2H), 3.86-3.83 (m, 1H), 3.82 (s, 3H), 3.81-3.77 (m, 1H), 3.25 (t, J=8.7 Hz, 2H).

Example 40: Preparation of Compound 6-fluoro-5-(3-fluoro-1H-pyrazol-4-yl)-N-(3-fluoro-5-methoxybenzyl)indoline-1-carboxamide (T351)

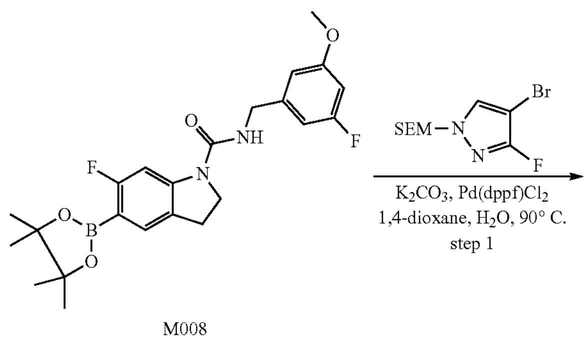

M008

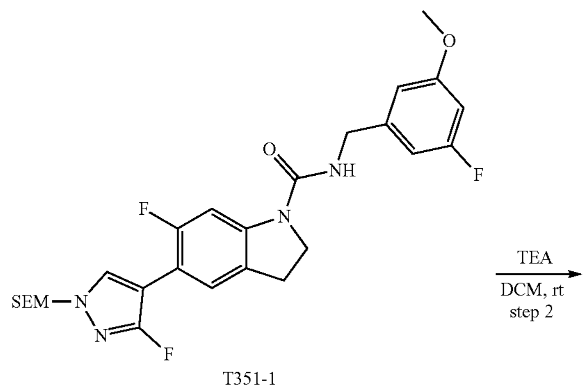

T351-1

-continued

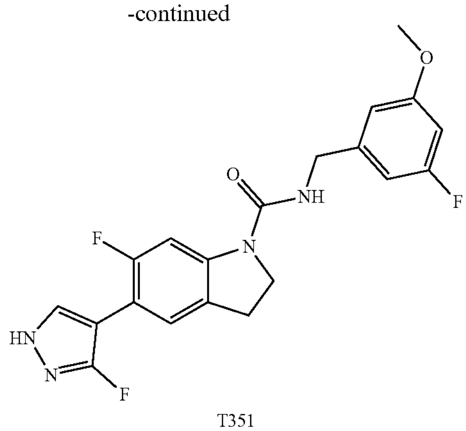

T351

1 Preparation of Compound 6-fluoro-5-(3-fluoro-1-((2-(trimethylsilyl)ethoxy)methyl)-1H-pyrazol-4-yl)-N-(3-fluoro-5-methoxybenzyl)indoline-1-carboxamide (T351-1)

4-bromo-3-fluoro-1-((2-(trimethylsilyl)ethoxy)methyl)-1H-pyrazole (M008) (220 mg) was dissolved in 1,4-dioxane (3 mL) and water (0.5 mL), and compound M008 (397 mg), potassium carbonate (206 mg) and [1,1'-bis(diphenylphosphino)ferrocene]dichloropalladium(II) (54.5 mg) were added under nitrogen atmosphere. The mixture was reacted at 90° C. for 3 h. The reaction solution was cooled to room temperature, water (30 mL) was added, and then ethyl acetate (30 mL×3) was added for extraction. The organic phases were combined, washed with saturated brine (30 mL×2), dried over anhydrous sodium sulfate, filtered and concentrated by rotary evaporation, and the resulting crude product was purified by silica gel column chromatography (eluent: petroleum ether:ethyl acetate=2:1) to give compound T351-2 in the form of a yellow oil (300 mg, 75.6% yield). MS $[M+H]^+$=533.1.

2 Preparation of Compound 6-fluoro-5-(3-fluoro-1H-pyrazol-4-yl)-N-(3-fluoro-5-methoxybenzyl)indoline-1-carboxamide (T351)

Compound T351-1 (300 mg) was dissolved in dichloromethane (3 mL), and trifluoroacetic acid (0.5 mL) was added. The mixture was reacted at room temperature for 2 h. After the reaction was completed, the reaction solution was directly concentrated by rotary evaporation, and the resulting crude product was purified by high pressure liquid phase chromatography to give compound T351 in the form of a white solid (63.4 mg, 28.0% yield). MS $[M+H]^+$=403.0.

$^1$H NMR (400 MHz, MeOD) δ7.80 (t, J=2.5 Hz, 1H), 7.68 (d, J=12.9 Hz, 1H), 7.41 (d, J=7.6 Hz, 1H), 6.77 (s, 1H), 6.70 (d, J=9.4 Hz, 1H), 6.58 (dt, J=10.8, 2.3 Hz, 1H), 4.42 (s, 2H), 4.06 (t, J=8.7 Hz, 2H), 3.81 (s, 3H), 3.23 (t, J=8.6 Hz, 2H).

Example 41: Preparation of Compound 6-fluoro-N-(3-fluoro-5-(trifluoromethoxy)benzyl)-5-(1H-pyrazol-4-yl)indoline-1-carboxamide (T349)

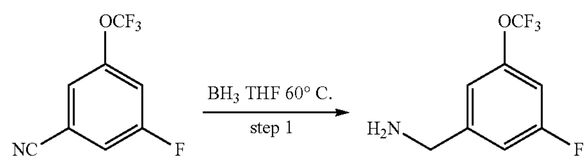

-continued

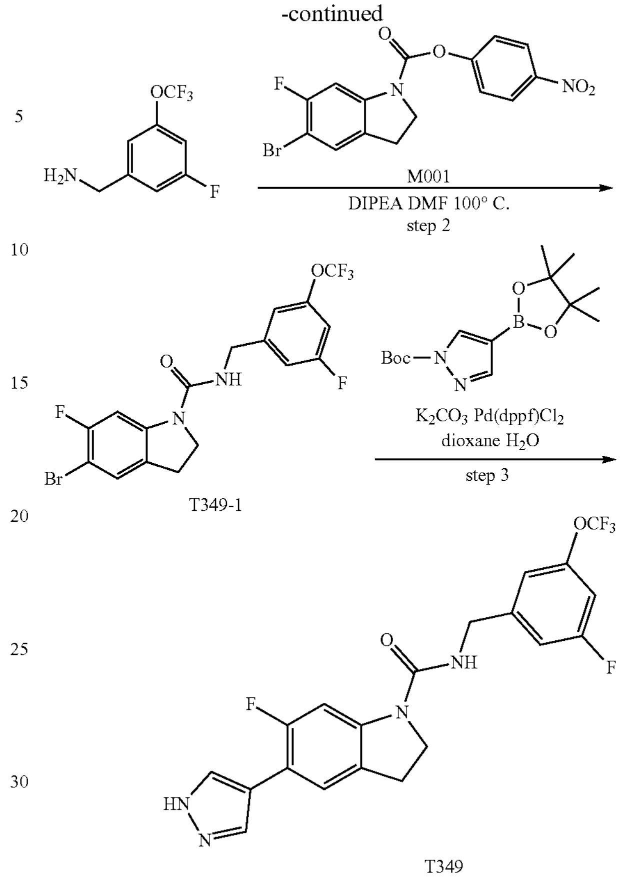

T349-1

T349

1 Preparation of Compound (3-fluoro-5-(trifluoromethoxy)phenyl)methylamine 3-fluoro-5-(trifluoromethoxy)benzonitrile (500 mg) was dissolved in anhydrous tetrahydrofuran (15 mL), and a solution of borane in tetrahydrofuran (25 mL) was added. The mixture was stirred overnight at 60° C. After the reaction was completed, methanol (10 mL) was slowly added dropwise in an ice bath, diluted hydrochloric acid (2 N, 20 mL) was added, ethyl acetate (20 mL×2) was added for extraction, and the aqueous phase was retained. The aqueous phase was adjusted to pH=9 with sodium hydroxide (2 N) and extracted with ethyl acetate (20 mL×2). The organic phases were combined, washed with saturated brine (10 mL), dried over anhydrous sodium sulfate, filtered and concentrated to give a colorless oily liquid (180 mg, 35.2% yield). LC-MS $[M+H]^+$: 209.9.

2 Preparation of Compound 5-bromo-6-fluoro-N-(3-fluoro-5-(trifluoromethoxy)benzyl)indoline-1-carboxamide (T349-1)

Compound M001 (272 mg) was dissolved in anhydrous DMF (5 mL), and (3-fluoro-5-(trifluoromethoxy)phenyl)methylamine (180 mg) was added. The mixture was warmed to 100° C. and reacted for 2 h. The reaction solution was diluted with water (30 mL) and extracted with ethyl acetate (10 mL×3). The organic phases were combined, washed with saturated brine (10 mL×2), dried over anhydrous sodium sulfate, filtered and concentrated. The resulting crude product was purified by silica gel column chromatography (PE/EA=5/1) to give a yellow solid (160 mg, 50.0% yield). LC-MS [M+H]$^+$: 451.2.

3 Preparation of Compound 6-fluoro-N-(3-fluoro-5-(trifluoromethoxy)benzyl)-5-(1H-pyrazol-4-yl)indoline-1-carboxamide (T349)

Compound T349-1 (160 mg) was dissolved in dioxane (5 mL) and water (1 mL), and tert-butyl 4-(4,4,5,5-tetramethyl-1,3,2-dioxaborolan-2-yl)-1H-pyrazole-1-carboxylate (123 mg), potassium carbonate (97 mg) and [1,1'-bis(diphenylphosphino)ferrocene]dichloropalladium(II) (25 mg) were added. The mixture was warmed to 80° C. and reacted for 4 h under nitrogen atmosphere. The reaction solution was diluted with water (20 mL) and extracted with ethyl acetate (15 mL×3). The organic phases were combined, washed with saturated brine (15 mL×2), dried over anhydrous sodium sulfate, filtered and concentrated. The resulting crude product was purified by preparative chromatography to give a white solid (54.2 mg, 35.3% yield). MS [M+H]$^+$= 439.1.

$^1$H NMR (400 MHz, MeOD) δ 7.97-7.91 (m, 2H), 7.65 (d, J=13.0 Hz, 1H), 7.49-7.43 (m, 1H), 7.18-7.16 (m, 2H), 7.00 (d, J=9.1 Hz, 1H), 4.48 (s, 2H), 4.06 (t, J=8.7, 2H), 3.23 (t, J=7.0 Hz, 2H).

Example 42: Preparation of (+/−)N-(2-(dimethylamino)-1-(3-fluoro-5-methoxyphenyl)ethyl)-6-fluoro-5-(3-fluoro-1H-pyrazol-4-yl)indoline-1-carboxamide (T388)

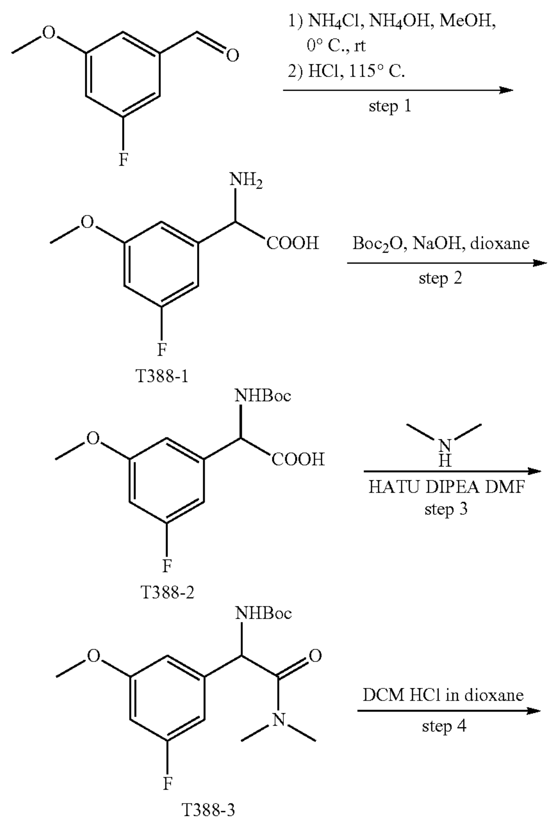

T388-1

T388-2

T388-3

-continued

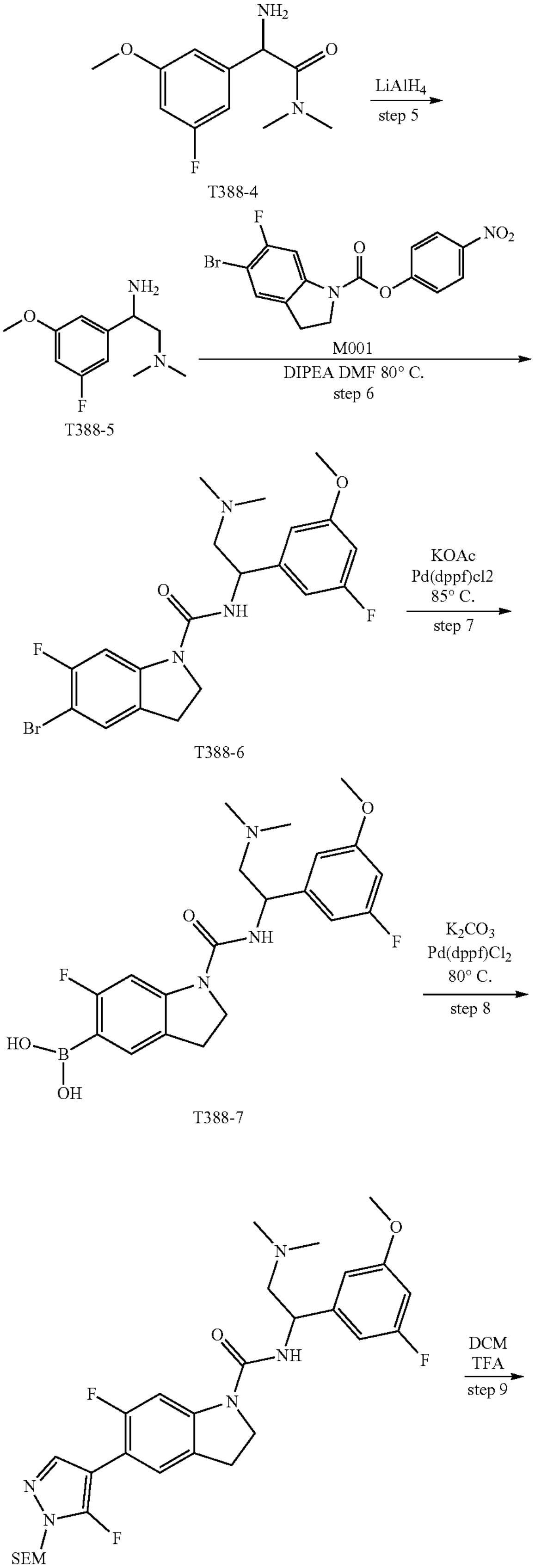

T388-4

T388-5

T388-6

T388-7

T388-8

-continued

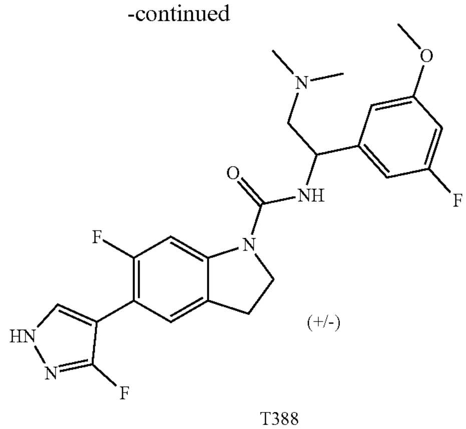

T388

1 Preparation of (+/−) 2-amino-2-(3-fluoro-5-methoxyphenyl)acetic acid (T388-1)

Ammonium chloride (3.50 g) and sodium cyanide (3.50 g) were dissolved in aqueous ammonia (120 mL) at 0° C., and a solution of 3-fluoro-5-methoxybenzaldehyde (10.00 g) in absolute methanol (60 mL) was slowly added dropwise. The mixture was stirred at room temperature for 4 h under nitrogen atmosphere. After the reaction was completed, the reaction solution was diluted with water (100 mL), concentrated by rotary evaporation to remove methanol and extracted with ethyl acetate (100 mL×3). The organic phases were combined, washed with saturated brine (200 mL), dried over anhydrous sodium sulfate, filtered and concentrated by rotary evaporation. The resulting crude product was dissolved in hydrochloric acid (6 N, 100 mL), and the mixture was heated to 115° C. and reacted for 12 h. After the reaction was completed, the reaction solution was concentrated under reduced pressure to give a brown oil (15.00 g, crude product). LC-MS $[M+H]^+$=199.9.

2 Preparation of (+/−) 2-((tert-butoxycarbonyl)amino)-2-(3-fluoro-5-methoxyphenyl)acetic acid (T388-2)

The (+/−) 2-amino-2-(3-fluoro-5-methoxyphenyl)acetic acid (crude product, 15.00 g) was dissolved in 1,4-dioxane (150 mL), and sodium hydroxide solution (2 N) was added at 0° C. to adjust the pH to 14, followed by addition of di-tert-butyl dicarbonate (18.09 g). The mixture was reacted at room temperature for 5 h under nitrogen atmosphere. After the reaction was completed, the reaction solution was concentrated under reduced pressure, saturated potassium hydrogen sulfate solution was added to adjust the pH to 4, and dichloromethane (50 mL×3) was added for extraction. The organic phases were combined, washed with saturated brine (200 mL), dried over anhydrous sodium sulfate, filtered and concentrated by rotary evaporation to give a brown oily liquid (15.00 g, crude product). LC-MS [M+Na]=322.2.

3 Preparation of (+/−) tert-butyl (2-(dimethylamino)-1-(3-fluoro-5-methoxyphenyl)-2-oxoethyl)carbamate (T388-3)

(+/−) 2-((tert-butoxycarbonyl)amino)-2-(3-fluoro-5-methoxyphenyl)acetic acid (15.00 g, crude product) was dissolved in anhydrous DMF (150 mL), and dimethylamine (2 M, dissolved in THF, 30.10 mL), HATU (22.87 g) and N,N-diisopropylethylamine (28.88 g) were added under nitrogen atmosphere. The mixture was reacted at room temperature for 4 h. After the reaction was completed, water (300 mL) was added, and ethyl acetate (200 mL×3) was added for extraction. The organic phases were combined, washed with saturated brine (300 mL×3), dried over anhydrous sodium sulfate, filtered and concentrated by rotary evaporation, and the resulting crude product was separated by silica gel column chromatography (PE/EA=4/1) to give a yellow solid (3.10 g, 14.6% three-step yield). LC-MS $[M+Na]^+$: 349.2.

4 Preparation of (+/−) 2-amino-2-(3-fluoro-5-methoxyphenyl)-N,N-dimethylacetamide (T388-4)

Compound T388-3 (3.10 g) was dissolved in dichloromethane (30 mL), and hydrochloric acid-1,4-dioxane solution (15 mL) was added. The mixture was reacted at room temperature for 12 h. After the reaction was completed, the reaction solution was diluted with water (30 mL) and extracted with dichloromethane (30 mL×2). The aqueous phase was adjusted to PH=10 with aqueous sodium hydroxide solution (2 N) and extracted with dichloromethane (30 mL×2). The organic phases were combined, washed with saturated brine (60 mL), dried over anhydrous sodium sulfate, filtered and concentrated by rotary evaporation to give a yellow solid (2.50 g. crude product). LC-MS $[M+H]^+$= 226.9.

Preparation of (+/−) 1-(3-fluoro-5-methoxyphenyl)-N2,N2-dimethylethane-1,2-diamine (T388-5) Lithium aluminum hydride (992 mg) was added into anhydrous tetrahydrofuran (30 mL) under nitrogen atmosphere, and compound T388-4 (2.50 g) was added at 0° C. The mixture was reacted at 40° C. for 2 h. After the reaction was completed, the reaction solution was cooled to 0° C., and sodium sulfate decahydrate was added. The resulting mixture was stirred for 1 h and filtered, and the filtrate was concentrated by rotary evaporation to give a yellow oily liquid (1.50 g, crude product). LC-MS $[M+H]^+$=212.8.

6 Preparation of (+/−) 5-bromo-N-(2-(dimethylamino)-1-(3-fluoro-5-methoxyphenyl)ethyl)-6-fluoroindoline-1-carboxamide (T388-6)

Compound T388-5 (1.50 g) and M001 (3.22 g) were dissolved in anhydrous DMF (30 mL), and N,N-diisopropylethylamine (3.65 g) was added. The mixture was reacted at 80° C. for 5 h. The reaction solution was cooled to room temperature, water (60 mL) was added, and ethyl acetate (30 mL×3) was added for extraction. The organic phases were combined, washed with saturated brine (30 mL 2), dried over anhydrous sodium sulfate, filtered and concentrated by rotary evaporation, and the resulting crude product was separated by silica gel column chromatography (DCM: MeOH=25/1) to give a brown solid (900 mg, 21% three-step yield). LC-MS $[M+H]^+$: 453.2.

7 Preparation of (+/−) (1-((2-(dimethylamino)-1-(3-fluoro-5-methoxyphenyl)ethyl)carbamoyl)-6-fluoroindolin-5-yl)boronic acid (T388-7)

Compound T388-6 (900 mg) was dissolved in anhydrous 1,4-dioxane (10 mL), and bis(pinacolato)diboron (754 mg), potassium acetate (388 mL) and [1,1'-bis(diphenylphosphino)ferrocene]dichloropalladium(II) (145 mg) were added under nitrogen atmosphere. The mixture was reacted at 85° C. for 4 h. The reaction solution was cooled to room temperature and filtered, water (10 mL) was added, and ethyl acetate (10 mL×3) was added for extraction. The organic phases were combined, washed with saturated brine (30 mL×3), dried over anhydrous sodium sulfate, filtered and concentrated by rotary evaporation, and the resulting crude product was subjected to preparative chromatography to give a white solid (30 mg, 4% yield). LC-MS $[M+H]^+$=419.7.

8 (+/−)N-(2-(dimethylamino)-1-(3-fluoro-5-methoxyphenyl)ethyl)-6-fluoro-5-(5-fluoro-1-((2-(trimethylsilyl)ethoxy)methyl)-1H-pyrazol-4-yl) indoline-1-formamide (T388-8)

Compound T388-7 (30 mg) was dissolved in 1,4-dioxane (2 mL) and water (0.4 mL), and N-(1-(3,5-difluorophenyl)-2-(di methyl amino)ethyl)-6-fluoro-5-(4,4,5,5-tetramethyl-1,3,2-dioxaborolan-2-yl)indoline-1-carboxamide (25 mg), potassium carbonate (20 mg) and [1,1'-bis(diphenylphosphino)ferrocene]dichloropalladium(II) (6 mg) were added under nitrogen atmosphere. The mixture was reacted at 80° C. for 3 h. the reaction solution was cooled to room temperature and filtered, water (10 mL) was added, and ethyl acetate (10×3) was added for extraction. The organic phases were combined, washed with saturated brine (20 mL), dried over anhydrous sodium sulfate, filtered and concentrated by rotary evaporation, and the resulting crude product was separated by silica gel column chromatography (DCM:MeOH=20/1) to give a brown solid (22 mg, 52% yield). LC-MS $[M+H]^+$: 589.8.

9 Preparation of (+/−)N-(2-(dimethylamino)-1-(3-fluoro-5-methoxyphenyl)ethyl)-6-fluoro-5-(3-fluoro-1H-pyrazol-4-yl)indoline-1-carboxamide (T388)

Compound T388-8 (22 mg) was dissolved in anhydrous dichloromethane (3 mL), and trifluoroacetic acid (1 mL) was added. The mixture was reacted at room temperature for 2 h. After the reaction was completed, water (5 mL) was added, and dichloromethane (5 mL×2) was added for extraction. The aqueous phase was adjusted to pH=10 with aqueous sodium hydroxide solution (2 N) and extracted with dichloromethane (5 mL×2). The organic phases were combined, washed with saturated brine (10 mL×2), dried over anhydrous sodium sulfate, filtered and concentrated by rotary evaporation, and the resulting crude product was subjected to preparative chromatography to give a white solid (2.1 mg, 12% yield). LC-MS $[M+H]^+$=454.9.

$^1$H NMR (400 MHz, MeOD) δ 7.81-7.76 (m, 1H), 7.66 (d, J=12.8 Hz, 1H), 7.41 (d, J=7.4 Hz, 1H), 6.85 (s, 1H), 6.83-6.78 (m, 1H), 6.68-6.62 (m, 1H), 4.61 (s, 2H), 4.29-4.00 (m, 3H), 3.81 (s, 3H), 3.25-3.15 (m, 2H), 2.72 (s, 6H).

Example 43: Preparation of Compound (S)—N-(1-(3-(cyclopentylcarbamoyl)-5-fluorophenyl)-2-hydroxyethyl)-6-fluoro-5-(1H-pyrazol-4-yl)indoline-1-carboxamide (T389-S)

Preparation of Compound (R)—N-(1-(3-(cyclopentylcarbamoyl)-5-fluorophenyl)-2-hydroxyethyl)-6-fluoro-5-(1H-pyrazol-4-yl)indoline-1-carboxamide (T389-R)

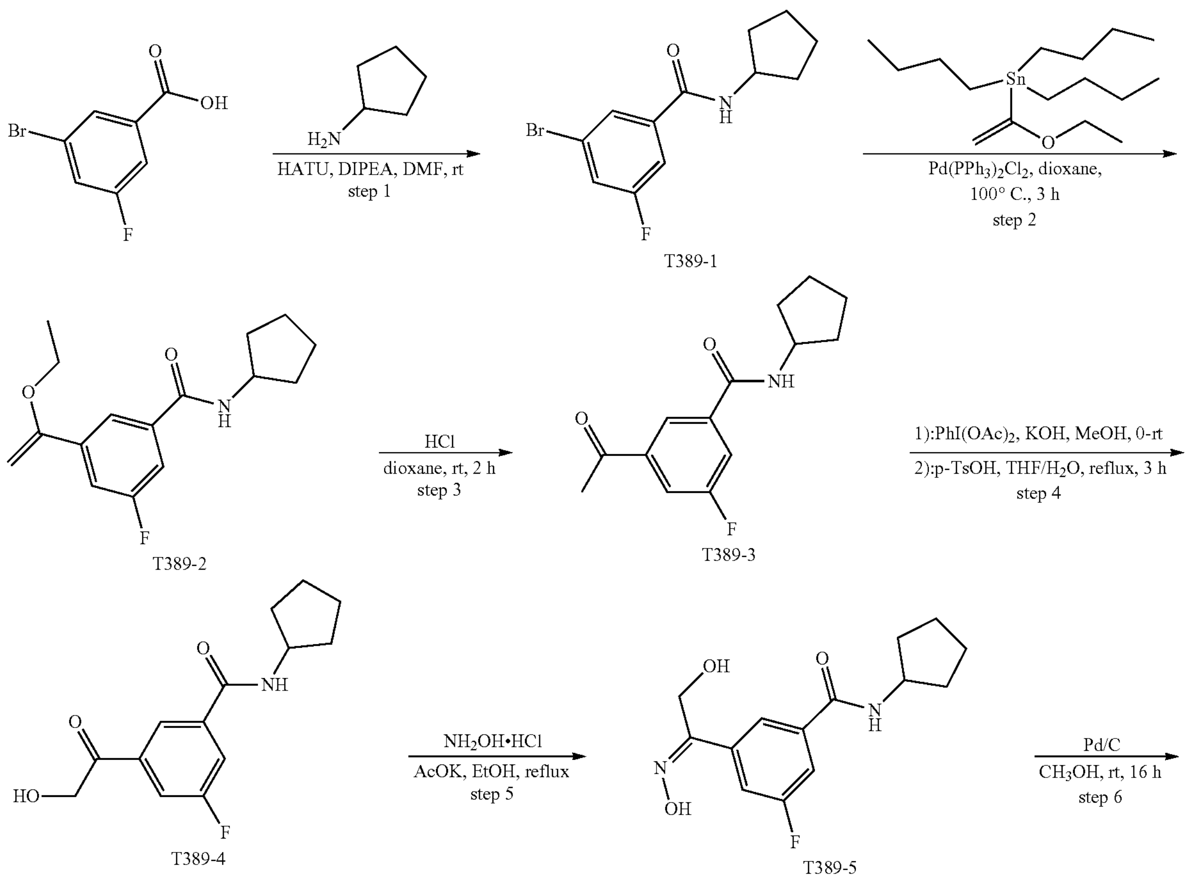

T389-1

T389-2

T389-3

T389-4

T389-5

-continued
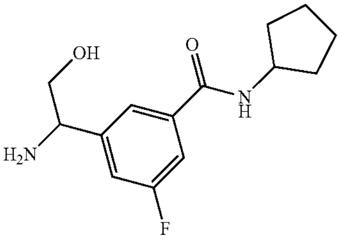
T389-6
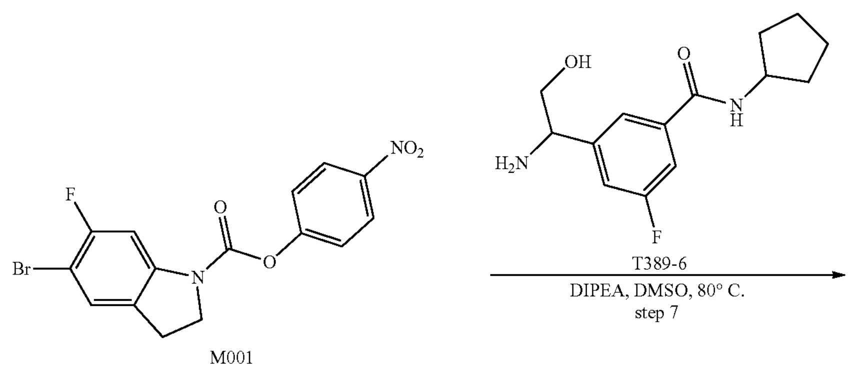
M001
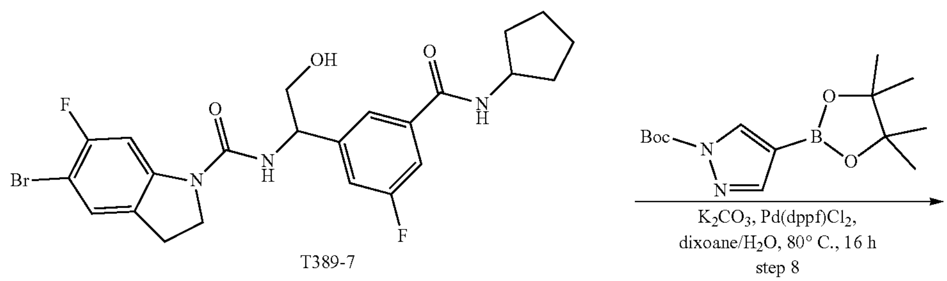
T389-7
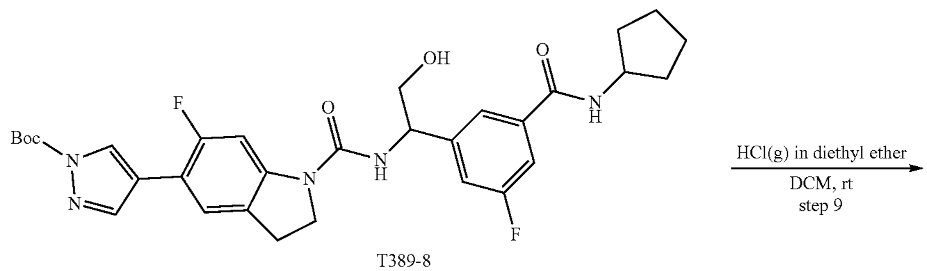
T389-8
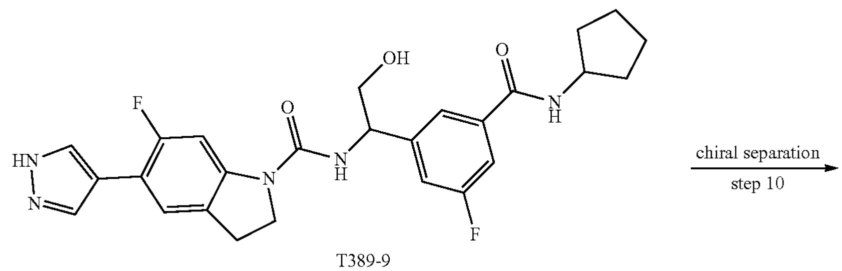
T389-9
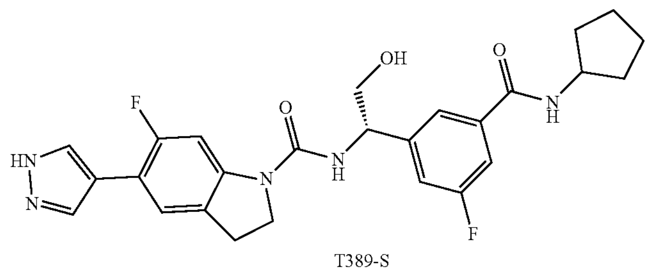
T389-S -continued

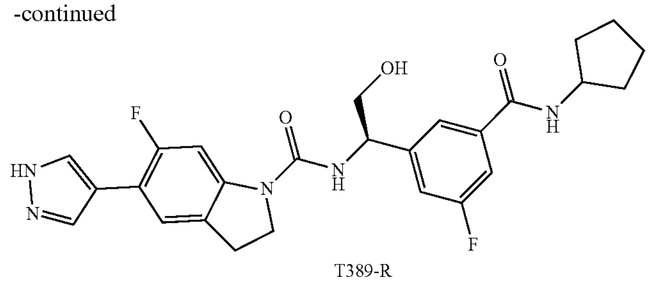

T389-R

1 Preparation of Compound 3-bromo-N-cyclopentyl-5-fluorobenzamide (T389-1)

3-bromo-5-fluorobenzoic acid (10.00 g) was dissolved in N,N-dimethylformamide (100 mL) under nitrogen atmosphere, and 2-(7-azabenzotriazol-1-yl)-N,N,N',N'-tetramethyluronium hexafluorophosphate (26.22 g) was added. The mixture was stirred at room temperature for 10 min, followed by addition of cyclopentylamine (4.70 g) and N,N-diisopropylethylamine (17.80 g). The resulting mixture was stirred at room temperature for 3 h. Water (400 mL) was added to quench the reaction, and ethyl acetate (100 mL×2) was added for extraction. The organic phases were combined, washed with saturated brine (100 mL×3), dried over anhydrous sodium sulfate, filtered and concentrated. The resulting crude product was purified by silica gel column chromatography (petroleum ether:dichloromethane=10:1) to give a white solid (8.30 g, 64% yield). MS $[M+H]^+$=285.8/287.8.

2 Preparation of Compound N-cyclopentyl-3-(1-ethoxyvinyl)-5-fluorobenzamide (T389-2)

Compound T389-1 (3.00 g) and tributyl(1-ethoxyvinyl) stannane (4.55 g) were dissolved in dioxane (36 mL), and bis(triphenylphosphine)palladium(II) dichloride (0.59 g) was added. The mixture was reacted at 100° C. for 3 h under nitrogen atmosphere. The reaction solution was concentrated under reduced pressure, and the resulting crude product was purified by silica gel column chromatography (petroleum ether:ethyl acetate=20:1-5:1) to give a pale yellow solid (2.00 g, 69.0% yield). MS $[M+H]^+$=277.9.

3 Preparation of Compound 3-acetyl-N-cyclopentyl-5-fluorobenzamide (T389-3)

Compound T389-2 (1.80 g) was dissolved in dioxane (20 mL), and diluted hydrochloric acid (19.50 mL) was added. The mixture was stirred at room temperature for 2 h. The reaction solution was poured into ethyl acetate (60 mL), washed successively with water (30 mL 2), saturated sodium bicarbonate (20 mL) and saturated brine (30 mL), dried over anhydrous sodium sulfate, filtered and concentrated. The resulting crude product was purified by silica gel column chromatography (petroleum ether:ethyl acetate=5:1) to give a pale yellow solid (1.50 g, 93.0% yield). MS $[M+H]^+$=249.9.

4 Preparation of Compound N-cyclopentyl-3-fluoro-5-(2-hydroxyacetyl)benzamide (T389-4)

Compound T389-3 (1.50 g) was dissolved in methanol (20 mL), and potassium hydroxide (1.35 g) and iodobenzene diacetic acid (2.90 g) were added successively under an ice water bat. The mixture was stirred at room temperature for 3 h. The reaction solution was diluted with water (40 mL), concentrated by rotary evaporation under reduced pressure to remove methanol, and extracted with ethyl acetate (20 mL×2). The organic phases were combined, washed with saturated brine (10 mL) and concentrated under reduced pressure to give a crude product. The crude product above was dissolved in tetrahydrofuran (15 mL) and water (5 mL), and p-toluenesulfonic acid (1.24 g) was added. The mixture was refluxed for 4 h under nitrogen atmosphere. The reaction solution was diluted with water (20 mL) and extracted with ethyl acetate (30 mL×2). The organic phases were combined, washed successively with saturated aqueous sodium bicarbonate solution (20 mL) and saturated brine (20 mL×2), dried over anhydrous sodium sulfate, filtered and concentrated. The resulting crude product was purified by silica gel column chromatography (petroleum ether:ethyl acetate=10:1-5:1) to give a white solid (1.10 g, 69.2% yield). MS $[M+H]^+$=265.9.

5 Preparation of Compound (E)-N-cyclopentyl-3-fluoro-5-(2-hydroxy-1-(hydroxyimino)ethyl)benzamide (T389-5)

Compound T389-4 (1.10 g) was dissolved in ethanol (20 mL), and potassium acetate (0.48 g) and hydroxylamine hydrochloride (0.34 g) were added. The mixture was heated to 80° C. and reacted for 3 h. The reaction solution was concentrated under reduced pressure to give a greyish-white solid (1.90 g), which was directly used in the next step. MS $[M+H]^+$=280.9.

6 Preparation of Compound 3-(1-amino-2-hydroxyethyl)-N-cyclopentyl-5-fluorobenzamide (T389-6)

Compound T389-5 (1.90 g, crude product) was dissolved in methanol (40 mL), wet Pd/C (10%, 0.50 g) was added, and hydrogen was introduced. The mixture was stirred at room temperature for 16 h. Saturated aqueous sodium bicarbonate solution (2 mL) was added. The mixture was stirred and filtered, and the filtrate was concentrated. The resulting crude product was purified by silica gel column chromatography (dichloromethane:(ethanol:aqueous ammonia=8:1)=6:1) to give a white solid (0.90 g, 82.5% two-step yield). MS $[M+H]^+$=267.0.

7 Preparation of Compound 5-bromo-N-(1-(3-(cyclopentylcarbamoyl)-5-fluorophenyl)-2-hydroxyethyl)-6-fluoroindoline-1-carboxamide (T389-7)

Compound M001 (0.96 g) and compound T389-6 (0.67 g) were dissolved in dimethyl sulfoxide (15 mL), and N,N-diisopropylethylamine (1.30 g) was added. The mixture was reacted at 80° C. for 16 h under nitrogen atmosphere. The reaction solution was poured into water (50 mL), and ethyl acetate (30 mL×2) was added for extraction. The organic phases were combined, washed with saturated brine (20 mL×3), dried over anhydrous sodium sulfate, filtered and concentrated. The resulting crude product was purified by silica gel column chromatography (dichloromethane:(ethanol:aqueous ammonia=8:1)=10:1) to give a yellow solid (0.90 g, 70.3% two-step yield). MS $[M+H]^+$=507.6/509.6.

8 Preparation of Compound tert-butyl 4-(1-((1-(3-(cyclopentylcarbamoyl)-5-fluorophenyl)-2-hydroxyethyl)carbamoyl)-6-fluoroindolin-5-yl)-1H-pyrazole-1-carboxylate (T389-8)

Compound T389-7 (400 mg) and tert-butyl 4-(4,4,5,5-tetramethyl-1,3,2-dioxaborolan-2-yl)-1H-pyrazole-1-carboxylate (350 mg) was dissolved in dioxane (8 mL), and a solution of potassium carbonate (273 mg) in water (1 mL) and [1,1'-bis(diphenylphosphino)ferrocene]dichloropalladium(II) (58 mg) were added. The mixture was reacted at 80° C. for 16 h under nitrogen atmosphere. The reaction solution was filtered, and the organic phase was concentrated by rotary evaporation. The resulting crude product was purified by silica gel column chromatography (ethyl acetate:dichloromethane=1:10) to give a pale yellow solid (200 mg, 42.5% yield). MS $[M+H]^+$=595.8.

9 Preparation of Compound N-(1-(3-(cyclopentylcarbamoyl)-5-fluorophenyl)-2-hydroxyethyl)-6-fluoro-5-(1H-pyrazol-4-yl)indoline-1-carboxamide (T389)

Compound T389-8 (200 mg) was dissolved in dichloromethane (2 mL), and a solution of hydrogen chloride in ether (4 N, 1 mL) was added. The mixture was stirred at room temperature for 16 h. The reaction solution was concentrated under reduced pressure, and the residue was purified by preparative chromatography (acetonitrile/0.1% trifluoroacetic acid-water/0.1% trifluoroacetic acid) to give a white solid (50 mg, 39.7% yield). MS $[M+H]^+$=495.8.

10 Preparation of Compound (S)—N-(1-(3-(cyclopentylcarbamoyl)-5-fluorophenyl)-2-hydroxyethyl)-6-fluoro-5-(1H-pyrazol-4-yl)indoline-1-carboxamide (T389-S)

Preparation of Compound (R)—N-(1-(3-(cyclopentylcarbamoyl)-5-fluorophenyl)-2-hydroxyethyl)-6-fluoro-5-(1N-pyrazol-4-yl)indoline-1-carboxamide (T389-R)

Compound T389-9 (50 mg) was dissolved in dimethyl sulfoxide (3 mL) and methanol (2 mL), and the mixture was separated by SFC chiral preparative chromatography (mobile phase: carbon dioxide-methanol (aqueous ammonia)) and lyophilized to give T389-S in the form of a white solid (18.1 mg). The lyophilized T389-R was dissolved in dichloromethane (10 mL), and sodium carbonate solution (2 mL) was added. A large amount of solid was precipitated out, and the mixture was filtered. The filter cake was lyophilized to give T389-R (9.9 mg). MS $[M+H]^+$=496.0.

T389-S: $^1$H NMR (400 MHz, DMSO-d6) δ 12.95 (s, 1H), 8.35 (d, J=7.2 Hz, 1H), 8.03 (s, 1H), 7.84 (s, 1H), 7.72 (d, J=1.5 Hz, 1H), 7.57 (d, J=13.2 Hz, 1H), 7.54-7.51 (m, 1H), 7.50 (d, J=8.1 Hz, 1H), 7.40 (dt, J=9.9, 2.0 Hz, 1H), 6.94 (d, J=7.7 Hz, 1H), 4.98 (t, J=5.9 Hz, 1H), 4.91 (q, J=7.0 Hz, 1H), 4.22 (q, J=7.0 Hz, 1H), 4.16-4.01 (m, 2H), 3.73-3.62 (m, 2H), 3.16 (t, J=8.5 Hz, 2H), 1.96-1.82 (m, 2H), 1.77-1.64 (m, 2H), 1.60-1.50 (m, 4H).

T389-R: $^1$H NMR (400 MHz, DMSO-d6) δ 12.85 (s, 1H), 8.36 (d, J=7.3 Hz, 1H), 7.94 (s, 2H), 7.72 (s, 1H), 7.57 (d, J=13.1 Hz, 1H), 7.54-7.51 (m, 1H), 7.50 (d, J=8.1 Hz, 1H), 7.40 (dt, J=9.8, 2.0 Hz, 1H), 6.94 (d, J=7.7 Hz, 1H), 4.99 (t, J=5.9 Hz, 1H), 4.91 (q, J=7.0 Hz, 1H), 4.23 (p, J=6.8 Hz, 1H), 4.16-4.03 (m, 2H), 3.73-3.63 (m, 2H), 3.16 (t, J=8.6 Hz, 2H), 1.94-1.84 (m, 2H), 1.75-1.65 (m, 2H), 1.60-1.49 (m, 4H).

Example 44: Preparation of Compounds (S)—N-(1-(3-(cyclopentylcarbamoyl)phenyl)-2-hydroxyethyl)-6-fluoro-5-(1H-pyrazol-4-yl)indoline-1-carboxamide (T356-S) and (R)—N-(1-(3-(cyclopentylcarbamoyl)phenyl)-2-hydroxyethyl)-6-fluoro-5-(1H-pyrazol-4-yl)indoline-1-carboxamide (T356-R)

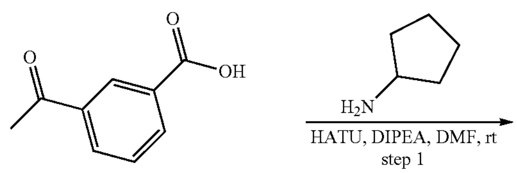

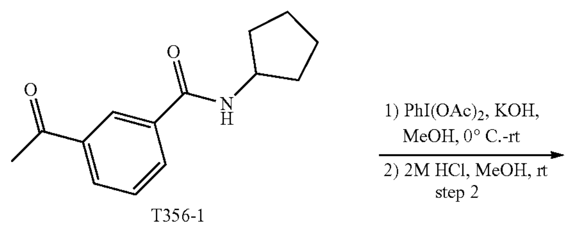

T356-1

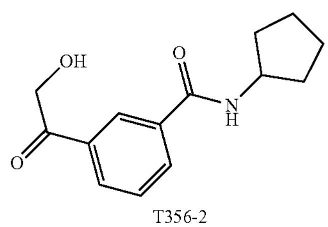

T356-2

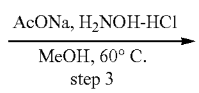

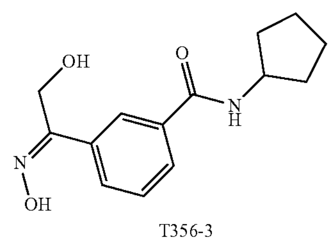

T356-3

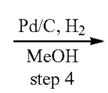

-continued
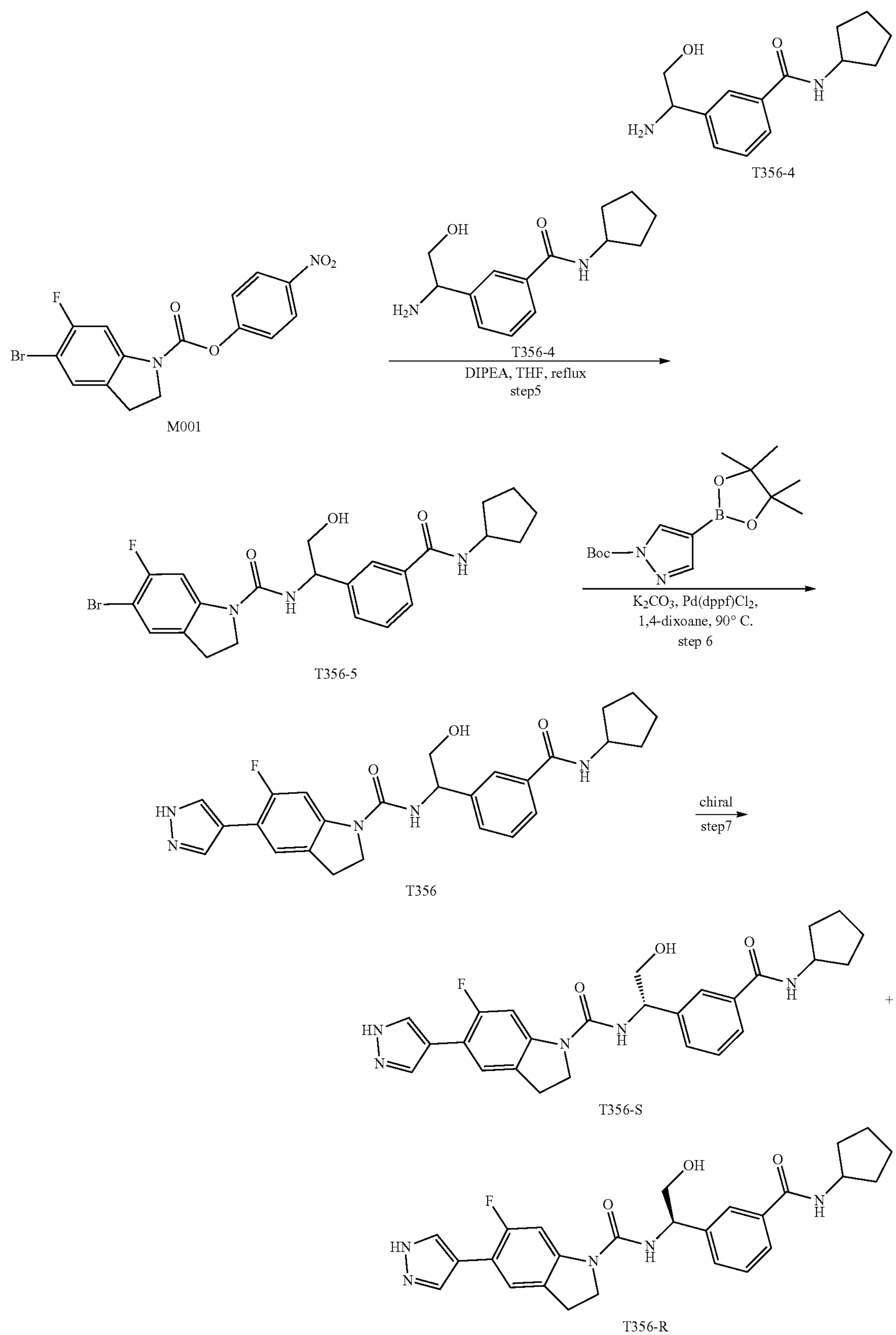
T356-4
T356-4
M001
T356-5
T356
T356-S
+
T356-R

1 Preparation of Compound 3-acetyl-N-cyclopentylbenzamide (T356-1)

3-acetylbenzoic acid (5.00 g) was dissolved in anhydrous DMF (50 mL) under nitrogen atmosphere, and 2-(7-azabenzotriazol-1-yl)-N,N,N',N'-tetramethyluronium hexafluorophosphate (17.40 g) was added. The mixture was reacted at room temperature for 10 min, followed by successive addition of N,N-diisopropylethylamine (11.80 g) and cyclopentylamine (3.90 g). The resulting mixture was reacted overnight at room temperature. Water (200 mL) was added to quench the reaction, and ethyl acetate (60 mL×3) was added for extraction. The organic phases were combined, washed with saturated brine (80 mL×2), dried over anhydrous sodium sulfate, filtered and concentrated. The resulting crude product was purified by silica gel column chromatography (petroleum ether:ethyl acetate=10:1) to give a yellow solid (6.00 g, 85.7% yield). MS $[M+H]^+$=232.1.

2 Preparation of Compound N-cyclopentyl-3-(2-hydroxyacetyl)benzamide (T356-2)

Compound T356-1 (6.00 g) was dissolved in absolute methanol (60 mL), and iodobenzene diacetic acid (9.18 g) and potassium hydroxide (7.99 g) were added at 0° C. The mixture was reacted at room temperature for 30 min. Water (100 mL) was added, and ethyl acetate (100 mL×3) was added for extraction. The organic phases were combined, washed with saturated brine (50 mL×2), dried over anhydrous sodium sulfate, filtered and concentrated, and the resulting crude product was dissolved in absolute methanol (30 mL) and diluted hydrochloric acid (2 M, 30 mL). The mixture was stirred overnight at room temperature. Water (100 mL) was added, and ethyl acetate (100 mL×3) was added for extraction. The organic phases were combined, washed with saturated brine (50 mL×2), dried over anhydrous sodium sulfate, filtered and concentrated. The resulting crude product was purified by silica gel column chromatography (petroleum ether:ethyl acetate=1:1) to give a white solid (4.90 g, 76.6% yield). MS $[M+H]^+$=248.0.

3 Preparation of Compound (E)-N-cyclopentyl-3-(2-hydroxy-1-(hydroxyimino)ethyl)benzamide (T356-3)

Compound T356-2 (4.90 g) was dissolved in absolute methanol (50 mL), and sodium acetate (3.23 g) and hydroxylamine hydrochloride (2.20 g) were added under nitrogen atmosphere. The mixture was reacted at 60° C. for 3 h. After the reaction was completed, the reaction solution was cooled to room temperature, filtered and concentrated by rotary evaporation to give compound T356-3 in the form of an anhydrous oil (5.0 g, crude product). MS $[M+H]^+$=263.0.

4 Preparation of Compound 3-(1-amino-2-hydroxyethyl)-N-cyclopentylbenzamide (T356-4)

Compound T356-3 (5.0 g, crude product) was dissolved in absolute methanol (50 mL), Pd/C (1.0 g) was added, and hydrogen was introduced. The mixture was stirred overnight at room temperature. After the reaction was completed, saturated aqueous sodium bicarbonate solution (2 mL) was added. The mixture was stirred and filtered, and the filtrate was concentrated. The resulting crude product was purified by silica gel column chromatography (dichloromethane: (ethanol:aqueous ammonia=8:1)=6:1) to give compound T356-4 (3.20 g, 65.2% two-step yield). MS $[M+H]^+$=263.0.

5 Preparation of Compound 5-bromo-N-(1-(3-(cyclopentylcarbamoyl)phenyl)-2-hydroxyethyl)-6-fluoroindoline-1-carboxamide (T356-5)

Compound M001 (460 mg) was dissolved in anhydrous tetrahydrofuran (5 mL), and compound T356-4 (334 mg) and N,N-diisopropylethylamine (434 mg) were added. The mixture was heated under reflux overnight. The reaction solution was cooled to room temperature, and then water (20 mL) was added and ethyl acetate (30 mL×3) was added for extraction. The organic phases were combined, washed with saturated brine (30 mL×2), dried over anhydrous sodium sulfate, filtered and concentrated. The resulting crude product was purified by silica gel column chromatography (petroleum ether:ethyl acetate=1:1) to give compound T356-5 in the form of a yellow oil (350 mg, 50.9% yield). MS $[M+H]^+$=490.1/492.1.

6 Preparation of Compound N-(1-(3-(cyclopentylcarbamoyl)phenyl)-2-hydroxyethyl)-6-fluoro-5-(1H-pyrazol-4-yl)indoline-1-carboxamide (T356)

Compound T356-5 (350 mg) was dissolved in 1,4-dioxane (3 mL) and water (0.5 mL), and tert-butyl 4-(4,4,5,5-tetramethyl-1,3,2-dioxaborolan-2-yl)-1H-pyrazole-1-carboxylate (253 mg), potassium carbonate (197 mg) and [1,1'-bis(di phenyl phosphino)ferrocene]dichloropalladium (11) (52 mg) were added under nitrogen atmosphere. The mixture was reacted at 90° C. for 3 h. The reaction solution was cooled to room temperature, and then water (10 mL) was added and ethyl acetate (50 mL×3) was added for extraction. The organic phases were combined, washed with saturated brine (50 mL×2), dried over anhydrous sodium sulfate, filtered and concentrated. The resulting crude product was purified by silica gel column chromatography (dichloromethane:methanol=80:1) to give compound T356 in the form of a yellow solid (110 mg, 32.3% two-step yield). MS $[M+H]^+$=478.1.

7 Preparation of Compounds (S)—N-(1-(3-(cyclopentylcarbamoyl)phenyl)-2-hydroxyethyl)-6-fluoro-5-(1H-pyrazol-4-yl)indoline-1-carboxamide (T356-S) and (R)—N-(1-(3-(cyclopentylcarbamoyl)phenyl)-2-hydroxyethyl)-6-fluoro-5-(1H-pyrazol-4-yl)indoline-1-carboxamide (T356-R)

Compound T356 (110 mg) was subjected to chiral resolution (chiral column: SP-120-10-C18-BIO-C18; flow rate: 12.5 g/min; mobile phase B: CO2; mobile phase A: MeOH; retention time A1: 5.38 min, A2: 9.30 min). The products were collected separately, concentrated by rotary evaporation and lyophilized to give T356-S (32.0 mg) and T356-R (38.4 mg).

T356-S: LC-MS $[M+H]^+$=478.1.

$^1$H NMR (400 MHz, DMSO) δ 12.96 (s, 1H), 8.27 (d, J=7.3 Hz, 1H), 8.03 (s, 1H), 7.84 (s, 2H), 7.70 (d, J=7.7 Hz, 1H), 7.57 (d, J=13.2 Hz, 1H), 7.51 (dd, J=14.2, 7.8 Hz, 2H), 7.39 (t, J=7.7 Hz, 1H), 6.94 (d, J=7.8 Hz, 1H), 4.96-4.87 (m, 2H), 4.25-4.20 (m, 1H), 4.12-4.07 (m, 2H), 3.73-3.60 (m, 2H), 3.16 (t, J=8.5 Hz, 2H), 1.93-1.86 (m, 2H), 1.74-1.67 (m, 2H), 1.55-1.51 (m, 4H).

T356-R: LC-MS $[M+H]^+$=478.1.

$^1$H NMR (400 MHz, DMSO) δ 12.96 (s, 1H), 8.27 (d, J=7.3 Hz, 1H), 7.94 (s, 2H), 7.84 (s, 1H), 7.70 (d, J=7.7 Hz,

1H), 7.57 (d, J=13.2 Hz, 1H), 7.51 (dd, J=14.2, 7.9 Hz, 2H), 7.39 (t, J=7.7 Hz, 1H), 6.95 (d, J=7.7 Hz, 1H), 4.96 (t, J=5.8 Hz, 1H), 4.93-4.85 (m, 1H), 4.25-4.20 (m, 1H), 4.12-4.07 (m, 2H), 3.74-3.58 (m, 2H), 3.16 (t, J=8.3 Hz, 2H), 1.93-1.84 (m, 2H), 1.74-1.67 (m, 2H), 1.58-1.49 (m, 4H).

Example 45: Preparation of Compound N-(2-amino-1-(3-fluoro-5-methoxyphenyl)ethyl)-6-fluoro-5-(1H-pyrazol-4-yl)indoline-1-carboxamide (T371)

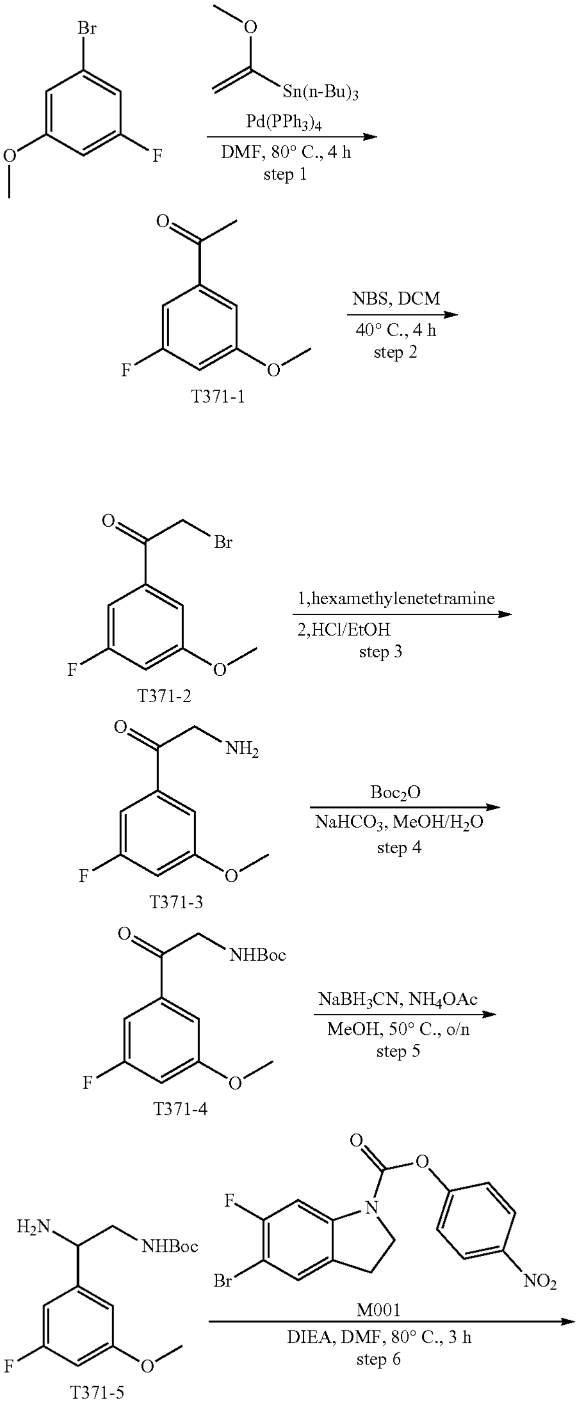

T371-1

T371-2

T371-3

T371-4

T371-5

-continued

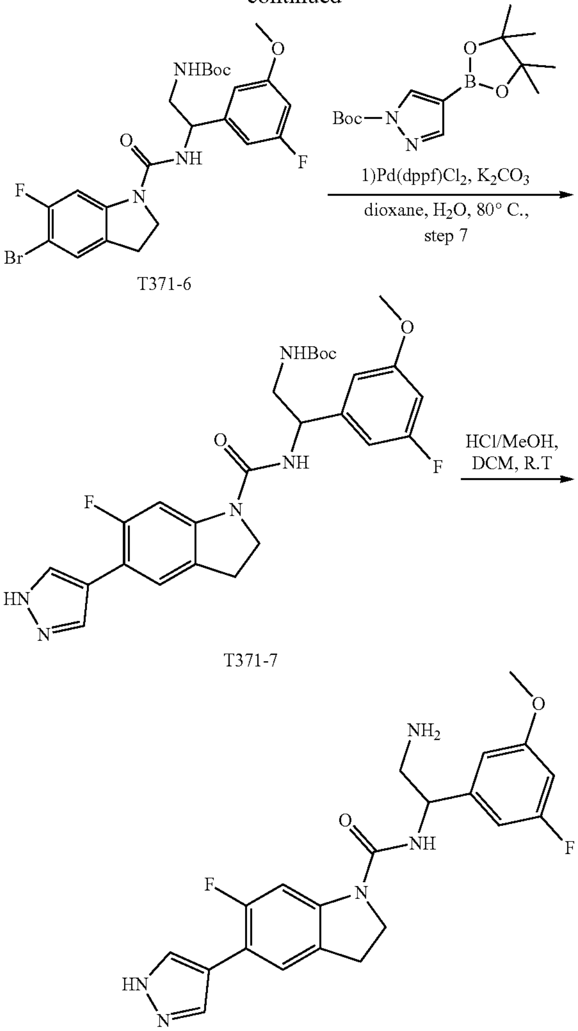

T371-6

T371-7

T371

1 Preparation of Compound 1-(3-fluoro-5-methoxyphenyl)ethan-1-one (T371-1)

1-bromo-3-fluoro-5-methoxybenzene (5 g) was dissolved in anhydrous 1,4-dioxane (50 mL), and tributyl(1-methoxyvinyl)stannane (10.57 g) and tetrakis(triphenylphosphine)palladium(0) (2.82 g) were added. The mixture was heated at 80° C. for 4 h. The reaction solution was filtered, and the filtrate was concentrated by rotary evaporation. The resulting crude product was purified by silica gel column chromatography (40 g, petroleum ether:ethyl acetate=50:1) to give product T371-1 (1.41 g, 34.41% yield).

$^1$H NMR (301 MHz, DMSO) δ 7.33-7.23 (m, 2H), 7.10 (dt, J=10.7, 2.3 Hz, 1H), 3.81 (s, 3H), 2.55 (s, 3H).

2 Preparation of Compound 2-bromo-1-(3-fluoro-5-methoxyphenyl)ethan-1-one (T371-2)

Compound T371-1 (1.4 g) was dissolved in anhydrous dichloromethane (30 mL), and N-bromosuccinimide (1.48 g) and p-toluenesulfonic acid (72 mg) were added. The mixture was heated at 40° C. for 4 h. After the reaction was completed, the reaction solution was cooled to room temperature and concentrated by rotary evaporation. The resulting crude product was purified by silica gel column chromatography (40 g, dichloromethane:ethyl acetate=10:1) to give T371-2 in the form of a pale yellow solid (1.21 g, 58.42% yield). LC-MS $[M+H]^+$: 246.9.

3 Preparation of Compound 2-amino-1-(3-fluoro-5-methoxyphenyl)ethan-1-one (T371-3)

Compound T371-2 (1.2 g) and urotropin (749 mg) were dissolved in anhydrous dichloromethane (20 mL), and the mixture was stirred overnight at room temperature. The reaction solution was filtered, and the filter cake was dried in vacuum and then dissolved in a mixed solution of methanol (20 mL) and concentrated hydrochloric acid (1 mL). The mixture was stirred at 60° C. for 3 h. After the reaction was completed as detected by TLC, the reaction solution was cooled to room temperature and concentrated by rotary evaporation (the residue was directly used in the next step) to give 2-amino-1-(3-fluoro-5-methoxyphenyl) ethane-1-one hydrochloride in the form of a white solid (1.2 g). LC-MS $[M+H]^+$: 184.0.

4 Preparation of Compound tert-butyl (2-(3-fluoro-5-methoxyphenyl)-2-oxoethyl)carbamate (T371-4)

Compound T371-3 (890 mg) was dissolved in methanol (8 mL), and saturated aqueous sodium carbonate solution (8 mL) and Boc-anhydride (1.27 g) were added. The mixture was stirred at room temperature for 3 h. After the reaction was completed as detected by a dot plate, the reaction solution was extracted with ethyl acetate (20 mL×3). The organic phases were combined, washed with saturated brine (30 mL×3), dried over sodium sulfate, filtered and concentrated by rotary evaporation, and the residue was purified by silica gel column chromatography (petroleum ether:ethyl acetate=20:1) to give product T371-4 in the form of a white solid (450 mg, 30.43% yield). LC-MS $[M+H]^+$: 284.0.

5 Preparation of Compound tert-butyl (2-amino-2-(3-fluoro-5-methoxyphenyl)ethane) carbamate (T371-5)

Compound T371-4 (450 mg) was dissolved in methanol (15 mL), and sodium cyanoborocyanide (1.03 g) and ammonium acetate (1.22 g) were added. The mixture was stirred overnight at 50° C. After the reaction was completed, the reaction solution was cooled to room temperature, sodium hydroxide solution (1 N) was added to quench the reaction, and dichloromethane (20 mL×6) was added for extraction. The organic phases were combined, dried over sodium sulfate, filtered and concentrated by rotary evaporation, and the residue was purified by silica gel column chromatography (dichloromethane:methanol=12:1) to give product T371-5 in the form of a colorless oil (200 mg, 44.14% yield). LC-MS $[M+H]^+$: 285.0.

6 Preparation of Compound tert-butyl N-{2-[(5-bromo-6-fluoro-2,3-indoline-1-yl)carbonylamino]-2-(3-fluoro-5-methoxyphenyl)ethyl}carbamate (T371-6)

Compound T371-5 (200 mg) was dissolved in N,N-dimethylformamide (5 mL), and compound M001 (322 mg) and N,N-diisopropylethylamine (271 mg) were added. The mixture was stirred at 80° C. for 3 h. After the reaction was completed, water (20 mL) was added to quench the reaction, and ethyl acetate (15 mL×3) was added for extraction. The organic phases were combined, washed with saturated brine (20 mL×2), dried over sodium sulfate, filtered and concentrated by rotary evaporation, and the residue was purified by silica gel column chromatography (petroleum ether:ethyl acetate=2:1) to give the product T371-6 in the form of a deep yellow solid (210 mg, 57.04% yield). LC-MS $[M+H]^+$: 425.9.

7 Preparation of Compound N-(2-amino-1-(3-fluoro-5-methoxyphenyl)ethyl)-6-fluoro-5-(1H-pyrazol-4-yl)indoline-1-carboxamide (T371)

Compound T371-6 (50 mg), tert-butyl 4-(4,4,5,5-tetramethyl-1,3,2-dioxaborolan-2-yl)-1H-pyrazole-1-carboxylate (40 mg), [1,1'-bis(diphenylphosphino)ferrocene]dichloropalladium(II) (14 mg) and potassium carbonate (40 mg) were dissolved in a mixed solution of 1,4-dioxane (5 mL) and water (1 mL), and the mixture was stirred overnight at 80° C. under nitrogen atmosphere. After the reaction was completed, the reaction solution was filtered, and the filtrate was concentrated by rotary evaporation. The residue was purified by silica gel column chromatography (dichloromethane:methanol=20:1), and the resulting product was concentrated by rotary evaporation to give compound T371-7.

Compound T371-7 was then dissolved in a mixed solution of dichloromethane and hydrochloric acid/ethanol (dichloromethane:ethanol hydrochloride=3 mL/1 mL (v/v)). After the reaction was completed as detected, the reaction solution was concentrated by rotary evaporation, and the resulting crude product was subjected to preparative chromatography (chromatographic column: Gemini-C18, 150×21.2 mm, 5 um; mobile phase: ACN-$H_2O$ (0.05% $NH_3$); gradient: 30-40) and lyophilized to give compound T371 in the form of a white powdery solid (20.7 mg, 52.76% yield). LC-MS $[M+H]^+$: 414.0.

$^1$H NMR (301 MHz, DMSO) δ 12.97 (s, 1H), 7.93 (s, 2H), 7.52 (dd, J=21.4, 10.5 Hz, 2H), 6.93 (d, J=7.6 Hz, 1H), 6.76 (d, J=7.8 Hz, 2H), 6.67 (d, J=11.0 Hz, 1H), 4.71 (d, J=6.1 Hz, 1H), 4.10 (t, J=8.5 Hz, 2H), 3.75 (s, 3H), 3.14 (t, J=7.9 Hz, 2H), 2.82 (d, J=7.7 Hz, 2H).

Example 46: Preparation of Compound N-(3-methoxybenzyl)-6-(1H-pyrazol-4-yl)imidazo[1,5-a]pyridine-1-carboxamide (T361)

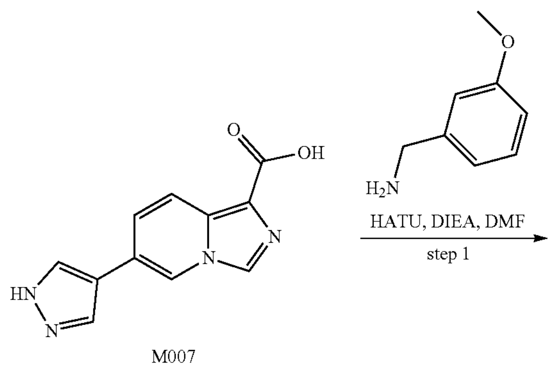

M007

-continued

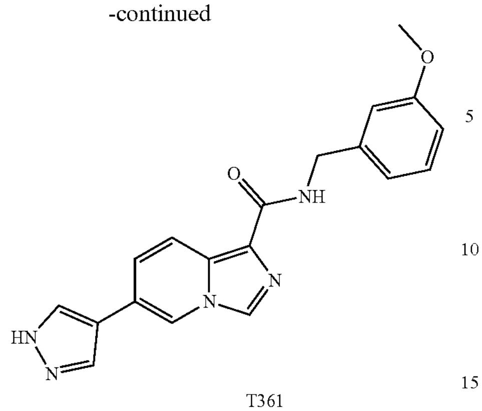

T361

Compound M007 (200 mg) was dissolved in anhydrous DMF (5 mL) under nitrogen atmosphere, and (3-methoxyphenyl)methylamine (120 mg), HATU (502 mg) and DIEA (341 mg) were added. The mixture was reacted at room temperature for 1 h. Water (15 mL) was added to quench the reaction, and ethyl acetate (15 mL×3) was added for extraction. The organic phase was washed with saturated brine (30 mL), dried over anhydrous sodium sulfate and concentrated under reduced pressure, and the residue was separated by silica gel column chromatography (DCM/MeOH=15/1) to give a white solid (15 mg). LC-MS $[M+H]^-$: 348.1.

$^1$H NMR (400 MHz, MeOD) δ 8.62 (s, 1H), 8.27 (s, 1H), 8.17 (d, J=9.4 Hz, 1H), 8.15-7.95 (m, 2H), 7.44 (d, J=9.1 Hz, 1H), 7.26-7.20 (m, 1H), 6.96 (s, 2H), 6.81 (d, J=8.3 Hz, 1H), 4.59 (s, 2H), 3.77 (s, 3H).

Example 47: Preparation of Compound N-(3-((dimethylamino)methyl)-5-fluorobenzyl)-6-(1H-pyrazol-4-yl)imidazo[1,5-a]pyridine-1-carboxamide (T360)

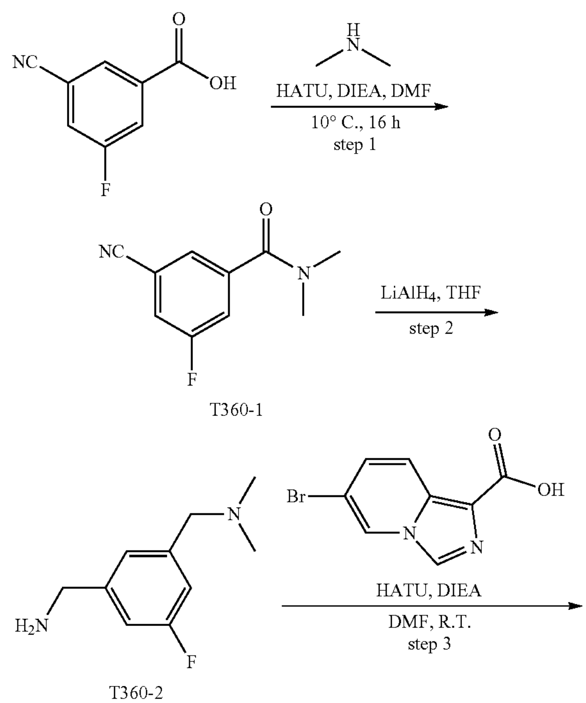

T360-1

T360-2

-continued

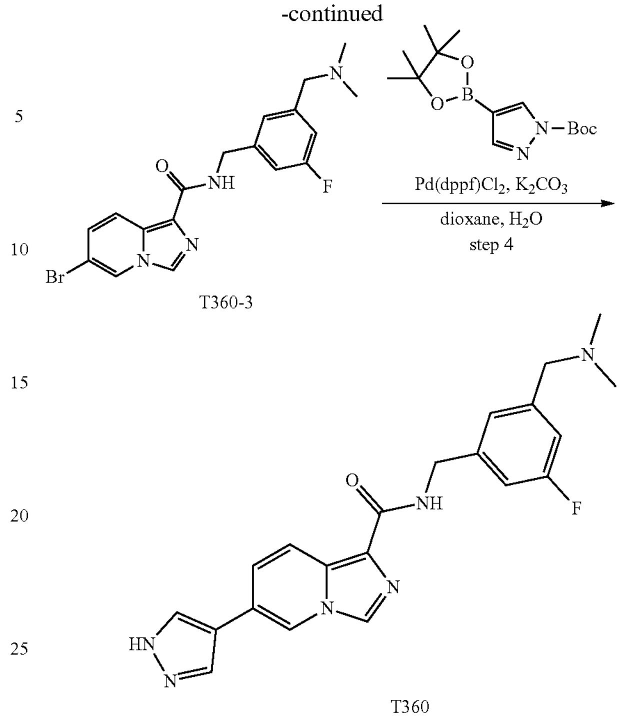

T360-3

T360

1 Preparation of Compound 3-cyano-5-fluoro-N,N-dimethylbenzamide (T360-1)

3-cyano-5-fluorobenzoic acid (1.5 g) was dissolved in anhydrous N,N-dimethylformamide (20 mL), and dimethylamine (6.9 mL), 2-(7-azabenzotriazol-1-yl) N,N,N',N'-tetramethyluronium hexafluorophosphate (5.18 g) and N,N-diisopropylethylamine (3.52 g) were successively added. The mixture was stirred at 10° C. for 16 h under nitrogen atmosphere. After the reaction was completed, water (20 mL) was added to quench the reaction, and ethyl acetate (30 mL×3) was added for extraction. The organic phases were combined, washed with saturated brine (30 mL×3), dried over anhydrous sodium sulfate and filtered, and the filtrate was concentrated by rotary evaporation. The resulting crude product was purified by silica gel column chromatography (petroleum ether:ethyl acetate=6:1) to give the product T360-1 in the form of a pale yellow solid (1.41 g, 79.80°/o yield). LC-MS $[M+H]^+$: 193.0.

2 Preparation of Compound 1-(3-(aminomethyl)-5-fluorophenyl)-N,N-dimethyl methyl amine (T360-2)

Compound T360-1 (1.41 g) was dissolved in anhydrous tetrahydrofuran (20 mL), and lithium aluminum hydride (1.39 g) was added at 0° C. The mixture was heated and stirred at 60° C. for 6 h under nitrogen atmosphere. After the reaction was completed, the reaction solution was cooled to room temperature and filtered, and the filtrate was concentrated by rotary evaporation. Saturated aqueous sodium carbonate solution was added to adjust the pH to 12, and ethyl acetate (20 mL×8) was added for extraction. The organic phases were combined, dried over anhydrous sodium sulfate, filtered and concentrated by rotary evaporation to give the product 1360-2 in the form of a pale yellow oil (crude product, 1.2 g, 89.70% yield). LC-MS $[M+H]^+$: 183.1.

3 Preparation of Compound 6-bromo-N-(3-((dimethyl amino)methyl)-5-fluorobenzyl)imidazo[1,5-a]pyridine-1-carboxamide (T360-3)

Compound T360-2 (300 mg) was dissolved in anhydrous N,N-dimethylformamide (10 mL), and 6-bromoimidazo[1,5-a]pyridine-1-carboxylic acid (595 mg), 2-(7-azabenzotriazol-1-yl)-N,N,N',N'-tetramethyluronium hexafluorophosphate (1.4 g) and N,N-diisopropylethylamine (851 mg) were successively added. The mixture was stirred overnight at room temperature under nitrogen atmosphere. After the reaction was completed, water (20 mL) was added to quench the reaction, and ethyl acetate (30 mL×3) was added for extraction. The organic phases were combined, washed with saturated brine (30 mL×3), dried over anhydrous sodium sulfate and filtered, and the filtrate was concentrated by rotary evaporation. The resulting crude product was purified by silica gel column chromatography (dichloromethane: methanol=20:1) to give the product T360-3 in the form of a white solid (410 mg, 61.35% yield). LC-MS $[M+H]^+$: 405.0.

4 Preparation of Compound N-(3-((dimethylamino)methyl)-5-fluorobenzyl)-6-(1H-pyrazol-4-yl)imidazo[1,5-a]pyridine-1-carboxamide (T360)

Compound T360-3 (410 mg) was dissolved in a mixed solution of dioxane (4 mL) and water (1 mL), and tert-butyl 4-(4,4,5,5-tetramethyl-1,3,2-dioxaborolan-2-yl)-1H-pyrazole-1-carboxylate (490 mg), [1,1'-bis(diphenylphosphino)ferrocene]dichloropalladium(II) (88 mg) and potassium carbonate (460 mg) were added. The mixture was stirred overnight at 80° C. The reaction solution was cooled to room temperature and then filtered to remove the precipitates, and the filtrate was concentrated by rotary evaporation. The residue was purified by silica gel column chromatography (wet loading, dichloromethane:methanol=10:1), concentrated by rotary evaporation and lyophilized to give product T360-4 in the form of a white powdery solid (95.7 mg, 21.93% yield). LC-MS $[M+H]^+$: 393.0.

$^1$H NMR (400 MHz, DMSO) δ 13.08 (s, 1H), 8.77 (t, J=1.2 Hz, 1H), 8.71 (s, 1H), 8.38 (s, 1H), 8.28 (s, 1H), 8.07 (d, J=9.4 Hz, 1H), 7.98 (s, 1H), 7.46 (dd, J=9.4, 1.4 Hz, 1H), 7.12 (s, 1H), 7.02 (d, J=9.7 Hz, 1H), 6.97 (d, J=9.6 Hz, 2H), 4.47 (d, J=6.4 Hz, 2H), 3.39 (s, OH), 2.15 (s, 6H).

Example 48: Preparation of Compound (R)-6-(5-fluoro-1H-pyrazol-4-yl)-N-(1-(3-fluoro-5-methoxyphenyl)ethyl)imidazo[1,5-a]pyridine-1-carboxamide (T370)

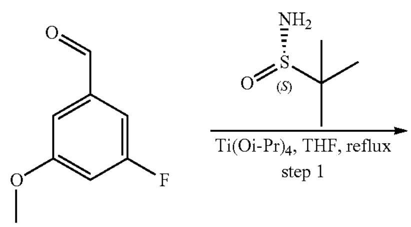

-continued

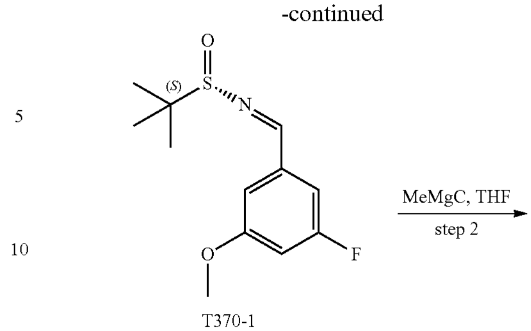

T370-1

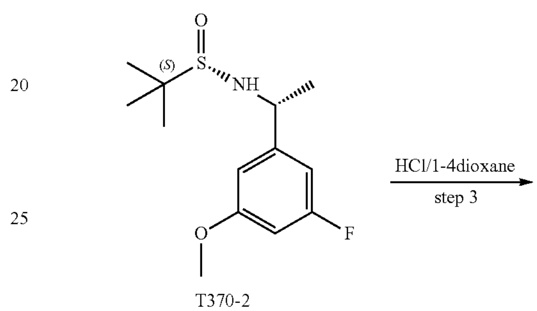

T370-2

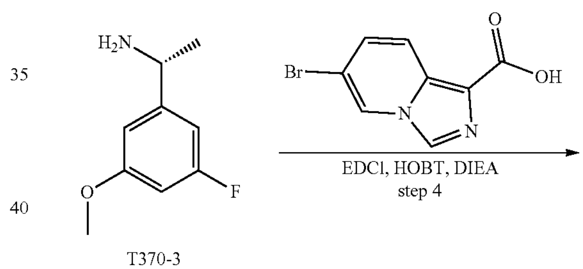

T370-3

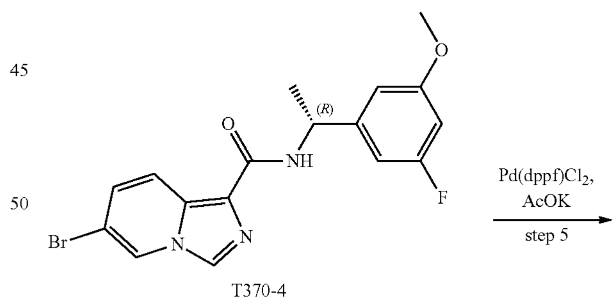

T370-4

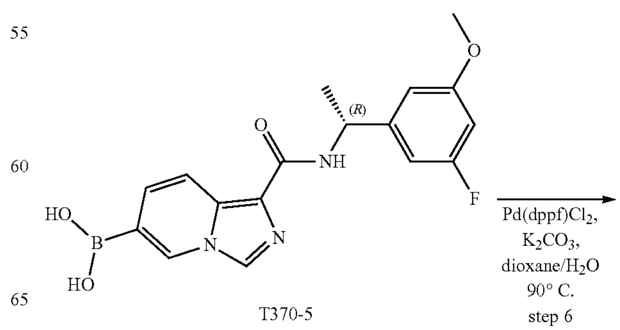

T370-5

-continued

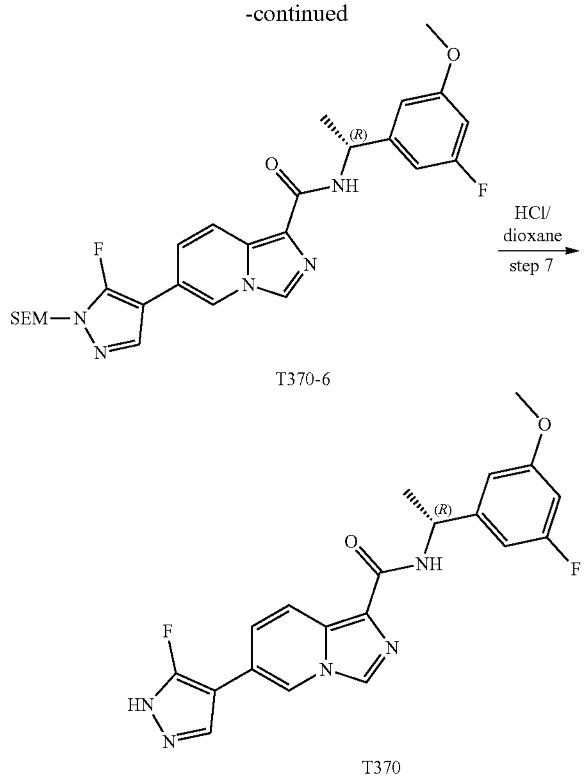

T370-6

T370

1 Preparation of Compound (S)—N-(3-fluoro-5-methoxybenzylidene)-2-methylpropane-2-sulfinamide (T370-1)

3-fluoro-5-methoxybenzaldehyde (5.00 g) was dissolved in tetrahydrofuran (50 mL), and (S)-2-methylpropane-2-sulfinamide (11.78 g) and titanium tetraisopropoxide (27.63 g) were added. The mixture was stirred at 70° C. for 12 h under nitrogen atmosphere. After the reaction was completed, water (50 mL) was added, and the mixture was filtered to remove the precipitates. The filtrate was extracted with ethyl acetate (50 mL×3), and the organic phase was washed with saturated brine (50 mL×2), dried over anhydrous sodium sulfate and concentrated under reduced pressure. The resulting crude product was separated by silica gel column chromatography (PE/EA=3:1) to give a yellow oil (6.0 g, 64% yield). LC-MS $[M+H]^+$=258.1.

2 Preparation of Compound (S)—N—((R)-1-(3-fluoro-5-methoxyphenyl)ethyl)-2-methylpropane-2-sulfinamide (T370-2)

Compound T370-1 (6.00 g) was dissolved in tetrahydrofuran (60 mL), and a solution of methylmagnesium bromide in diethyl ether (4 M, 6 mL) was added at −20° C. under nitrogen atmosphere. The mixture was stirred for 0.5 h and then warmed to 25° C. and stirred for 3 h. After the reaction was completed, saturated aqueous ammonium chloride solution (50 mL) was added to quench the reaction, and ethyl acetate (50 mL 3) was added for extraction. The organic phase was washed with saturated brine (30 mL×2), dried over anhydrous sodium sulfate, filtered and concentrated. The resulting crude product was separated by silica gel column chromatography (PE/EA=3:1) to give a colorless oil (1.00 g, 18% yield). LC-MS $[M+H]^+$=274.2.

3 Preparation of Compound (R)-1-(3-fluoro-5-methoxyphenyl)ethan-1-amine (T370-3)

Compound T370-2 (1.00 g) was dissolved in a solution of 1-4 dioxane in hydrochloric acid (10 mL, 4 mol/L), and the mixture was stirred at 25° C. for 1 h. After the reaction was completed, saturated sodium carbonate solution (10 mL 4) was added to adjust the pH to 10, and ethyl acetate (10 mL×4) was added for extraction. The organic phase was washed with saturated brine (10 mL×2), dried over anhydrous sodium sulfate, filtered and concentrated to give a colorless oily liquid (0.50 g, 80% yield). LC-MS $[M+H]^+$=169.6.

4 Preparation of Compound (R)-6-bromo-N-(1-(3-fluoro-5-methoxyphenyl)ethyl)imidazo[1,5-a]pyridine-1-carboxamide (T370-4)

Compound T370-3 (421 mg) was dissolved in dichloromethane (6 mL), and 6-bromoimidazo[1,5-a]pyridine-1-carboxylic acid (500 mg), 1-hydroxybenzotriazole (596 mg) and N,N-diisopropylethylamine (420 mg) were added. The mixture was stirred at 25° C. for 1 h. After the reaction was completed, the resulting crude product was separated by silica gel column chromatography (PE/EA=3:1) to give a colorless oil (360 mg, 44% yield). LC-MS $[M+H]^+$=392.2.

5 Preparation of Compound (R)-(1-((1-(3-fluoro-5-methoxyphenyl)ethyl)carbamoyl)imidazo[1,5-a]pyridin-6-yl)boronic acid (T370-5)

Compound T370-4 (170 mg) was dissolved in 1-4 dioxane (6 mL), and 4,4,5,5-tetramethyl-2-(4,4,5,5-tetramethyl-1,3,2-dioxaborolan-2-yl)-1,3,2-dioxaborolane (132 mg), potassium acetate (128 mg) and [1,1'-bis(diphenylphosphino)ferrocene]dichloropalladium(II) (31 mg) were added. The mixture was stirred at 90° C. for 2 h under nitrogen atmosphere. After the reaction was completed, the reaction solution was concentrated and crystallized to give a black oil (178 mg, 80% purity). LC-MS $[M+H]^+$: 357.7.

6 Preparation of Compound (R)-6-(5-fluoro-14(2-(trimethylsilyl)ethoxy)methyl)-1H-pyrazol-4-yl)-N-(1-(3-fluoro-5-methoxyphenyl)ethyl)imidazo[1,5-a]pyridine-1-carboxamide (T370-6)

Compound T370-5 (178 mg) was dissolved in 1-4 dioxane/water (2 mL, 5/1), and 4-bromo 5-fluoro-1-[4-bromo](2-methoxyethyl)trimethyl-{5}-silyl]pyrazole (100 mg), potassium carbonate (140 mg) and [1,1'-bis(diphenylphosphino)ferrocene]dichloropalladium(ii) (25 mg) were added. The mixture was stirred at 90° C. for 3 h under nitrogen atmosphere. After the reaction was completed, water (10 mL) was added to quench the reaction, and ethyl acetate (20 mL×3) was added for extraction. The organic phase was washed with saturated brine (15 mL×2), dried over anhydrous sodium sulfate, filtered and concentrated. The resulting crude product was separated by silica gel column chromatography (PE/EA=1:1) to give a light green solid (50 mg, 22% yield). LC-MS $[M+H]^+$=527.7.

7 Preparation of Compound (R)-6-(5-fluoro-1H-pyrazol-4-yl)N-(1-(3-fluoro-5-methoxyphenyl)ethyl)imidazo[1,5-a]pyridine-1-carboxamide (T370)

Compound T370-6 (50 mg) was dissolved in a solution of hydrochloric acid in 1-4 dioxane (1 mL, 4 mol/L), and the mixture was stirred at 25° C. for 1 h under nitrogen atmosphere. After the reaction was completed, the reaction solution was concentrated by rotary evaporation to remove the solvent, and the resulting crude product was purified by preparative chromatography (acetonitrile-water (0.1% formic acid)) to give a white solid (26.4 mg, 70% yield). LC-MS $[M+H]^+$=397.7.

$^1H$ NMR (400 MHz, DMSO) δ 12.75 (s, 1H), 8.65 (s, 1H), 8.51 (s, 1H), 8.45 (d, J=8.5 Hz, 1H), 8.27 (d, J=1.9 Hz, 1H), 8.06 (d, J=9.4 Hz, 1H), 7.38 (dd, J=9.5, 1.4 Hz, 1H), 6.90-6.79 (m, 2H), 6.67 (dt, J=11.0, 2.3 Hz, 1H), 5.46-4.97 (m, 1H), 3.75 (s, 3H), 1.49 (d, J=7.1 Hz, 3H).

Example 49: Preparation of Compound 6-fluoro-5-(3-fluoro-1H-pyrazol-4-yl)-N-(3-methoxybenzyl) indoline-1-carboxamide (1357)

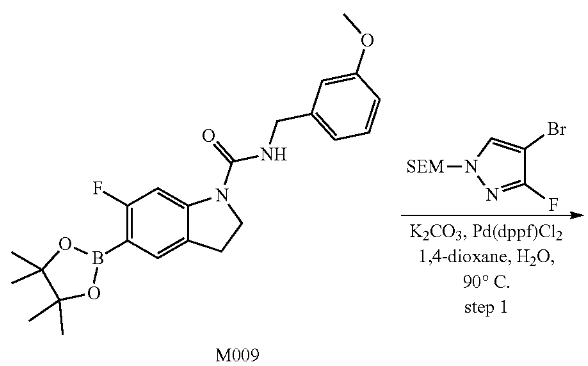

M009

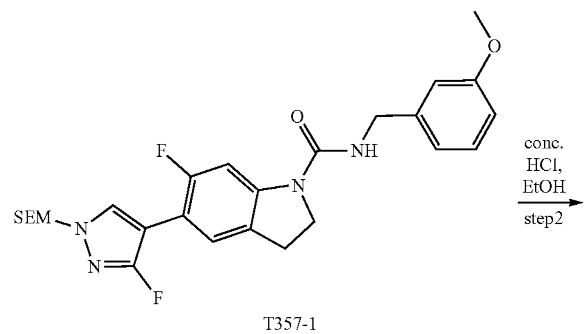

T357-1

-continued

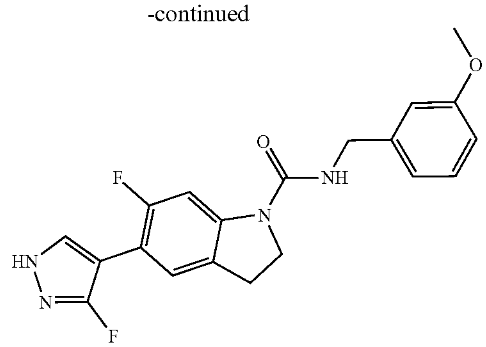

T357

1 Preparation of Compound 6-fluoro-5-(3-fluoro-1-(((2-(trimethylsilyl)ethoxy)methyl)-1H-pyrazol-4-yl)-N-(3-methoxybenzyl)indoline-1-carboxamide (T357-1)

4-bromo-3-fluoro-1-((2-(trimethylsilyl)ethoxy)methyl)-1H-pyrazole (248.82 mg) was dissolved in 1,4-dioxane (3 mL) and water (0.5 mL) under nitrogen atmosphere, and compound M009 (600 mg), potassium carbonate (348 mg) and [1,1'-bis(diphenylphosphino)ferrocene]dichloropalladium(II) (60 mg) were added. The mixture was reacted at 90° C. for 3 h. The reaction solution was cooled to room temperature, water (30 mL) was added, and then ethyl acetate (30 mL×3) was added for extraction. The organic phases were combined, washed with saturated brine (30 mL×2), dried over anhydrous sodium sulfate, filtered and concentrated by rotary evaporation, and the resulting crude product was purified by silica gel column chromatography (eluent: petroleum ether:ethyl acetate=2:1) to give compound T357-1 (200 mg, 26.45% yield). MS $[M+H]^+$=456.8.

2 Preparation of Compound 6-fluoro-5-(3-fluoro-1H-pyrazol-4-yl)-N-(3-methoxybenzyl)indoline-1-carboxamide (T357)

Compound T357-1 (200 mg) was dissolved in dichloromethane (5 mL), and trifluoroacetic acid (2 mL) was added. The mixture was reacted at room temperature for 5 h. After the reaction was completed, the reaction solution was directly concentrated by rotary evaporation, and the resulting crude product was purified by high pressure liquid phase chromatography to give compound T357 in the form of a white solid (28.7 mg, 19.21% yield). MS $[M+H]^+$=385.2.

$^1H$ NMR (400 MHz, DMSO) δ 12.61 (s, 1H), 7.90 (s, 1H), 7.66 (d, J=12.9 Hz, 1H), 7.39 (t, J=5.9 Hz, 1H), 7.31 (d, J=7.7 Hz, 1H), 7.24 (t, J=8.0 Hz, 1H), 6.93-6.87 (m, 2H), 6.84-6.78 (m, 1H), 4.31 (d, J=5.8 Hz, 2H), 4.01 (t, J=8.7 Hz, 2H), 3.74 (s, 3H), 3.15 (t, J=8.6 Hz, 2H).

Example 50: Preparation of Compound N-(3-(cyclopropylmethoxy)benzyl)-6-fluoro-5-(3-fluoro-1H-pyrazol-4-yl)indoline-1-carboxamide (T380)
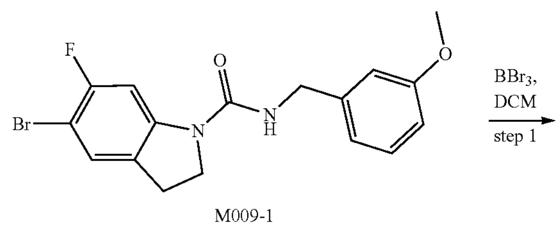
M009-1
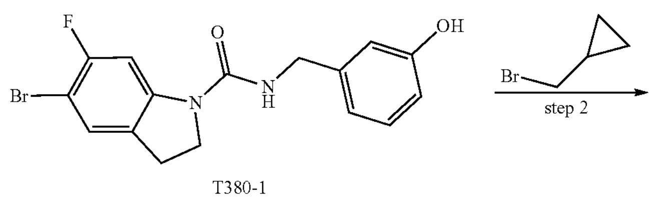
T380-1
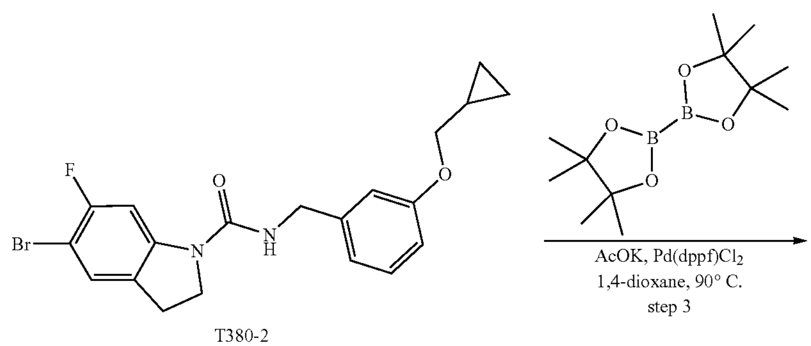
T380-2
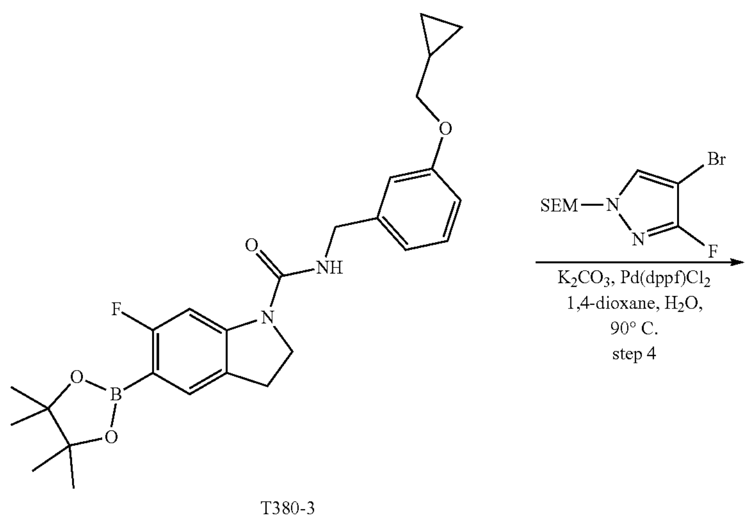
T380-3

-continued

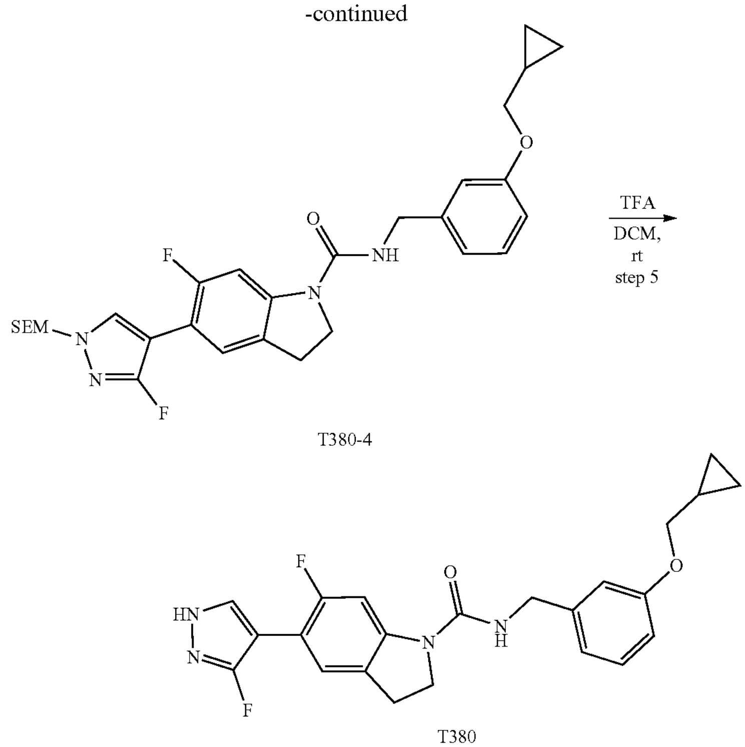

T380-4

T380

1 Preparation of Compound 5-bromo-6-fluoro-N-(3-hydroxybenzyl)indoline-1-carboxamide (T380-1)

Compound M009-1 (800 mg) was dissolved in dichloromethane (20 mL) under nitrogen atmosphere, and the mixture was cooled to −78° C., and then boron tribromide (diethyl ether solution, 1 M, 3 mL) was added slowly. The mixture was stirred at low temperature for 1 h. After the reaction was completed, methanol (20 mL) was added to quench the reaction, and the reaction solution was concentrated by rotary evaporation. The resulting crude product was purified by column chromatography (petroleum ether: ethyl acetate=3:2) to give compound T380-1 in the form of a red solid (600 mg, 77.09% yield). MS $[M+H]^+$=365.1.

2 Preparation of Compound 5-bromo-N-(3-(cyclopropylmethoxy)benzyl)-6-fluoroindoline-1-carboxamide (T380-2)

Compound T380-1 (550 mg) and cesium carbonate (1968 mg) were dissolved in acetonitrile (23 mL), and the mixture was mixed well by stirring, followed by addition of (bromomethyl)cyclopropane (306 mg). The resulting mixture was stirred at 50° C. for 10 h. After the reaction was completed, the reaction solution was filtered under vacuum and the filtrate was concentrated by rotary evaporation. The resulting crude product was purified by column chromatography (petroleum ether:ethyl acetate=3:1) to give compound T380-2 in the form of a white solid (550 mg, 85.13% yield). MS $[M+H]^+$=419.1.

3 Preparation of Compound N-(3-(cyclopropylmethoxy)benzyl)-6-fluoro-5-(4,4,5,5-tetramethyl-1,3,2-dioxaborolan-2-yl)indoline-1-carboxamide (T380-3)

Compound T380-2 (400 mg) was dissolved in anhydrous 1,4-dioxane (5 mL) under nitrogen atmosphere, and 4,4,4',4',5,5,5',5'-octamethyl-2,2'-bi(1,3,2-dioxaborolane) (362 mg), potassium acetate (233 mg) and [1,1'-bis(diphenylphosphino)ferrocene]dichloropalladium(II) (70 mg) were added. The mixture was reacted at 90° C. for 6 h. After the reaction was completed, the reaction solution was filtered and concentrated by rotary evaporation, and the resulting crude product was purified by column chromatography (petroleum ether:dichloromethane=15:1) to give compound T380-3 in the form of a brown oil (500 mg). MS $[M+H]^+$=467.3.

4 Preparation of Compound N-(3-(cyclopropylmethoxy)benzyl)-6-fluoro-5-(3-fluoro-1-(((2-(trimethylsilyl)ethoxy)methyl)-1H-pyrazol-4-yl)indoline-1-carboxamide (T380-4)

4-bromo-3-fluoro-1-((2-(trimethylsilyl)ethoxy)methyl)-1H-pyrazole (316 mg) was dissolved in 1,4-dioxane (3 mL) and water (0.5 mL) under nitrogen atmosphere, and compound T380-3 (500 mg), potassium carbonate (296 mg) and [1,1'-bis(diphenylphosphino)ferrocene]dichloropalladium (II) (78 mg) were added. The mixture was reacted at 80° C. for 3 h. The reaction solution was cooled to room temperature, water (30 mL) was added, and then ethyl acetate (30 mL×3) was added for extraction. The organic phases were combined, washed with saturated brine (30 mL 2), dried over anhydrous sodium sulfate, filtered and concentrated by rotary evaporation, and the resulting crude product was purified by silica gel column chromatography (eluent: petroleum ether:ethyl acetate=2:1) to give compound T380-4 (200 mg, 33.00% yield). MS $[M+H]^+$=555.3.

5 Preparation of Compound N-(3-(cyclopropylmethoxy)benzyl)-6-fluoro-5-(3-fluoro-1H-pyrazol-4-yl)indoline-1-carboxamide (T380)

Compound T380-4 (210 mg) was dissolved in dichloromethane (5 mL), and trifluoroacetic acid (2 mL) was added. The mixture was reacted at room temperature for 5 h. After the reaction was completed, the reaction solution was directly concentrated by rotary evaporation, and the resulting crude product was purified by high pressure liquid phase chromatography to give compound T380 in the form of a white solid (14.4 mg, 8.92% yield). MS $[M+H]^+$=425.1.

$^1H$ NMR (400 MHz, DMSO) δ 12.61 (s, 1H), 7.90 (s, 1H), 7.65 (d, J=12.9 Hz, 1H), 7.37 (t, J=5.9 Hz, 1H), 7.31 (d, J=7.7 Hz, 1H), 7.21 (t, J=8.1 Hz, 1H), 6.91-6.84 (m, 2H), 6.78 (dd, J=8.2, 1.5 Hz, 1H), 4.30 (d, J=5.8 Hz, 2H), 4.01 (t, J=8.7 Hz, 2H), 3.79 (d, J=7.0 Hz, 2H), 3.15 (t, J=8.6 Hz, 2H), 1.25-1.18 (m, 1H), 0.60-0.51 (m, 2H), 0.36-0.27 (m, 2H).

Example 51: Preparation of Compound N-(3,5-difluorobenzyl)-6-fluoro-5-(5-fluoro-1H-pyrazol-4-yl)indoline-1-carboxamide (T387)

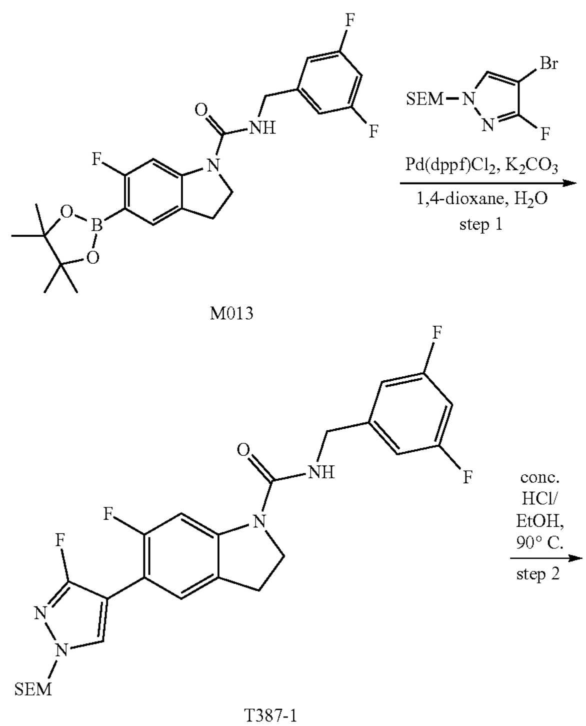

M013

T387-1

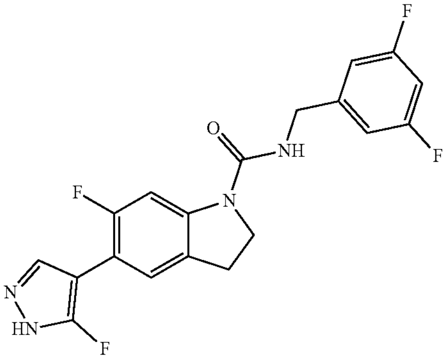

T387

1 Preparation of Compound N-(3,5-difluorobenzyl)-6-fluoro-5-(3-fluoro-1-((2-(trimethylsilyl)ethoxy)methyl)-1H-pyrazol-4-yl)indoline-1-carboxamide (T387-1)

4-bromo-3-fluoro-1-((2-(trimethylsilyl)ethoxy)methyl)-1H-pyrazole (172 mg) was dissolved in 1,4-dioxane (3 mL) and water (0.5 mL) under nitrogen atmosphere, and compound M013 (250 mg), potassium carbonate (240 mg) and [1,1'-bis(diphenylphosphino)ferrocene]dichloropalladium (11) (42 mg) were added. The mixture was reacted at 80° C. for 3 h. The reaction solution was cooled to room temperature, water (30 mL) was added, and then ethyl acetate (30 mL×3) was added for extraction. The organic phases were combined, washed with saturated brine (30 mL×2), dried over anhydrous sodium sulfate, filtered and concentrated by rotary evaporation, and the resulting crude product was purified by silica gel column chromatography (eluent: petroleum ether:ethyl acetate=2:1) to give compound T387-1 in the form of a yellow oil (100 mg, 32.40% yield). MS $[M+Na]^+$=543.0.

2 Preparation of Compound N-(3,5-difluorobenzyl)-6-fluoro-5-(5-fluoro-1H-pyrazol-4-yl)indoline-1-carboxamide (T387)

Compound T387-1 (100 mg) was dissolved in ethanol (5 mL), and concentrated hydrochloric acid (1 mL) was added. The mixture was reacted at 90° C. for 1 h. After the reaction was completed, the reaction solution was directly concentrated by rotary evaporation, and the resulting crude product was dissolved in dichloromethane, basified with triethylamine and purified by preparative plate (petroleum ether:ethyl acetate=1:1) to give compound T387 in the form of a white solid (21.76 mg, 29.05% yield). MS $[M+H]^+$=493.4.

$^1H$ NMR (400 MHz, DMSO) δ 12.61 (s, 1H), 7.90 (d, J=1.6 Hz, 1H), 7.65 (d, J=12.8 Hz, 1H), 7.46 (t, J=5.9 Hz, 1H), 7.32 (d, J=7.7 Hz, 1H), 7.13-7.02 (m, 3H), 4.35 (d, J=5.8 Hz, 2H), 4.04 (t, J=8.7 Hz, 2H), 3.16 (t, J=8.6 Hz, 2H).

Example 52: Preparation of Compound N-(3-(difluoromethoxy)-5-fluorobenzyl)-6-fluoro-5-(1H-pyrazol-4-yl)indoline-1-carboxamide (T375)

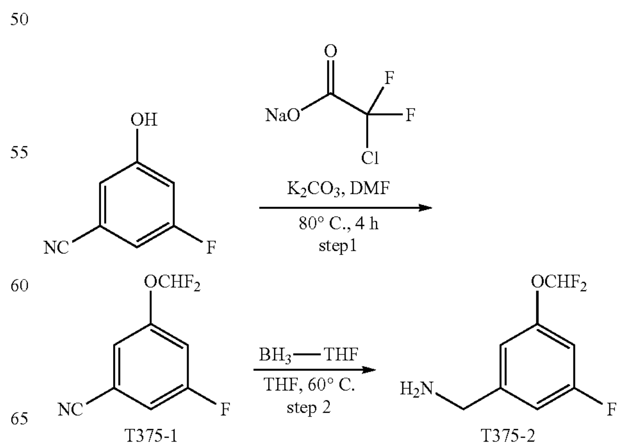

T375-1

T375-2

-continued

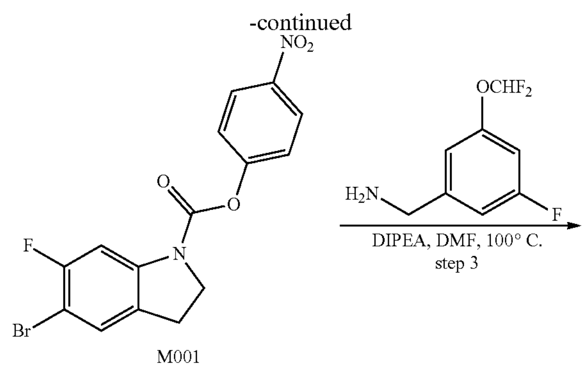

M001

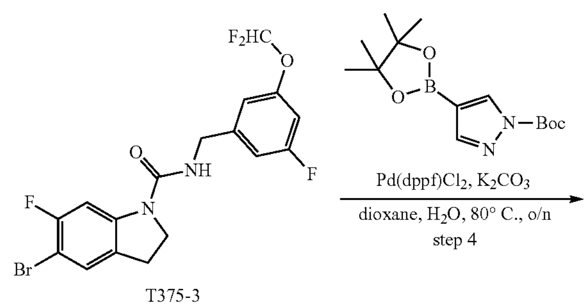

T375-3

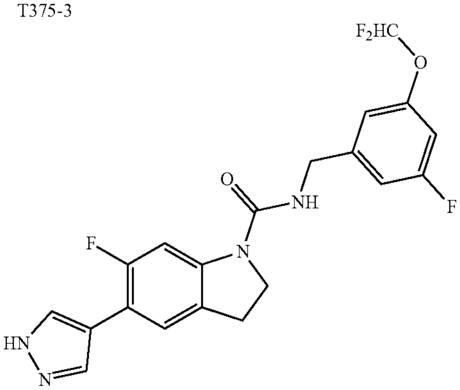

T375

1 Preparation of Compound 3-(difluoromethoxy)-5-fluorobenzonitrile (T375-1)

3-fluoro-5-hydroxybenzonitrile (1 g) was dissolved in anhydrous N,N-dimethylformamide (10 mL), and sodium 2-chloro-2,2-difluoroacetate (1.33 g) and potassium carbonate (1.2 g) were added successively. The mixture was stirred at 80° C. for 4 h under nitrogen atmosphere. After the reaction was completed, the reaction solution was cooled to room temperature, water (20 mL) was added to quench the reaction, and ethyl acetate (30 mL×3) was added for extraction. The organic phases were combined, washed with saturated brine (30 mL×3), dried over anhydrous sodium sulfate, filtered and concentrated by rotary evaporation. The resulting crude product was purified by silica gel column chromatography (petroleum ether:ethyl acetate=6:1) to give compound T375-1 in the form of a colorless oil (1.21 g, 88.76% yield).

$^1$H NMR (400 MHz, MeOD) δ 7.52-7.46 (m, 1H), 7.43 (s, 1H), 7.35 (dt, J=9.6, 2.2 Hz, 1H), 7.01 (t, J=72.6 Hz, 1H).

2 Preparation of Compound (3-(difluoromethoxy)-5-fluorophenyl)methylamine (T375-2)

Compound T375-1 (800 mg) was dissolved in anhydrous tetrahydrofuran (8 mL), and borane/tetrahydrofuran solution (1 N, 45 mL) was added. The mixture was heated and stirred overnight at 60° C. under nitrogen atmosphere. After the reaction was completed, the reaction solution was cooled to room temperature, saturated aqueous ammonium chloride solution (50 mL) was added to quench the reaction, and ethyl acetate (30 mL×3) was added for extraction. The organic phases were combined, washed with saturated brine (30 mL×3), dried over anhydrous sodium sulfate, filtered and concentrated by rotary evaporation to give compound T375-2 in the form of a light yellow oil (478 mg, 58.42% yield). LC-MS $[M+H]^+$: 192.0.

3 Preparation of Compound 5-bromo-N-(3-(difluoromethoxy)-5-fluorobenzyl)-6-fluoroindoline-1-carboxamide (T375-3)

Compound M001 (500 mg) was dissolved in anhydrous N,N-dimethylformamide (10 mL), and compound T375-2 (233 mg) and N,N-diisopropylethylamine (472 mg) were added successively. The mixture was stirred overnight at 100° C. After the reaction was completed, the reaction solution was cooled to room temperature, water (20 mL) was added to quench the reaction, and ethyl acetate (15 mL×3) was added for extraction. The organic phases were combined, washed with saturated brine (30 mL×3), dried over anhydrous sodium sulfate, filtered and concentrated by rotary evaporation. The resulting crude product was purified by silica gel column chromatography (dichloromethane: ethyl acetate=2:1) to give product T375-3 in the form of a white solid (400 mg, 75.89% yield). LC-MS $[M+H]^+$: 432.9.

4 Preparation of Compound N-(3-(difluoromethoxy)-5-fluorobenzyl)-6-fluoro-5-(1H-pyrazol-4-yl)indoline-1-carboxamide (T375)

Compound T375-3 (200 mg) was dissolved in a mixed solution of dioxane (4 mL) and water (1 mL), and tert-butyl 4-(4,4,5,5-tetramethyl-1,3,2-dioxaborolan-2-yl)-1H pyrazole-1-carboxylate (203 mg), [1,1'-bis(diphenylphosphino) ferrocene]dichloropalladium(II) (67 mg) and potassium carbonate (190 mg) were added. The mixture was stirred overnight at 80° C. The reaction solution was cooled to room temperature and then filtered to remove the precipitates, and the filtrate was extracted with ethyl acetate (30 mL×3). The organic phases were combined, washed with saturated brine (30 mL×4), dried over sodium sulfate, filtered and concentrated by rotary evaporation, and the residue was purified by silica gel column chromatography (wet loading, dichloromethane:ethyl acetate=1:1), concentrated by rotary evaporation and lyophilized to give compound T375 in the form of a white powdery solid (34.1 mg, 17.63% yield). LC-MS $[M+H]^+$: 421.0.

$^1$H NMR (400 MHz, DMSO) δ 7.94 (s, 2H), 7.62 (d, J=13.2 Hz, 1H), 7.50 (d, J=7.9 Hz, 1H), 7.43 (t, J=5.9 Hz, 1H), 7.30 (t, J=73.7 Hz, 1H), 7.06 (d, J=9.3 Hz, 1H), 7.04-6.96 (m, 2H), 4.35 (d, J=5.7 Hz, 2H), 4.03 (t, J=8.7 Hz, 2H), 3.16 (t, J=8.5 Hz, 2H).

Example 53: Preparation of Compound (S)-6-fluoro-N-(1-(3-fluoro-5-(2-(isopropylamino)-2-oxo-ethoxy)phenyl)-2-hydroxyethyl)-5-(1H-pyrazol-4-yl) indoline-1-carboxamide (T358)

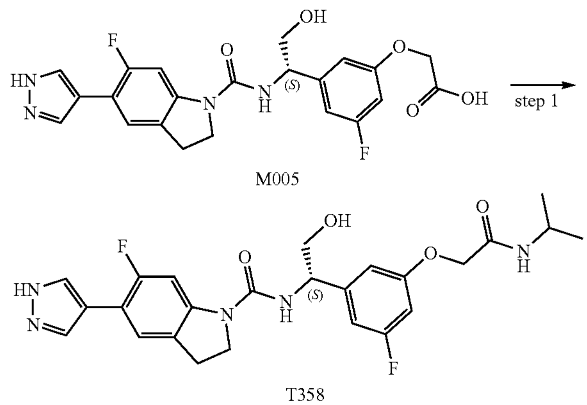

M005

T358

Compound M005 (86 mg, crude product) and HATU (87 mg) were dissolved in N,N-dimethylformamide (2 mL), and the mixture was mixed well by stirring, followed by addition of N,N-diisopropylethylamine (98 mg). The mixture was stirred for 5 min and then isopropylamine (23 mg) was added. The resulting mixture was stirred at room temperature for 5 h. After the reaction was completed as detected, water (10 mL) was added, and ethyl acetate (10 mL×3) was added for extraction. The organic phases were combined, washed with saturated brine, dried over anhydrous sodium sulfate and concentrated under reduced pressure, and the resulting crude product was purified by column chromatography (dichloromethane:methanol=10:1) to give compound T358 in the form of a white solid (37 mg, 37.89% yield). MS $(M+H)^+$=500.2.

$^1$H NMR (400 MHz, DMSO) δ 8.01-7.88 (m, 3H), 7.57 (d, J=13.2 Hz, 1H), 7.50 (d, J=7.9 Hz, 1H), 6.93-6.82 (m, 3H), 6.69 (dt, J=10.9, 2.3 Hz, 1H), 4.82 (dd, J=13.6, 7.4 Hz, 1H), 4.45 (s, 2H), 4.14-4.05 (m, 2H), 3.97-3.91 (m, 1H), 3.66-3.60 (m, 2H), 3.16 (t, J=8.5 Hz, 2H), 1.08 (dd, J=6.6, 1.6 Hz, 6H).

Example 54: Preparation of Compound (S)-6-fluoro-N-(1-(3-fluoro-5-(2-(isobutylamino)-2-oxo-ethoxy)phenyl)-2-hydroxyethyl)-5-(1H-pyrazol-4-yl) indoline-1-carboxamide (T367)

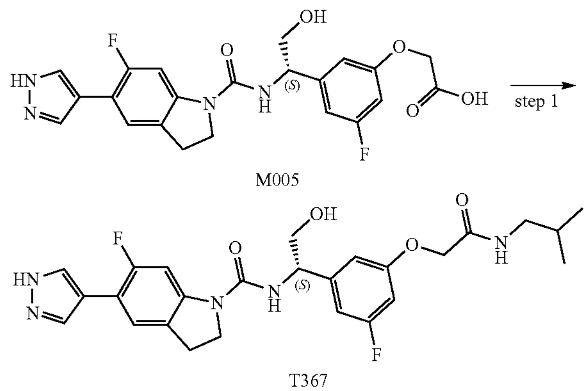

M005

T367

Compound M005 (86 mg, crude product) and HATU (87 mg) were dissolved in N,N-dimethylformamide (2 mL), and the mixture was mixed well by stirring, followed by addition of N,N-diisopropylethylamine (98 mg). The mixture was stirred for 5 min and then isobutylamine (28 mg) was added. The resulting mixture was stirred at room temperature for 5 h. After the reaction was completed as detected, water (10 mL) was added, and ethyl acetate (10 mL×3) was added for extraction. The organic phases were combined, washed with saturated brine, dried over anhydrous sodium sulfate and concentrated under reduced pressure, and the resulting crude product was purified by column chromatography (dichloromethane:methanol=10:1) to give compound T367 in the form of a white solid (27 mg, 27.26% yield). MS $(M+H)^+$= 514.3.

$^1$H NMR (400 MHz, DMSO) δ 12.96 (s, 1H), 8.09 (t, J=5.9 Hz, 1H), 8.03 (s, 1H), 7.85 (s, 1H), 7.58 (d, J=13.2 Hz, 1H), 7.50 (d, J=7.9 Hz, 1H), 6.90-6.82 (m, 3H), 6.71-6.65 (m, 1H), 4.95 (t, J=5.9 Hz, 1H), 4.82 (dd, J=13.3, 7.3 Hz, 1H), 4.51 (s, 2H), 4.15-4.03 (m, 2H), 3.69-3.57 (m, 2H), 3.16 (t, J=8.6 Hz, 2H), 2.93 (t, J=6.5 Hz, 2H), 1.77-1.67 (m, 1H), 0.80 (d, J=6.7 Hz, 6H).

Example 55: Preparation of Compound (S)—N-(1-(3-(2-(3,3-difluoroazetidin-1-yl)-2-oxoethoxy)-5-fluorophenyl)-2-hydroxyethyl)-6-fluoro-5-(1H-pyrazol-4-yl)indoline-1-carboxamide (T350)

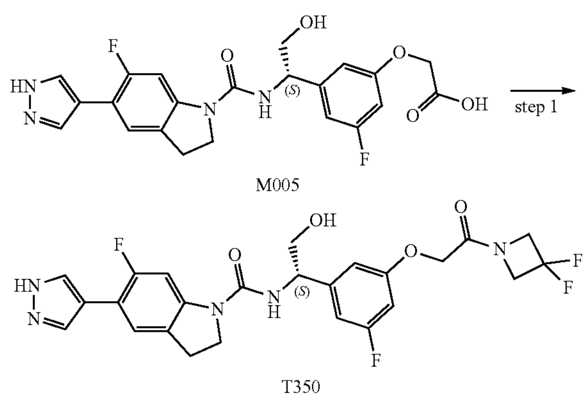

M005

T350

Compound M005 (86 mg, crude product) and HATU (87 mg) were dissolved in N,N-dimethylformamide (2 mL), and the mixture was mixed well by stirring, followed by addition of N,N-diisopropylethylamine (98 mg). The mixture was stirred for 5 min and then 3,3-difluoroazetidine hydrochloride (37 mg) was added. The resulting mixture was stirred at room temperature for 5 h. After the reaction was completed as detected, water (10 mL) was added, and ethyl acetate (10 mL×3) was added for extraction. The organic phases were combined, washed with saturated brine, dried over anhydrous sodium sulfate and concentrated under reduced pressure, and the resulting crude product was purified by column chromatography (dichloromethane:methanol=10:1) to give compound T350 in the form of a white solid (31 mg, 29.79% yield). MS (M+H)_534.1.

$^1$H NMR (400 MHz, DMSO) δ 12.92 (s, 1H), 7.95 (s, 2H), 7.58 (d, J=13.2 Hz, 1H), 7.50 (d, J=7.9 Hz, 1H), 6.92-6.81 (m, 3H), 6.74 (dt, J=10.9, 2.2 Hz, 1H), 4.95 (t, J=5.9 Hz, 1H), 4.83 (dd, J=13.5, 7.3 Hz, 1H), 4.80-4.64 (m, 4H), 4.36 (t, J=12.5 Hz, 2H), 4.17-4.02 (m, 2H), 3.71-3.58 (m, 2H), 3.16 (t, J=8.5 Hz, 2H).

Example 56: Preparation of Compound (S)—N-(1-(3-(2-((3,3-difluorocyclobutyl)amino)-2-oxoethoxy)-5-fluorophenyl)-2-hydroxyethyl)-6-fluoro-5-(1H-pyrazol-4-yl)indoline-1-carboxamide (T369)

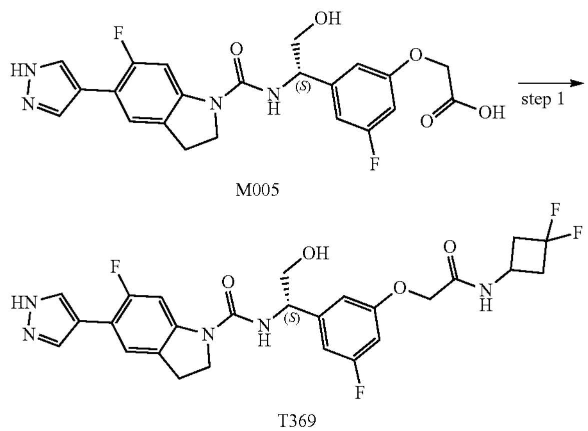

M005

T369

Compound M005 (100 mg, crude product) and HATU (124 mg) were dissolved in N,N-dimethylformamide (2 mL), and the mixture was mixed well by stirring, followed by addition of N,N-diisopropylethylamine (113 mg). The mixture was stirred for 5 min and then 3,3-difluorocyclobutan-1-amine (35 mg) was added. The resulting mixture was stirred at room temperature for 5 h. After the reaction was completed as detected, water (10 mL) was added, and ethyl acetate (10 mL×3) was added for extraction. The organic phases were combined, washed with saturated brine, dried over anhydrous sodium sulfate and concentrated under reduced pressure, and the resulting crude product was purified by column chromatography (dichloromethane:methanol=10:1) to give compound T369 in the form of a white solid (25 mg, 20.77% yield). MS $(M+H)^+$=548.3.

$^1$H NMR (400 MHz, DMSO) δ 12.96 (s, 1H), 8.58 (d, J=7.0 Hz, 1H), 8.02 (s, 1H), 7.86 (s, 1H), 7.57 (d, J=13.2 Hz, 1H), 7.50 (d, J=7.9 Hz, 1H), 6.92-6.82 (m, 3H), 6.71 (dt, J=10.8, 2.2 Hz, 1H), 4.96 (t, J=5.9 Hz, 1H), 4.83 (dd, J=13.5, 7.5 Hz, 1H), 4.51 (s, 2H), 4.19-4.03 (m, 3H), 3.68-3.58 (m, 2H), 3.16 (t, J=8.6 Hz, 2H), 2.93-2.81 (m, 2H), 2.77-2.64 (m, 2H), 1.28-1.21 (m, 2H).

Example 57: Preparation of Compound (S)—N-(1-(3-ethoxy-5-fluorophenyl)-2-hydroxyethyl)-6-fluoro-5-(1N-pyrazol-4-yl)indoline-1-carboxamide (T390)

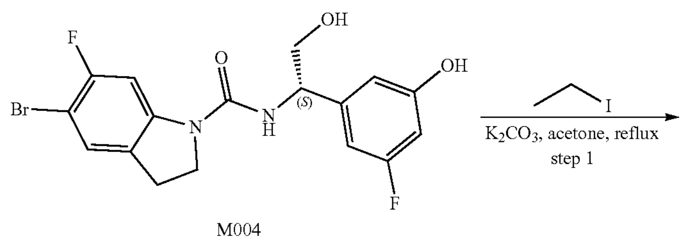

M004

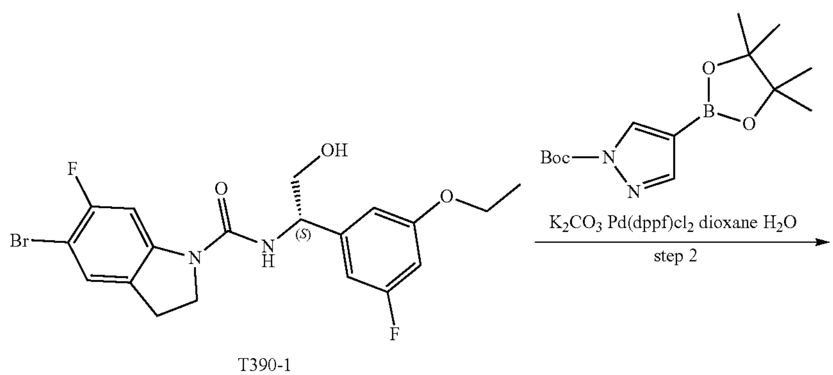

T390-1

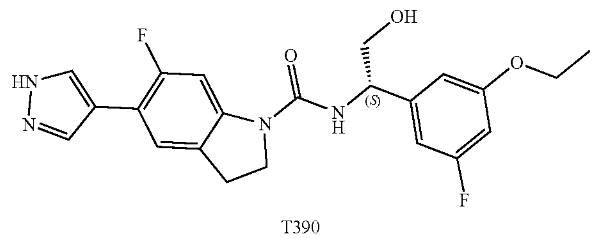

T390

1 Preparation of Compound (S)-5-bromo-N-(1-(3-ethoxy-5-fluorophenyl)-2-hydroxyethyl)-6-fluoroindoline-1-carboxamide (T390-1)

Compound M004 (200 mg) was dissolved in acetonitrile (5 mL), and iodoethane (374 mg) and potassium carbonate (132 mg) were added under nitrogen atmosphere. The mixture was reacted at 60° C. for 2 h. After the reaction was completed, the reaction solution was concentrated, and the resulting crude product was purified by silica gel column chromatography (eluent: dichloromethane:methanol=20:1) to give a colorless oily liquid (100 mg, 47% yield). MS $[M+H]^+$=440.9.

2 Preparation of Compound (S)—N-(1-(3-ethoxy-5-fluorophenyl)-2-hydroxyethyl)-6-fluoro-5-(1H-pyrazol-4-yl)indoline-1-carboxamide (1390-2)

Compound T390-1 (100 mg) was dissolved in dioxane (3 mL) and water (0.5 mL), and tert-butyl 4-(4,4,5,5-tetramethyl-1,3,2-dioxaborolan-2-yl)-1H-pyrazole-1-carboxylate (81 mg), potassium carbonate (63 mg) and [1,1'-bis(diphenylphosphino)ferrocene]dichloropalladium(11) (17 mg) were added. The mixture was reacted at 90° C. for 3 h under nitrogen atmosphere. After the reaction was completed, the reaction solution was filtered, water (10 mL) was added to quench the reaction, and ethyl acetate (10 mL×3) was added for extraction. The organic phases were combined, washed with saturated brine (20 mL×2), dried over anhydrous sodium sulfate, filtered and concentrated by rotary evaporation, and the resulting crude product was purified by preparative chromatography to give a white solid (13 mg, 13% yield). MS $[M+H]^+$=428.9.

$^1$H NMR (400 MHz, MeOD) δ 7.98 (s, 2H), 7.62 (d, J=13.0 Hz, 1H), 7.47 (d, J=7.6 Hz, 1H), 6.81 (s, 1H), 6.75 (d, J=9.4 Hz, 1H), 6.58 (d, J=10.8 Hz, 1H), 4.98-4.94 (m, 1H), 4.14 (t, J=8.5 Hz, 2H), 4.06 (q, J=7.0 Hz, 2H), 3.84-3.79 (m, 2H), 3.25 (t, J=8.4 Hz, 2H), 1.40 (t, J=7.0 Hz, 3H).

Example 58: Preparation of Compound (S)—N-(1-(3-(cyclopropylmethoxy)-5-fluorophenyl)-2-hydroxyethyl)-6-fluoro-5-(1H-pyrazol-4-yl)indoline-1-carboxamide (T386)

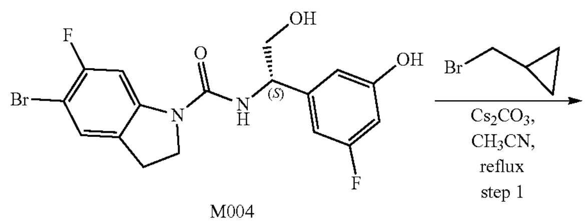

M004

-continued

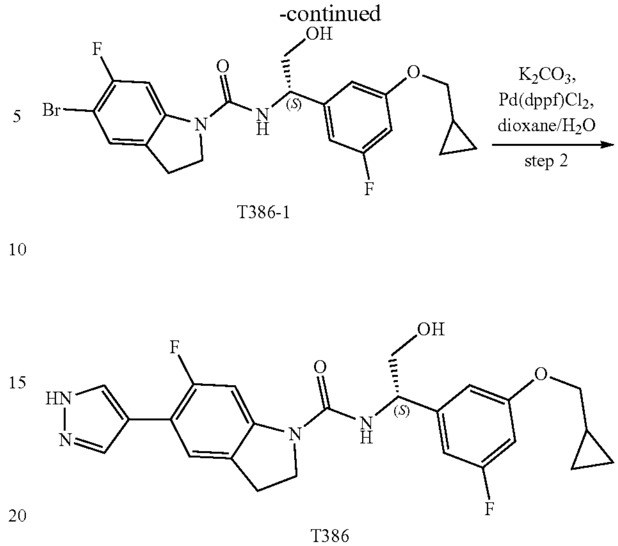

T386-1

T386

1 Preparation of Compound (S)-5-bromo-N-(1-(3-(cyclopropylmethoxy)-5-fluorophenyl)-2-hydroxyethyl)-6-fluoroindoline-1-carboxamide (T386-1)

Compound M004 (200 mg) was dissolved in acetonitrile (15 mL), and cesium carbonate (635 mg) was added. The mixture was mixed well by stirring, and a solution of (bromomethyl)cyclopropane (210 mg) in acetonitrile (5 mL) was added. The mixture was stirred overnight at 70° C. The reaction solution was filtered through celite under vacuum, and the filter cake was washed with acetonitrile. The filtrate was combined and concentrated under reduced pressure. The resulting crude product was purified by column chromatography (petroleum ether:ethyl acetate=3:2) to give T386-1 in the form of a yellow solid (100 mg, 43.91% yield). MS $(M+H)^+$=467.1.

2 Preparation of Compound (S)—N-(1-(3-(cyclopropylmethoxy)-5-fluorophenyl)-2-hydroxyethyl)-6-fluoro-5-(1 N-pyrazol-4-yl)indoline-1-carboxamide (T386)

Compound T386-1 (70 mg), tert-butyl (4-(4,4,5,5-tetramethyl-1,3,2-dioxaborolan-2-yl)pyrazol-1-yl)carboxylate (89 mg) and potassium carbonate (83 mg) were dissolved in dioxane/water (4:1, 3 mL) under nitrogen atmosphere. The mixture was mixed well by stirring, and [1,1'-bis(diphenylphosphino)ferrocene]dichloropalladium(II) (11 mg) was added. The mixture was stirred at 90° C. for 15 h. The reaction solution was concentrated under reduced pressure, and the residue was purified by preparative chromatography to give compound T386 in the form of a white solid (24 mg, 35.20% yield). MS $(M+H)^+$=455.3.

$^1$H NMR (400 MHz, DMSO) δ 12.95 (s, 1H), 8.08-7.83 (m, 2H), 7.57 (d, J=13.2 Hz, 1H), 7.49 (d, J=7.9 Hz, 1H), 6.84 (d, J=7.9 Hz, 1H), 6.82-6.75 (m, 2H), 6.66 (dt, J=11.1, 2.2 Hz, 1H), 4.93 (s, 1H), 4.81 (dd, J=13.6, 7.5 Hz, 1H), 4.16-4.01 (m, 2H), 3.81 (d, J=7.0 Hz, 2H), 3.67-3.56 (m, 2H), 3.16 (t, J=8.6 Hz, 2H), 1.24-1.18 (m, 1H), 0.61-0.51 (m, 2H), 0.36-0.26 (m, 2H).

Example 59: Preparation of Compound (S)-6-fluoro-N-(1-(3-fluoro-3-isobutoxyphenyl)-2-hydroxyethyl)-5-(1H-pyrazol-4-yl)indoline-1-carboxamide (T354)

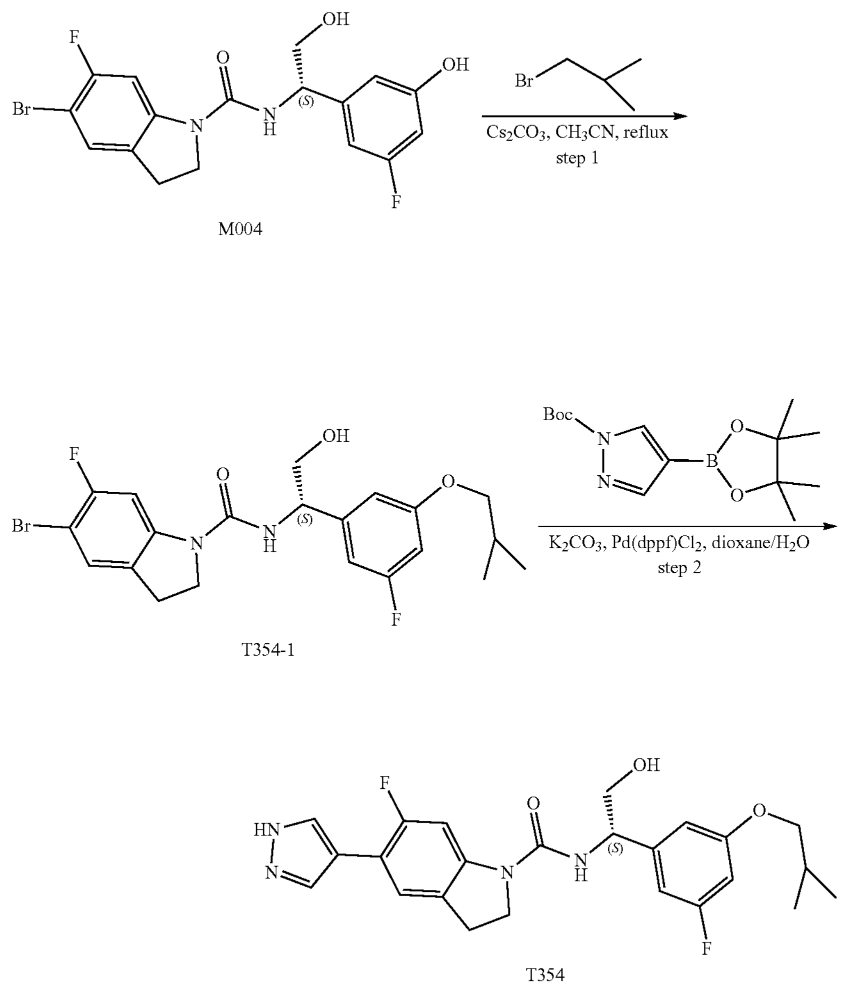

M004

T354-1

T354

1 Preparation of Compound (S)-5-bromo-6-fluoro-N-(1-(3-fluoro-5-isobutoxyphenyl)-2-hydroxyethyl) indoline-1-carboxamide (T354-1)

Compound M004 (250 mg) was dissolved in acetonitrile (15 mL), and cesium carbonate (781 mg) was added. The mixture was mixed well by stirring, and a solution of 1-bromo-2-methylpropane (263 mg) in acetonitrile (5 mL) was added. The mixture was stirred at 70° C. for 12 h. The reaction solution was filtered through celite under vacuum, and the filter cake was washed with acetonitrile. The filtrate was combined and concentrated under reduced pressure. The resulting crude product was purified by column chromatography (petroleum ether:ethyl acetate=3:2) to give compound T354-1 in the form of a greyish-white solid (120 mg, 50.60% yield). MS $(M+H)^+$=469.1.

2 Preparation of Compound (S)-6-fluoro-N-(1-(3-fluoro-3-isobutoxyphenyl)-2-hydroxyethyl)-5-(1H-pyrazol-4-yl)indoline-1-carboxamide (T354)

Compound T354-1 (110 mg), tert-butyl (4-(4,4,5,5-tetramethyl-1,3,2-dioxaborolan-2-yl)pyrazol-1-yl)carboxylate (135 mg) and potassium carbonate (127 mg) were dissolved in dioxane/water (4:1, 3 mL) under nitrogen atmosphere. The mixture was mixed well by stirring, and [1,1'-bis (diphenylphosphino)ferrocene]dichloropalladium(II) (17 mg) was added. The mixture was stirred at 90° C. for 15 h. The reaction solution was concentrated under reduced pressure, and the residue was purified by preparative chromatography to give compound T354 in the form of a white solid (100 mg, 44.67% yield). MS $(M+H)^+$=457.3.

$^1$H NMR (400 MHz, DMSO) δ 12.96 (s, 1H), 8.03 (s, 1H), 7.85 (s, 1H), 7.57 (d, J=13.2 Hz, 1H), 7.49 (d, J=7.9 Hz, 1H), 6.86 (d, J=7.9 Hz, 1H), 6.83-6.76 (m, 2H), 6.67 (dt, J=11.0, 2.2 Hz, 1H), 4.93 (t, J=5.9 Hz, 1H), 4.81 (dd, J=13.4, 7.5 Hz, 1H), 4.15-4.02 (m, 2H), 3.75 (d, J=6.5 Hz, 2H), 3.68-3.57 (m, 2H), 3.16 (t, J=8.7 Hz, 2H), 2.05-1.96 (m, 1H), 0.98 (d, J=6.7 Hz, 6H).

Example 60: Preparation of Compound(S)-6-fluoro-N-(1-(3-fluoro-5-methoxyphenyl)-2-hydroxyethyl)-5-(1H-pyrazol-4-yl)indoline-1-carboxamide (T377)

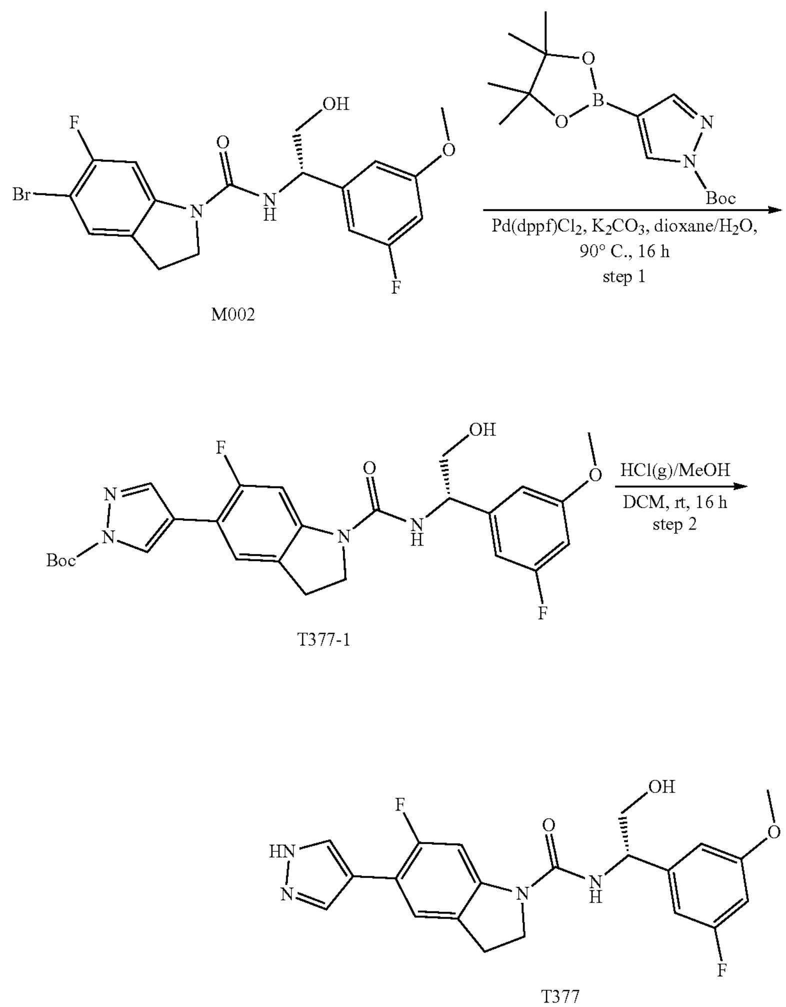

M002

T377-1

T377

1 Preparation of Compound tert-butyl (S)-4-(6-fluoro-1-((1-(3-fluoro-5-methoxyphenyl)-2-hydroxyethyl)carbamoyl)indolin-5-yl)-1H-pyrazole-1-carboxylate (T377-1)

Compound M002 (300 mg) and 1-tert-butoxycarbonylpyrazole-4-boronic acid pinacol ester (248 mg) were dissolved in dioxane (8 mL), and a solution of potassium carbonate (242 mg) in water (0.8 mL) and [1,1'-bis(diphenylphosphino)ferrocene]dichloropalladium(II) (51 mg) were added. The mixture was reacted at 90° C. for 16 h under nitrogen atmosphere. The reaction solution was extracted with ethyl acetate (30 mL×2). The organic phase was washed with saturated brine (10 mL×2), dried over anhydrous sodium sulfate, filtered and concentrated. The resulting crude product was purified by silica gel column chromatography (methanol:dichloromethane=1:50) to give T377-1 in the form of a pale yellow solid (320 mg, 80% yield). MS $[M+H]^+$=515.0.

2 Preparation of Compound (S)-6-fluoro-N-(1-(3-fluoro-5-methoxyphenyl)-2-hydroxyethyl)-5-(1H-pyrazol-4-yl)indoline-1-carboxamide (T377)

T377-1 (320 mg) was dissolved in dichloromethane (4 mL), and methanolic hydrochloric acid (2 mL) was added. The mixture was stirred at room temperature for 16 h. The reaction solution was concentrated under reduced pressure, and the residue was purified by preparative chromatography (acetonitrile/0.1% formic acid-water/0.1% formic acid) to give T377 in the form of a white solid (87.3 mg, 34% yield). MS $[M+H]^+$=416.0.

$^1$H NMR (400 MHz, DMSO) δ 13.02 (br, 1H), 7.95 (s, 2H), 7.58 (d, J=13.2 Hz, 1H), 7.50 (d, J=7.9 Hz, 1H), 6.87 (d, J=7.9 Hz, 1H), 6.81 (d, J=8.3 Hz, 2H), 6.69 (dt, J=11.0, 2.2 Hz, 1H), 4.90-4.78 (m, 2H), 4.19-3.99 (m, 2H), 3.77 (s, 3H), 3.70-3.56 (m, 2H), 3.23-3.10 (m, 2H).

Example 61: Preparation of Compound 6-fluoro-N-(1-(3-fluoro-5-((1-methylazetidin-3-yl)methoxy)phenyl)-2-hydroxyethyl)-5-(1H-pyrazol-4-yl)indoline-1-carboxamide (T343)
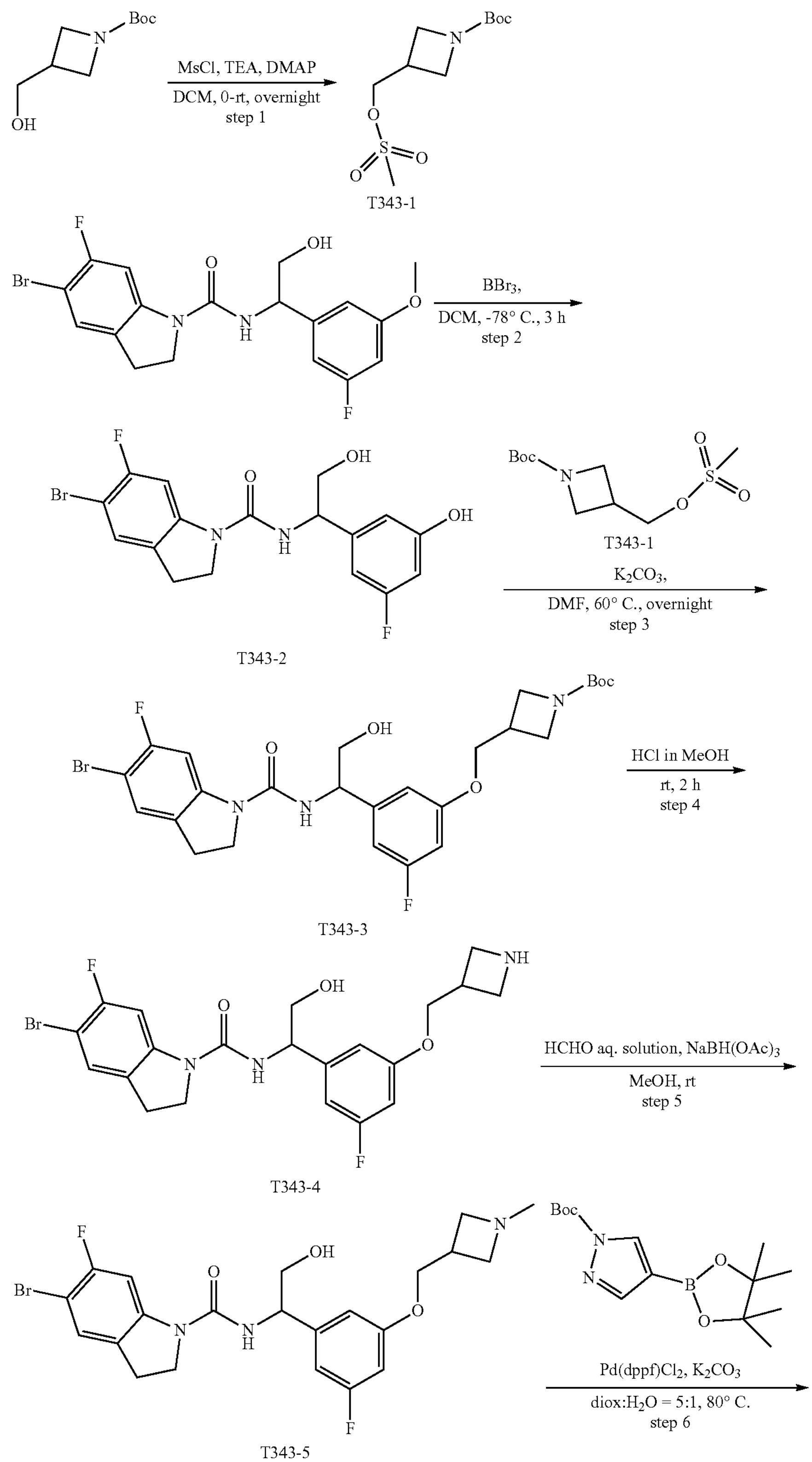
T343-1
T343-2
T343-1
T343-3
T343-4
T343-5

-continued

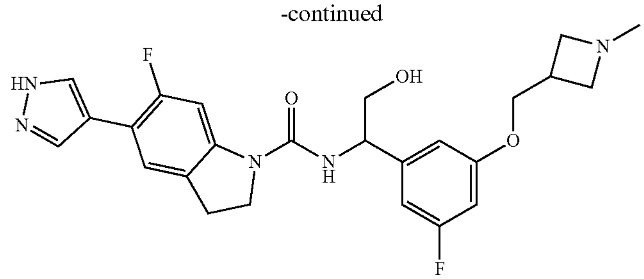

T343

? indicates text missing or illegible when filed

1 Preparation of Compound tert-butyl 3-(((methylsulfonyl)oxy)methyl)azetidine-1-carboxylate (T343-1)

Tert-butyl 3-(hydroxymethyl)azetidine-1-carboxylate (3.00 g), triethylamine (3.23 g) and N,N-lutidine (195 mg) were dissolved in dichloromethane (40 mL) under nitrogen atmosphere, and methylsulfonyl chloride (2.00 g) was added dropwise at 0° C. in an ice water bath. The mixture was slowly warmed to room temperature and stirred overnight. Water (50 mL) was added to quench the reaction, and dichloromethane (20 mL×2) was added for extraction. The organic phases were combined, washed with saturated brine (40 mL), dried over anhydrous sodium sulfate, filtered and concentrated. The resulting crude product was purified by silica gel column chromatography (petroleum ether:ethyl acetate=6:1) to give a colorless oil (3.20 g, 67.8% yield). MS $[M+H-56]^+$=210.0.

2 Preparation of Compound 5-bromo-6-fluoro-N-[1-(3-fluoro-5-hydroxyphenyl)-2-hydroxyethyl]-2,3-indoline-1-carboxamide (T343-2)

M002 (320 mg) was dissolved in anhydrous dichloromethane (10 mL) under nitrogen atmosphere, and a solution of boron tribromide in dichloromethane (4.5 mL, 1 N) was added dropwise at −78' C. After the addition was completed, the mixture was stirred at −40° C. for 3 h. Saturated sodium bicarbonate solution (20 mL) was added to quench the reaction, and dichloromethane (20 mL×3) was added for extraction. The organic phases were combined, washed with saturated brine, dried over anhydrous sodium sulfate, filtered and concentrated. The resulting crude product was purified by column chromatography (dichloromethane:methanol=30:1) to give compound T343-2 in the form of a white solid (290 mg, 89.9% yield). MS $[M+H]^+$=413.0.

3 Preparation of Compound Teri-butyl [3-(3-{1-[(5-bromo-6-fluoro-2,3-indoline-1-yl)carbonylamino]-2-hydroxyethyl}-5-fluorophenoxymethyl)azetidin-1-yl]carboxylate (T343-3)

Compound T343-2 (290 mg) was dissolved in N,N-dimethylformamide (5 mL), and potassium carbonate (193 mg) was added. The mixture was stirred at room temperature for 10 min, and then ern-butyl 3-(((methylsulfonyl)oxy)methyl)azetidine-1-carboxylate (T343-1) (224 mg) was added. The resulting mixture was heated to 60° C. and stirred overnight. Water (50 mL) was added to quench the reaction, and ethyl acetate (20 mL×3) was added for extraction. The organic phases were combined, washed with saturated sodium bicarbonate solution (30 mL), dried over anhydrous sodium sulfate, filtered and concentrated. The resulting crude product was purified by column chromatography (dichloromethane:methanol=50:1) to give compound T343-3 in the form of a pale yellow solid (290 mg, 71.1% yield). MS $[M+H]^+$=582.1.

4 Preparation of Compound N-{1-[3-(azetidin-3-ylmethoxy)-5-fluorophenyl]-2-hydroxyethyl}-5-bromo-6-fluoro-2,3-indoline-1-carboxamide (T343-4)

Compound T343-3 (290 mg) was dissolved in dichloromethane (5 mL), and a solution of hydrogen chloride in methanol (1 mL, 10 N) was added. The mixture was stirred at room temperature for 2 h. The reaction solution was concentrated under reduced pressure, dichloromethane (30 mL) was added, and saturated sodium bicarbonate solution (20 mL) was used for washing. The aqueous phase was extracted with dichloromethane (20 mL×2). The organic phases were combined, washed with saturated brine (15 mL), dried over anhydrous sodium sulfate, filtered and concentrated to give T343-4 in the form of a light yellow solid (250 mg, crude product). MS $[M+H]^+$=482.1.

5 Preparation of Compound 5-bromo-6-fluoro-N-(1-{3-fluoro-5-[(1-methylazetidin-3-yl)methoxy]phenyl}-2-hydroxyethyl)-2,3-indoline-1-carboxamide (T343-5)

Compound T343-4 (249 mg) was dissolved in methanol (15 mL), and aqueous formaldehyde solution (38 mg, 37%) was added. The mixture was stirred at room temperature for 1 h, followed by addition of sodium borohydride acetate (199 mg). The resulting mixture was stirred for 1 h. Saturated ammonium chloride solution (20 mL) was added, and dichloromethane (50 mL×2) was added for extraction. The organic phases were combined, washed with saturated brine (30 mL×2), dried over sodium sulfate, filtered and concentrated to give compound T343-5 in the form of a pale yellow solid (140 mg, crude product, 48.0% two-step yield). MS $(M+H)^+$=496.1.

6 Preparation of Compound 6-fluoro-N-(1-(3-fluoro-5-((1-methyl azetidin-3-yl)methoxy)phenyl)-2-hydroxyethyl)-5-(1H-pyrazol-4-yl)indoline-1-carboxamide (T343)

Compound T343-5 (100 mg), ten-butyl 4-(4,4,5,5-tetramethyl-1,3,2-dioxaborolan-2-yl)-1H-pyrazole-1-carboxylate (89 mg), potassium carbonate (55 mg) and [1,1'-bis(diphenylphosphino)ferrocene]dichloropalladium(II) (29 mg) were dissolved in dioxane (5 mL) and water (1 mL). The mixture was stirred at 80° C. for 18 h under nitrogen atmosphere. The reaction solution was cooled to room temperature, water (30 mL) was added, and ethyl acetate (20 mL×3) was added for extraction. The organic phases were combined, washed with saturated brine (20 mL), dried over anhydrous sodium sulfate, filtered and concentrated, and the resulting crude product was purified by preparative chromatography to give a white solid (9.6 mg, 9.9% yield). MS $(M+H)^+$=484.1.

$^1$H NMR (400 MHz, MeOD) S 8.57 (s, 1H), 7.93 (s, 2H), 7.60 (d, J=13.0 Hz, 1H), 7.46 (d, J=7.3 Hz, 1H), 6.92 (s, 1H), 6.84 (d, J=9.4 Hz, 1H), 6.72 (d, J=10.5 Hz, 1H), 4.97 (t, J=6.6 Hz, 1H), 4.20-4.08 (m, 6H), 4.06-3.95 (m, 2H), 3.87-3.77 (m, 2H), 3.24 (t, J=7.1 Hz, 3H), 2.86 (s, 3H).

Example 62: Preparation of Compound (S)-6-fluoro-N-(1-(3-fluoro-5-methoxyphenyl)-2-hydroxyethyl)-5-(3-methyl-1H-pyrazol-4-yl)indoline-1-carboxamide (T381)

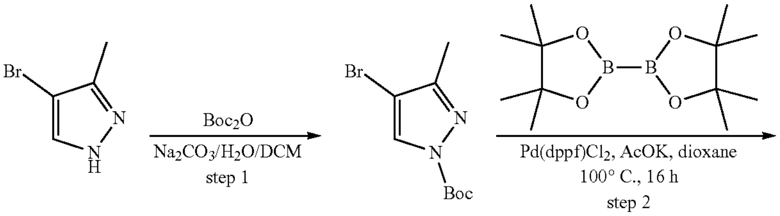

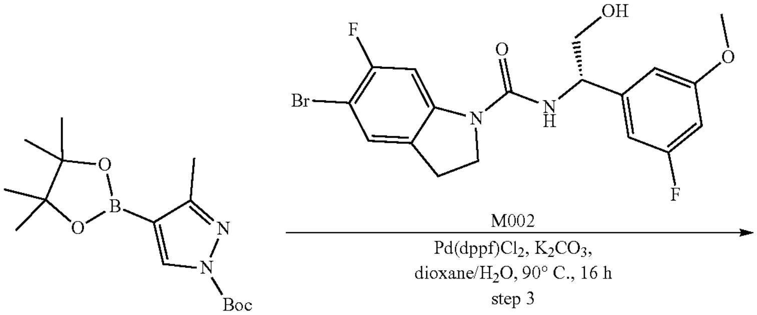

T381-2

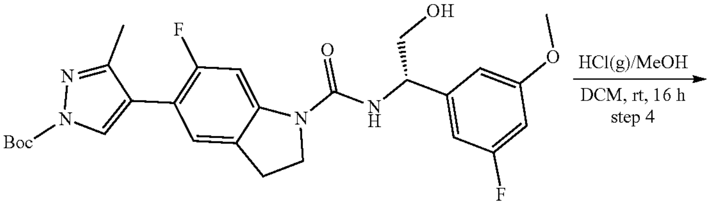

T381-3

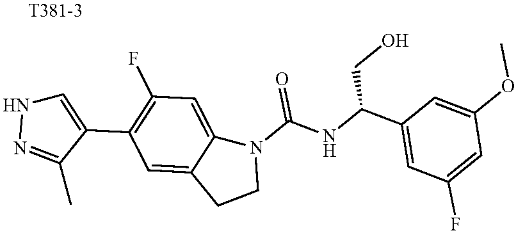

T381

? indicates text missing or illegible when filed

1 Preparation of Compound tert-butyl 4-bromo-3-methyl-1H-pyrazole-1-carboxylate (T381-1)

4-bromo-3-methylpyrazole (3.00 g) was dissolved in dichloromethane (30 mL), and sodium carbonate (10.32 g) and 4-dimethylaminopyridine (2.93 g) were added, and then di-tert-butyl dicarbonate (4.87 g) was added at room temperature. The mixture was reacted at room temperature for 16 h. Dichloromethane (50 mL) was added, and the mixture was washed with water (50 mL) and saturated brine (30 mL), dried over anhydrous sodium sulfate, filtered and concentrated to give a crude product in the form of a colorless oil (6 g). MS $[M+Na]^+$=282.9/285.0.

2 Preparation of Compound ten-butyl 3-methyl-4-(4,4,5,5-tetramethyl-1,3,2-dioxaborolan-2-yl)-1H-pyrazole-1-carboxylate (T381-2)

Compound T381-1 (6.00 g), potassium acetate (2.69 g), bis(pinacolato)diboron (5.58 g) and [1,1'-bis(diphenylphosphino)ferrocene]dichloropalladium(II) (1.07 g) were added in a 250 mL single-necked flask, followed by addition of 1,4-dioxane (60 mL). The mixture was heated to 100° C. and reacted for 16 h under nitrogen atmosphere. The reaction solution was filtered and concentrated, and the resulting crude product was separated by silica gel column chromatography (petroleum ether:dichloromethane=10:1) to give a colorless oil (3.50 g, 30% two-step yield). MS $[M-55]^-$: 252.9.

3 Preparation of Compound tert-butyl (S)-4-(6-fluoro-1-((1-(3-fluoro-5-methoxyphenyl)-2-hydroxyethyl)carbamoyl)indolin-5-yl)-3-methyl-1H-pyrazole-1-carboxylate (T381-3)

Compound M002 (150 mg) and compound T381-2 (130 mg) were dissolved in dioxane (3 mL), and a solution of potassium carbonate (121 mg) in water (0.3 mL) and [1,1'-bis(diphenylphosphino)ferrocene]dichloropalladium(II) (26 mg) were added. The mixture was reacted at 90° C. for 16 h under nitrogen atmosphere. The reaction solution was extracted with ethyl acetate (20 mL×2). The organic phase was washed with saturated brine (10 mL×2), dried over anhydrous sodium sulfate, filtered and concentrated. The resulting crude product was purified by silica gel column chromatography (methanol:dichloromethane=1:50) to give a pale yellow solid (129 mg, 62% yield). MS $[M+H]^+$=529.0.

4 Preparation of Compound (S)-6-fluoro-N-(1-(3-fluoro-5-methoxyphenyl)-2-hydroxyethyl)-5-(3-methyl-1H-pyrazol-4-yl)indoline-1-carboxamide (T381)

Compound T381-3 (129 mg) was dissolved in dichloromethane (3 mL), and methanolic hydrochloric acid (1 mL) was added. The mixture was stirred at room temperature for 16 h. The reaction solution was concentrated under reduced pressure, and the residue was purified by preparative chromatography (acetonitrile/0.1% trifluoroacetic acid-water/0.1% trifluoroacetic acid) to give a white solid (30 mg, 29% yield). MS $[M+H]^+$=429.0.

$^1$H NMR (400 MHz, DMSO) δ 7.59 (d, J=12.4 Hz, 2H), 7.15 (d, J=7.8 Hz, 1H), 6.86 (d, J=7.9 Hz, 1H), 6.81 (d, J=8.2 Hz, 2H), 6.73-6.65 (m, 1H), 4.83 (dd, J=13.4, 7.3 Hz, 1H), 4.09 (dd, J=21.0, 8.8 Hz, 2H), 3.77 (s, 3H), 3.63 (t, J=6.9 Hz, 2H), 3.21-3.11 (m, 2H), 2.22 (s, 3H).

Example 63: Preparation of Compound (S)—N-(1-(3-fluoro-5-methoxyphenyl)-2-hydroxyethyl)-6-(1H-pyrazol-4-yl)imidazo[1,5-a]pyridine-1-carboxamide (T344)

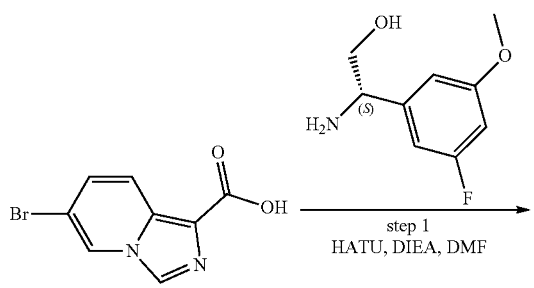

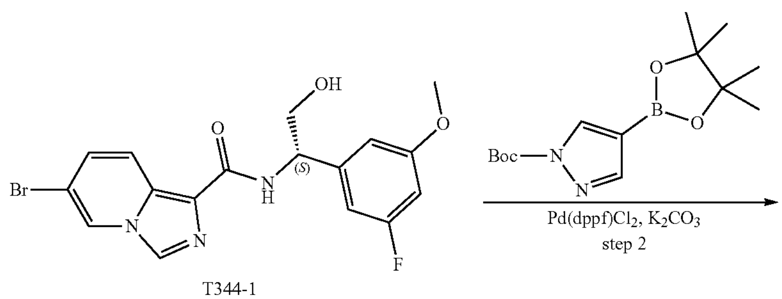

T344-1

-continued

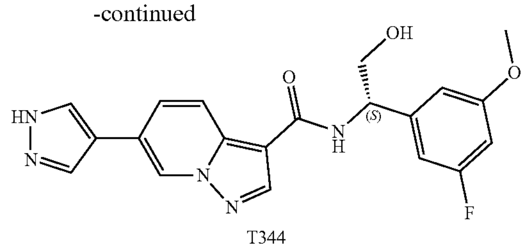

T344

1 Preparation of Compound (S)-6-bromo-N-(1-(3-fluoro-5-methoxyphenyl)-2-hydroxyethyl)imidazo[1,5-a]pyridine-1-carboxamide (T344-1)

6-bromoimidazo[1,5-a]pyridine-1-carboxylic acid (200 mg) was dissolved in DMF (10 mL) under nitrogen atmosphere, and HATU (473 mg) and DIEA (322 mg) were added. After the mixture was stirred at room temperature for 30 min, (S)-2-amino-2-(3-fluoro-5-methoxyphenyl)ethanol (230 mg) was added, and the resulting mixture was stirred at room temperature for 1 h. Water (20 mL) was added to quench the reaction, and ethyl acetate (20 mL×3) was added for extraction. The organic phases were combined, washed with saturated brine (20 mL×2), dried over anhydrous sodium sulfate and concentrated under reduced pressure. The resulting crude product was separated by silica gel column chromatography (petroleum ether/ethyl acetate=3/1) to give the product (200 mg). LC-MS $[M+H]^-$: 408.0/410.0.

2 Preparation of Compound (S)—N-(1-(3-fluoro-5-methoxyphenyl)-2-hydroxyethyl)-6-(1H-pyrazol-4-yl)imidazo[1,5-a]pyridine-1-carboxamide (T344)

Compound T344-1 (200 mg) was dissolved in 1,4-dioxane (8 mL) and water (2 mL), and tort-butyl 4 (4,4,5,5-tetramethyl-1,3,2-dioxaborolan-2-yl)-1H-pyrazole-1-carboxylate (217 mg), $Pd(dppf)Cl_2$ (36 mg) and potassium carbonate (203 mg) were added. The mixture was reacted at 90° C. for 3 h under nitrogen atmosphere. The reaction solution was diluted with water (20 mL) and extracted with ethyl acetate (20 mL×3). The organic phases were combined, washed with saturated brine (20 mL), dried over anhydrous sodium sulfate, filtered and concentrated, and the resulting crude product was separated by preparative chromatography to give a pale blue solid (56.4 mg). MS $[M+H]^+$= 395.9.

$^1$H NMR (400 MHz, DMSO) δ 13.07 (s, 1H), 8.78 (s, 1H), 8.40 (s, 1H), 8.31 (d, J=8.2 Hz, 1H), 8.23-8.00 (m, 3H), 7.46 (dd, J=9.4, 1.4 Hz, 1H), 6.84-6.78 (m, 2H), 6.69 (dt, J=11.0, 2.3 Hz, 1H), 5.12-4.96 (m, 2H), 3.75 (s, 4H).

Example 64: Preparation of Compound N-(3-fluorobenzyl)-6-(1H-pyrazol-4-yl)imidazo[1,5-a]pyridine-1-carboxamide (T368)

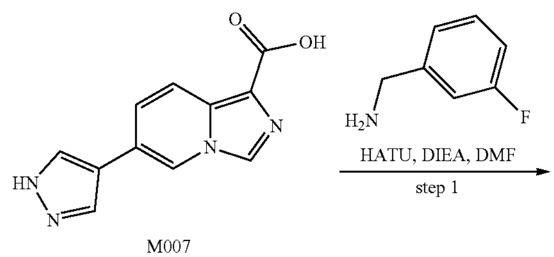

M007

-continued

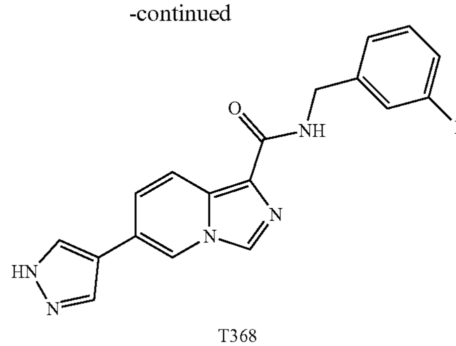

T368

Compound M007 (200 mg) was dissolved in anhydrous DMF (5 mL) under nitrogen atmosphere, and (3-fluorophenyl)methylamine (165 mg), HATU (502 mg) and DIEA (341 mg) were added. The mixture was reacted at room temperature for 1 h. Water (15 mL) was added to quench the reaction, and ethyl acetate (15 mL×3) was added for extraction. The organic phase was washed with saturated brine (30 mL), dried over anhydrous sodium sulfate and concentrated under reduced pressure, and the residue was separated by silica gel column chromatography (DCM/MeOH=15/1) to give a white solid (20.2 mg). LC-MS [M+H]–: 336.0.

$^1$H NMR (400 MHz, MeOD) δ 8.63 (s, 1H), 8.28 (s, 1H), 8.18-8.11 (m, 2H), 8.01-7.94 (m, 1H), 7.44 (dd, J=9.5, 1.4 Hz, 1H), 7.36-7.29 (m, 1H), 7.20 (d, J=7.7 Hz, 1H), 7.12 (d, J=10.1 Hz, 1H), 6.97 (td, J=8.4, 2.4 Hz, 1H), 4.62 (s, 2H).

Example 65: Preparation of Compound N-(3-(cyclopropylmethoxy)benzyl)-6-(1H-pyrazol-4-yl)imidazo[1,5-a]pyridine-1-carboxamide (T376)

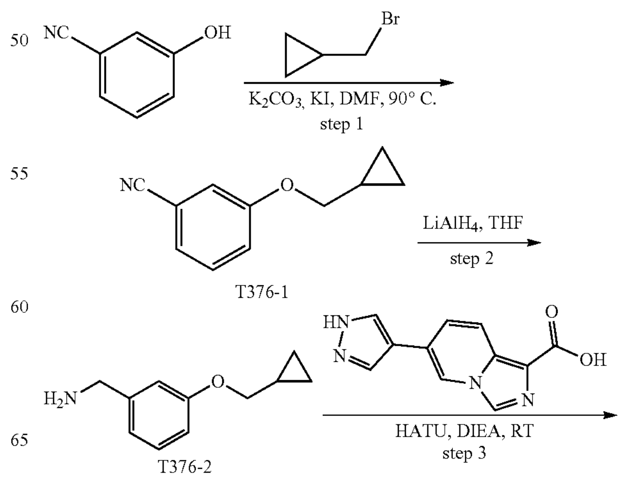

T376-1

T376-2

-continued

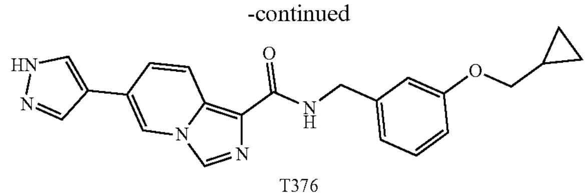

T376

1 Preparation of Compound 3-(cyclopropylmethoxy)benzonitrile (T376-1)

3-hydroxybenzonitrile (1 g) was dissolved in DMF (10 mL) under nitrogen atmosphere, and (bromomethyl)cyclopropane (1.1 g), potassium carbonate (2.6 g) and potassium iodide (2.8 g) were added. The mixture was reacted at 90° C. for 4 h. Water (30 mL) was added to quench the reaction, and ethyl acetate (30 mL×3) was added for extraction. The organic phase was washed with saturated brine (30 mL), dried over anhydrous sodium sulfate and concentrated, and the residue was purified by silica gel column chromatography (PE/EA=2/1) to give a colorless oily liquid (1.0 g, 68.5% yield). LC-MS $[M+H]^+$: 174.1.

2 Preparation of Compound (3-(cyclopropylmethoxy)phenyl)methyl amine (T376-2)

Compound T376-1 (1 g) was dissolved in tetrahydrofuran (10 mL) under nitrogen atmosphere, and then the mixture was cooled to 0° C., followed by addition of lithium aluminum hydride (241 mg). The mixture was warmed to room temperature and reacted at room temperature for 4 h. Water (10 mL) was added to quench the reaction, sodium hydroxide solution (10 mL, 1 N) was added, and ethyl acetate (20 mL×3) was added for extraction. The organic phase was washed with saturated brine (30 mL), dried over anhydrous sodium sulfate and concentrated under reduced pressure to give a colorless oily liquid (1 g). LC-MS $[M+H]^+$: 178.1.

Example 3: Preparation of Compound N-(3-(cyclopropylmethoxy)benzyl)-6-(1H-pyrazol-4-yl)imidazo [1,5-a]pyridine-1-carboxamide (T376)

Compound M007 (200 mg) was dissolved in anhydrous DMF (5 mL) under nitrogen atmosphere, and compound T376-2 (156 mg), HATU (502 mg) and DIEA (341 mg) were added. The mixture was reacted at room temperature for 1 h. Water (15 mL) was added to quench the reaction, and ethyl acetate (15 mL×3) was added for extraction. The organic phase was washed with saturated brine (30 mL), dried over anhydrous sodium sulfate and concentrated under reduced pressure, and the residue was separated by silica gel column chromatography (DCM/MeOH=15/1) to give a white solid (20 mg). LC-MS $[M+H]^-$: 388.1.

$^1H$ NMR (400 MHz, MeOD) δ 8.62 (s, 1H), 8.27 (s, 1H), 8.16-8.09 (m, 2H), 7.98 (s, 1H), 7.43 (dd, J=9.5, 1.4 Hz, 1H), 7.22 (t, J=8.1 Hz, 1H), 6.96-6.92 (m, 2H), 6.79 (dd, J=8.1, 2.0 Hz, 1H), 4.57 (s, 2H), 3.80 (d, J=6.9 Hz, 2H), 1.28-1.17 (m, 1H), 0.62-0.52 (m, 2H), 0.35-0.27 (m, 2H).

Example 66: Preparation of Compound 6-(5-fluoro-1H-pyrazol-4-yl)-N-(3-fluoro-5-methoxybenzyl) imidazo [1,5-a]pyridine-1-carboxamide (T355)

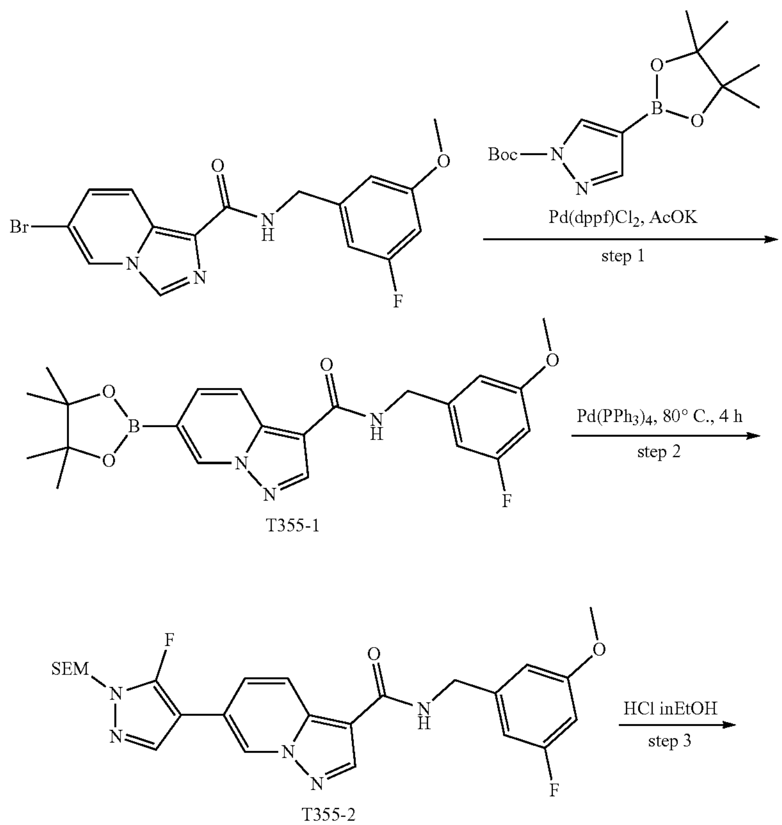

T355-1

T355-2

-continued

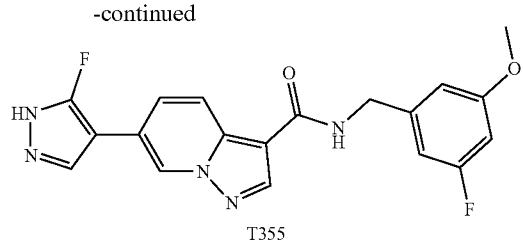

T355

1 Preparation of Compound N-(3-fluoro-5-methoxybenzyl)-6-(4,4,5,5-tetramethyl-1,3,2-dioxaborolan-2-yl)imidazo[1,5-a]pyridine-1-carboxamide (T355-1)

6-bromo-N-(3-fluoro-5-methoxybenzyl)imidazo[1,5-a]pyridine-1-carboxamide (200 mg) was dissolved in 1,4-dioxane (10 mL), and tert-butyl 4-(4,4,5,5-tetramethyl-1,3,2-dioxaborolan-2-yl)-1H-pyrazole-1-carboxylate (202 mg), Pd(dppf)$Cl_2$ (78 mg) and potassium acetate (208 mg) were added. The mixture was reacted at 80° C. for 12 h under nitrogen atmosphere. The reaction solution was diluted with water (10 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (wet loading, PE/EA=5/1) to give a brown oily liquid (200 mg). MS $[M+H]^+$=426.2.

2 Preparation of Compound 6-(5-fluoro-1-((2-(trimethylsilyl)ethoxy)methyl)-1H-pyrazol-4-yl)-N-(3-fluoro-5-methoxybenzyl)imidazo[1,5-a]pyridine-1-carboxamide (T355-2)

Compound T355-1 (200 mg) was dissolved in 1,4-dioxane (8 mL) and water (2 mL), and 4-bromo-5-fluoro-1-((2-(trimethylsilyl)ethoxy)methyl)-1H-pyrazole (157 mg), $Pd(PPh_3)_4$ (56 mg) and potassium carbonate (207 mg) were added. The mixture was reacted at 90° C. for 4 h under nitrogen atmosphere. The reaction solution was diluted with water (20 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (PE/EA=5/1) to give a yellow oily liquid (100 mg, 39.0% two-step yield). MS $[M+H]^+$=514.0.

3 Preparation of Compound 6-(5-fluoro-1H-pyrazol-4-yl)-N-(3-fluoro-5-methoxybenzyl)imidazo[1,5-a]pyridine-1-carboxamide (T355)

Compound T355-2 (100 mg) was dissolved in ethanol (5 mL), and a solution of hydrochloric acid in ethanol (2 mL, mass fraction of 33%) was added. The mixture was reacted at room temperature for 2 h under nitrogen atmosphere. The reaction solution was concentrated under reduced pressure, and the residue was separated by preparative chromatography to give a white solid (6.5 mg). MS $[M+H]^+$=384.0.

$^1$H NMR (400 MHz, DMSO) δ 12.75 (s, 1H), 8.71 (t, J=6.5 Hz, 1H), 8.66 (s, 1H), 8.50 (s, 1H), 8.28 (d, J=1.9 Hz, 1H), 8.09 (d, J=9.5 Hz, 1H), 7.39 (d, J=9.4 Hz, 1H), 6.78-6.65 (m, 3H), 4.43 (d, J=6.4 Hz, 2H), 3.74 (s, 3H).

Example 67: Preparation of Compound 6-fluoro-5-(5-fluoro-1H-pyrazol-4-yl)-N-(4-fluoro-3-methoxybenzyl)indoline-1-carboxamide (T384)

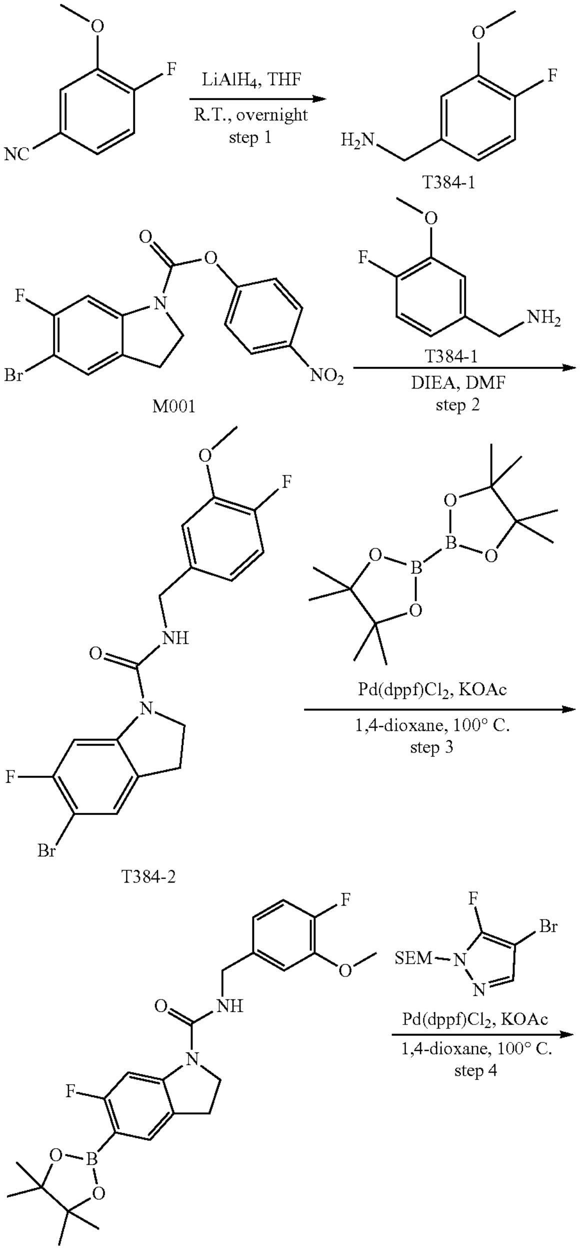

T384-1

M001

T384-2

T384-3

-continued

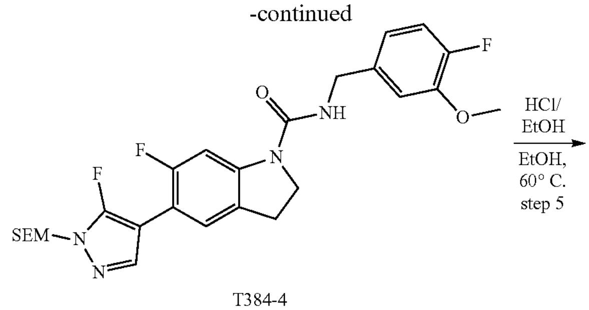

T384-4

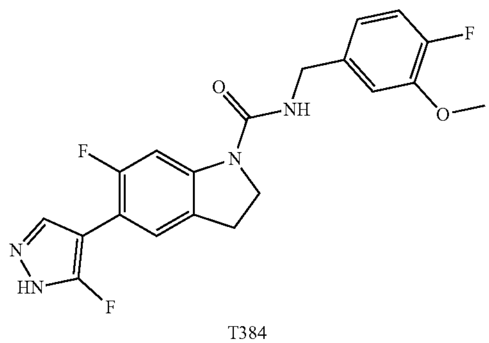 [SMILES: COc1cc(CNC(=O)N2CCc3cc(-c4cn[nH]c4F)c(F)cc32)ccc1F ; "T384"]

T384

1 Preparation of Compound (4-fluoro-3-methoxyphenyl)methylamine (T384-1)

4-fluoro-3-methoxybenzonitrile (500 mg) was dissolved in anhydrous tetrahydrofuran (10 mL), and lithium aluminum hydride (503 mg) was added at 0° C. The mixture was stirred overnight at room temperature under nitrogen atmosphere. After the reaction was completed, the reaction solution was filtered, and the filtrate was concentrated by rotary evaporation. Saturated aqueous sodium carbonate solution was added to adjust the pH to 12, and ethyl acetate (20 mL×8) was added for extraction. The organic phases were combined, dried over anhydrous sodium sulfate, filtered and concentrated by rotary evaporation to give the product (4-fluoro-3-methoxyphenyl)methylamine in the form of a pale brown oil (crude product, 400 mg, 77.96% yield). LC-MS $[M+H]^+$: 139.1

2 Preparation of Compound 5-bromo-6-fluoro-N-(4-fluoro-3-methoxybenzyl)indoline-1-carboxamide (T384-2)

Compound MOOT (400 mg) was dissolved in anhydrous N,N-dimethylformamide (10 mL), and (4-fluoro-3-methoxyphenyl)methylamine (244 mg) and N,N-diisopropylethylamine (406 mg) were added. The mixture was heated and stirred at 100° C. for 3 h under nitrogen atmosphere. After the reaction was completed, water (20 mL) was added to quench the reaction, and ethyl acetate (20 mL 3) was added for extraction. The organic phases were combined, washed with saturated brine (20 mL 3), dried over anhydrous sodium sulfate and filtered, and the filtrate was concentrated by rotary evaporation. The resulting crude product was purified by silica gel column chromatography (4 g, dichloromethane:ethyl acetate=4:1) to give the compound T384-2 in the form of a white solid (400 mg, 95.98% yield). LC-MS $[M+H]^+$: 396.9

3 Preparation of Compound 6-fluoro-N-(4-fluoro-3-methoxybenzyl)-5-(4,4,5,5-tetramethyl-1,3,2-dioxaborolan-2-yl)indoline-1-carboxamide (T384-3)

Compound T384-2 (250 mg) was dissolved in 1,4-dioxane (10 mL), and [1,1'-bis(diphenylphosphino)ferrocene]dichloropalladium(II) (45 mg), bis(pinacolato)diboron (192 mg) and potassium acetate (185 mg) were added. The mixture was stirred overnight at 100° C. under nitrogen atmosphere. The reaction solution was cooled to room temperature and then filtered to remove the precipitates, and the filtrate was concentrated by rotary evaporation. The residue was purified by silica gel column chromatography (4 g, dichloromethane:ethyl acetate=1:1) and concentrated by rotary evaporation to give compound T384-3 in the form of a brown oil (225 mg, 81.77% yield). LC-MS $[M+H]^+$: 445.1.

4 Preparation of Compound 6-fluoro-5-(5-fluoro-1-((2-(trimethylsilyl)ethoxy)methyl)-1H-pyrazol-4-yl)-N-(4-fluoro-3-methoxybenzyl)indoline-1-carboxamide (T384-4)

Compound T384-3 (200 mg) was dissolved in a mixed solution of dioxane (5 mL) and water (1 mL), and 4-bromo-5-fluoro-14(2-(trimethylsilyl)ethoxy)methyl)-1H-pyrazole (200 mg), [1,1'-bis(diphenylphosphino)ferrocene]dichloropalladium(II) (36 mg) and potassium carbonate (186 mg) were added. The mixture was stirred overnight at 100° C. The reaction solution was cooled to room temperature and then filtered to remove the precipitates. The filtrate was concentrated by rotary evaporation, and the residue was purified by silica gel column chromatography (4 g, dichloromethane:ethyl acetate=1:1) to give 6-fluoro-5-(5-fluoro-1-((2-(trimethylsilyl)ethoxy)methyl)-1H-pyrazol-4-yl)-N-(4-fluoro-3-methoxybenzyl)indoline-1-carboxamide in the form of a yellow oil (110 mg, 45.77% yield). LC-MS $[M+H]^+$: 534.1

5 Preparation of Compound 6-fluoro-5-(5-fluoro-1H-pyrazol-4-yl)-N-(4-fluoro-3-methoxybenzyl)indoline-1-carboxamide (T384)

6-fluoro-5-(5-fluoro-1-((2-(trimethylsilyl)ethoxy)methyl)-1H-pyrazol-4-yl)-N-(4-fluoro-3-methoxybenzyl)indoline-1-carboxamide (110 mg) was dissolved in ethanol (3 mL), and ethanol hydrochloride (33%, 1 mL) was added. The mixture was stirred at 60° C. for 30 min. The reaction solution was cooled to room temperature and concentrated by rotary evaporation, saturated sodium carbonate solution was added to adjust the pH to 11, and ethyl acetate (20 mL×3) was added for extraction. The organic phases were combined, washed with saturated brine (30 mL 2), dried over sodium sulfate and filtered. The filtrate was concentrated by rotary evaporation, and the residue was purified by silica gel column chromatography (4 g, dichloromethane:methanol=20:1), concentrated by rotary evaporation, purified by preparative chromatography and then lyophilized to give product T384 in the form of a white powder (7.8 mg, 9.2% yield). LC-MS $[M+H]^+$: 403.0.

$^1H$ NMR (301 MHz, CD3OD) δ 7.79 (t, J=2.4 Hz, 1H), 7.66 (d, J=12.9 Hz, 1H), 7.39 (d, J=7.6 Hz, 1H), 7.16-7.07 (m, 1H), 7.02 (dd, J=11.3, 8.3 Hz, 1H), 6.95-6.86 (m, 1H), 4.40 (s, 2H), 4.02 (t, J=8.6 Hz, 2H), 3.87 (s, 3H), 3.20 (t, J=8.6 Hz, 2H).

Example 68: Preparation of Compound N-(3-(cyclopropylmethoxy)$_5$-fluorobenzyl)-6-fluoro-5-(3-fluoro-1H-pyrazol-4-yl)indoline-1-carboxamide (T347)
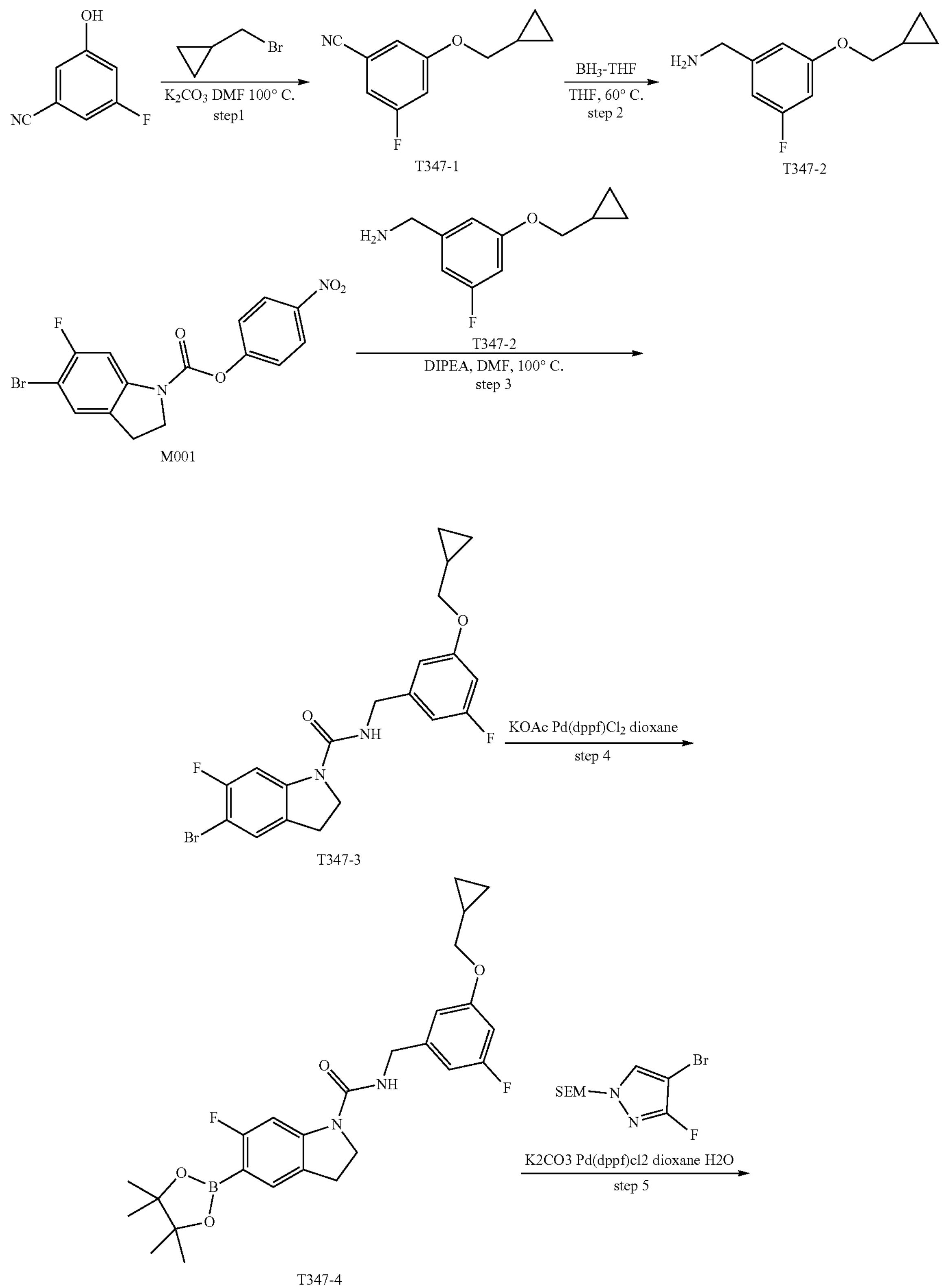
T347-1
T347-2
M001
T347-2
T347-3
T347-4

-continued

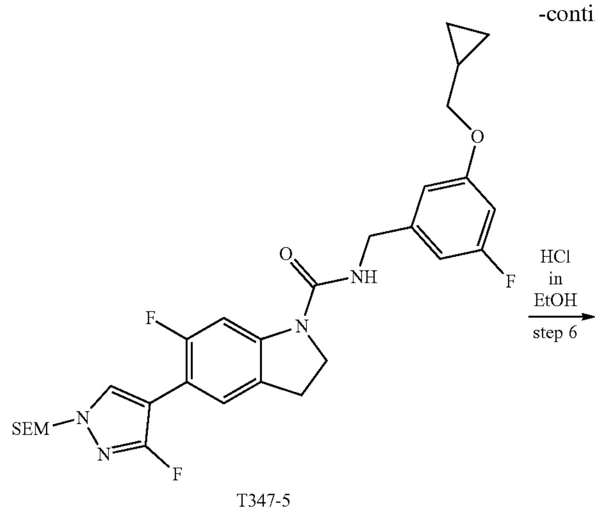

T347-5

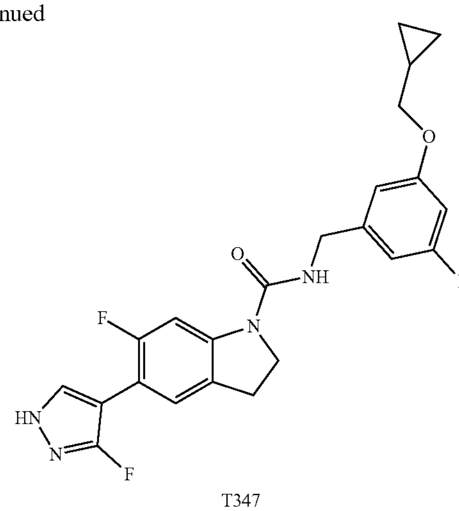

T347

1 Preparation of Compound 3-(cyclopropylmethoxy)-5-fluorobenzonitrile (T347-1)

3-fluoro-5-hydroxybenzonitrile (2.00 g) was dissolved in anhydrous N,N-dimethylformamide (30 mL), and (bromomethyl)cyclopropane (2.35 g) and potassium carbonate (6.05 g) were added. The mixture was stirred at 100° C. for 5 h under nitrogen atmosphere. After the reaction was completed, the reaction solution was diluted with water (60 mL) and extracted with ethyl acetate (40 mL 2). The organic phase was washed with saturated brine (50 mL 2), dried over anhydrous sodium sulfate, filtered and concentrated, and the residue was separated by column chromatography (PE/EA=20/1) to give a colorless oily liquid (2.50 g, 89% yield). LC-MS $[M+H]^+$: 192.2

2 Preparation of Compound (3-(cyclopropylmethoxy)-5-fluorophenyl)methylamine (T347-2)

Compound T347-1 (500 mg) was dissolved in anhydrous tetrahydrofuran (5 mL), and a solution of Borane-tetrahydrofuran complex (1 M, 21 mL) was added. The mixture was reacted at 60° C. for 12 h under nitrogen atmosphere. After the reaction was completed, methanol (5 mL) was added to quench the reaction in an ice bath, and diluted hydrochloric acid (1 N, 5 mL) was added. The mixture was stirred at room temperature for 15 min, and then extracted with ethyl acetate (10 mL×2). The aqueous phase was adjusted to pH of about 10 with sodium hydroxide (2 N) and extracted with ethyl acetate (10 mL×2). The organic phases were combined, washed with saturated brine (30 mL×2), dried over anhydrous sodium sulfate, filtered and concentrated, and the residue was separated by column chromatography (PE/EA=5/1) to give a pale yellow oily liquid (410 mg, 80% yield). LC-MS $[M+H]_=$195.9.

3 Preparation of Compound 5-bromo-N-(3-(cyclopropylmethoxy)-5-fluorobenzyl)-6-fluoroindoline-1-carboxamide (T347-3)

M001 (300 mg) was dissolved in N,N-dimethylformamide (10 mL), and compound T347-2 (184 mg) and NN-diisopropylethylamine (305 mg) were added. The mixture was reacted at 100° C. for 3 h under nitrogen atmosphere. The reaction solution was diluted with water (20 mL) and extracted with ethyl acetate (20 mL×2). The organic phase was washed with saturated brine (30 mL×2), dried over anhydrous sodium sulfate, filtered and concentrated, and the residue was separated by column chromatography (PE/EA=3/1) to give a pale yellow oily liquid (300 mg, 87% yield). LC-MS $[M+H]^+$: 436.8.

4 Preparation of Compound N-(3-(cyclopropylmethoxy)-5-fluorobenzyl)-6-fluoro-5-(4,4,5,5-tetramethyl-1,3,2-dioxaborolan-2-yl)indoline-1-carboxamide (T347-4)

Compound T347-3 (300 mg) was dissolved in anhydrous 1,4 dioxane (5 mL), and potassium acetate (135 mg), bis(pinacolato)diboron (210 mg), and [1,1'-bis(diphenylphosphino)ferrocene]dichloropalladium(II) (50 mg) were added. The mixture was reacted at 85° C. for 3 h under nitrogen atmosphere. The reaction solution was cooled to room temperature, filtered, diluted with water (10 mL) and extracted with ethyl acetate (10 mL×2). The organic phase was washed with saturated brine (30 mL), dried over anhydrous sodium sulfate and concentrated, and the residue was separated by column chromatography (wet loading, PE/EA=3/1) to give a brown oily liquid (110 mg, 33% two-step yield). LC-MS $[M+H]^+$: 484.8.

5 Preparation of Compound N-(3-(cyclopropylmethoxy)-5-fluorobenzyl)-6-fluoro-5-(3-fluoro-1-((2-(trimethylsilyl)ethoxy)methyl)-1H-pyrazol-4-yl)indoline-1-carboxamide (T347-5)

Compound T347-4 (110 mg) was dissolved in dioxane (5 mL) and water (1 mL), and 4-bromo-3-fluoro-1-((2-(trimethylsilyl)ethoxy)methyl)-1H-pyrazole (81 mg), potassium carbonate (63 mg) and [1,1'-bis(diphenylphosphino)ferrocene]dichloropalladium(II) (17 mg) were added. The mixture was stirred at 80° C. for 3 h. The reaction solution was cooled to room temperature and filtered, water (10 mL) was added, and ethyl acetate (10 mL×2) was added for extraction. The organic phase was washed with saturated brine (20 mL), dried over anhydrous sodium sulfate and concentrated, and the residue was separated by column chromatography (PE/EA=2/1) to give a colorless oily liquid (45 mg, 34% yield). LC-MS $[M+H]^+$: 572.8.

6 Preparation of Compound N-(3-(cyclopropyl-methoxy)$_5$-fluorobenzyl)-6-fluoro-5-(3-fluoro-1H-pyrazol-4-yl)indoline-1-carboxamide (T347)

Compound T347-5 (45 mg) was dissolved in ethanol (2 mL), and a solution of hydrochloric acid in ethanol (33%, 0.5 mL) was added. The mixture was reacted at room temperature for 1.5 h under nitrogen atmosphere. After the reaction was completed, the reaction solution was diluted with water (5 mL) and extracted with ethyl acetate (5 mL×2). The aqueous phase was adjusted to PH of about 10 with sodium hydroxide (2 N) and extracted with ethyl acetate (5 mL 2). The organic phase was washed with saturated brine (10 mL), dried over anhydrous sodium sulfate and concentrated, and the residue was subjected to preparative chromatography to give a white solid (11.8 mg, 34% two-step yield). LC-MS $[M+H]^+$: 442.8.

$^1$H NMR (400 MHz, MeOD) δ 7.81-7.76 (m, 1H), 7.66 (d, J=12.9 Hz, 1H), 7.39 (d, J=7.1 Hz, 1H), 6.73 (s, 1H), 6.65 (d, J=9.4 Hz, 1H), 6.53 (dt, J=10.8, 2.3 Hz, 1H), 4.39 (s, 2H), 4.04 (t, J=8.7 Hz, 2H), 3.81 (d, J=6.9 Hz, 2H), 3.21 (t, J=8.6 Hz, 2H), 127-1.20 (m, 1H), 0.63-0.55 (m, 2H), 0.38-0.29 (m, 2H).

Example 69: Preparation of Compound 5-(3-amino-1H-pyrazol-4-yl)-N-(3,5-difluorobenzyl)-6-fluoroindole-1-carboxamide (T364)

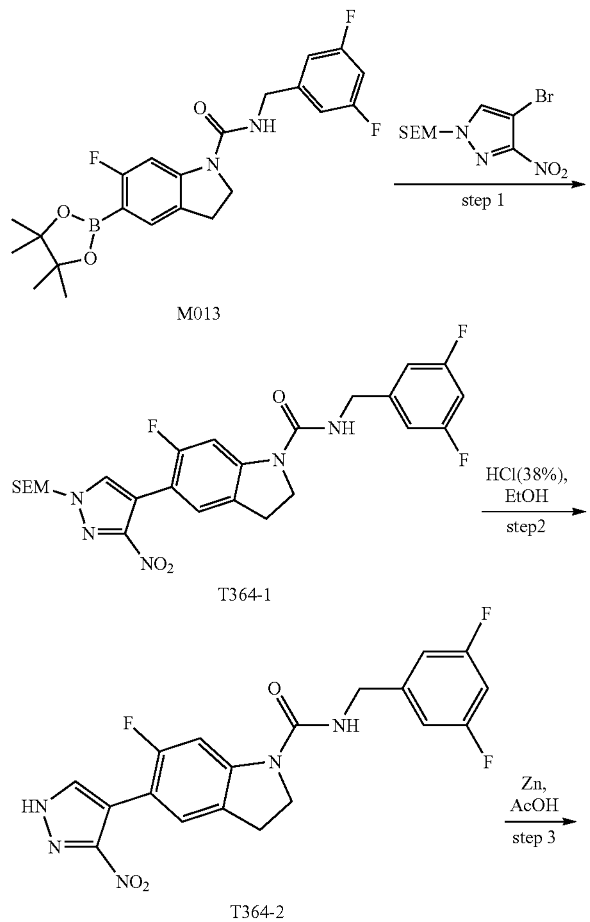

M013

T364-1

T364-2

-continued

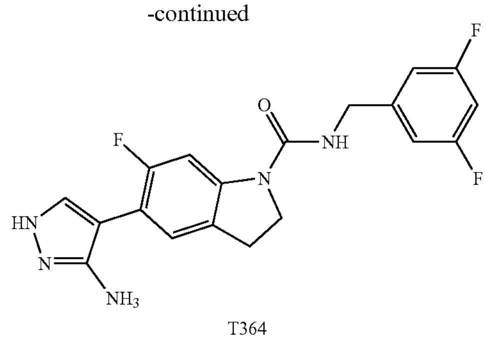

T364

1 Preparation of Compound 6-fluoro-N-(3,5-difluorobenzyl)-5-(3-nitro-1-(((2-(trimethylsilyl)ethoxy)methyl)-1H-pyrazol-4-yl)indoline-1-carboxamide (T364-1)

Compound M013 (900 mg), 4-bromo-3-nitro-1-(((2-(trimethylsilyl)ethoxy)methyl)-1N-pyrazole (673 mg), anhydrous potassium carbonate (575 mg) and [1,1'-bis(diphenylphosphino)ferrocene]dichloropalladium(II) (152 mg) were added to 1,4-dioxane/water (20:1, 10 mL) under nitrogen atmosphere. The mixture was stirred at 80° C. for 2 h in an oil bath. After the reaction was completed, the reaction solution was diluted with water (50 mL) and extracted with ethyl acetate (30 mL 3). The organic phases were combined, washed with saturated brine (20 mL), dried over anhydrous sodium sulfate and concentrated, and the residue was purified by column chromatography (petroleum ether:ethyl acetate=20:1) to give a yellow oil (750 mg, 65.00% yield). MS $(M+H)^+$=548.2.

2 Preparation of Compound 6-fluoro-N-(3,5-difluorobenzyl)-5-(3-nitro-1H-pyrazol-4-yl)indoline-1-carboxamide (T364-2)

Compound T364-1 (750 mg) was dissolved in ethanol (10 mL), and concentrated hydrochloric acid (2 mL) was added. The mixture was stirred under reflux in an oil bath for 5 h, and after the reaction was completed as detected by liquid mass spectrometry, the reaction solution was directly used in the next step without treatment. MS $(M+H)^+$=417.6.

3 Preparation of Compound 5-(3-amino-1H-pyrazol-4-yl)-6-fluoro-N-(3,5-difluorobenzyl)indoline-1-carboxamide (T364)

Activated zinc powder (1097 mg) was added to the reaction solution obtained in the previous step in an ice bath, and then acetic acid (3 mL) was added. The mixture was warmed to room temperature and stirred for 2 h. The reaction solution was concentrated under reduced pressure, and then saturated sodium bicarbonate (10 mL) was added and ethyl acetate (5 mL×3) was added for extraction. The organic phases were combined, dried over anhydrous sodium sulfate and concentrated, and the resulting crude product was purified by silica gel column chromatography (dichloromethane:methanol=20:1) to give a white solid (154.23 mg, 22.60% yield). MS $(M+H)^+$=388.2.

$^1$H NMR (400 MHz, DMSO) δ 11.72 (s, 1H), 7.60 (d, J=12.8 Hz, 1H), 7.47 (d, J=1.8 Hz, 1H), 7.41 (t, J=5.9 Hz,

1H), 7.31 (d, J=8.0 Hz, 1H), 7.15-6.99 (m, 3H), 4.62 (s, 2H), 4.35 (d, J=5.8 Hz, 2H), 4.02 (t, J=8.7 Hz, 2H), 3.14 (t, J=8.5 Hz, 2H).

Example 70: Preparation of Compound 5-(3-amino-1H-pyrazol-4-yl)-N-(3-cyano-5-fluorobenzyl)-6-fluoroindoline-1-carboxamide (T348)

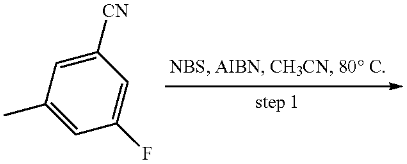

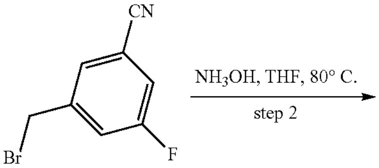

T348-1

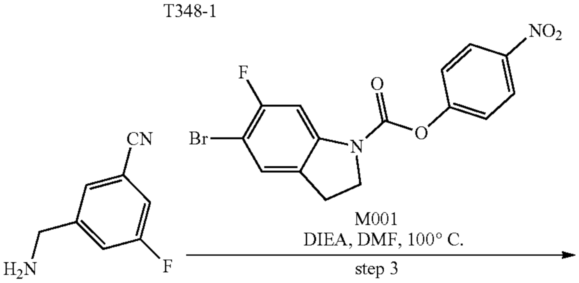

T348-2

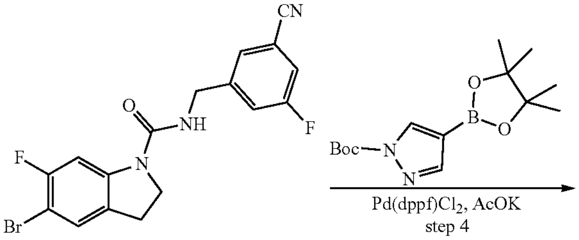

T348-3

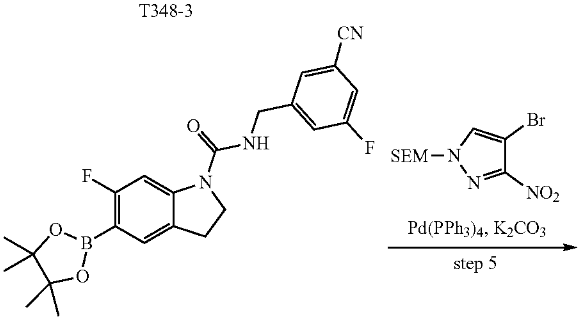

T348-4

-continued

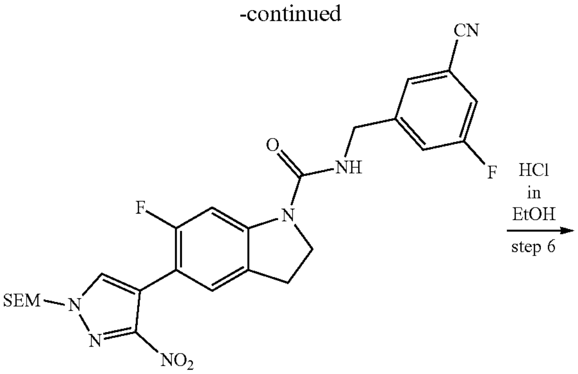

T348-5

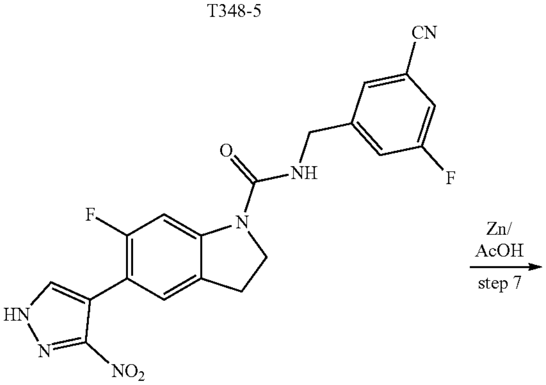

T348-6

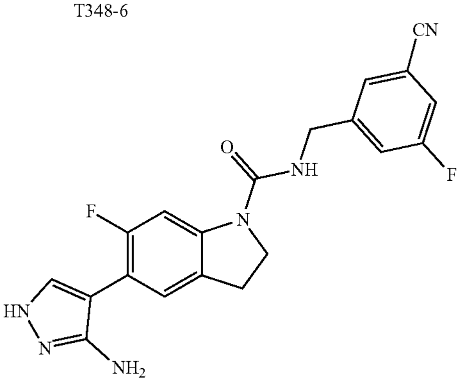

T348

1 Preparation of Compound 3-(bromomethyl)-5-fluorobenzonitrile (T348-1)

3-fluoro-5-methylbenzonitrile (10 g) was dissolved in acetonitrile (100 mL) under nitrogen atmosphere, and NBS (13.8 g) and AIBN (240 mg) were added. The mixture was heated to 80° C. and reacted for 3 h. The mixture was filtered and concentrated, and the residue was separated by silica gel column chromatography (petroleum ether/ethyl acetate=5/1) to give a yellow solid (6.0 g, 37.9% yield). LC-MS $[M+H]^+$: 213.9/215.9.

2 Preparation of Compound 3-(aminomethyl)-5-fluorobenzonitrile (T348-2)

Compound T348-1 (6.0 g) was dissolved in aqueous ammonia (500 mL) and tetrahydrofuran (10 mL), and the mixture was warmed to 80° C. and reacted for 2 h. The reaction solution was extracted with dichloromethane (300 mL×3). The organic phases were combined, washed with saturated brine (20 mL×2), dried over anhydrous sodium sulfate and concentrated under reduced pressure to give a yellow solid (3.0 g). LC-MS $[M+H]^+$: 151.1.

3 Preparation of Compound 5-bromo-N-(3-cyano-5-fluorobenzyl)-6-fluoroindoline-1-carboxamide (T348-3)

Compound M001 (700 mg) was dissolved in DMF (10 mL) under nitrogen atmosphere, and compound T348-2 (413 mg) and DIEA (712 mg) were added. The mixture was heated to 100° C. and reacted for 16 h. Water (30 mL) was added to quench the reaction, and ethyl acetate (30 mL×3) was added for extraction. The organic phases were combined, washed with saturated brine (30 mL×2), dried over anhydrous sodium sulfate, filtered and concentrated. The resulting crude product was separated by silica gel column chromatography (petroleum ether:ethyl acetate=3:1) to give a yellow solid (700 mg). LC-MS $[M+H]^+$: 391.8/393.8.

4 Preparation of Compound N-(3-cyano-5-fluorobenzyl)-6-fluoro-5-(4,4,5,5-tetramethyl-1,3,2-dioxaborolan-2-yl)indoline-1-carboxamide (T348-4)

Compound T348-3 (700 mg) was dissolved in 1,4-dioxane (10 mL), and sera-butyl 4-(4,4,5,5-tetramethyl-1,3,2-dioxaborolan-2-yl)-1H-pyrazole-1-carboxylate (679 mg), $Pd(dppf)Cl_2$ (130 mg) and potassium acetate (525 mg) were added. The mixture was reacted at 80° C. for 12 h under nitrogen atmosphere. The reaction solution was diluted with water (10 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (wet loading, PE/EA=3/1) to give a brown oily liquid (700 mg). MS $[M+H]^+$=440.1.

6 Preparation of Compound N-(3-cyano-5-fluorobenzyl)-6-fluoro-5-(3-nitro-1-((2-(trimethylsilyl)ethoxy)methyl)-1H-pyrazol-4-yl)indoline-1-carboxamide (T348-5)

4-bromo-3-nitro-1-(((2-(trimethylsilyl)ethoxy)methyl)-1H-pyrazole (772 mg) was dissolved in 1,4-dioxane (8 mL) and water (2 mL), and compound T348-4 (700 mg), $Pd(PPh_3)_4$ (116 mg) and potassium carbonate (660 mg) were added. The mixture was reacted at 90° C. for 4 h under nitrogen atmosphere. The reaction solution was diluted with water (20 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (PE/EA=1/1) to give a yellow oily liquid (250 mg). MS $[M+H]^+$=555.0.

6 Preparation of Compound N-(3-cyano-5-fluorobenzyl)-6-fluoro-5-(3-nitro-1H-pyrazol-4-yl)indoline-1-carboxamide (T348-6)

Compound T348-5 (200 mg) was dissolved in ethanol (5 mL), and a solution of hydrochloric acid in ethanol (2 mL, mass fraction of 33%) was added. The mixture was reacted at room temperature for 2 h under nitrogen atmosphere. The reaction solution was directly used in the next step without post-treatment. MS $[M+H]^+$=425.0.

7 Preparation of Compound 5-(3-amino-1H-pyrazol-4-yl)-N-(3-cyano-5-fluorobenzyl)-6-fluoroindoline-1-carboxamide (1348)

Zinc powder (70 mg) was added into the reaction solution obtained in the previous step at room temperature, and the mixture was reacted at room temperature for 2 h under nitrogen atmosphere. The reaction solution was concentrated under reduced pressure, and the residue was separated by preparative chromatography to give a white solid (20 mg). MS $[M+H]^+$=394.7.

$^1H$ NMR (400 MHz, DMSO) δ 8.01 (d, J=1.1 Hz, 1H), 7.76-7.71 (m, 1H), 7.67 (d, J=1.6 Hz, 1H), 7.64 (s, 1H), 7.60-7.55 (m, 2H), 7.32 (d, J=7.8 Hz, 1H), 4.39 (d, J=5.7 Hz, 2H), 4.07 (t, J=8.7 Hz, 2H), 3.16 (t, J=8.6 Hz, 2H).

Example 71: Preparation of Compound 5-(3-amino-1H-pyrazol-4-yl)-6-fluoro-N-(3-fluoro-5-methoxybenzyl)indoline-1-carboxamide (T385)

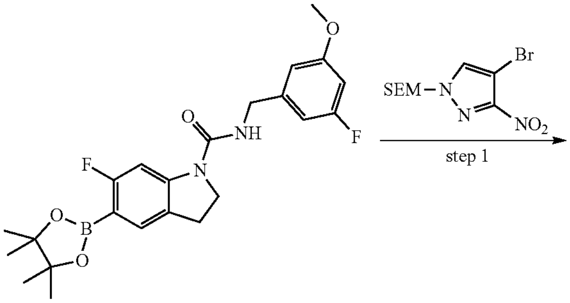

M008

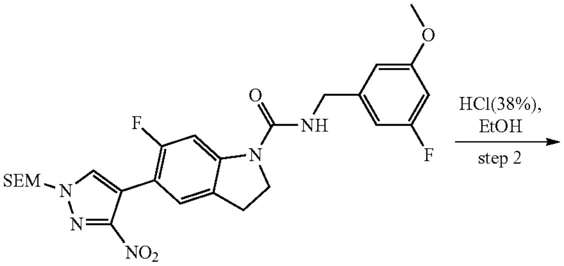

T385-1

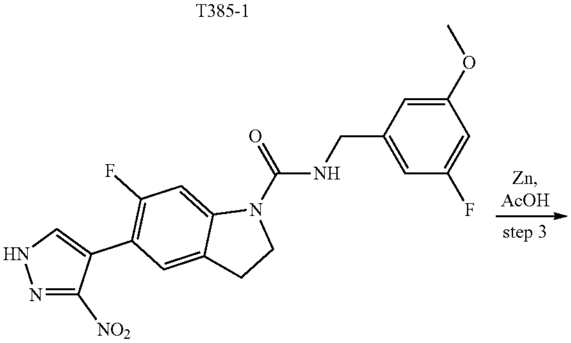

T385-2

-continued

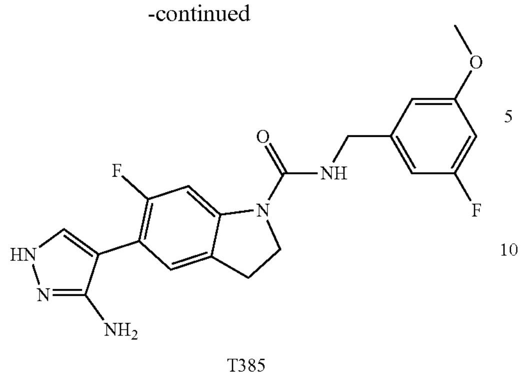

T385

1 Preparation of Compound 6-fluoro-N-(3-fluoro-5-methoxybenzyl)-5-(3-nitro-1-(((2-(trimethylsilyl)ethoxy)methyl)-1H-pyrazol-4-yl)indoline-1-carboxamide (T385-1)

Compound M008 (400 mg), 4-bromo-3-nitro-1-(((2-(trimethylsilyl)ethoxy)methyl)-1H-pyrazole (291 mg), anhydrous potassium carbonate (249 mg) and [1,1'-bis(diphenylphosphino)ferrocene]dichloropalladium(11) (66 mg) were added to 1,4-dioxane/water (20:1, 10 mL) under nitrogen atmosphere. The mixture was stirred at 80° C. for 2 h in an oil bath. After the reaction was completed, the reaction solution was diluted with water (50 mL) and extracted with ethyl acetate (30 mL×3). The organic phases were combined, washed with saturated brine (20 mL), dried over anhydrous sodium sulfate and concentrated, and the residue was purified by column chromatography (petroleum ether: ethyl acetate=20:1) to give a yellow oil (100 mg, 18.82% yield). MS $(M+H)^+$=560.3.

2 Preparation of Compound 6-fluoro-N-(3-fluoro-5-methoxybenzyl)-5-(3-nitro-1H-pyrazol-4-yl)indoline-1-carboxamide (T385-2)

Compound T385-1 (100 mg) was dissolved in ethanol (10 mL), and concentrated hydrochloric acid (1 mL) was added.

The mixture was stirred under reflux in an oil bath for 5 h, and after the reaction was completed as detected by liquid mass spectrometry, the reaction solution was directly used in the next step without treatment. MS $(M+H)^+$=430.0.

3 Preparation of Compound 5-(3-amino-1H-pyrazol-4-yl)-6-fluoro-N-(3-fluoro-5-methoxybenzyl)indoline-1-carboxamide (T385)

Activated zinc powder (152 mg) was added to the reaction solution obtained in the previous step in an ice bath, and then acetic acid (3 mL) was added. The mixture was warmed to room temperature and stirred for 2 h. The reaction solution was concentrated under reduced pressure, and then saturated sodium bicarbonate (10 mL) was added and ethyl acetate (5 mL×3) was added for extraction. The organic phases were combined, dried over anhydrous sodium sulfate and concentrated, and the resulting crude product was purified by silica gel column chromatography (dichloromethane:methanol=20:1) to give a white solid (13.63 mg, 14.04% yield). MS $(M+H)^+$=400.2.

$^1H$ NMR (400 MHz, DMSO) δ 7.61 (d, J=12.8 Hz, 1H), 7.51 (s, 1H), 7.37 (t, J=5.9 Hz, 1H), 7.30 (d, J=8.0 Hz, 1H), 6.76-6.66 (m, 3H), 4.30 (d, J=5.8 Hz, 2H), 4.01 (t, J=8.7 Hz, 2H), 3.76 (s, 3H), 3.13 (t, J=8.4 Hz, 2H).

Example 72: Preparation of Compounds (S)—N-(1-(3,5-difluorophenyl)-2-(dimethylamino)ethyl)-6-fluoro-5-(3-fluoro-1H-pyrazol-4-yl)indoline-1-carboxamide (T366-S) and (R)—N-(1-(3,5-difluorophenyl)-2-(dimethylamino)ethyl)-6-fluoro-5-(3-fluoro-1H-pyrazol-4-yl)indoline-1-carboxamide (T366-R)

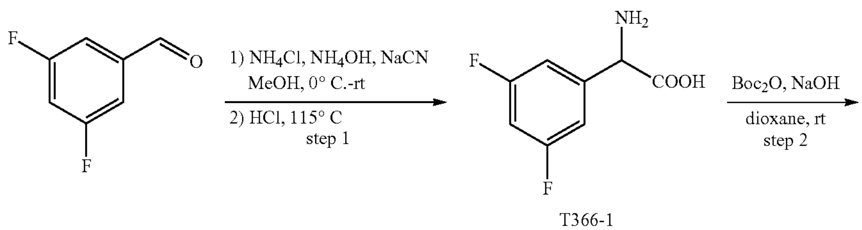

T366-1

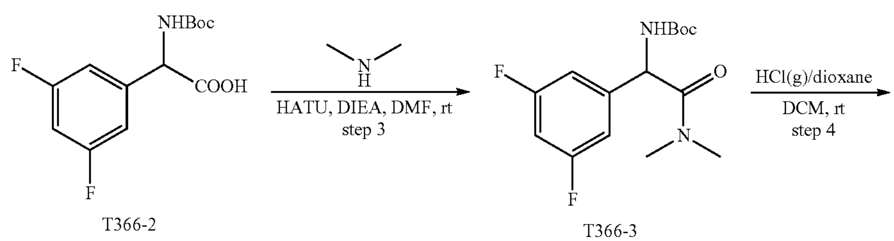

T366-2

T366-3

-continued
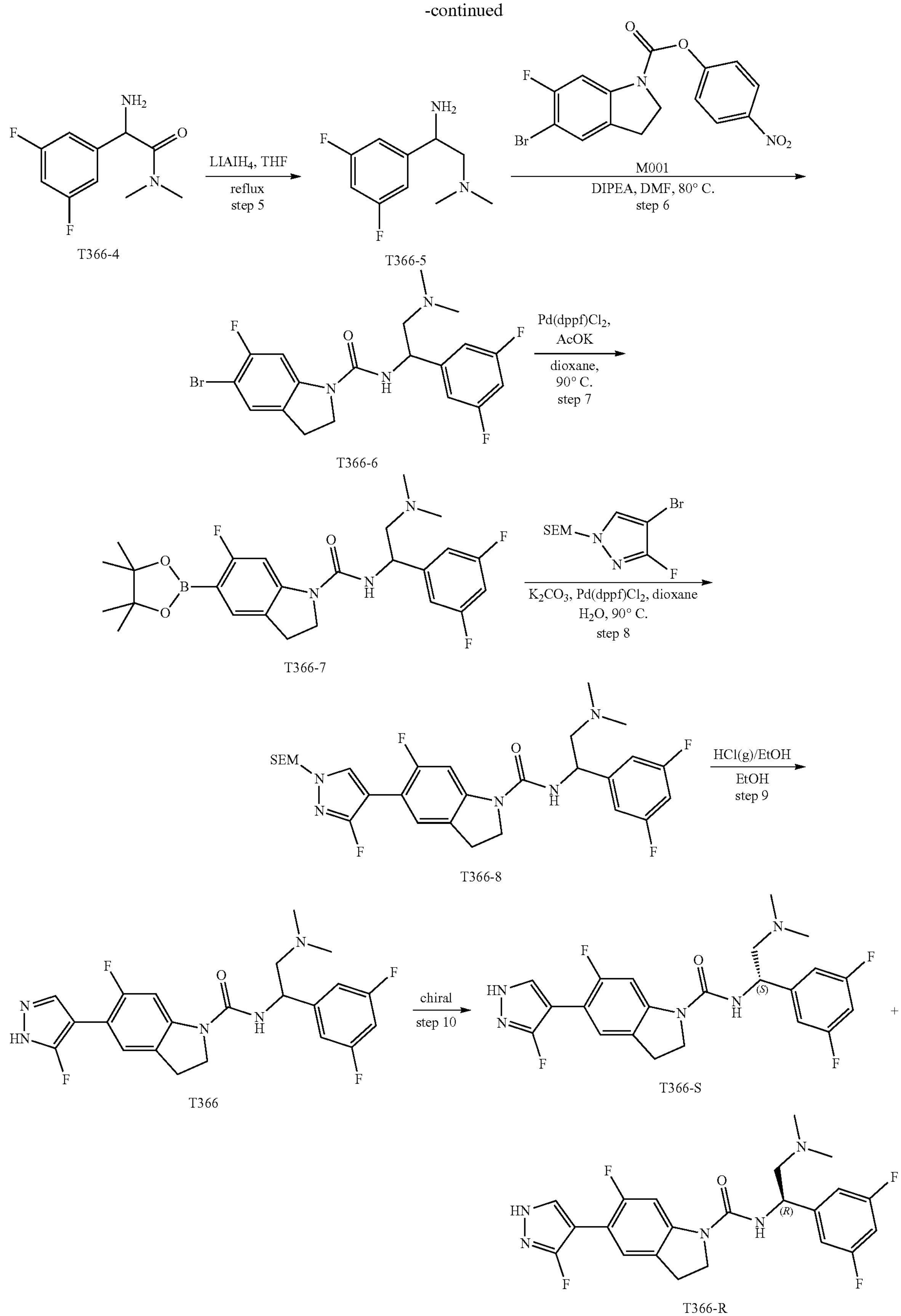
T366-4
T366-5
T366-6
T366-7
T366-8
T366
T366-S
+
T366-R

1 Preparation of Compound 2-amino-2-(3,5-difluorophenyl)acetic acid (T366-1)

Ammonium chloride (4.89 g) and sodium cyanide (4.94 g) were dissolved in aqueous ammonia (66 mL) at 0° C., and a solution of 3,5-difluorobenzaldehyde (13.00 g) in absolute methanol (130 mL) was slowly added dropwise. The mixture was stirred at room temperature for 4 h. The reaction solution was concentrated by rotary evaporation to remove methanol and extracted with ethyl acetate (50 mL 3). The organic phases were combined, washed with saturated brine (50 mL), dried over anhydrous sodium sulfate, filtered and concentrated by rotary evaporation. The resulting crude product was dissolved in hydrochloric acid (6 N, 200 mL), and the mixture was heated to 115° C. and reacted for 16 h. After the reaction was completed, the reaction solution was concentrated under reduced pressure to give compound T366-1 in the form of a yellow oil (15.00 g, crude product). MS $[M+H]^+$=187.9.

2 Preparation of Compound 2-((tert-butoxycarbonyl)amino)-2-(3,5-di fluorophenyl)acetic acid (T366-2)

Compound T366-1 (15.00 g) was dissolved in 1,4-dioxane (150 mL), and sodium hydroxide solution was added at 0° C. to adjust pH to 14, followed by addition of di-tert-butyl dicarbonate (19.24 g). The mixture was reacted at room temperature for 5 h. After the reaction was completed, the reaction solution was concentrated under reduced pressure, saturated potassium hydrogen sulfate solution was added to adjust pH to 4, and dichloromethane (50 mL×3) was added for extraction. The organic phases were combined, washed with saturated brine (50 mL), dried over anhydrous sodium sulfate, filtered and concentrated by rotary evaporation to give compound T366-2 in the form of a yellow oil (6.00 g, crude product). MS [M+Na]=310.0.

3 Preparation of Compound tert-butyl (1-(3,5-difluorophenyl)-2-(dimethylamino)-2-oxoethyl)carbamate (T366-3)

Compound T366-2 (6.00 g) was dissolved in anhydrous DMF (70 mL), and dimethylamine (2 M, dissolved in THF, 12.50 mL), HATU (11.91 g) and N,N-diisopropylethylamine (10.80 g) were added under nitrogen atmosphere. The mixture was reacted at room temperature for 3 h. After the reaction was completed, water (100 mL) was added, and ethyl acetate (100 mL×3) was added for extraction. The organic phases were combined, washed with saturated brine (100 mL×2), dried over anhydrous sodium sulfate, filtered and concentrated by rotary evaporation, and the resulting crude product was subjected to silica gel column chromatography (2.5 g, petroleum ether:ethyl acetate=10:1) to give compound T366-3 in the form of a yellow oil (5.00 g, 75.76% yield). MS $[M+Na]^+$=336.9.

4 Preparation of Compound 2-amino-2-(3,5-difluorophenyl)-N,N-dim ethyl acetamide (T366-4)

Compound T366-3 (5.00 g) was dissolved in dichloromethane (20 mL), and hydrochloric acid-1,4-dioxane solution (4 M, 10 mL) was added at 0° C. The mixture was reacted at room temperature for 16 h. After the reaction was completed, saturated sodium carbonate solution was added at 0° C. to adjust pH to 9, and dichloromethane (50 mL×3) was added for extraction. The organic phases were combined, washed with saturated brine (50 mL), dried over anhydrous sodium sulfate, filtered and concentrated by rotary evaporation to give compound T366-4 in the form of a yellow oil (4.00 g, crude product). MS $[M+H]^+$=215.1.

5 Preparation of Compound 1-(3,5-difluorophenyl) N2,N2-dimethylethane-1,2-diamine (T366-5)

Lithium aluminum hydride (1.63 g) was added into anhydrous tetrahydrofuran (20 mL) under nitrogen atmosphere, and compound T366-4 (4.00 g) and pyridine (365.44 mg) were added at 0° C. The mixture was reacted under reflux for 8 h. After the reaction was completed, the reaction solution was cooled to 0° C., and sodium sulfate decahydrate was added. The resulting mixture was stirred for 1 h and filtered, and the filtrate was concentrated by rotary evaporation to give compound T366-5 in the form of a yellow oil (1.5 g, crude product). MS $[M+H]^+$=200.9.

6 Preparation of Compound 5-bromo-h-(1-(3,5-difluorophenyl)-2-(di methyl amino)ethyl)-6-fluoroindoline-1-carboxamide (T366-6)

Compound T366-5 (1.5 g) and compound M001 (3.43 g) were dissolved in anhydrous DMF (15 mL), and N,N-diisopropylethylamine (2.90 g) was added. The mixture was reacted at 80° C. for 16 h. The reaction solution was then cooled to room temperature, water (20 mL) was added, and ethyl acetate (30 mL×3) was added for extraction. The organic phases were combined, washed with saturated brine (30 mL×2), dried over anhydrous sodium sulfate, filtered and concentrated by rotary evaporation, and the resulting crude product was subjected to silica gel column chromatography (12 g, petroleum ether:ethyl acetate=1:1) to give compound 1366-6 in the form of a yellow oil (1.0 g, 30.30% yield). MS $[M+H]^+$=442.9.

7 Preparation of Compound N-(1-(3,5-difluorophenyl)-2-(dimethylamino)ethyl)-6-fluoro-5-(4,4,5,5-tetramethyl-1,3,2-dioxaborolan-2-yl)indoline-1-carboxamide (T366-7)

Compound T366-6 (1.0 g) was dissolved in anhydrous 1,4-dioxane (10 mL), and bis(pinacolato)diboron (1.72 g), potassium acetate (443.79 mg) and [1,1'-bis(diphenylphosphino)ferrocene]dichloropalladium(11) (82.72 mg) were added under nitrogen atmosphere. The mixture was reacted at 90° C. for 3 h. The reaction solution was cooled to room temperature, water (10 mL) was added, and ethyl acetate (30 mL×3) was added for extraction. The organic phases were combined, washed with saturated brine (30 mL), dried over anhydrous sodium sulfate, filtered and concentrated by rotary evaporation, and the resulting crude product was subjected to silica gel column chromatography (4 g, dichloromethane:methanol=80:1) to give compound 1366-7 in the form of a yellow oil (600 mg, 54.54% yield). MS $[M+H]^+$= 489.9.

8 Preparation of Compound N-(1-(3,5-difluorophenyl)-2-(dimethylamino)ethyl)-6-fluoro-5-(3-fluoro-1-((2-(trimethylsilyl)ethoxy)methyl)-1H-pyrazol-4-yl)indoline-1-carboxamide (T366-8)

4-bromo-3-fluoro-1-((2-(trimethylsilyl)ethoxy)methyl)-1H-pyrazole (360 mg) was dissolved in 1,4-dioxane (5 mL) and water (1 mL), and compound T366-7 (500 mg), potassium carbonate (282 mg) and [1,1'-bis(diphenylphosphino)

ferrocene]dichloropalladium(II) (75 mg) were added under nitrogen atmosphere. The mixture was reacted at 90° C. for 3 h. The reaction solution was then cooled to room temperature, water (10 mL) was added, and ethyl acetate (50 mL×3) was added for extraction. The organic phases were combined, washed with saturated brine (50 mL), dried over anhydrous sodium sulfate, filtered and concentrated by rotary evaporation, and the resulting crude product was subjected to silica gel column chromatography (4 g, dichloromethane:methanol=60:1) to give compound T366-8 in the form of a yellow oil (200 mg, 33.90% yield). MS $[M+H]^+$=577.6.

9 Preparation of Compound N-(1-(3,5-difluorophenyl)-2-(dimethylamino)ethyl)-6-fluoro-5-(3-fluoro-1H-pyrazol-4-yl)indoline-1-carboxamide (T366)

Compound T366-8 (200 mg) was dissolved in ethanol (2 mL), and a solution of hydrochloric acid in ethanol (4 M, 0.5 mL) was added. The mixture was reacted at room temperature for 2 h. After the reaction was completed, the reaction solution was directly concentrated by rotary evaporation, and the resulting crude product was purified by high pressure liquid phase chromatography to give compound T366 in the form of a white solid (80 mg, 51.61% yield). MS $[M+H]^+$=447.7.

10 Preparation of Compounds (S)—N-(1-(3,5-difluorophenyl)-2-(dimethylamino)ethyl)-6-fluoro-5-(3-fluoro-1H-pyrazol-4-yl)indoline-1-carboxamide (T366-S) and (R)—N-(1-(3,5-difluorophenyl)-2-(dimethylamino)ethyl)-6-fluoro-5-(3-fluoro-1H-pyrazol-4-yl)indoline-1-carboxamide (T366-R)

N-(1-(3,5-difluorophenyl)-2-(dimethylamino)ethyl)-6-fluoro-5-(3-fluoro-1 N-pyrazol-4-yl)indoline-1-carboxamide (80 mg) was subjected to chiral resolution, and the products were collected separately, concentrated by rotary evaporation and lyophilized to give T366-S (9.1 mg) and T366-R (6.6 mg).

T366-S: LC-MS $[M+H]^+$=447.7.

$^1$H NMR (400 MHz, MeOD) δ 7.78 (t, J=2.4 Hz, 1H), 7.63 (d, J=12.8 Hz, 1H), 7.40 (d, J=7.6 Hz, 1H), 7.09-7.02 (m, 2H), 6.86 (ddd, J=9.1, 5.7, 2.3 Hz, 1H), 5.16 (dd, J=10.7, 4.4 Hz, 1H), 4.21-4.07 (m, 2H), 3.23 (t, J=8.6 Hz, 2H), 3.04-2.96 (m, 1H), 2.67 (dd, J=12.8, 4.2 Hz, 1H), 2.48 (s, 6H).

T366-R: LC-MS $[M+H]^+$=447.7.

$^1$H NMR (400 MHz, DMSO) δ 7.78-7.74 (m, 1H), 7.63 (d, J=12.8 Hz, 1H), 7.39 (d, J=7.6 Hz, 1H), 7.10-7.02 (m, 2H), 6.91-6.84 (m, 1H), 5.29-5.21 (m, 1H), 4.18-4.05 (m, 2H), 3.22 (t, J=8.5 Hz, 2H), 3.18-3.12 (m, 1H), 2.96-2.87 (m, 1H), 2.63 (s, 6H).

Example 101: Preparation of Compound 1-(5-(3-amino-1H-pyrazol-4-yl)-6-fluoroindolin-1-yl)-3-(3-methoxyphenyl)propan-1-one (T362)

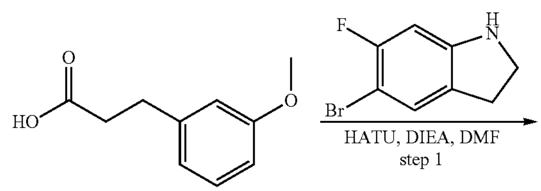

-continued

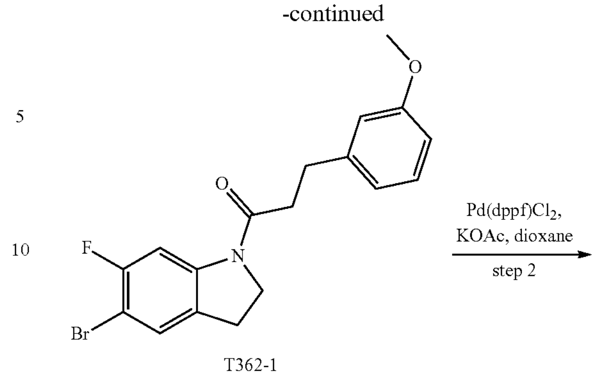

T362-1

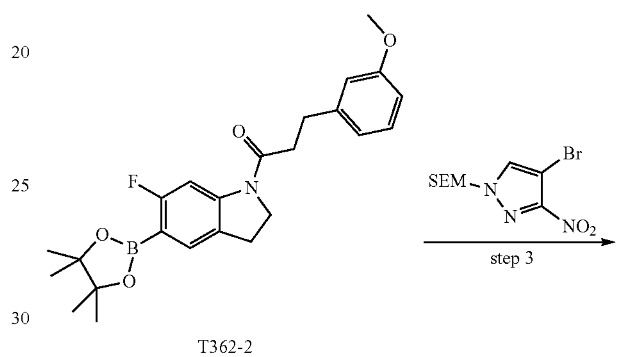

T362-2

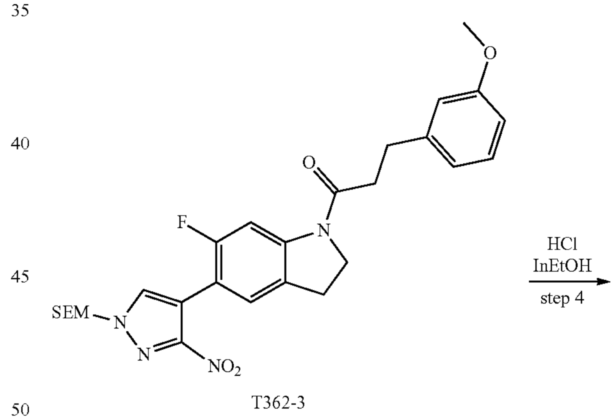

T362-3

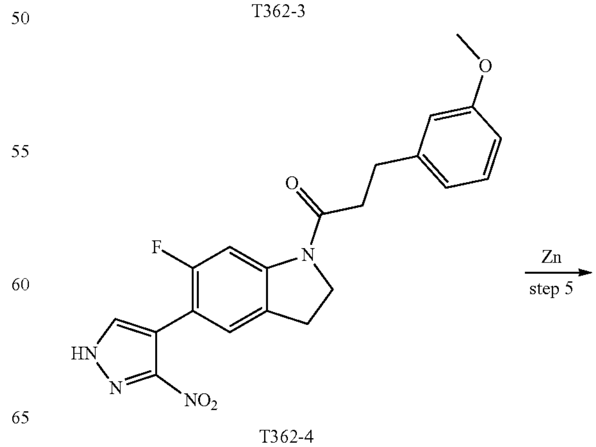

T362-4

-continued

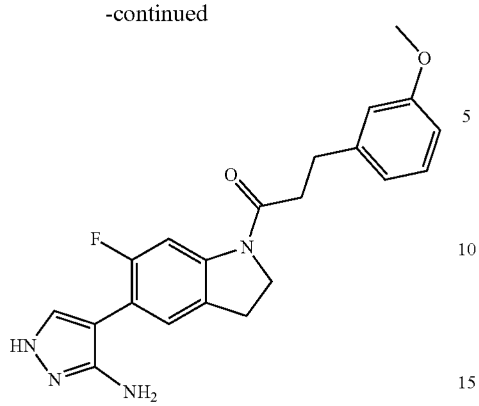

T362

1 Preparation of Compound 1-(5-bromo-6-fluoroindolin-1-yl)-3-(3-methoxyphenyl)propan-1-one (T362-1)

3-(3-methoxyphenyl)propionic acid (1.0 g) was dissolved in DMF (10 mL) under nitrogen atmosphere, and 5-bromo-6-fluoroindoline (1.3 g), HATU (3.1 g) and DIEA (2.1 g) were added. The mixture was reacted at room temperature for 2 h. Water (30 mL) was added to quench the reaction, and ethyl acetate (30 mL×3) was added for extraction. The organic phases were combined, washed with saturated brine (30 mL×2), dried over anhydrous sodium sulfate, filtered and concentrated. The resulting crude product was separated by silica gel column chromatography (petroleum ether/ethyl acetate=5/1) to give a yellow solid (1.2 g). LC-MS $[M+H]^+$: 377.6/379.6.

2 Preparation of Compound 1-(6-fluoro-5-(4,4,5,5-tetramethyl-1,3,2-dioxaborolan-2-yl)indolin-1-yl)-3-(3-methoxyphenyl)propan-1-one (T362-2)

Compound T362-1 (1.0 g) was dissolved in 1,4-dioxane (10 mL), and Teri-butyl 4-(4,4,5,5-tetramethyl-1,3,2-dioxaborolan-2-yl)-1H-pyrazole-1-carboxylate (1.0 g), Pd(dppf)$Cl_2$ (193 mg) and potassium acetate (778 mg) were added. The mixture was reacted at 80° C. for 12 h under nitrogen atmosphere. The reaction solution was diluted with water (10 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (wet loading, PE/EA=3/1) to give a brown oily liquid (800 mg). MS $[M+H]^+$=426.0.

3 Preparation of Compound 1-(6-fluoro-5-(3-nitro-1-((2-(trimethylsilyl)ethoxy)methyl)-1H-pyrazol-4-yl)indolin-1-yl)-3-(3-methoxyphenyl)propan-1-one (T362-3)

4-bromo-3-nitro-1-((2-(trimethylsilyl)ethoxy)methyl)-111-pyrazole (729 mg) was dissolved in 1,4-dioxane (8 mL) and water (2 mL), and compound T362-2 (800 mg), Pd(dppf)$Cl_2$ (137 mg) and potassium carbonate (780 mg) were added. The mixture was reacted at 90° C. for 4 h under nitrogen atmosphere. The reaction solution was diluted with water (20 mL) and extracted with ethyl acetate (20 mL×3). The organic phases were combined, washed with saturated brine (20 mL), dried over anhydrous sodium sulfate, filtered and concentrated, and the resulting crude product was separated by silica gel column chromatography (PE/EA=2/1) to give a yellow oily liquid (300 mg). MS $[M+H]^+$=541.1.

4 Preparation of Compound 1-(6-fluoro-5-(3-nitro-1H-pyrazol-4-yl)indolin-1-yl)-3-(3-methoxyphenyl)propan-1-one (T362-4)

Compound T362-3 (150 mg) was dissolved in ethanol (5 mL), and a solution of hydrochloric acid in ethanol (2 mL, mass fraction of 33%) was added. The mixture was reacted at room temperature for 2 h under nitrogen atmosphere. The reaction solution was directly used in the next step without post treatment. MS $[M+H]^+$=411.0.

5 Preparation of Compound 1-(5-(3-amino-1H-pyrazol-4-yl)-6-fluoroindolin-1-yl)-3-(3-methoxyphenyl)propan-1-one (T362)

Zinc powder (52 mg) was added into the reaction solution obtained in the previous step at room temperature, and the mixture was reacted at room temperature for 2 h under nitrogen atmosphere. The reaction solution was concentrated under reduced pressure, and the residue was separated by preparative chromatography to give a white solid (10 mg). MS $[M+H]^+$=381.0.

$^1H$ NMR (400 MHz, DMSO) δ 7.86 (d, J=12.5 Hz, 1H), 7.59 (s, 1H), 7.38 (d, J=7.9 Hz, 1H), 7.20 (t, J=8.0 Hz, 1H), 6.88-6.83 (m, 2H), 6.78-6.74 (m, 1H), 4.13 (t, J=8.5 Hz, 2H), 3.73 (s, 3H), 3.11 (t, J=8.4 Hz, 2H), 2.91-2.85 (m, 2H), 2.82-2.74 (m, 2H).

Example 73: Preparation of Compound 5-(5-fluoro-1H-pyrazol-4-yl)-N-(3-fluoro-5-methoxybenzyl) indoline-1-carboxamide (T342)

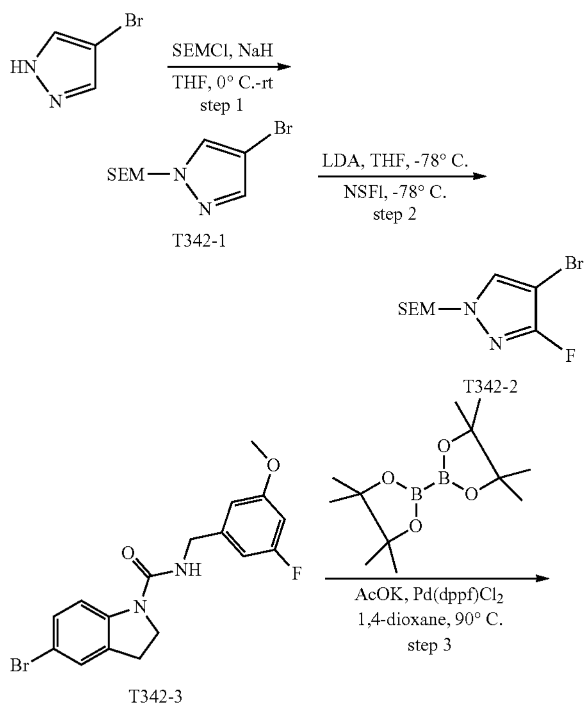

T342-1

T342-2

T342-3

-continued

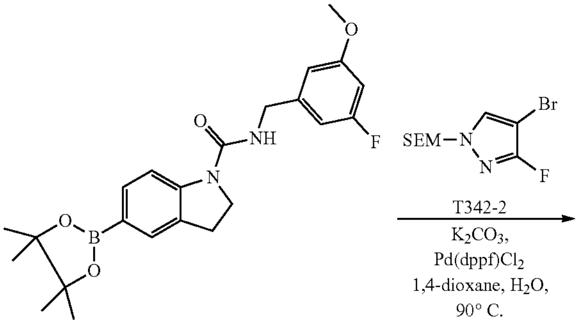

T342-4

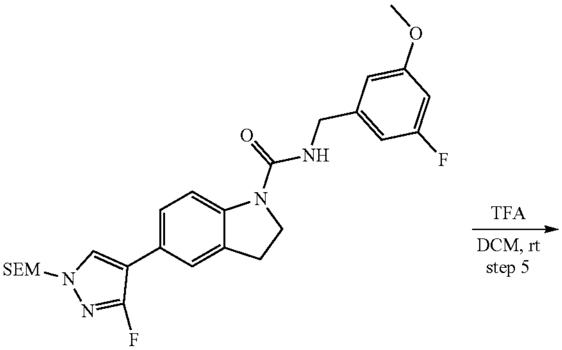

T342-5

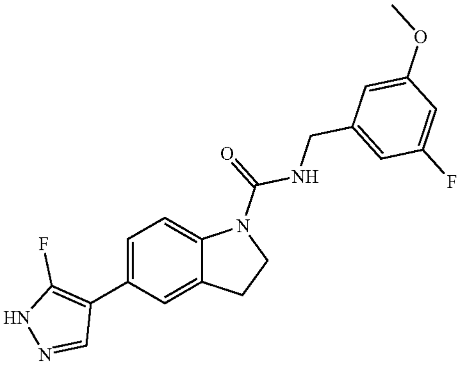

T342

1 Preparation of Compound 4-bromo-1-((2-(trimethylsilyl)ethoxy)methyl)-1H-pyrazole (T342-1)

4-bromo-1H-pyrazole (10.0 g) was dissolved in anhydrous tetrahydrofuran (100 mL) under nitrogen atmosphere, and sodium hydride (60%, 4.1 g) was added at 0° C. The mixture was reacted at 0° C. for 30 min, and then 2-(trimethylsilyl)ethoxymethyl chloride (12.0 g) was added. The resulting mixture was reacted at room temperature for 16 h. After the reaction was completed, ice water (100 mL) was added to quench the reaction, and ethyl acetate (100 mL×3) was added for extraction. The organic phases were combined, washed with saturated brine (100 mL 2), dried over anhydrous sodium sulfate, filtered and concentrated by rotary evaporation to give compound T342-1 in the form of a yellow oil (13 g, crude product).

$^1$H NMR (301 MHz, CDCl3) δ 7.59 (s, 1H), 7.49 (s, 1H), 5.37 (s, 2H), 3.57-3.48 (m, 2H), 0.92-0.85 (m, 2H), 0.03 (s, 9H).

2 Preparation of Compound 4-bromo-3-fluoro-1-((2-(trimethylsilyl)ethoxy)methyl)-1H-pyrazole (T342-2)

Compound T342-1 (10.0 g) was dissolved in anhydrous tetrahydrofuran (50 mL), and lithium diisopropylamide (2 M, in tetrahydrofuran, 36 mL) was added dropwise at −78° C. under nitrogen atmosphere. After the dropwise addition was completed, the mixture was reacted at −78° C. for 1 h, and then N-fluorobisbenzenesulfonamide (22.7 g, dissolved in 50 mL of anhydrous tetrahydrofuran) was added dropwise. After the dropwise addition was completed, the resulting mixture was reacted at −78° C. for 1 h. Saturated ammonium chloride (60 mL) was added to quench the reaction, and ethyl acetate (100 mL×3) was added for extraction. The organic phases were combined, washed with saturated brine (100 mL×2), dried over anhydrous sodium sulfate, filtered and concentrated by rotary evaporation. The resulting crude product was purified by silica gel column chromatography (25 g; eluent: petroleum ether:ethyl acetate=80:1) to give compound T342-2 in the form of a yellow oil (1.0 g, 9.4% yield).

$^1$H NMR (301 MHz, CDCl3) δ 7.40 (d, J=2.4 Hz, 1H), 5.36 (s, 2H), 3.65-3.58 (m, 2H), 0.97-0.85 (m, 2H), 0.01 (s, 9H).

3 Preparation of Compound N-(3-fluoro-5-methoxybenzyl)-5-(4,4,5,5-tetramethyl-1,3,2-dioxaborolan-2-yl)indoline-1-carboxamide (T342-4)

Compound T342-3 (170 mg) was dissolved in anhydrous 1,4-dioxane (2 mL) under nitrogen atmosphere, and 4,4,4',4',5,5,5',5'-octamethyl-2,2'-bi(1,3,2-dioxaborolane) (144 mg), potassium acetate (90 mg) and [1,1'-bis(diphenylphosphino)ferrocene]dichloropalladium(II) (17 mg) were added. The mixture was reacted at 90° C. for 3 h. The reaction solution was cooled to room temperature, filtered and concentrated by rotary evaporation to give compound T342-3 in the form of a yellow oil (200 mg, crude product).

MS $[M+H]^+$=427.1.

4 Preparation of Compound 5-(3-fluoro-1-((2-(trimethylsilyl)ethoxy)methyl)-1H-pyrazol-4-yl)-N-(3-fluoro-5-methoxybenzyl)indoline-1-carboxamide (T342-5)

Compound T342-2 (150 mg) was dissolved in 1,4-dioxane (3 mL) and water (0.5 mL) under nitrogen atmosphere, and compound T342-4 (260 mg), potassium carbonate (140 mg) and [1,1'-bis(diphenylphosphino)ferrocene]dichloropalladium(II) (37.2 mg) were added. The mixture was reacted at 90° C. for 3 h. The reaction solution was cooled to room temperature, water (30 mL) was added, and then ethyl acetate (20 mL×3) was added for extraction. The organic phases were combined, washed with saturated brine (20 mL×2), dried over anhydrous sodium sulfate, filtered and concentrated by rotary evaporation, and the resulting crude product was purified by silica gel column chromatography (eluent: petroleum ether:ethyl acetate=2:1) to give compound T342-4 in the form of a yellow oil (100 mg, 38.24% yield). MS $[M+H]^+$=457.1.

5 Preparation of Compound 5-(5-fluoro-1H-pyrazol-4-yl)-N-(3-fluoro-5-methoxybenzyl)indoline-1-carboxamide (T342)

Compound T342-5 (100 mg) was dissolved in dichloromethane (2 mL), and trifluoroacetic acid (0.5 mL) was added. The mixture was reacted at room temperature for 2 h. After the reaction was completed, the reaction solution was directly concentrated by rotary evaporation, and the resulting crude product was purified by high pressure liquid phase chromatography to give compound T342 in the form of a white solid (3.5 mg, 4.7% yield). MS $[M+H]^+$=385.0.

$^1$H NMR (400 MHz, MeOD) δ 7.86-7.83 (m, 2H), 7.41 (s, 1H), 7.34 (d, J=8.4 Hz, 1H), 6.77 (s, 1H), 6.70 (d, J=9.4 Hz, 1H), 6.58 (dt, J=10.8, 2.3 Hz, 1H), 4.43 (s, 2H), 4.03 (t, J=8.7 Hz, 2H), 3.81 (s, 3H), 3.25 (t, J=8.6 Hz, 2H).

Example 74: Preparation of Compound 6-cyano-N-(3-fluoro-5-methoxybenzyl)-5-(1H-pyrazol-4-yl)indoline-1-carboxamide (T353)

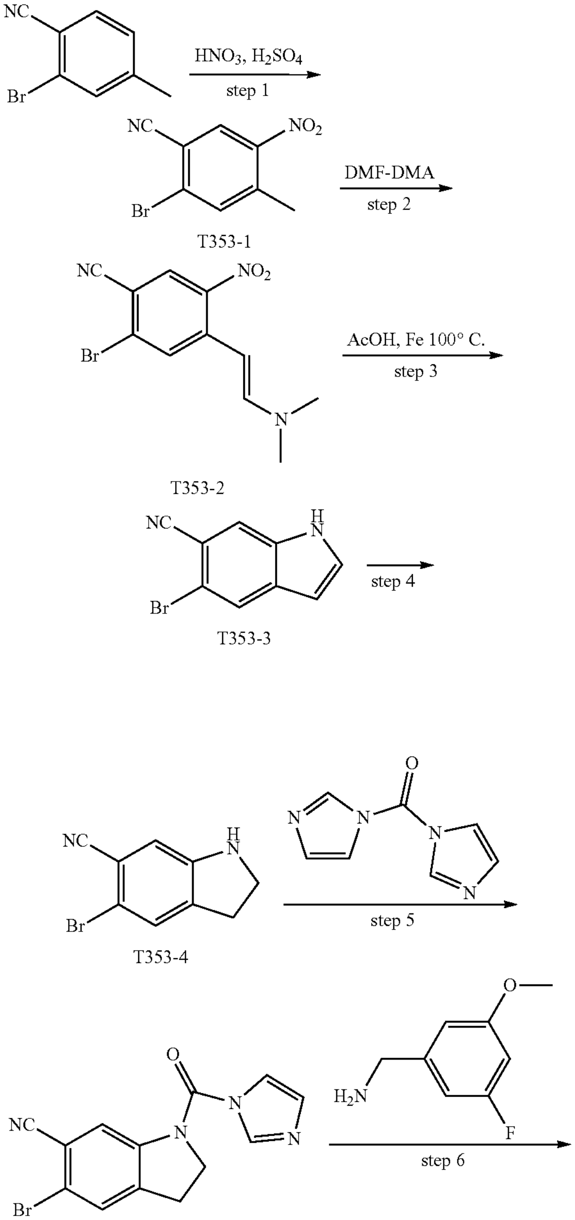

T353-1

T353-2

T353-3

T353-4

T353-5

-continued

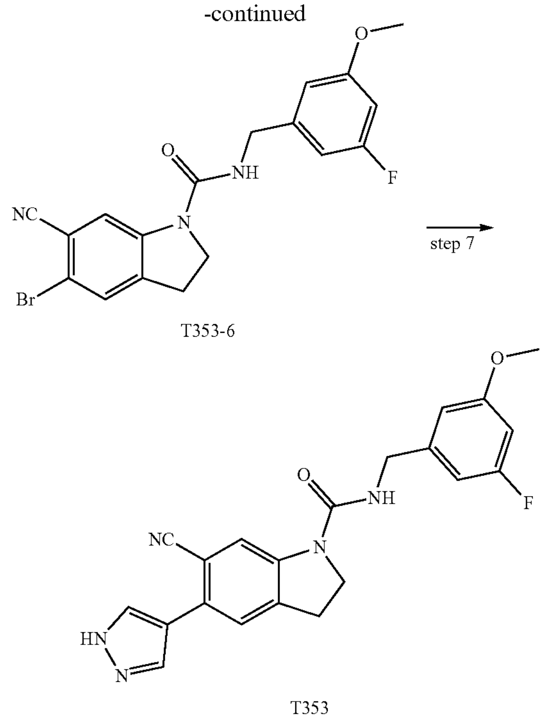

T353-6

T353

1 Preparation of Compound 2-bromo-4-methyl-5-nitrobenzonitrile (T353-1)

2-bromo-4-methylbenzonitrile (10.00 g) was dissolved in concentrated sulfuric acid (60 mL), and concentrated nitric acid (20 mL) was added dropwise in an ice water bath. The mixture was stirred at room temperature for 2 h. After the reaction was completed, the reaction solution was poured into ice water (150 mL). The mixture was filtered and washed with water, and the precipitate was collected. The resulting crude product was separated by silica gel column chromatography (petroleum ether/ethyl acetate=20:1) to give a white solid (9.50 g, 70% yield). LC-MS $[M+H]^+$=241.2.

2 Preparation of Compound (E)-2-bromo-4-(2-(dimethylamino)vinyl)-5-nitrobenzonitrile (T353-2)

Compound T353-1 (9.00 g) was dissolved in N,N-dimethylformamide (80 mL), and N,N-dimethylformamide dimethyl acetal (11.11 g) was added. The mixture was stirred at 100° C. for 2 h under nitrogen atmosphere. After the reaction was completed, the reaction solution was concentrated to give a tan solid (13.40 g, with a product content of about 80%). and the crude product was directly used in the next step. LC-MS $[M+H]^+$=296.1.

3 Preparation of Compound 5-bromo-1H-indole-6-carbonitrile (T353-3)

Compound T353-2 (11.00 g) was dissolved in acetic acid (50 mL), and iron powder (34.24 g) was added. The mixture was stirred at 100° C. for 12 h under nitrogen atmosphere. After the reaction was completed, the reaction solution was filtered to remove the iron powder and concentrated under reduced pressure. Saturated sodium carbonate solution (30 mL) was added, and ethyl acetate (50 mL×2) was added for extraction. The organic phases were combined, washed with saturated brine (50 mL), dried over anhydrous sodium sulfate, filtered and concentrated. The resulting crude product was separated by silica gel column chromatography (PE/EA=8:1) to give a white solid (1.40 g, 17% yield). LC-MS $[M+H]^+$=220.6.

4 Preparation of Compound 5-bromoindoline-6-carbonitrile (T353-4)

Compound T353-3 (1.40 g) was dissolved in dichloromethane (15 mL), and triethylsilane (3.66 g) and trifluoroacetic acid (7.5 mL) were added. The mixture was stirred at 45° C. for 4 h. The reaction solution was concentrated under reduced pressure, saturated sodium carbonate solution (25 mL) was added, and ethyl acetate (20 mL×4) was added for extraction. The organic phases were combined, washed with saturated brine (20 mL×2), dried over anhydrous sodium sulfate, filtered and concentrated. The resulting crude product was separated by silica gel column chromatography (petroleum ether:ethyl acetate=8:1) to give a white solid (0.80 g, 51% yield). LC-MS $[M+H]^+$-223.1.

5 Preparation of Compound 5-bromo-1-(1N-imidazole-1-carbonyl)indoline-6-carbonitrile (T353-5)

Compound 1353-4 (300 mg) was dissolved in acetonitrile (3 mL), and 1-[(imidazol-1-yl)carbonyl]imidazole (326 mg) and 4-dimethylaminopyridine (327 mg) were added. The mixture was stirred at 90° C. for 12 h under nitrogen atmosphere. After the reaction was completed, the reaction solution was concentrated under reduced pressure to give a brown solid (1.10 g). LC-MS $[M+H]^+$=317.0.

6 Preparation of Compound 5-bromo-6-cyano-N-(3-fluoro-5-methoxybenzyl)indoline-1-carboxamide (T353-6)

T353-5 (1.10 g, crude product) was dissolved in anhydrous N,N-dimethylformamide (5 mL), and (3-fluoro-5-methoxyphenyl)methylamine (0.42 g) and triethylamine (0.48 g) were added. The mixture was stirred at 90° C. for 12 h under nitrogen atmosphere. Water (30 mL) was added to quench the reaction, and ethyl acetate (20 mL×3) was added for extraction. The organic phases were combined, washed with saturated brine (20 mL×2), dried over anhydrous sodium sulfate, filtered and concentrated. The resulting crude product was separated by silica gel column chromatography (PE/EA=1:1) to give a white solid (130 mg, 22% yield). LC-MS $[M+H]^+$=404.2.

7 Preparation of Compound 6-cyano-N-(3-fluoro-5-methoxybenzyl)-5-(1H-pyrazol-4-yl)indoline-1-carboxamide (T353)

Compound T353-6 (100 mg) was dissolved in 1-4 dioxane and water (5/1, 7.2 mL), and tert-butyl [4-(4,4,5,5-tetramethyl-1,3,2-dioxaborolan-2-yl)pyrazol-1-yl]carboxylate (148 mg), potassium carbonate (104 mg) and [1,1'-bis(diphenylphosphino)ferrocene]dichloropalladium(II) (18 mg) were added. The mixture was stirred at 90° C. for 12 h under nitrogen atmosphere. The reaction solution was diluted with water (20 mL) and extracted with ethyl acetate (10 mL×3). The organic phases were combined, washed with saturated brine (10 mL×2), dried over anhydrous sodium sulfate, filtered and concentrated. The resulting crude product was separated by silica gel column chromatography (DCM/MeOH=50/1) to give a white solid (23 mg, 26% yield). LC-MS $[M+H]^+$=319.1.

$^1H$ NMR (400 MHz, DMSO) δ 13.09 (s, 1H), 8.15 (s, 1H), 8.06 (s, 1H), 7.95 (s, 1H), 7.55 (s, 1H), 7.48 (t, J=5.8 Hz, 1H), 6.81-6.56 (m, 3H), 4.31 (d, J=5.4 Hz, 2H), 4.03 (t, J=8.6 Hz, 2H), 3.76 (s, 3H), 3.26 (t, J=8.5 Hz, 2H).

Example 75: Preparation of Compound N-(3-((cyclopropylmethyl)carbamoyl)-5-fluorobenzyl)-6-fluoro-5-(1H-pyrazol-4-yl)indoline-1-carboxamide (T378)

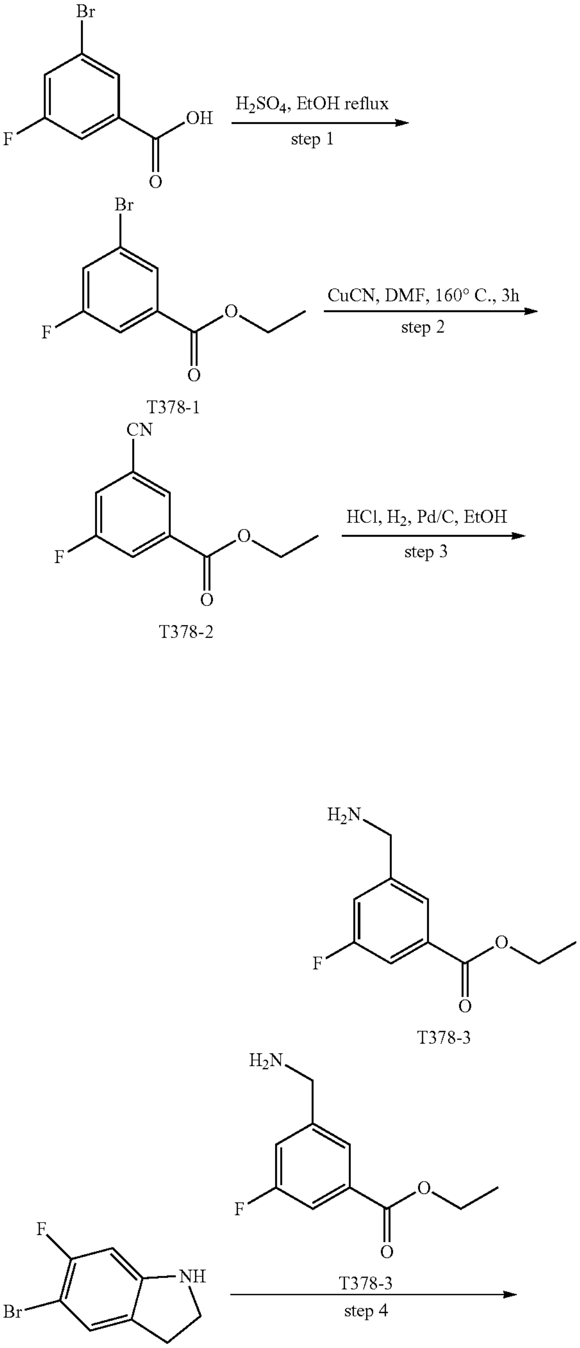

-continued

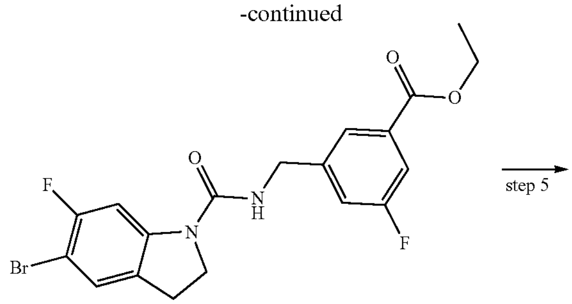

T378-4

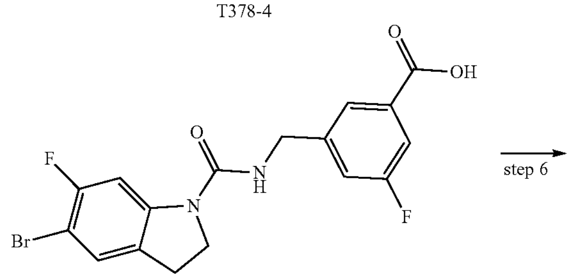

T378-5

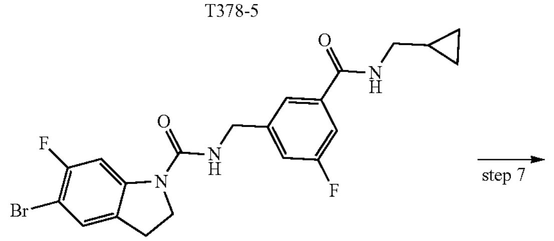

T378-6

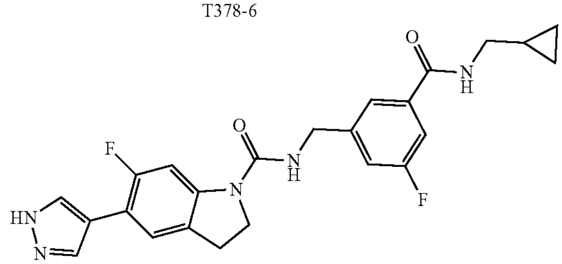

T378

1 Preparation of Compound ethyl 3-bromo-5-fluorobenzoate (T378-1)

3-bromo-5-fluorobenzoic acid (3.0 g) was dissolved in ethanol (30 mL), and concentrated sulfuric acid (3 mL) was added. The mixture was stirred overnight under reflux. The reaction solution was concentrated under reduced pressure, diluted with water (50 mL) and extracted with ethyl acetate (30 mL×2). The organic phases were combined, washed with saturated brine (30 mL), dried over anhydrous sodium sulfate and concentrated, and the resulting crude product was purified by silica gel column chromatography (PE/EA=10/1) to give a yellow oily liquid (2.5 g, 74% yield). LC-MS $[M+H]^+$: 246.9.

2 Preparation of Compound ethyl 3-cyano-5-fluorobenzoate (T378-2)

Compound T378-1 (2.5 g) was dissolved in anhydrous DMF (25 mL), and cuprous cyanide (1.0 g) was added. The mixture was warmed to 160° C. and reacted for 3 h. The reaction solution was diluted with water (100 mL) and extracted with ethyl acetate (50 mL×3). The organic phases were combined, washed with saturated brine (50 mL×3), dried over anhydrous sodium sulfate and concentrated, and the residue was separated by silica gel column chromatography (PE/EA=3/1) to give a yellow oily liquid (1.2 g, 63% yield). LC-MS $[M+H]^+$: 194.0.

3 Preparation of Compound ethyl 3-(aminomethyl)-5-fluorobenzoate (T378-3)

Compound T378-2 (1.2 g) was dissolved in ethanol (10 mL), and 5% Pd/C (240 mg) and concentrated hydrochloric acid (0.5 mL) were added. The mixture was stirred overnight at room temperature under hydrogen atmosphere. The reaction solution was filtered and concentrated by rotary evaporation, and the resulting solid was dissolved in dichloromethane (50 mL), followed by addition of sodium carbonate solution (20 mL, 2 N). The mixture was stirred at room temperature for 30 min, washed with water (20 mL×3), dried over anhydrous sodium sulfate, filtered and concentrated to give a yellow oily liquid (1.2 g, crude product). LC-MS $[M+H]^+$: 198.1.

4 Preparation of Compound ethyl 34(5-bromo-6-fluoroindoline-1-carboxamido<oxalylamino>) methyl)-5-fluorobenzoate (T378-4)

5-bromo-6-fluoroindoline (500 mg) was dissolved in tetrahydrofuran (10 mL) under nitrogen atmosphere, and 4-nitrophenyl chlorate (698 mg) and pyridine (548 mg) were added. The mixture was stirred overnight at room temperature. Compound T378-3 (683 mg) and DIEA (894 mg) were added to the reaction solution, and the resulting mixture was reacted at 70° C. for 12 h. Water (40 mL) was added to quench the reaction, and ethyl acetate (20 mL×3) was added for extraction. The organic phases were combined, washed with saturated brine (30 mL), dried over anhydrous sodium sulfate, filtered and concentrated, and the residue was separated by silica gel column chromatography (PE/EA=3/1) to give a yellow solid (500 mg, 49% yield). LC-MS $[M+H]^+$: 438.9.

5 Preparation of Compound 3-((5-bromo-6-fluoroindoline-1-carboxamido<oxalylamino>)methyl)-5-fluorobenzoic acid (T378-5)

Compound T378-4 (450 mg) was dissolved in tetrahydrofuran/methanol (1/1=10 mL), and sodium hydroxide solution (2 N, 3 mL) was added. The mixture was stirred overnight at room temperature. The reaction solution was diluted with water (30 mL), adjusted to pH=5-6 with diluted hydrochloric acid, and extracted with ethyl acetate (30 mL×3). The organic phases were combined, washed with saturated brine (30 mL), dried over anhydrous sodium sulfate, filtered and concentrated, and the residue was separated by silica gel column chromatography (PE/EA=1/1) to give a yellow oily liquid (350 mg, 83% yield). LC-MS $[M+H]^+$: 412.6.

6 Preparation of Compound 5-bromo-N-(3-((cyclopropylmethyl)carbamoyl)-5-fluorobenzyl)-6-fluoroindoline-1-carboxamide (T378-6)

Compound T378-5 (350 mg) was dissolved in DMF (10 mL) under nitrogen atmosphere, and HATU (646 mg) and DIEA (330 mg) were added. The mixture was stirred at room temperature for 30 min, and then cyclopropylmethylamine (120 mg) was added. The resulting mixture was stirred overnight at room temperature. Water (30 mL) was added to quench the reaction, and ethyl acetate (20 mL×3) was added for extraction. The organic phases were combined, washed with saturated brine (20 mL 3), dried over anhydrous sodium sulfate, filtered and concentrated, and the resulting crude product was separated by silica gel column chromatography (PE/EA=1/1) to give a yellow oily liquid (300 mg, 76% yield). LC-MS $[M+H]^+$: 463.9.

7 Preparation of Compound N-(3-((cyclopropylmethyl)carbamoyl)-5-fluorobenzyl)-6-fluoro-5-(1H-pyrazol-4-yl)indoline-1-carboxamide (T378)

Compound T378-6 (150 mg) was dissolved in 1,4-dioxane (10 mL) and water (2 mL) under nitrogen atmosphere, and sera-butyl 4-(4,4,5,5-tetramethyl-1,3,2-dioxaborolan-2-yl)-1 N-pyrazole-1-carboxylate (142 mg), Pd(dppf)$Cl_2$ (23 mg) and potassium carbonate (132 mg) were added. The mixture was reacted overnight at 90° C. The reaction solution was diluted with water (25 mL) and extracted with ethyl acetate (20 mL×3). The organic phases were combined, washed with saturated brine (30 mL), dried over anhydrous sodium sulfate, filtered and concentrated, and the residue was separated by preparative chromatography to give a white solid (11.5 mg). MS $[M/2+H]^+$=452.2.

$^1$H NMR (400 MHz, DMSO) δ 8.65 (t, J=5.6 Hz, 1H), 7.94 (s, 2H), 7.69 (s, 1H), 7.62 (d, J=13.2 Hz, 1H), 7.57-7.48 (m, 2H), 7.45 (t, J=5.8 Hz, 1H), 7.32 (d, J=9.5 Hz, 1H), 4.39 (d, J=5.6 Hz, 2H), 4.03 (t, J=8.7 Hz, 2H), 3.19-3.11 (m, 4H), 1.12-0.85 (m, 1H), 0.55-0.35 (m, 2H), 0.32-0.10 (m, 2H).

Example 76: Preparation of Compound N-(3-((cyclopropylmethyl)carbamoyl)benzyl)-6-fluoro-5-(1H-pyrazol-4-yl)indoline-1-carboxamide (T382)

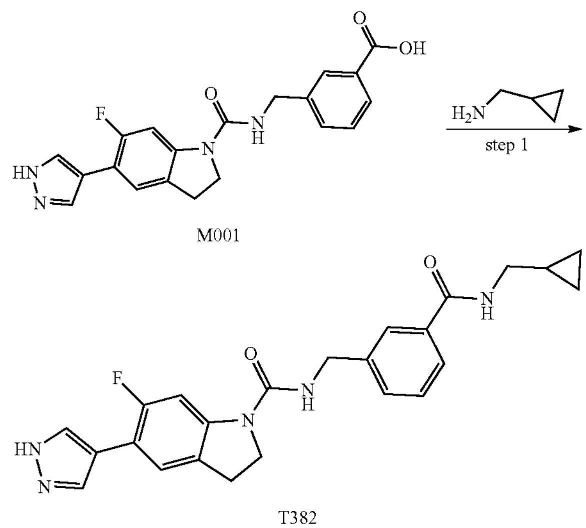

M001

T382

M011 (200 mg, crude product) was dissolved in DMF (8 mL), and HATU (214 mg) and DIEA (205 mg) were added. The mixture was stirred at room temperature for 30 min, and then cyclopropylmethylamine (27 mg) was added. The resulting mixture was stirred overnight at room temperature. Water (30 mL) was added to quench the reaction, and ethyl acetate (20 mL×3) was added for extraction. The organic phases were combined, washed with saturated brine (30 mL), dried over anhydrous sodium sulfate, filtered and concentrated, and the residue was separated by preparative chromatography to give a white solid (34.6 mg). LC-MS $[M+H]^+$: 434.0.

$^1$H NMR (400 MHz, DMSO) δ 8.55 (t, J=5.6 Hz, 1H), 7.95 (s, 2H), 7.82 (s, 1H), 7.72 (d, J=7.6 Hz, 1H), 7.63 (d, J=13.2 Hz, 1H), 7.52-7.46 (m, 2H), 7.46-7.38 (m, 2H), 4.39 (d, J=5.7 Hz, 2H), 4.02 (t, J=8.7 Hz, 2H), 3.20-3.10 (m, 4H), 1.09-0.98 (m, 1H), 0.46-0.39 (m, 2H), 0.26-0.16 (m, 2H).

Example 77: Preparation of Compound 6-fluoro-N-(3-((1-methylazetidin-3-yl)carbamoyl)benzyl)-5-(1H-pyrazol-4-yl)indoline-1-carboxamide (T379)

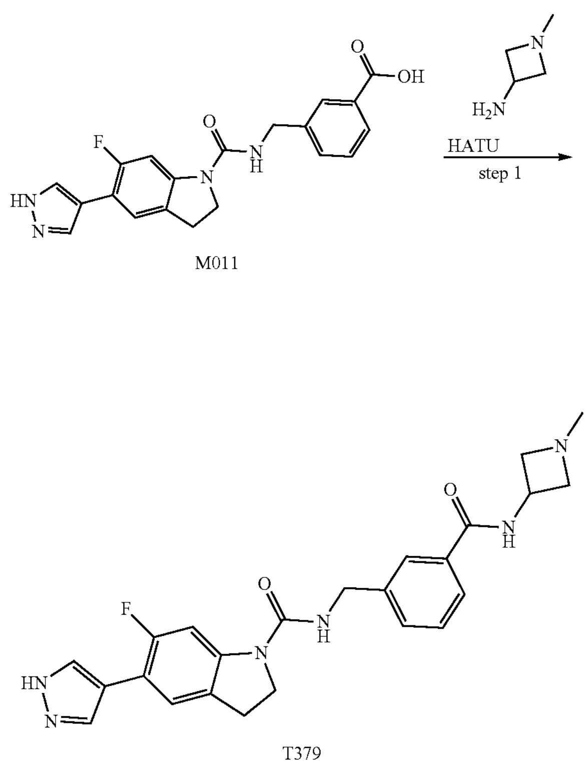

M011

T379

M011 (200 mg, crude product) was dissolved in DMF (10 mL), and HATU (302 mg) and DIEA (205 mg) were added. The mixture was stirred at room temperature for 30 min under nitrogen atmosphere, and then 1-methylazetidin-3-amine (68 mg) was added. The resulting mixture was stirred overnight at room temperature. Water (30 mL) was added to quench the reaction, and ethyl acetate (20 mL×3) was added for extraction. The organic phases were combined, washed with saturated brine (30 mL), dried over anhydrous sodium sulfate, filtered and concentrated, and the residue was separated by preparative chromatography to give a yellow oily liquid (15.9 mg). LC-MS $[M+H]^+$: 449.1.

$^1$H NMR (400 MHz, MeOD) δ 7.97-7.85 (m, 3H), 7.77 (t, J=7.6 Hz, 1H), 7.68-7.58 (m, 2H), 7.53-7.44 (m, 2H), 4.84-4.76 (m, 1H), 4.68-4.60 (m, 2H), 4.52 (s, 2H), 4.39-4.24 (m, 2H), 4.07 (t, J=8.7 Hz, 2H), 3.24 (t, J=8.6 Hz, 2H), 3.03 (d, J=18.0 Hz, 3H).

Example 78: Preparation of Compound 4-fluoro-N-(3-fluoro-5-methoxybenzyl)-5-(1H-pyrazol-4-yl)indoline-1-carboxamide (T372)

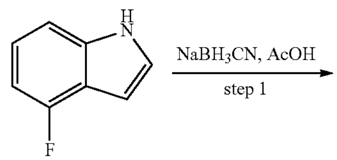

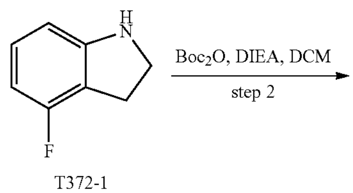

T372-1

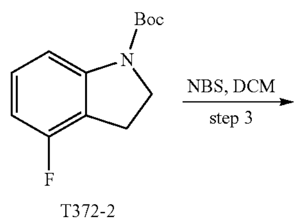

T372-2

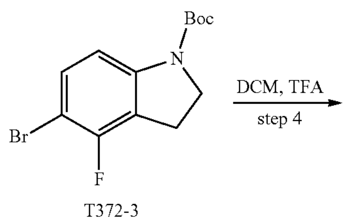

T372-3

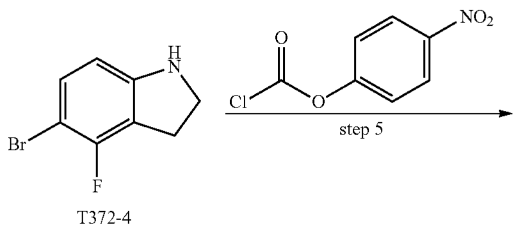

T372-4

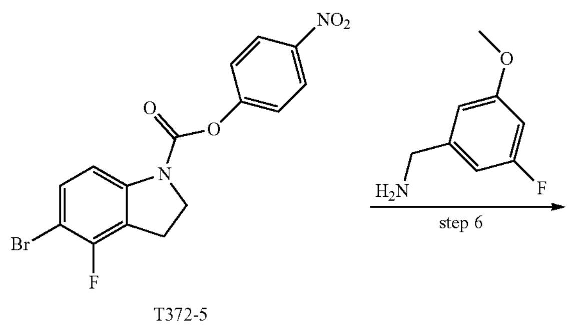

T372-5

-continued

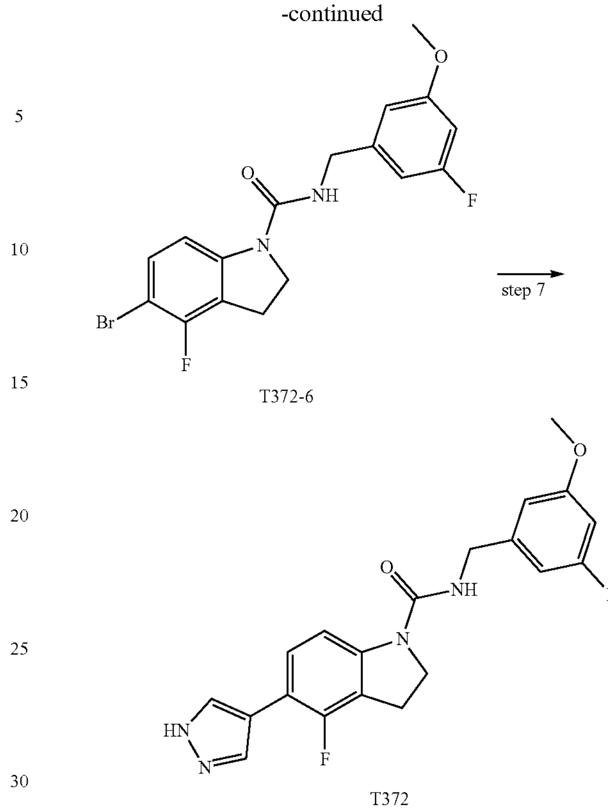

T372-6

T372

1 Preparation of Compound 4-fluoroindoline (T372-1)

4-fluoro-1H-indole (7.00 g) was dissolved in glacial acetic acid (50 mL), and sodium cyanoborohydride (10.09 g) was added in portions in an ice water bath under nitrogen atmosphere. The mixture was stirred at room temperature for 3 h. Saturated sodium carbonate solution was added to adjust pH to 10, and ethyl acetate (30 mL×5) was added for extraction. The organic phases were combined, washed with saturated brine (50 mL×2), dried over anhydrous sodium sulfate, filtered and concentrated. The resulting crude product was separated by silica gel column chromatography (PE/EA=8:1) to give a colorless oil (3.00 g, 38% yield). LC-MS $[M+H]^+$=138.2.

2 Preparation of Compound tert-butyl 4-fluoroindoline-1-carboxylate (T372-2)

Compound T372-1 (2.00 g) was dissolved in DCM (20 mL), and BOC anhydride (3.19 g), N,N-diisopropylethylamine (5.66 g) and 4-dimethylaminopyridine (178 mg) were added. The mixture was stirred at room temperature for 12 h. The reaction solution was concentrated under reduced pressure, and the resulting crude product was separated by silica gel column chromatography (PE/EA=10:1) to give a colorless oil (3.00 g, 77% yield). LC-MS $[M+H]^+$=238.2.

3 Preparation of Compound tert-butyl 5-bromo-4-fluoroindoline-1-carboxylate (T372-3)

Compound T372-2 (500 mg) was dissolved in anhydrous DCM (15 mL), and N-bromosuccinimide (449 mg) was added in portions. The mixture was stirred at room temperature for 2 h. Saturated sodium carbonate solution was added to adjust pH to about 10, and dichloromethane (20 mL×3) was added for extraction. The organic phases were combined, washed with saturated brine (20 mL×2), dried over anhydrous sodium sulfate, filtered and concentrated. The resulting crude product was separated by silica gel column chromatography (PE/EA=20:1) to give a white solid (470 mg, 64% yield). LC-MS $[M+H]^+$=316.1

4 Preparation of Compound 5-bromo-4-fluoroindoline (T372-4)

Compound T372-3 (470 mg) was dissolved in DCM (5 mL), and trifluoroacetic acid (1 mL) was added. The mixture was stirred at room temperature for 2 h. The reaction solution was concentrated under reduced pressure, and the resulting crude product was dissolved in dichloromethane (50 mL), washed with saturated sodium bicarbonate solution (20 mL), dried over anhydrous sodium sulfate, filtered and concentrated to give a white solid (280 mg, 86.9% yield). LC-MS $[M+H]^+$=216.1.

5 Preparation of Compound p-nitrophenyl 5-bromo-4-fluoro-2,3-indoline-1-carboxylate (T372-5)

Compound T372-4 (220 mg) was dissolved in DCM (2 mL), and 4-nitrophenyl chloroformate (308 mg) and pyridine (403 mg) were added. The mixture was stirred at room temperature for 4 h under nitrogen atmosphere. After the reaction was completed, the reaction solution was concentrated under reduced pressure to give a brown solid (880 mg, crude product, with a product content of about 40%), and the crude product was directly used in the next step. LC-MS $[M+H]^+$=380.9.

6 Preparation of Compound 5-bromo-4-fluoro-N-(3-fluoro-5-methoxybenzyl)indoline-1-carboxamide (T372-6)

Compound T372-5 (880 mg, crude product) was dissolved in anhydrous THE (4 mL), and (3-fluoro-5-methoxyphenyl)methylamine (427 mg) was added. The mixture was stirred at 70° C. for 12 h under nitrogen atmosphere. The reaction solution was diluted with water (30 mL) and extracted with ethyl acetate (20 mL×3). The organic phases were combined, washed with saturated brine (20 mL×2), dried over anhydrous sodium sulfate, filtered and concentrated. The resulting crude product was separated by silica gel column chromatography (PE/EA=3/2) to give an off-white substance (200 mg, 55% yield). LC-MS $[M+H]^+$ =397.0

7 Preparation of Compound 4-fluoro-N-(3-fluoro-5-methoxybenzyl)-5-(1H-pyrazol-4-yl)indoline-1-carboxamide (T372)

Compound T372-6 (200 mg) was dissolved in 1-4 dioxane and water (5/1, 3.6 mL), and tert-butyl [4-(4,4,5,5-tetramethyl-1,3,2-dioxaborolan-2-yl)pyrazol-1-yl]carboxylate (221 mg), potassium carbonate (207 mg) and [1,1'-bis (diphenylphosphino)ferrocene]dichloropalladium(II) (36.7 mg) were added. The mixture was stirred at 90° C. for 12 h under nitrogen atmosphere. The reaction solution was diluted with water (30 mL) and extracted with ethyl acetate (15 mL×3). The organic phases were combined, washed with saturated brine (15 mL×2), dried over anhydrous sodium sulfate, filtered and concentrated. The resulting crude product was purified by silica gel column chromatography (petroleum ether:ethyl acetate=1/3) to give a white solid (70 mg, 33% yield). LC-MS $[M+H]^+$=385.1.

$^1H$ NMR (400 MHz, DMSO) δ 12.95 (s, 1H), 7.94 (s, 2H), 7.63 (d, J=8.4 Hz, 1H), 7.45 (t, J=8.2 Hz, 1H), 7.35 (t, J=5.5 Hz, 1H), 6.78-6.66 (m, 3H), 4.30 (d, J=5.0 Hz, 2H), 4.05 (t, J=8.4 Hz, 2H), 3.76 (s, 3H), 3.21 (t, J=8.3 Hz, 2H).

Example 79. Preparation of Compound (S)—N-(1-(3-fluoro-5-methoxyphenyl)-2-hydroxyethyl)-7-(1H-pyrazol-4-yl)imidazo(1,2-a)pyridine-3-carboxamide (T352)

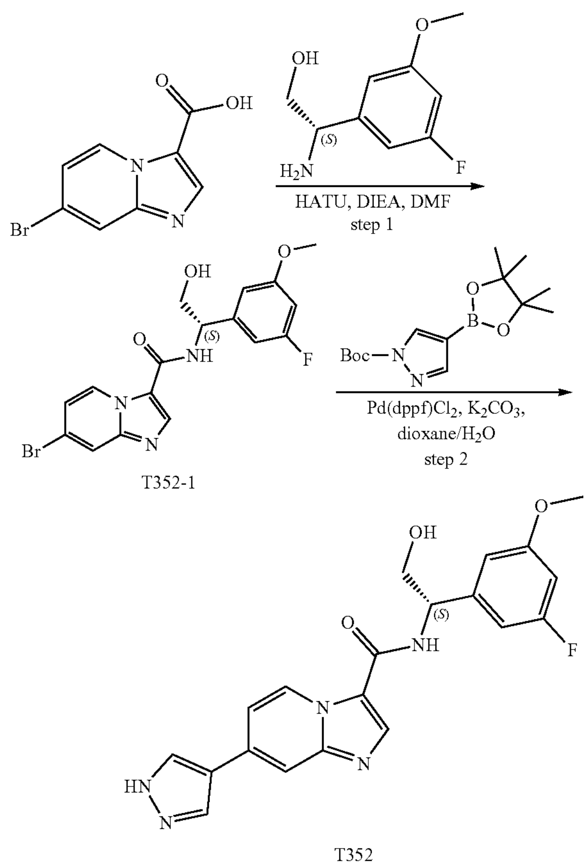

T352-1

T352

1 Preparation of Compound (S)-7-bromo-N-(1-(3-fluoro-5-methoxyphenyl)-2-hydroxyethyl)imidazo(1,2-a)pyridine-3-carboxamide (T352-1)

7-bromoimidazo(1,2-a)pyridine-3-carboxylic acid (150 mg) and HATU (353 mg) were dissolved in DMF (3 mL) under nitrogen atmosphere, and DIEA (320 mg) was added. After the mixture was stirred at room temperature for 10 min, (2S)-2-amino-2-(3-fluoro-5-methoxyphenyl)ethanol hydrochloride (151 mg) was added, and the resulting mixture was stirred at room temperature for 2 h. After the reaction was completed, the reaction solution was diluted with water (20 mL) and extracted with ethyl acetate (20 mL×3). The organic phases were combined, washed with saturated brine (20 mL×3), dried over anhydrous sodium sulfate, filtered and concentrated. The resulting crude product was purified by silica gel column chromatography (dichloromethane:methanol=20:1) to give a white solid (230 mg, 89.9% yield). MS(M+H)$^+$=408.1.

2 Preparation of Compound (S—N-(1-(3-fluoro-5-methoxyphenyl)-2-hydroxyethyl)-7-(1H-pyrazol-4-yl)imidazo(1,2-a)pyridine-3-carboxamide (T352)

Compound T352-1 (190 mg), tert-butyl (4-(4,4,5,5-tetramethyl-1,3,2-dioxaborolan-2-yl)pyrazole-1-yl)carboxylate (206 mg), potassium carbonate (257 mg) and [1,1'-bis(diphenylphosphino)ferrocene]dichloropalladium(II) (34 mg) were dissolved in dioxane and water (5:1, 5 mL) under nitrogen atmosphere. The mixture was stirred at 90° C. for 5 h. After the reaction was completed, the reaction solution was concentrated under reduced pressure, and the resulting crude product was purified by silica gel column chromatography (dichloromethane:methanol=10:1) and then purified by preparative chromatography to give a white solid (70 mg, 37.5% yield). MS(M+H)$^+$=396.2.

$^1$H NMR (400 MHz, DMSO) δ 13.14 (s, 1H), 9.33 (d, J=7.3 Hz, 1H), 8.64 (d, J=8.2 Hz, 1H), 8.47 (s, 1H), 8.45 (s, 1H), 8.16 (s, 1H), 7.96 (s, 1H), 7.43 (dd, J=7.3, 1.7 Hz, 1H), 6.88-6.80 (m, 2H), 6.71 (dt, J=11.0, 2.2 Hz, 1H), 5.10 (dd, J=14.1, 7.3 Hz, 1H), 5.03 (t, J=5.7 Hz, 1H), 3.76 (s, 3H), 3.74-3.65 (m, 2H).

Example 80: Preparation of Compound (S)—N-(1-(3-fluoro-5-methoxyphenyl)-2-hydroxyethyl)-7-(1H-pyrazol-4-yl)imidazo[1,5-a]pyridine-3-carboxamide (T373)

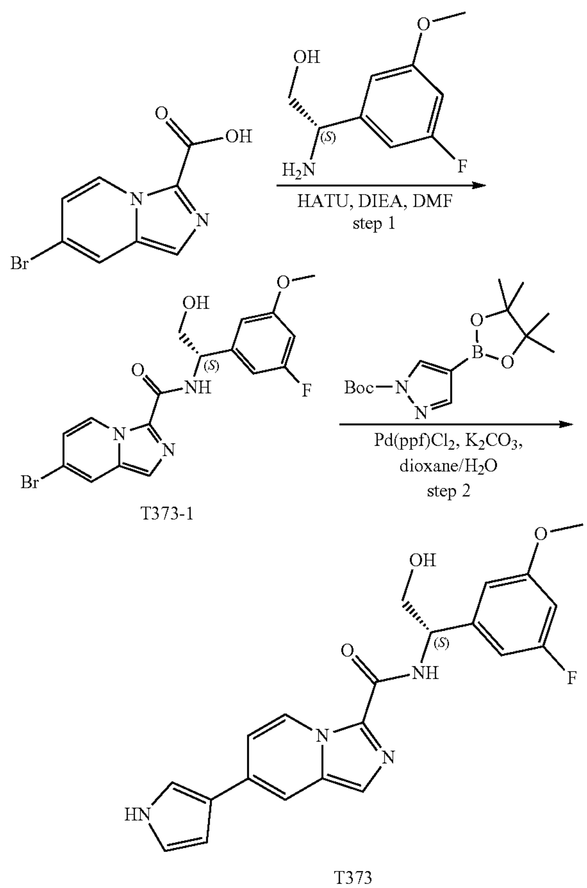

T373-1

T373

1 Preparation of Compound (S)-7-bromo-N-(1-(3-fluoro-5-methoxyphenyl)-2-hydroxyethyl)imidazo[1,5-a]pyridine-3-carboxamide (T373-1)

7-bromoimidazo[1,5-a]pyridine-3-carboxylic acid (150 mg) and HATU (353 mg) were dissolved in DMF (3 mL) under nitrogen atmosphere, and DIEA (320 mg) was added. After the mixture was stirred at room temperature for 10 min, (2S)-2-amino-2-(3-fluoro-5-methoxyphenyl)ethanol hydrochloride (151 mg) was added, and the resulting mixture was stirred at room temperature for 2 h. Water (20 mL) was added to quench the reaction, and ethyl acetate (20 mL×3) was added for extraction. The organic phases were combined, washed with saturated brine (20 mL 3), dried over anhydrous sodium sulfate, filtered and concentrated. The resulting crude product was purified by silica gel column chromatography (dichloromethane:methanol=20:1) to give a brown solid (250 mg, 96.5% yield). MS(M+H)$^+$=408.1.

2 Preparation of Compound (S)—N-(1-(3-fluoro-3-methoxyphenyl)-2-hydroxyethyl)-7-(1H-pyrazol-4-yl)imidazo(1,5-a)pyridine-3-carboxamide (T373)

Compound T373-1 (250 mg), tert-butyl (4-(4,4,5,5-tetramethyl-1,3,2-dioxaborolan-2-yl)pyrazole-1-yl)carboxylate (270 mg), potassium carbonate (337 mg) and [1,1'-bis(diphenylphosphino)ferrocene]dichloropalladium(II) (45 mg) were dissolved in dioxane and water (5:1, 5 mL) under nitrogen atmosphere. The mixture was stirred at 90° C. for 5 h. The reaction solution was directly concentrated under reduced pressure, and the resulting crude product was purified by silica gel column chromatography (dichloromethane:methanol=10:1) and then purified by preparative chromatography to give a yellow solid (97 mg, 39.2% yield). MS(M+H)$^+$=396.2.

$^1$H NMR (400 MHz, DMSO) δ 9.29 (d, J=7.5 Hz, 1H), 8.75 (d, J=8.3 Hz, 1H), 8.22 (s, 2H), 7.99 (s, 1H), 7.53 (s, 1H), 7.32 (dd, J=7.5, 1.7 Hz, 1H), 6.88-6.81 (m, 2H), 6.70 (dt, J=11.0, 2.3 Hz, 1H), 5.05 (dd, J=13.8, 6.5 Hz, 1H), 3.84-3.69 (m, 5H).

Example 81: Preparation of Compound 6-fluoro-N-(1-(2-fluoro-6-methoxyphenyl)-2-hydroxyethyl)-5-(1H-pyrazol-4-yl)indoline-1-carboxamide (T363)

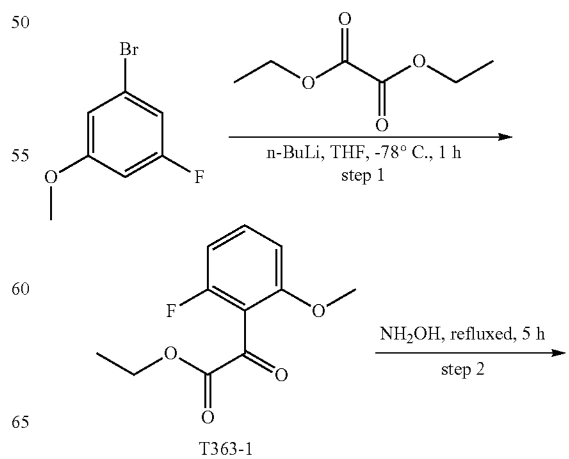

T363-1

-continued

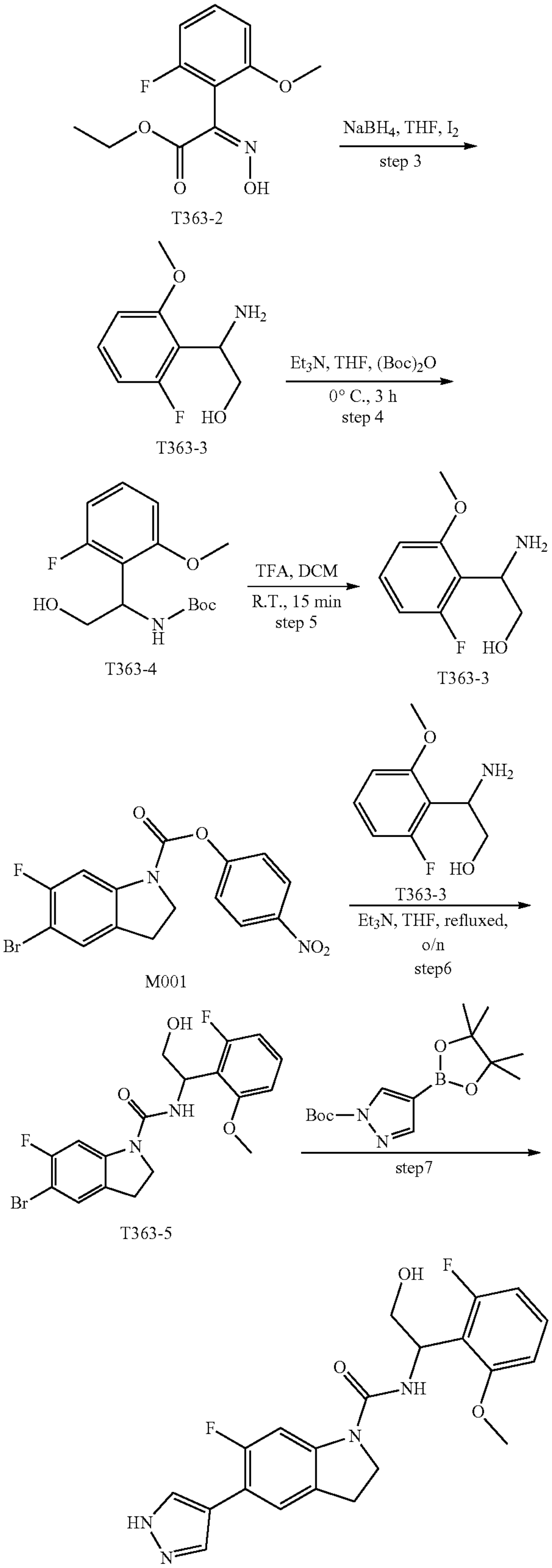

T363-2

T363-3

T363-4

T363-3

M001

T363-3

T363-5

T363

1 Preparation of Compound ethyl 2-(2-fluoro-6-methoxyphenyl)-2-oxoacetate (T363-1)

1-bromo-3-fluoro-5-methoxybenzene (20.0 g) was dissolved in anhydrous tetrahydrofuran (200 mL). The mixture was cooled to −78° C. under nitrogen atmosphere, and then n-butyl lithium/tetrahydrofuran solution (2.4 N, 41 mL) was slowly added dropwise. After the dropwise addition was completed, the mixture was stirred for 15 min at −78° C., and then diethyl oxalate (17.1 g) was added dropwise. The resulting mixture was slowly warmed to 0° C., and reacted for 1 h at 0° C. Saturated aqueous ammonium chloride solution (150 mL) was added to quench the reaction, and ethyl acetate (150 mL 2) was added for extraction. The organic phases were combined, washed with saturated brine (100 mL×2), dried over anhydrous sodium sulfate, filtered and concentrated by rotary evaporation. The resulting crude product was purified by silica gel column chromatography (40 g, petroleum ether:ethyl acetate=4:1) to give the product T363-1 (3.8 g, 16.9% yield). LC-MS $[M+H]^+$: 153.0.

2 Preparation of Compound ethyl 2-(2-fluoro-6-methoxyphenyl)-2-(hydroxyimino)acetate (T363-2)

Compound T363-1 (3.8 g) and hydroxylamine hydrochloride (1.4 g) were dissolved in absolute ethanol (50 mL), and the mixture was heated under reflux for 5 h. After the reaction was completed, the reaction solution was cooled to room temperature, water (20 mL) was added to quench the reaction, and ethyl acetate (40 mL×3) was added for extraction. The organic phases were combined, washed with saturated brine (50 mL×2), dried over anhydrous sodium sulfate, filtered and concentrated by rotary evaporation. The crude product was purified by silica gel column chromatography (dichloromethane:ethyl acetate=10:1) to give compound T363-2 (3.0 g, 66.6% yield). LC-MS $[M+H]^+$: 242.1.

3 Preparation of Compound 2-amino-2-(2-fluoro-6-methoxyphenyl)ethan-1-ol (T363-3)

Compound T363-2 racemate (2.80 g) was dissolved in anhydrous tetrahydrofuran (40 mL), and the mixture was stirred at room temperature. Sodium borohydride (1.76 g) was added, and then a solution of iodine (5.89 g) in anhydrous tetrahydrofuran (50 mL) was added dropwise. After the dropwise addition was completed, the resulting mixture was heated under reflux for 4 h. After the reaction was completed as detected by TLC, the reaction solution was cooled to room temperature, saturated aqueous ammonium chloride solution (40 mL) was added to quench the reaction, and the resulting mixture was filtered. The filtrate was adjusted to pH=11 with saturated aqueous sodium carbonate solution and extracted with dichloromethane (40 mL×8). The organic phases were combined, dried over anhydrous sodium sulfate, filtered and concentrated by rotary evaporation to give T363-3 in the form of a light yellow oil (3.00 g, crude product), which was directly used in the next step. LC-MS $[M+H]^+$: 186.0.

4 Preparation of Compound tert-butyl (1-(2-fluoro-6-methoxyphenyl)-2-hydroxyethyl)carbamate (T363-4)

Compound T363-3 (3.00 g) was dissolved in anhydrous tetrahydrofuran (30 mL), and triethylamine (3.27 g) and Boc anhydride (3.54 g) were added. The mixture was stirred at room temperature for 3 h. Water (20 mL) was added to quench the reaction, and ethyl acetate (30 mL×3) was added for extraction. The organic phases were combined, washed with saturated brine (30 mL×3), dried over sodium sulfate, filtered and concentrated by rotary evaporation. The resulting crude product was purified by silica gel column chromatography (dichloromethane:methanol=50:1) to give the product T363-4 (600 mg, 30.7% yield). LC-MS $[M+H]^+$: 286.0.

5 Separation and Purification of Compound 2-amino-2-(2-fluoro-6-methoxyphenyl)ethan-1-ol (T363-3)

Compound T363-4 (600 mg) was dissolved in dichloromethane (6 mL), and then trifluoroacetic acid (3 mL) was added. The mixture was stirred at room temperature for 15 min. The reaction solution was concentrated under reduced pressure, saturated aqueous sodium carbonate solution (15 mL) was added, and dichloromethane (20 mL/8) was added for extraction. The organic phases were combined, dried over anhydrous sodium sulfate, filtered and concentrated by rotary evaporation to give T363-3 in the form of a light yellow oil (310 mg, crude product, 79.7% yield). LC-MS $[M+H]^+$: 186.0.

6 Preparation of Compound 5-bromo-6-fluoro-N-(1-(2-fluoro-6-methoxyphenyl)-2-hydroxyethyl)indoline-1-carboxamide (T363-5)

Compound M001 (150 mg) was dissolved in anhydrous tetrahydrofuran (5 mL), and compound T363-3 (80 mg) and triethylamine (118 mg) were added. The mixture was stirred overnight under reflux. The reaction solution was cooled to room temperature, water (20 mL) was added to quench the reaction, and ethyl acetate (20 mL×3) was added for extraction. The organic phases were combined, washed with saturated brine (20 mL×3), dried over sodium sulfate, filtered and concentrated by rotary evaporation. The resulting crude product was purified by silica gel column chromatography (dichloromethane:ethyl acetate=20:1) to give the product (80 mg, pure product, 48.0% yield). LC-MS $[M+H]^+$: 426.9.

7 Preparation of Compound 6-fluoro-N-(1-(2-fluoro-6-methoxyphenyl)-2-hydroxyethyl)-5-(1H-pyrazol-4-yl)indoline-1-carboxamide (T363)

Compound T363-5 (80 mg), tert-butyl 4-(4,4,5,5-tetramethyl-1,3,2-dioxaborolan-2-yl)-1H-pyrazole-1-carboxylate (72 mg), [1,1'-bis(di phenyl phosphino)ferrocene]dichloropalladium(II) (24 mg) and potassium carbonate (66 mg) were dissolved in a mixed solution of 1,4-dioxane (5 mL) and water (1 mL), and the mixture was stirred overnight at 80° C. under nitrogen atmosphere. The reaction solution was cooled to room temperature and filtered, and the filtrate was concentrated by rotary evaporation. The residue was purified by silica gel column chromatography (dichloromethane: methanol=20:1) and lyophilized to give the product (12.5 mg, pure product, 15.3% yield). LC-MS $[M+H]^+$: 414.9.

$^1$H NMR (400 MHz, DMSO) δ 12.94 (s, 1H), 7.94 (s, 2H), 7.58 (d, J=13.1 Hz, 1H), 7.49 (d, J=7.9 Hz, 1H), 7.30-7.24 (m, 1H), 6.88 (d, J=8.4 Hz, 1H), 6.81-6.75 (m, 1H), 6.37 (d, J=8.7 Hz, 1H), 5.41-5.36 (m, 1H), 4.93 (t, J=6.2 Hz, 1H), 4.12 (q, J=8.9 Hz, 1H), 3.91 (q, J=8.7 Hz, 1H), 3.88 (s, 3H), 3.75-3.69 (m, 1H), 3.59 (dd, J=11.8, 5.5 Hz, 1H), 3.14 (t, J=8.7 Hz, 2H).

Example 82: Preparation of Compound 6-(5-fluoro-1H-pyrazol-4-yl)-N-(3-methoxybenzyl)imidazo (1,5-a)pyridine-1-carboxamide (T391)

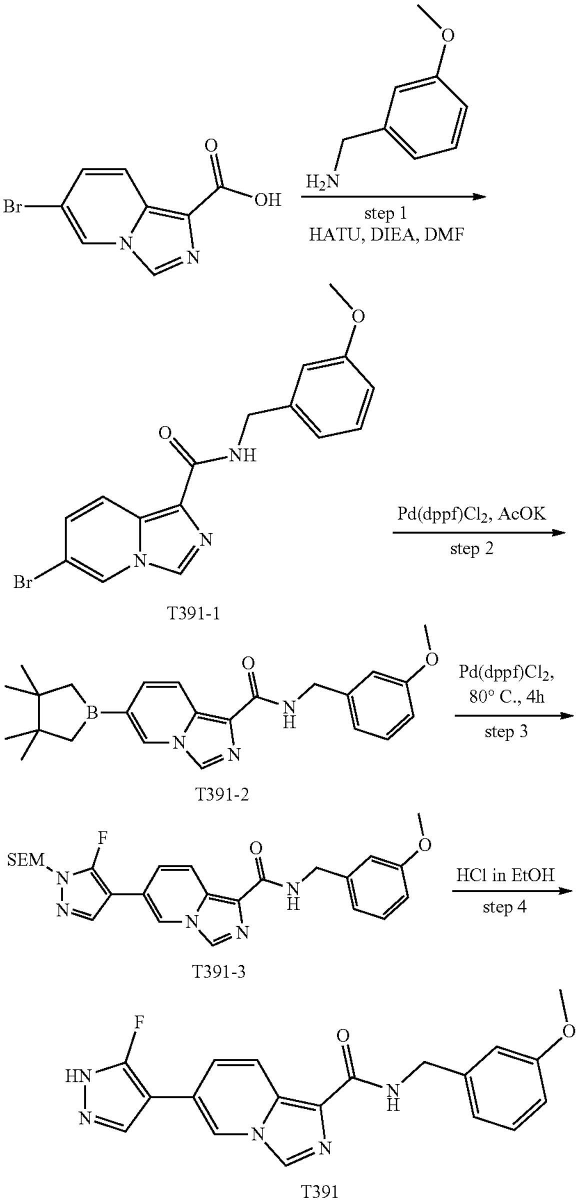

T391-1

T391-2

T391-3

T391

1 Preparation of 6-bromo-N-(3-methoxybenzyl) imidazo(1,5-a)pyridine-1-carboxamide (T391-1)

6-bromoimidazo(1,5-a)pyridine-1-carboxylic acid (1000 mg) was dissolved in dimethylformamide (10 mL), and HATU (2051 mg) and N,N-diisopropylethylamine (2144 mg) were added. The mixture was stirred at room temperature for 10 min. (3-methoxyphenyl)methylamine (740 mg) was then added, and the resulting mixture was stirred at room temperature for 2 h. After the reaction was completed, water (50 mL) was added, and ethyl acetate (10 mL×3) was added for extraction. The organic phases were combined, washed with saturated brine, dried over anhydrous sodium sulfate and concentrated by rotary evaporation, and the resulting crude product was purified by column chromatography (petroleum ether:ethyl acetate=2:1) to give T391-1 in the form of a yellow solid (900 mg, 59.62% yield). MS $(M+H)^+$=361.9.

2 Preparation of N-(3-methoxybenzyl)-6-(4,4,5,5-tetramethyl-1,3,2-dioxaborolan-2-yl)imidazo(1,5-a)pyridine-1-carboxamide (T391-2)

T391-1 (900 mg) was dissolved in anhydrous 1,4-dioxane (15 mL) under nitrogen atmosphere, and 4,4,4',4',5,5,5',5'-octamethyl-2,2'-bi(1,3,2-dioxaborolane) (1269 mg), potassium acetate (736 mg) and [1,1'-bis(diphenylphosphino)ferrocene]dichloropalladium(II) (183 mg) were added. The mixture was reacted at 90° C. for 3 h. After the reaction was completed, the reaction solution was cooled to room temperature, filtered and concentrated by rotary evaporation to give T391-2 in the form of a brown oil (1000 mg, crude product, 97.29% yield). MS $(M+H)^+$=408.1.

3 Preparation of 6-(5-fluoro-1-(((2-(trimethylsilyl)ethoxy)methyl)-1H-pyrazol-4-yl)-N-(3-methoxybenzyl)imidazo(1,5-a)pyridine-1-carboxamide (T391-3)

T391-2 (900 mg) was dissolved in 1,4-dioxane (3 mL) and water (0.5 mL) under nitrogen atmosphere, and N-(3-methoxybenzyl)-5-(4,4,5,5-tetramethyl-1,3,2-dioxaborolan-2-yl)indoline-1-carboxamide (720 mg), potassium carbonate (611 mg) and [1,1'-bis(diphenylphosphino)ferrocene]dichloropalladium(II) (162 mg) were added. The mixture was reacted at 80° C. for 4 h. The reaction solution was cooled to room temperature, water (30 mL) was added, and then ethyl acetate (30 mL×3) was added for extraction. The organic phases were combined, washed with saturated brine (30 mL×2), dried over anhydrous sodium sulfate, filtered and concentrated by rotary evaporation, and the resulting crude product was purified by silica gel column chromatography (eluent: petroleum ether:ethyl acetate=2:1) to give T391-3 (210 mg, 18.94% yield). MS $(M+H)^+$=496.0.

4 Preparation of 6-(5-fluoro-1H-pyrazol-4-yl)-N-(3-methoxybenzyl)imidazo (1,5-a)pyridine-1-carboxamide (T391)

T391-3 (200 mg) was dissolved in ethanol (5 mL), and concentrated hydrochloric acid (1 mL) was added. The mixture was reacted at 80° C. for 5 h. After the reaction was completed, the reaction solution was directly concentrated by rotary evaporation, and the resulting crude product was purified by high pressure liquid phase chromatography to give a white solid (71.5 mg, 50.22% yield). MS $(M+H)^+$=366.2.

$^1$H NMR (400 MHz, DMSO) δ 12.77 (s, 1H), 8.67-8.59 (m, 2H), 8.49 (s, 1H), 8.28 (d, J=2.0 Hz, 1H), 8.10 (d, J=9.4 Hz, 1H), 7.38 (dd, J=9.5, 1.3 Hz, 1H), 7.22 (t, J=8.1 Hz, 1H), 6.95-6.88 (m, 2H), 6.79 (dd, J=8.2, 1.8 Hz, 1H), 4.44 (d, J=6.4 Hz, 2H), 3.72 (s, 3H).

Biological Activity Assay

In some embodiments, the compounds of the present disclosure are found to result in kinase inhibition, particularly inhibition of ROCK1 and/or ROCK2 kinase, in vitro and/or in vivo, as tested by methods conventional in the art. Meanwhile, it is also found that the compounds of the present disclosure have low cytotoxicity and good pharmacokinetic property, and experiments also show that the compounds of the present disclosure have a proper metabolic stability and are promising in druggability.

1. In Vitro Evaluation of ROCK2 Kinase Activity

ROCK2 activity screening. ROCK2 activity was detected using a 96-well (Cisbio) time-resolved fluorometric assay. The assay for ROCK2 was performed in the following assay buffer: 5 mM $MgCl_2$ (Sigma), 1 mM DTT (Sigma) and 1× kinase buffer. The kinase buffer was used for dilution. 7.5 μL of ROCK2 kinase (Invitrogen, PV3759) was added to a 96-well microplate to reach a final concentration of 0.4 ng/μL, and then 0.25 μL of test compound (DMSO content: 1% (volume fraction)) was added. The mixture was incubated at room temperature for 0.5 h. To start the reaction, the kinase buffer was used to mix ATP (Aladdin) and the substrate STK-substrate 2-biotin. 7.5 μL of the mixed solution was added to the microplate to reach final concentrations of 6.739 μM and 1 μM. The resulting mixture was incubated for 2 h at room temperature. 5 mL of detection buffer was mixed with STK antibody—Cryptate, and then an appropriate volume of the mixture was mixed with an equal volume of streptavidin-XL665. 10 μL of the resulting mixture was added to the microplate to stop the reaction. After further incubation for about 1 h, the microplate was read on a Molecular Devices SpectraMax i3x multifunctional microplate reader. The kinase buffer, the STK-substrate 2-biotin, the detection buffer, the STK antibody-Cryptate, and the streptavidin-XL665 were all from HTRF KinEASE-STK kit (Cisbio, 1000 tests, 61GSTXLA).

2. In Vitro Evaluation of ROCK1 Kinase Selectivity

ROCK1 activity was detected using a 96-well (Cisbio) time-resolved fluorometric assay. The assay for ROCK1 was performed in the following assay buffer: 5 mM $MgCl_2$ (Sigma), 1 mM DTT (Sigma) and 1× kinase buffer. The kinase buffer was used for dilution. 7.5 μL of ROCK1 kinase (Invitrogen) was added to a 96-well microplate to reach a final concentration of 0.4 ng/μL, and then 0.25 μL of test compound (DMSO content: 1%) was added. The mixture was incubated at room temperature for 0.5 h. To start the reaction, the kinase buffer was also used to mix ATP (Aladdin) and the substrate STK-substrate 2-biotin. 7.5 μL of the mixed solution was added to the microplate to reach final concentrations of 3.53 μM and 1 μM. The resulting mixture was incubated for 2 h at room temperature. 5 mL of detection buffer was mixed with STK antibody-Cryptate, and then an appropriate volume of the mixture was mixed with an equal volume of streptavidin-XL665. 10 μL of the resulting mixture was added to stop the reaction. After further incubation for about 1 h, the microplate was read on a Molecular Devices SpectraMax i3x multifunctional microplate reader. The kinase buffer, the STK-substrate 2-biotin, the detection buffer, the STK antibody-Cryptate, and the streptavidin-XL665 were all from HTRF KinEASE-STK kit (Cisbio, 1000 tests, 61GSTXLA).

Biological Example 1

The compounds of the Examples of the present disclosure were subjected to the experiments on evaluation of in vitro kinase activity described above to determine the inhibitory activity of each compound against ROCK 1/2. It was found that the compounds of the present disclosure all have good activity, wherein for both kinases, some compounds have an $IC_{50}$<10 μM, some compounds have an $IC_{50}$≤50 nM (activity level A), some compounds have an $IC_{50}$>50 nM and ≤500 nM (activity level B), and some compounds have an $IC_{50}$>500 nM and ≤5 μM (activity level C).

$IC_{50}$ values of representative compounds are shown in Table 1 below. Note: (A: ≤50 nM; B: >50 nM and ≤500 nM; C: >500 nM and ≤5 μM)

TABLE 1

Inhibition of ROCK1 and ROCK2 by compounds of the present disclosure

| Compound | $IC_{50}$ for ROCK1 | $IC_{50}$ for ROCK2 |
|---|---|---|
| T201 | C | B |
| T202 | A | A |
| T204 | B | A |
| T205 | B | A |
| T206 | C | B |
| T207 | A | A |
| T208 | A | A |
| T209 | B | B |
| T210 | B | B |
| T211 | A | A |
| T212 | C | C |
| T213 | A | A |
| T214 | B | B |
| T215 | C | C |
| T216 | B | B |
| T217 | B | B |
| T218 | B | C |
| T219 | A | A |
| T220 | B | B |
| T221 | B | B |
| T222 | A | A |
| T223 | A | A |
| T224 | B | B |
| T225 | A | A |
| T226 | B | A |
| T227 | A | A |
| T228 | A | A |
| T229 | A | A |
| T230 | B | B |
| T231 | A | A |
| T232 | A | A |
| T233 | A | A |
| T234 | A | A |
| T235 | A | A |
| T236 | A | A |
| T237 | A | A |
| T238 | A | A |
| T239 | A | A |
| T240 | C | C |
| T241 | B | B |
| T242 | B | B |
| T243 | C | C |
| T244 | B | B |
| T245 | B | B |
| T246 | C | C |
| T247 | B | B |
| T248 | B | B |
| T249 | C | C |
| T340 | B | A |
| T341 | A | A |
| T342 | A | A |
| T343 | C | B |
| T344 | A | A |
| T345 | B | A |
| T346 | A | A |
| T347 | A | A |
| T348 | C | C |
| T349 | C | C |
| T350 | A | A |
| T351 | A | A |
| T352 | A | A |
| T353 | C | B |
| T354 | B | B |
| T355 | A | A |
| T356 | S: A<br>R: B | S: A<br>R: B |
| T357 | A | A |
| T358 | A | A |
| T359 | B | A |
| T360 | C | B |

TABLE 1-continued

Inhibition of ROCK1 and ROCK2 by compounds of the present disclosure

| Compound | $IC_{50}$ for ROCK1 | $IC_{50}$ for ROCK2 |
|---|---|---|
| T361 | B | A |
| T362 | C | B |
| T363 | — | B |
| T364 | C | B |
| T365 | B | A |
| T366 | S: A<br>R: C | S: A<br>R: B |
| T367 | A | A |
| T368 | C | B |
| T369 | A | A |
| T370 | A | A |
| T371 | A | A |
| T372 | A | A |
| T373 | A | A |
| T374 | A | A |
| T375 | B | A |
| T376 | C | B |
| T377 | A | A |
| T378 | A | A |
| T379 | A | A |
| T380 | B | A |
| T381 | A | A |
| T382 | A | A |
| T383 | C | C |
| T384 | A | A |
| T385 | B | A |
| T386 | B | A |
| T387 | A | A |
| T388 | B | A |
| T389 | A | A |
| T390 | B | A |
| T391 | A | A |

Biological Example 2. In Tiny Cytotoxicity Assay for Compounds Disclosed Herein In vitro cytotoxicity assay for the compounds disclosed herein was performed in HepG2 cells using the CCK-8 method. HepG2 cells (Beina Bio) in the logarithmic growth phase were collected, the concentration of cell suspension was adjusted, and then the cells were plated on a 96-well cell culture plate at 50,000 cells/well. The cells were then incubated overnight in a cell incubator (5%, 37° C.), and after 80-90% cell confluence was achieved, test compound at each concentration gradient or vehicle (DMSO) was added after medium change. The resulting mixture was incubated in the cell incubator (5%, 37° C.) for 48 h. After the treatment, the medium in the plate was discarded. The plate was washed twice with PBS, added with CCK-8 working solution (Beyotime) at 100 μL per well, and then incubated at 37° C. for 1.5 h in the dark. Absorbance at $OD_{450\ nm}$ was measured for each well on a microplate reader, and $CC_{50}$ value of each compound was analyzed and calculated. The compounds of the Examples of the present disclosure were subjected to the experiment described above, and it was found that the compounds of the present disclosure all have good safety, wherein the $CC_{50}$ values of all the compounds are >10 μM, some preferred compounds have a $CC_{50}$>30 μM, and more preferred compounds have a $CC_{50}$>50 μM. $CC_{50}$ values of representative compound are shown in Table 2 below.

TABLE 2

| CC$_{50}$ values obtained for compounds | |
|---|---|
| Compound | HepG2 CC$_{50}$ (μM) |
| T202 | >50 |
| T203 | >50 |
| T204 | >50 |
| T205 | >50 |
| T356-R | >200 |
| T346 | 45 |
| T357 | 96 |
| T361 | >100 |
| T345 | 40.8 |
| T387 | >100 |
| T355 | >100 |
| T385 | >100 |
| T384 | >100 |
| T391 | >100 |
| T380 | 35.3 |

Biological Example 3

In Vivo Pharmacokinetic Study of Compounds Disclosed Herein in Mice SPF-grade mice (SPF (Beijing) Biotechnology Co., Ltd.) were fasted overnight (without water deprivation) after adaptive feeding, and then received the compound of the present disclosure by intragastrical administration and bolus injection at tail vein. After administration, plasma of mice was collected at specific time points, and the concentration of the compound in the plasma was detected by LC-MS/MS (AB SCIEX Qtrap4500). The PK parameters of the compounds were statistically analyzed and calculated (WinNonlin V5.2, Pharsight) to show the pharmacokinetic properties of the compounds in mice.

The compounds of the Examples of the present disclosure were subjected to the experiment described above, and the results showed that the compounds of the present disclosure all have good pharmacokinetic properties in mice, and can realize high exposure in vivo and high oral bioavailability at a low dose, wherein the oral bioavailability of some compounds is >30%, and the oral bioavailability of some compounds is >50%. Table 3 below shows experimental data for representative compounds.

TABLE 3

PK experiment of compounds disclosed herein in mice

| Compound | Adminis-tration dose mg/kg | Route of adminis-tration | Cmax (ng/mL) | AUC$_{last}$ (ng/mL*hr) | Oral bioavail-ability (%) |
|---|---|---|---|---|---|
| T201 | 3 | Po | 95.5 | 175 | 42.4 |
| | | Iv | 704 | 413 | |
| T202 | 3 | Po | 807 | 1570 | 90.3 |
| | | Iv | 2339 | 1739 | |
| T345 | 1 | Po | 322 | 618 | 49.1 |
| | | Iv | 977 | 1257 | |
| T387 | 1 | Po | 188 | 623 | 82.8 |
| | | Iv | 492 | 753 | |
| T238 | 3.4 | Po | 2133 | 8875 | 84.6 |
| | | Iv | 4940 | 10493 | |
| T357 | 1 | Po | 352 | 775 | 71.1 |
| | | Iv | 811 | 1090 | |

In the specification, description involving the term “one embodiment”, “some embodiments”, “examples”, “a specific example”, “some examples” or the like means that a particular feature, structure, material or characteristic described in reference to the embodiment or example is included in at least one embodiment or example of the present disclosure. In this specification, the schematic descriptions of the terms described above do not necessarily refer to the same embodiment or example. Moreover, the specific features, materials, structures and other characteristics described may be combined in any one or more embodiments or examples in an appropriate manner. Moreover, various embodiments or examples and features of various embodiments or examples described in this specification can be combined by one skilled in the art to the extent that they do not contradict each other.

Although examples of the present disclosure are illustrated and described above, it will be appreciated that the above examples are exemplary and not to be construed as limiting the present disclosure, and that changes, modifications, substitutions and alterations can be made to the above examples by those of ordinary skill in the art within the scope of the present disclosure.

The invention claimed is:

1. A compound of formula (I) or a racemate, a stereoisomer, a tautomer, an isotopically labeled compound, a nitrogen oxide, a solvate, a polymorph, a pharmaceutically acceptable salt thereof, (I)

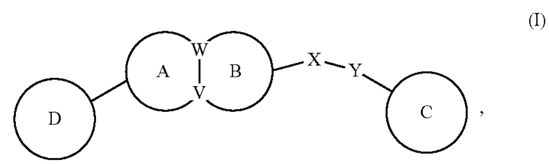

wherein, ring B is attached to the X via an N atom present on the ring B; and

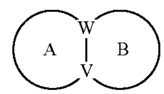

is selected from the following groups unsubstituted or optionally substituted with one, two or more $R_{ab}$:

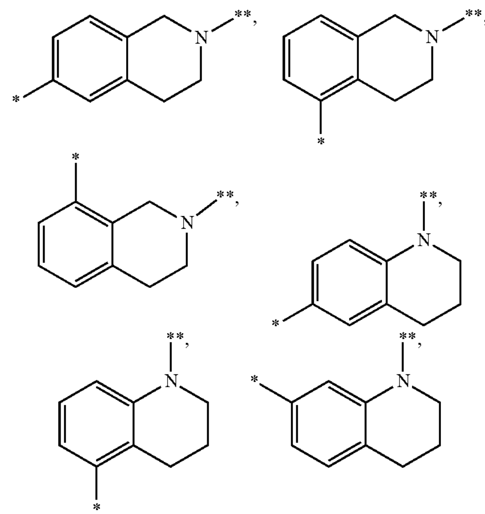

-continued

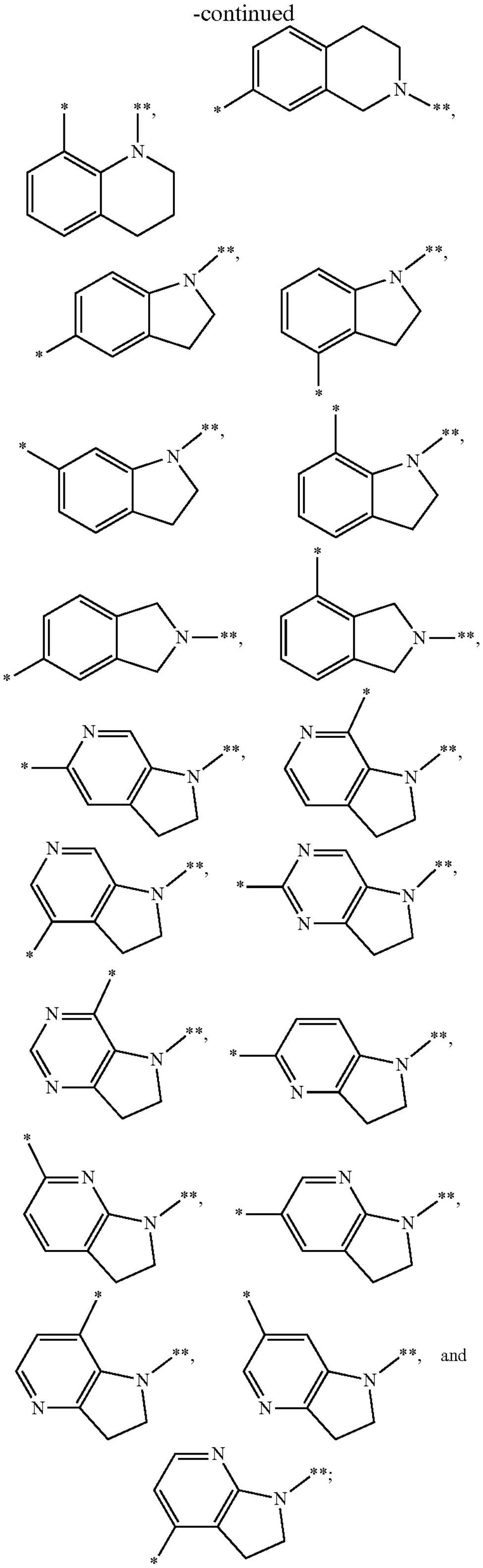

and

X is —C(═O) NRx-;

Y is methylene unsubstituted or optionally substituted with one, two or more Ry;

ring C is the following group unsubstituted or optionally substituted with one, two or more $R_c$:

phenyl, pyridinyl, pyrazolyl, imidazolyl, and benzimidazolyl;

ring D is pyrazolyl or triazolyl unsubstituted or optionally substituted with one, two or more $R_d$;

each $R_y$ is independently H, halogen, OH, or the following group unsubstituted or optionally substituted with one, two or more R: methyl, ethyl, propyl, butyl, pentyl, hexyl, $NH_2(CH_2)_m$—, $(CH_3)_2N(CH_2)_m$—, $CH_3NH(CH_2)_m$—, oxetanyl, azetidinyl, tetrahydropyranyl, tetrahydrofuranyl, pyrrolyl, piperidyl,

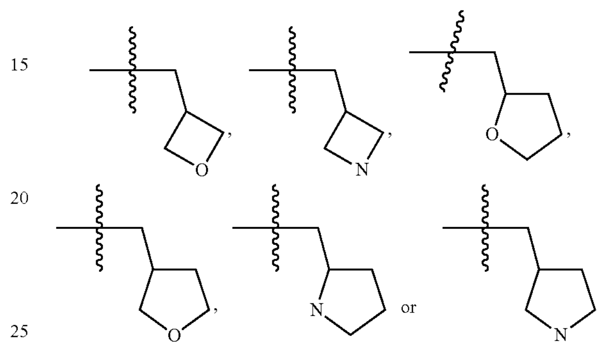

or wherein each m is independently selected from 0, 1, 2 and 3;

wherein each R is independently ═O, halogen, CN, OH, SH, $NH_2$, or the following group unsubstituted or optionally substituted with one, two or more R': 3-7 membered heterocyclyl containing one heteroatom which is selected from nitrogen or oxygen; wherein each R' is independently halogen or $(C_1\text{-}C_6)$ aliphatic hydrocarbyl;

each $R_{ab}$ is H, halogen, CN, or $(C_1\text{-}C_6)$ aliphatic hydrocarbyl, wherein the $(C_1\text{-}C_6)$ aliphatic hydrocarbyl is unsubstituted or optionally substituted with one, two or more halogen;

each $R_c$ is independently H, halogen, —$C(O)NR_{11}R_{12}$, or the following group unsubstituted or optionally substituted with one, two or more R: methyl, ethyl, propyl, butyl, pentyl, hexyl, methoxy, ethoxy, propoxy, butoxy, pentyloxy, hexyloxy, —$O(CH_2)_nO(CH_2)_mCH_3$, $NH_2(CH_2)_m$—, $(CH_3)_2N(CH_2)_m$—, $CH_3NH(CH_2)_m$—, —$(NH)_kC(O)NH_2$, —$(NH)_kC(O)NH(CH_2)_mCH_3$, —$(NH)_kC(O)N(CH_3)(CH_2)_mCH_3$, —$(NH)_kC(O)(CH_2)_m$ $CH_3$, —$OC(O)(CH_2)_mCH_3$, —$O(CH_2)_mC(═O)(CH_2)_m(NH)_kH$, or —$C(O)O(CH_2)_mCH_3$, wherein each n is independently selected from 1, 2 and 3; each m is independently selected from 0, 1, 2 and 3; each k is independently selected from 0 and 1; wherein each R is independently ═O, halogen, CN, OH, SH, $NH_2$, or the following group unsubstituted or optionally substituted with one, two or more R': 3-7 membered heterocyclyl containing one heteroatom selected from nitrogen and oxygen, $(C_1\text{-}C_6)$ aliphatic hydrocarbyl, or $C_{3\text{-}7}$ alicyclic hydrocarbyl; wherein each R' is independently halogen or $(C_1\text{-}C_6)$ aliphatic hydrocarbyl; and wherein $R_{11}$ is H or $C_{3\text{-}7}$ alicyclic hydrocarbyl and $R_{12}$ is H or $C_{3\text{-}7}$ alicyclic hydrocarbyl;

each $R_d$ is independently H, halogen, —$NH_2$, or $(C_1\text{-}C_6)$ aliphatic hydrocarbyl, wherein the $(C_1\text{-}C_6)$ aliphatic hydrocarbyl is unsubstituted or optionally substituted with one, two or more halogen; and each $R_x$ is independently selected from H, halogen, and the following groups unsubstituted or optionally substituted with one, two or more halogen: methyl, ethyl, propyl, butyl, pentyl, hexyl, vinyl, propenyl, butenyl, pentenyl, hexenyl, $NH_2(CH_2)_m$—, $(CH_3)_2N(CH_2)_m$—, $CH_3NH(CH_2)_m$—, oxetanyl, azetidinyl, tetrahydropyranyl, tetrahydrofuranyl, pyrrolyl, piperidyl, wherein each m is selected from 0, 1, 2, and 3.

2. The compound of formula (I) or the racemate, the stereoisomer, the tautomer, the isotopically labeled compound, the nitrogen oxide, the solvate, the polymorph, the pharmaceutically acceptable salt thereof according to claim 1, wherein, each $R_y$ is independently selected from H, halogen, OH, methyl, ethyl, propyl, butyl, pentyl, hexyl, $NH_2(CH_2)_m$—, $(CH_3)_2N(CH_2)_m$—, $CH_3NH(CH_2)_m$—, oxetanyl, azetidinyl, tetrahydropyranyl, tetrahydrofuranyl, pyrrolyl, and piperidyl, each m being independently selected from 0, 1, 2, and 3, or each Ry is independently selected from the following groups substituted with one, two or more R: methyl ethyl and propyl; wherein each R is independently selected from halogen, OH, and the following groups unsubstituted or optionally substituted with one, two or more halogen: 3-7 membered heterocyclyl containing one heteroatom selected from nitrogen and oxygen;

each $R_{ab}$ is independently selected from H, halogen, CN, and the following group unsubstituted or optionally substituted with one, two or more halogen: methyl, ethyl, propyl, butyl, pentyl, and hexyl;

each $R_c$ is independently selected from H, halogen, and the following groups unsubstituted or optionally substituted with one, two or more R: methyl, ethyl, propyl, butyl, pentyl, hexyl, methoxy, ethoxy, propoxy, butoxy, pentyloxy, hexyloxy, —$O(CH_2)_nO(CH_2)_mCH_3$, $NH_2(CH_2)_m$—, $(CH_3)_2N(CH_2)_m$—, $CH_3NH(CH_2)_m$—, —$(NH)_kC(O)NH_2$, —$(NH)_kC(O)NH(CH_2)_mCH_3$, —$(NH)_kC(O)N(CH_3)(CH_2)_mCH_3$, —$(NH)_kC(O)(CH_2)_m$ $CH_3$, —$OC(O)(CH_2)_mCH_3$, —$O(CH_2)_mC({=}O)(CH_2)m(NH)_kH$, and —$C(O)O(CH_2)_mCH_3$, wherein each n is independently selected from 1, 2 and 3; each m is independently selected from 0, 1, 2 and 3; each k is independently 0 and 1; wherein each R is independently selected from =O, halogen, OH, $NH_2$, and the following groups unsubstituted or optionally substituted with one, two or more R': 3-7 membered heterocyclyl containing one heteroatom selected from nitrogen, oxygen, $(C_1$-$C_6)$ aliphatic hydrocarbyl, and $C_{3-7}$ alicyclic hydrocarbyl; wherein each R' is independently selected from halogen and $(C_1$-$C_6)$ aliphatic hydrocarbyl; and each $R_d$ is independently selected from H, halogen, —$NR_{11}R_{12}$, and $(C_1$-$C_6)$ aliphatic hydrocarbyl which is unsubstituted or optionally substituted with one, two or more halogen, $R_{11}$ and $R_{12}$ being H.

3. The compound of formula (I) or the racemate, the stereoisomer, the tautomer, the isotopically labeled compound, the nitrogen oxide, the solvate, the polymorph, the pharmaceutically acceptable salt thereof according to claim 1, wherein: each Rab is independently selected from H, halogen, CN, methyl, ethyl, propyl, butyl, pentyl, and hexyl; each Rd is independently selected from H, halogen, methyl, ethyl, and $NH_2$;

each Ry is independently selected from H, F, Cl, OH, methyl, ethyl, n-propyl, isopropyl, $NH_2$—, $NH_2CH_2$—, —$NHCH_3$, —$N(CH_3)_2$, $(CH_3)_2NCH_2CH_2$—, $CH_3NHCH_2CH_2$—, $(CH_3)_2NCH_2$—, $(CH_3)_2NCH_2CH_2CH_2$—, azetidinyl, pyrrolyl, and piperidyl; or each Ry is independently selected from the following groups substituted with one, two or more R: methyl, ethyl, n-propyl, and isopropyl, each R being independently selected from F, Cl, OH, and the following groups unsubstituted or optionally substituted with one, two or more halogen: azetidinyl, pyrrolyl, and piperidyl;

each Rc is independently selected from H, F, Cl,

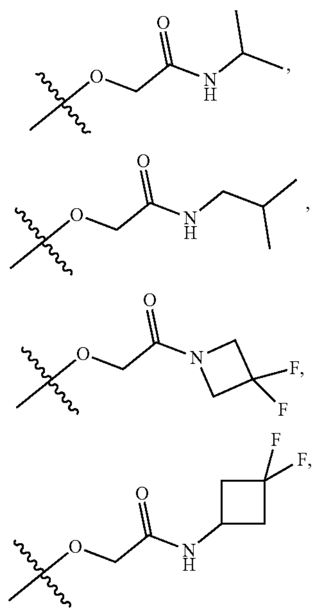

and the following groups unsubstituted or optionally substituted with one, two or more R: methyl, ethyl, n-propyl, isopropyl, methoxy, ethoxy, propoxy, butoxy, pentyloxy, —$OCH_2OCH_3$, —$OCH_2CH_2OCH_3$, —$OCH_2CH_2CH_2OCH_3$, —$OCH_2OCH_2CH_3$, —$OCH_2OCH_2CH_2CH_3$, —$OCH_2CH_2OCH_2CH_3$, —$OCH_2CH_2OCH_2CH_2CH_3$, —$C(O)NH_2$, —$C(O)NHCH_3$, and —$C(O)N(CH_3)_2$, each R being independently selected from F, Cl, and the following groups unsubstituted or optionally substituted with one, two or more R': methyl, ethyl, propyl, azetidinyl, pyrrolyl, piperidyl, cyclopropyl, cyclobutyl, and cyclopentyl, each R' being independently selected from F, Cl, methyl, ethyl, and propyl;

each Rx is independently selected from H, F, Cl, and the following groups unsubstituted or optionally substituted with one, two or more halogen: methyl, ethyl, n-propyl, isopropyl, $NH_2CH_2$—, —$NHCH_3$, —$N(CH_3)_2$, $(CH_3)_2NCH_2CH_2$—, $CH_3NHCH_2CH_2$—, $(CH_3)_2NCH_2$—, $(CH_3)_2NCH_2CH_2CH_2$—, oxetanyl, tetrahydropyranyl, and tetrahydrofuranyl.

4. A compound or the racemate, the stereoisomer, the tautomer, the isotopically labeled compound, the nitrogen oxide, the solvate, the polymorph, the pharmaceutically acceptable salt thereof, wherein the compound is selected from:

-continued
T201
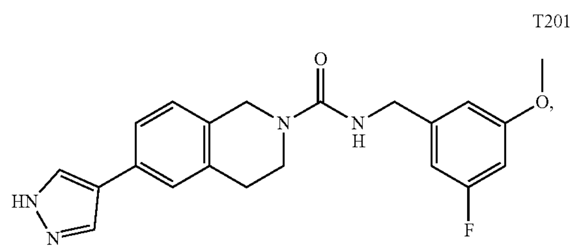
T202
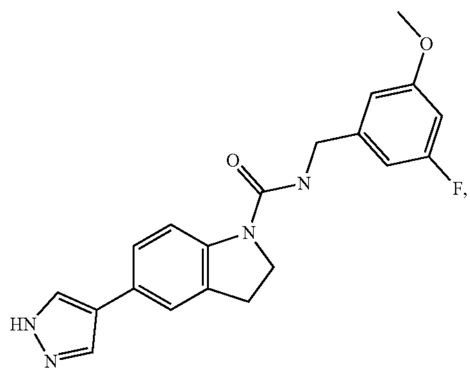
T204
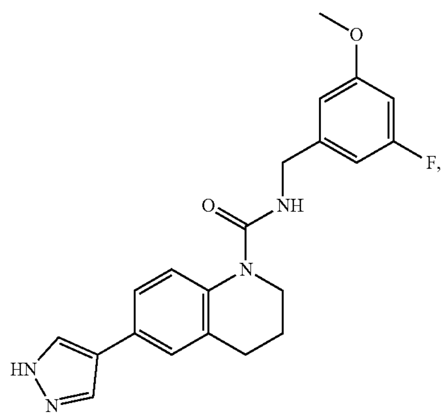
T206
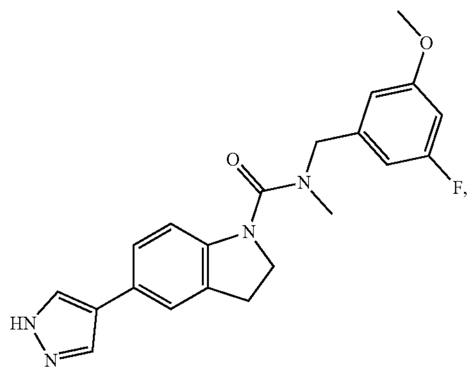
T207
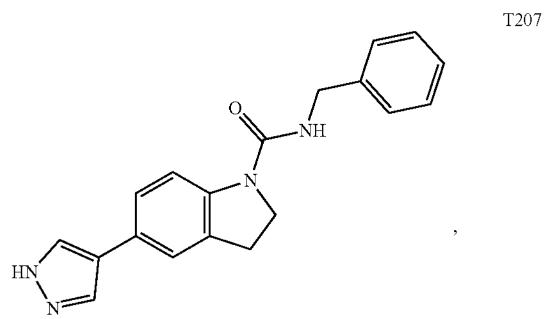
T208
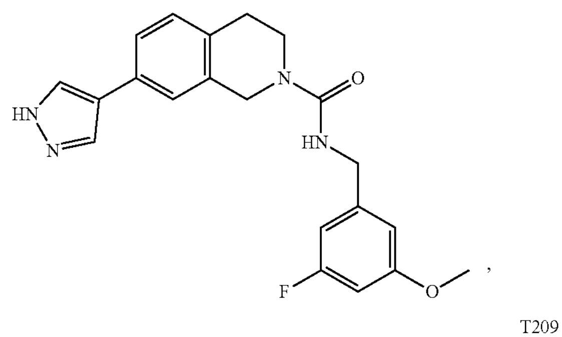
T209
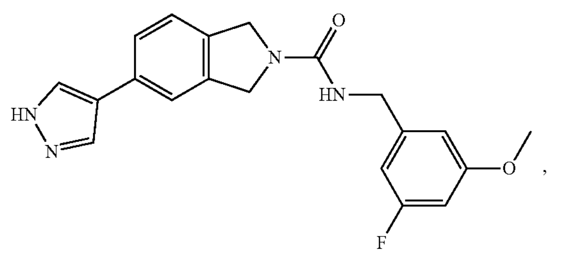
T211
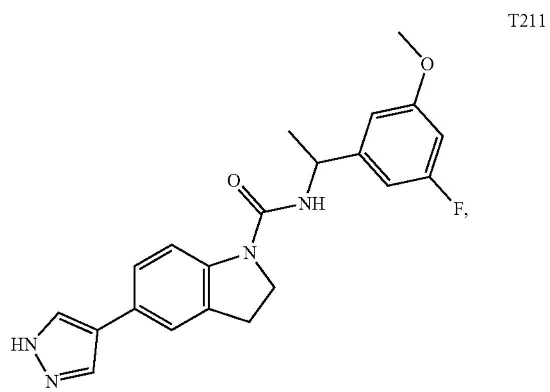
T212
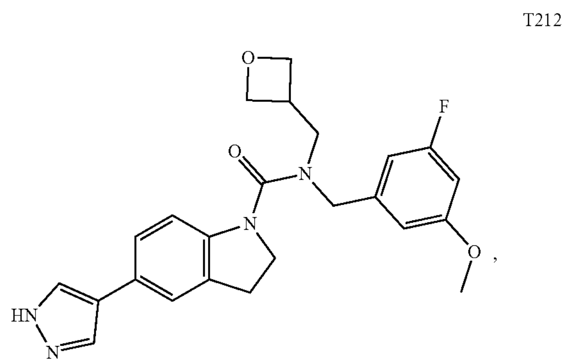

-continued
T213
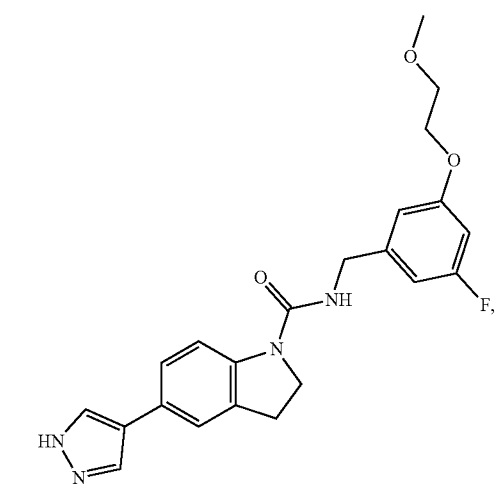
T214
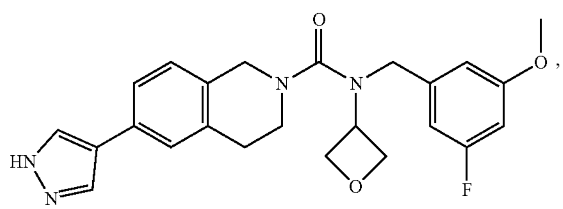
T215
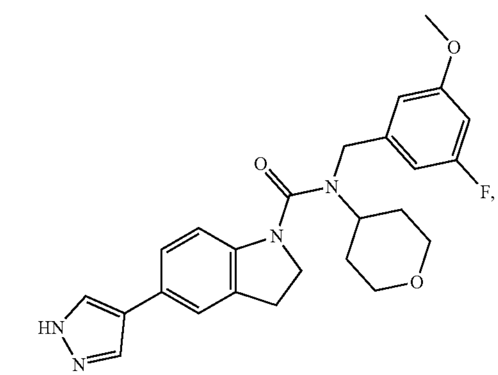
T216
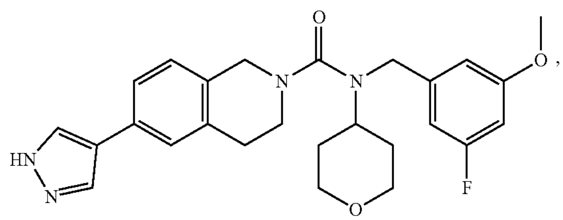
-continued
T217
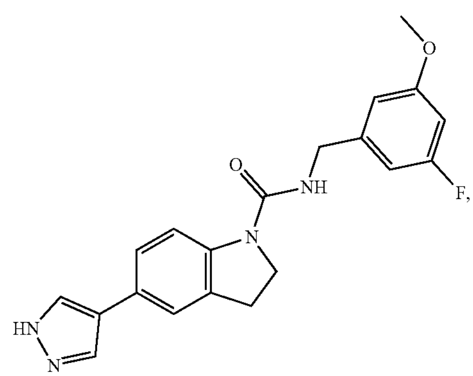
T218
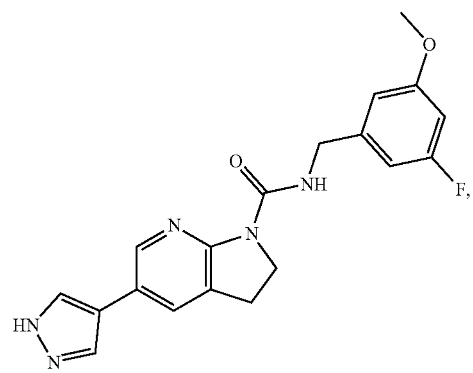
T219
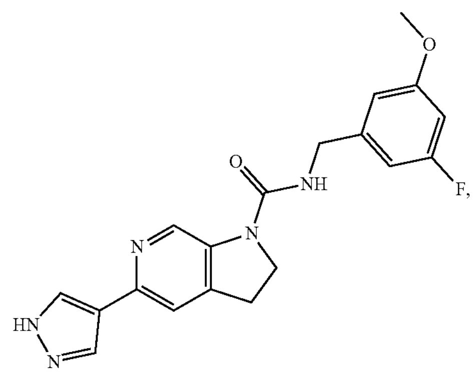
T220
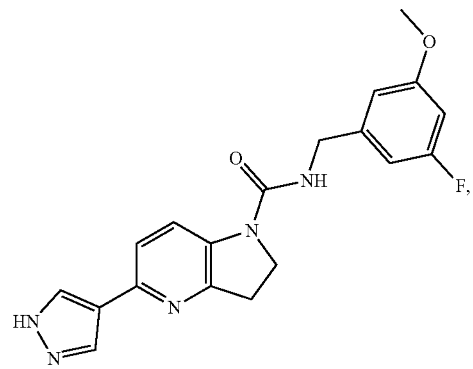

-continued
T221
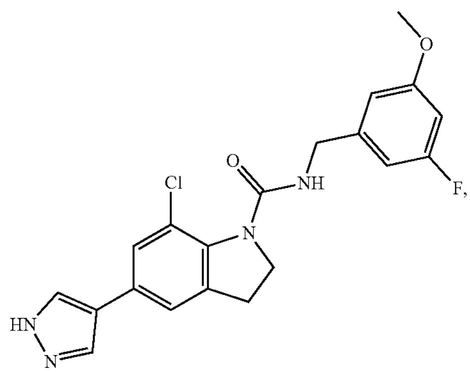
T222
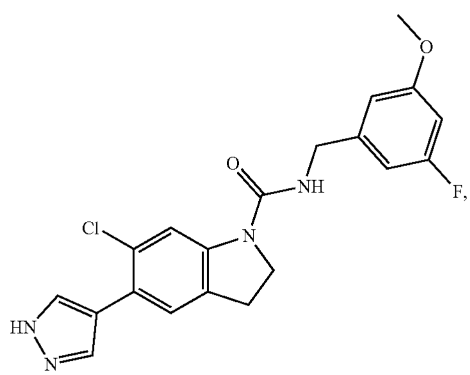
T223
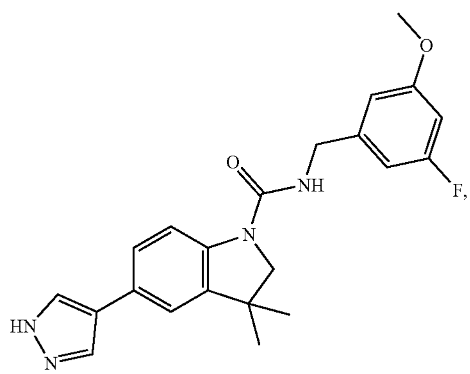
T225
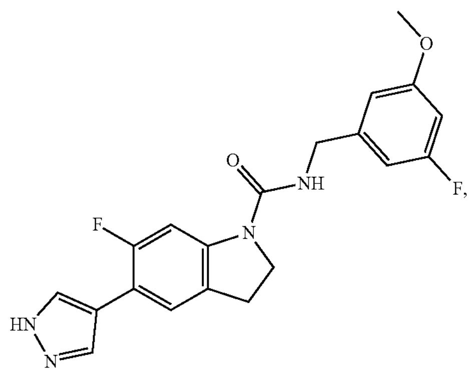
-continued
T226
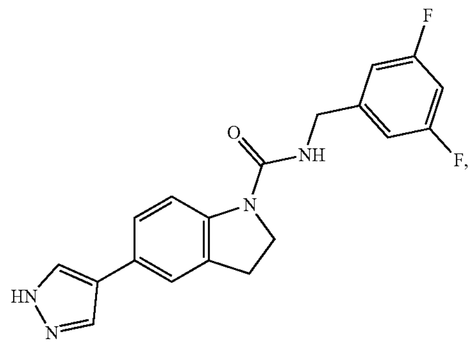
T227
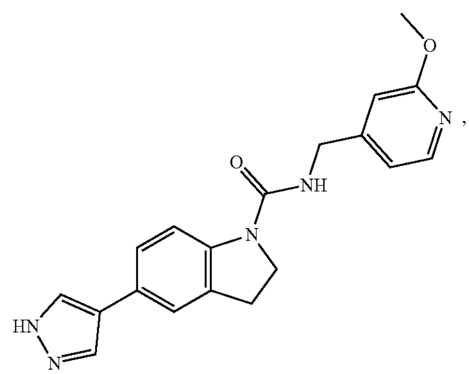
T228
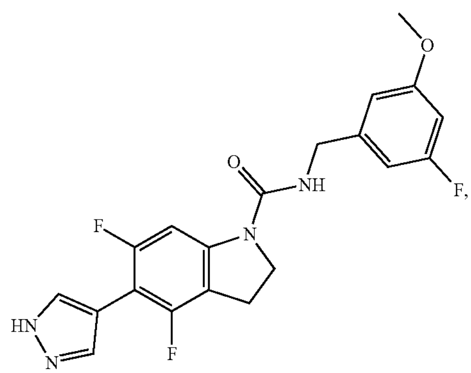
T231
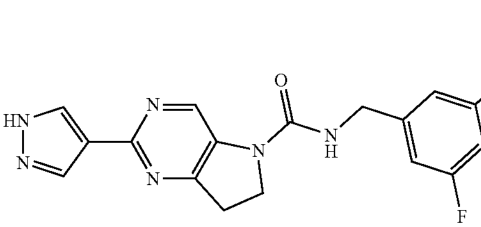
T240
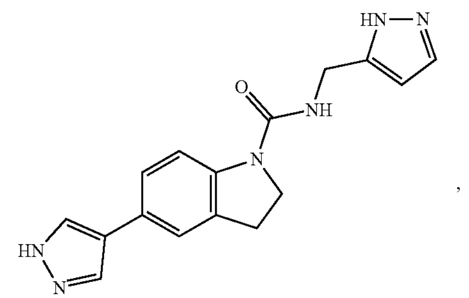

-continued
T241
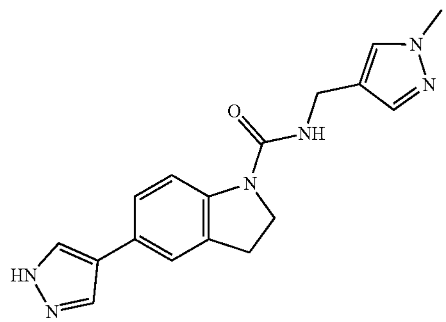
,
T242
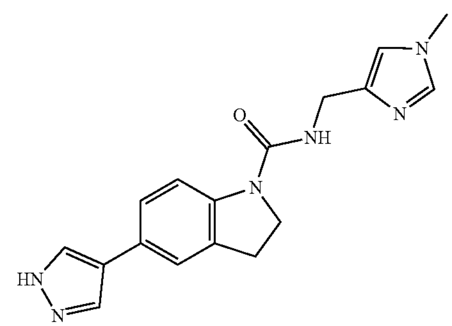
,
T243
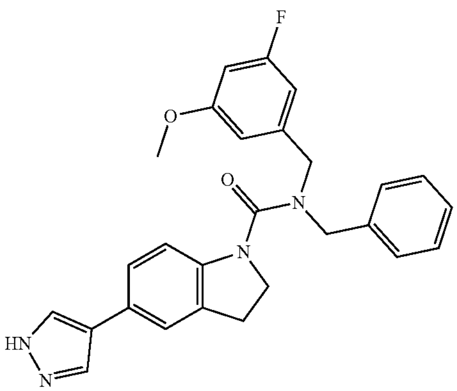
,
T244
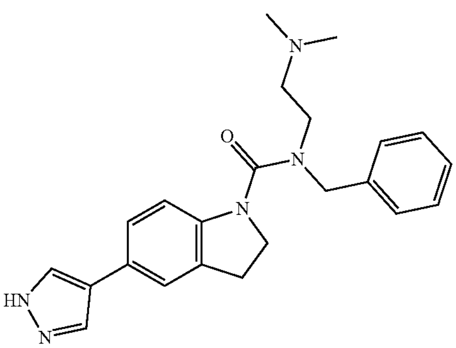
,
-continued
T247
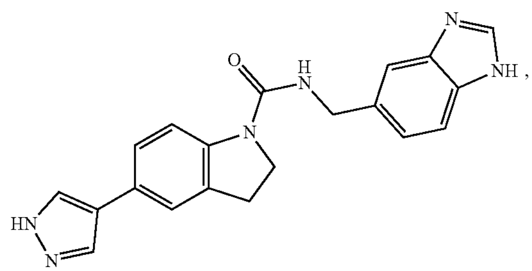
,
T248
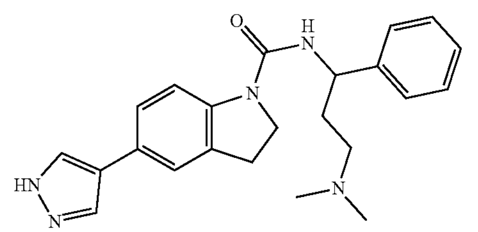
,
T340
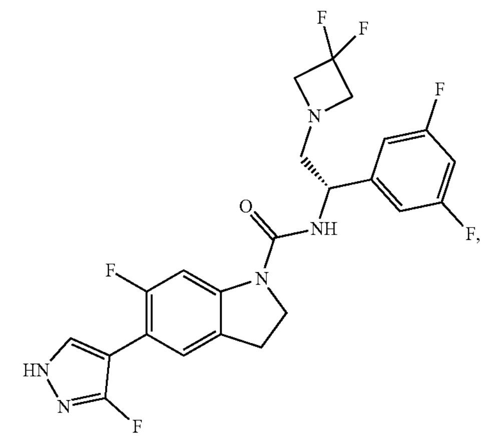
,
T341
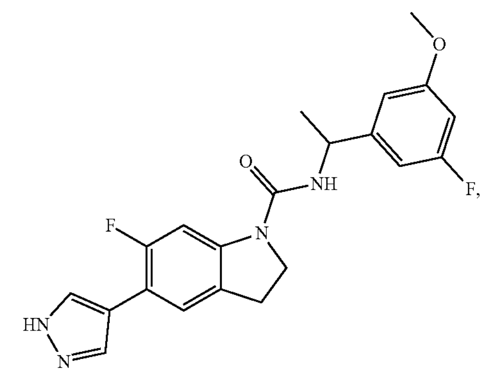
, -continued
T342
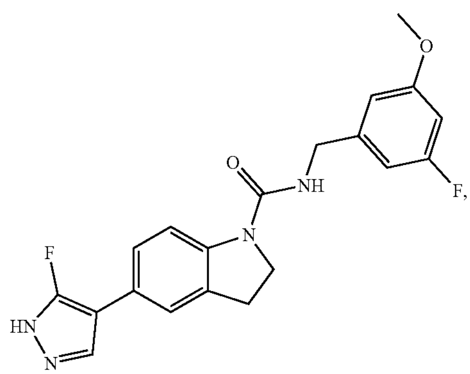
T343
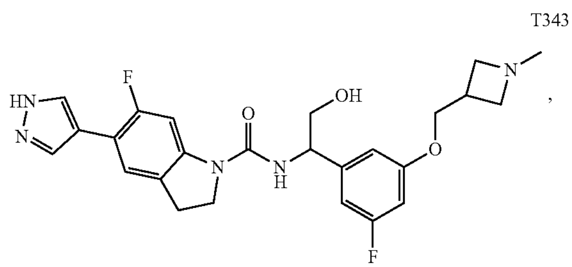
T345
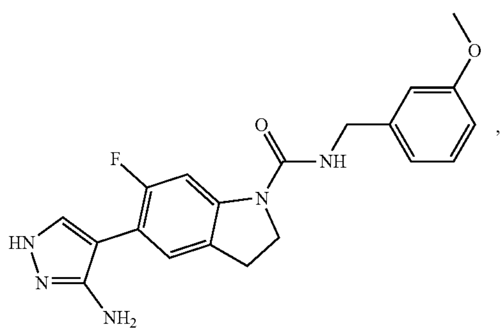
T346
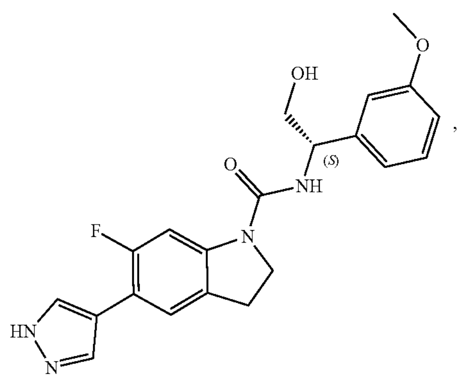
-continued
T347
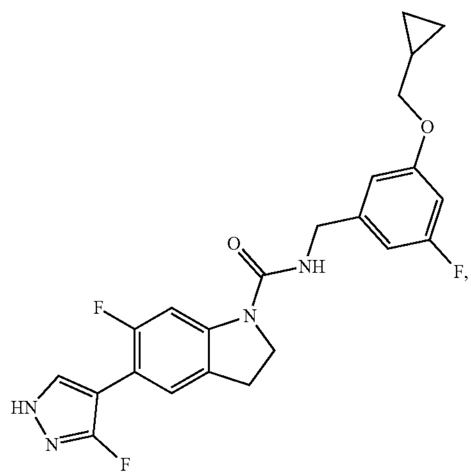
T348
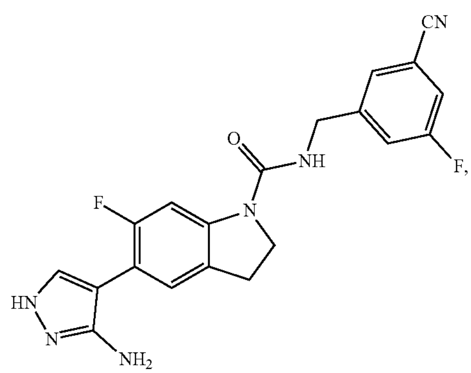
T349
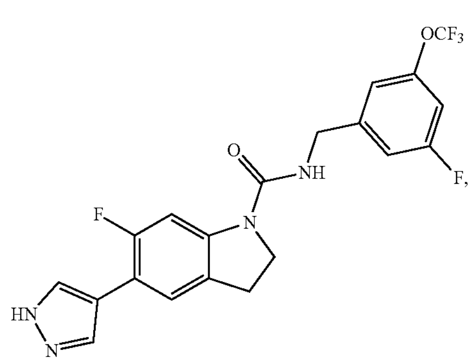
T350
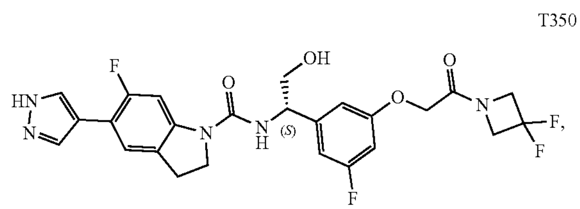

-continued
T351
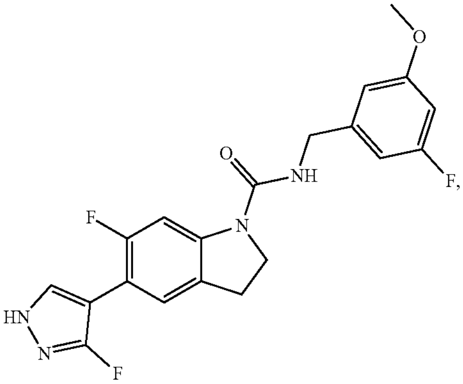
T353
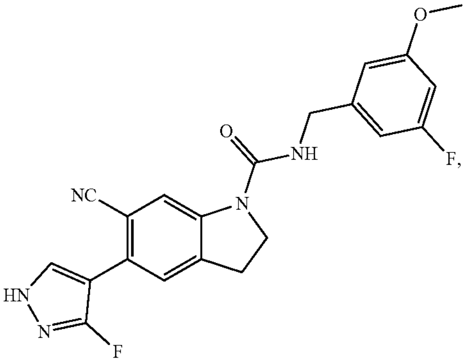
T354
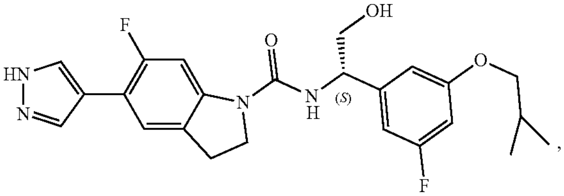
T356-S
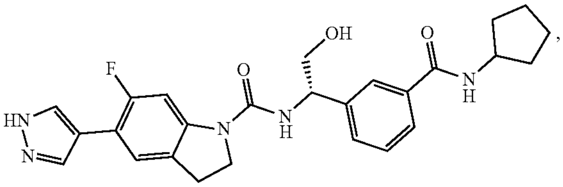
T356-R
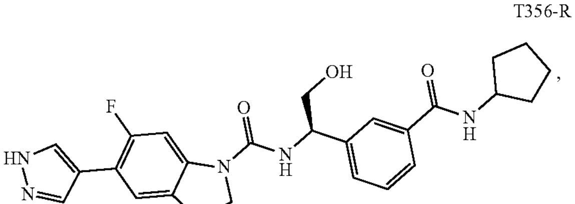
-continued
T357
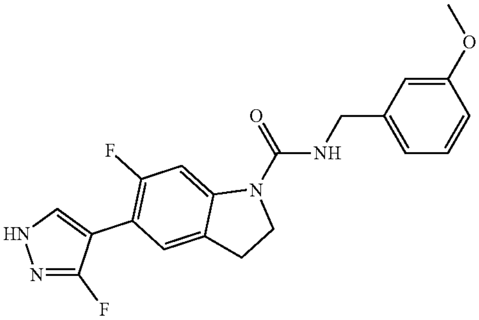
T358
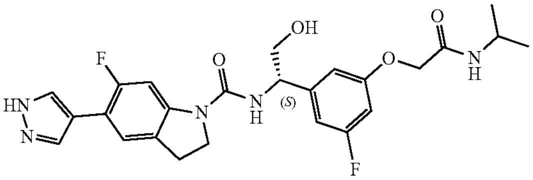
T359
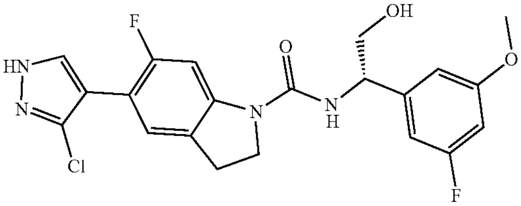
T363
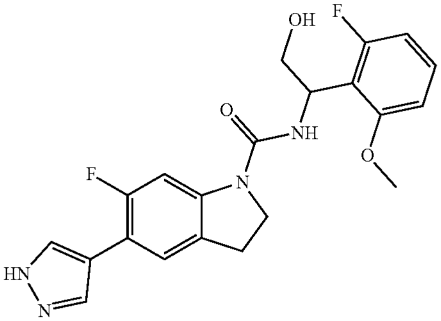
T364
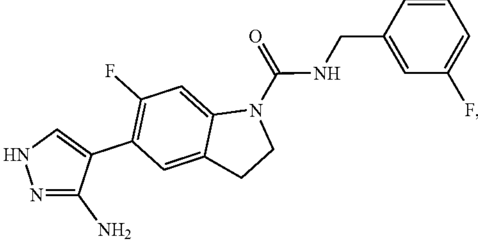

-continued
T365
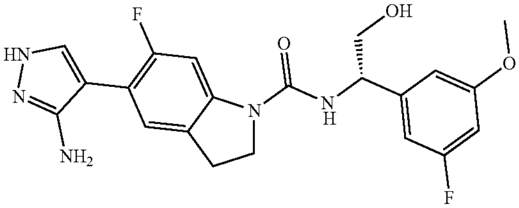
,
T366-S
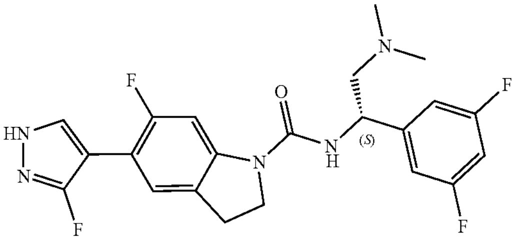
,
T366-R
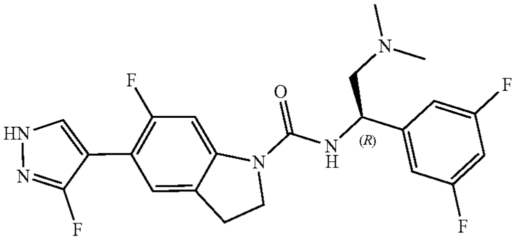
,
T367
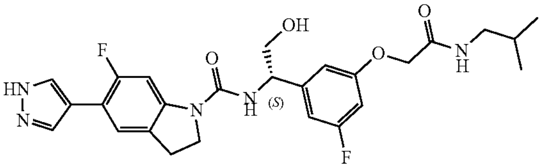
,
T369
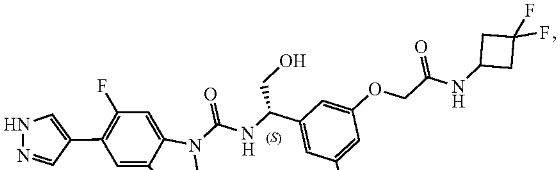
,
T371
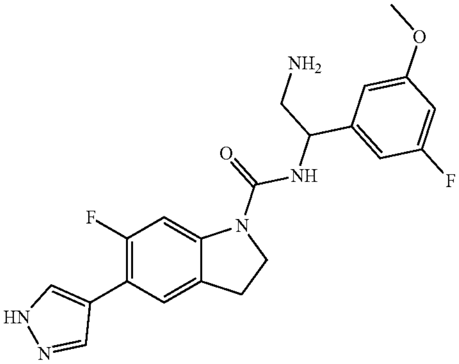
,
-continued
T372
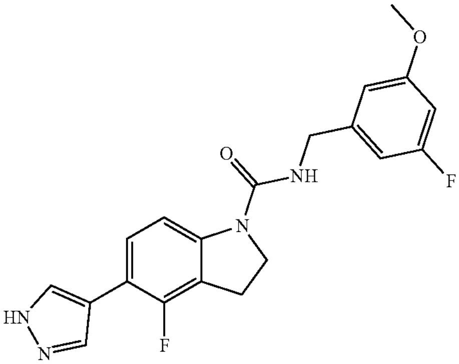
,
T374
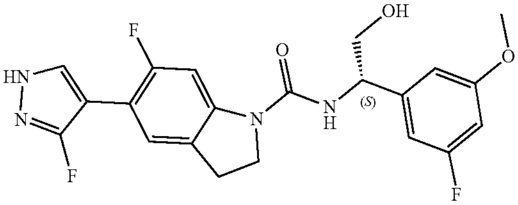
,
T375
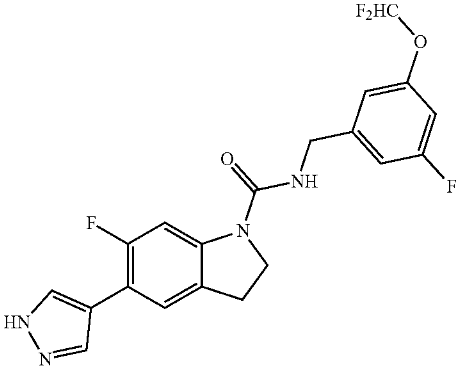
,
T377
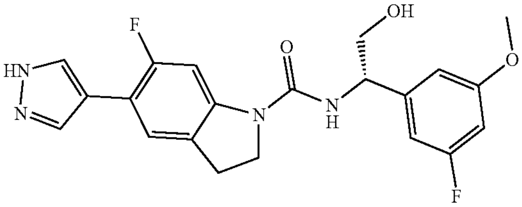
,
T378
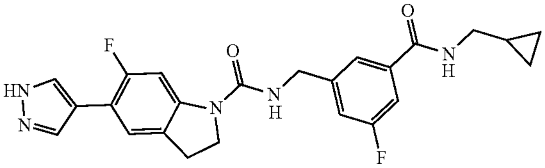
,
T379
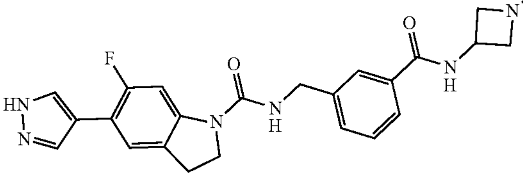
, -continued
T380
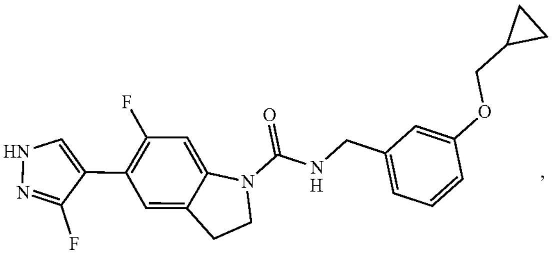
,
T381
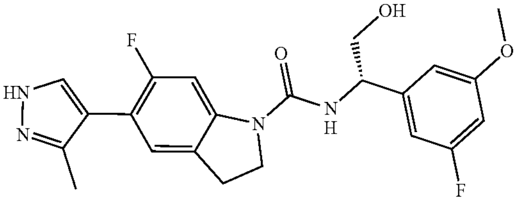
,
T382
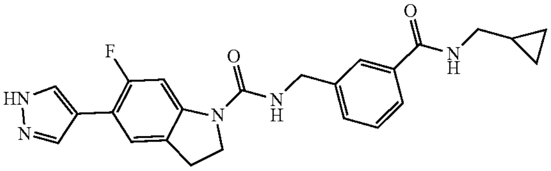
,
T384
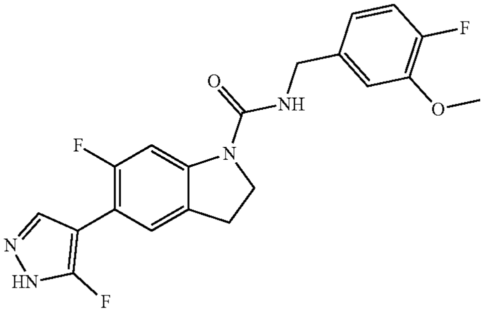
,
T385
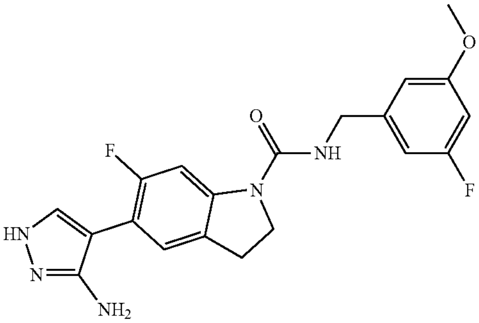
,
T386
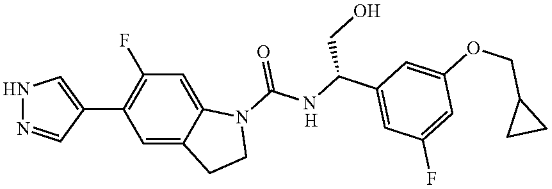
,
-continued
T387
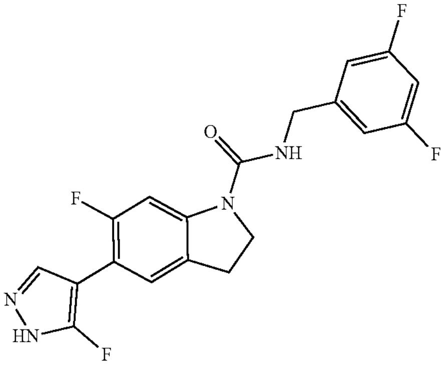
,
T389
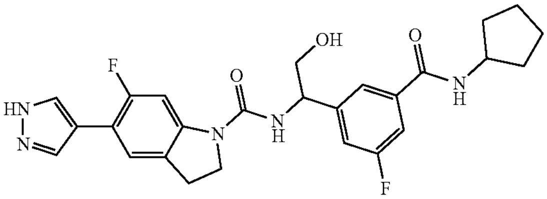
,
T390
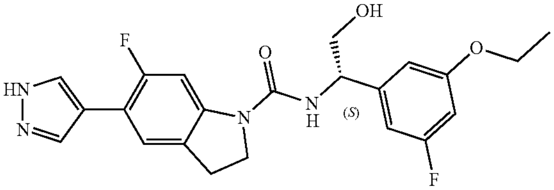
,
T388
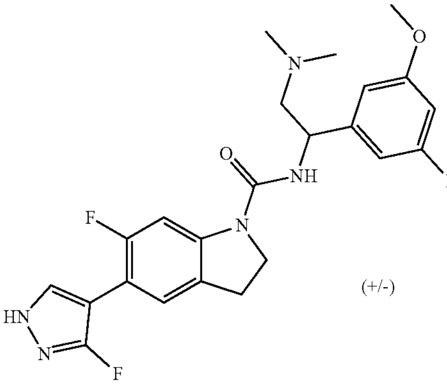
,
(+/-)
T389-S
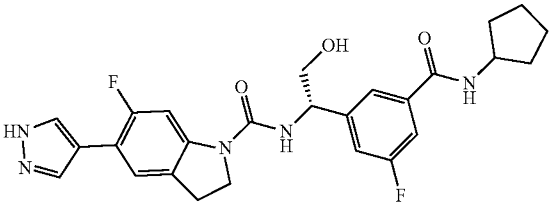
,
and -continued

T389-R

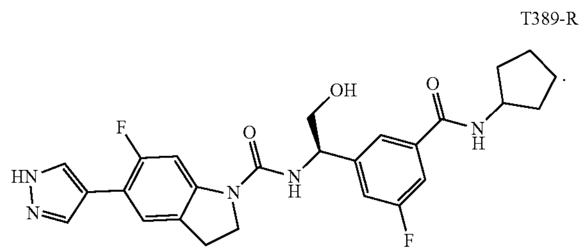

5. A pharmaceutical composition, comprising a therapeutically effective amount of at least one selected from the compound of formula (I), the racemate, the stereoisomer, the tautomer, the nitrogen oxide, the isotopically labeled compound, the solvate, the polymorph, and the pharmaceutically acceptable salt thereof according to claim 1.

6. The compound of formula (I) or the racemate, the stereoisomer, the tautomer, the isotopically labeled compound, the nitrogen oxide, the solvate, the polymorph, or the pharmaceutically acceptable salt thereof according to claim 1, wherein:

the group is selected from:

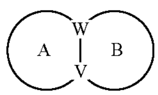

is selected from:

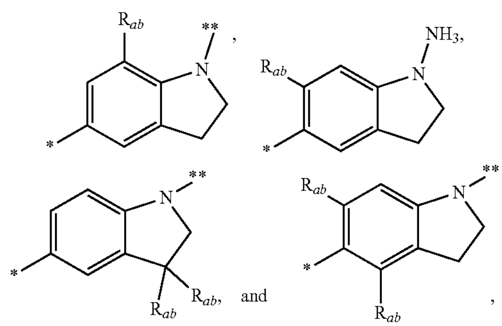

and

7. The compound of formula (I) or the racemate, the stereoisomer, the tautomer, the isotopically labeled compound, the nitrogen oxide, the solvate, the polymorph, or the pharmaceutically acceptable salt thereof according to claim 1, wherein:

ring C is selected from:

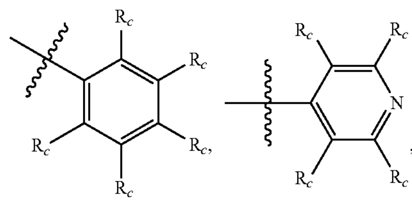

-continued

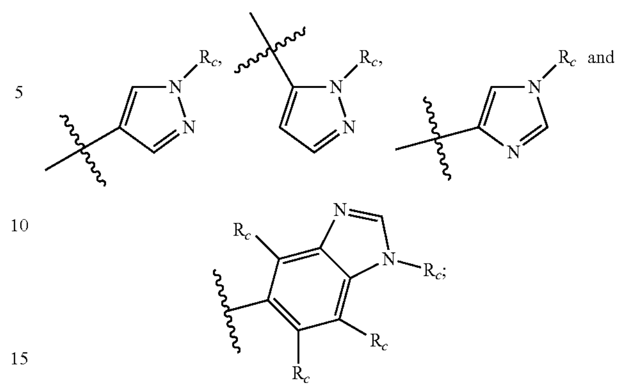

and

8. The compound of formula (I) or the racemate, the stereoisomer, the tautomer, the isotopically labeled compound, the nitrogen oxide, the solvate, the polymorph, or the pharmaceutically acceptable salt thereof according to claim 1, wherein:

each Rc is independently H, F, Cl, methyl, ethyl, n-propyl, isopropyl, methoxy, ethoxy, $—OCH_2CH(CH_3)_2$, $—OCHF_2$, $—O(CH_2)_2OCH_3$,

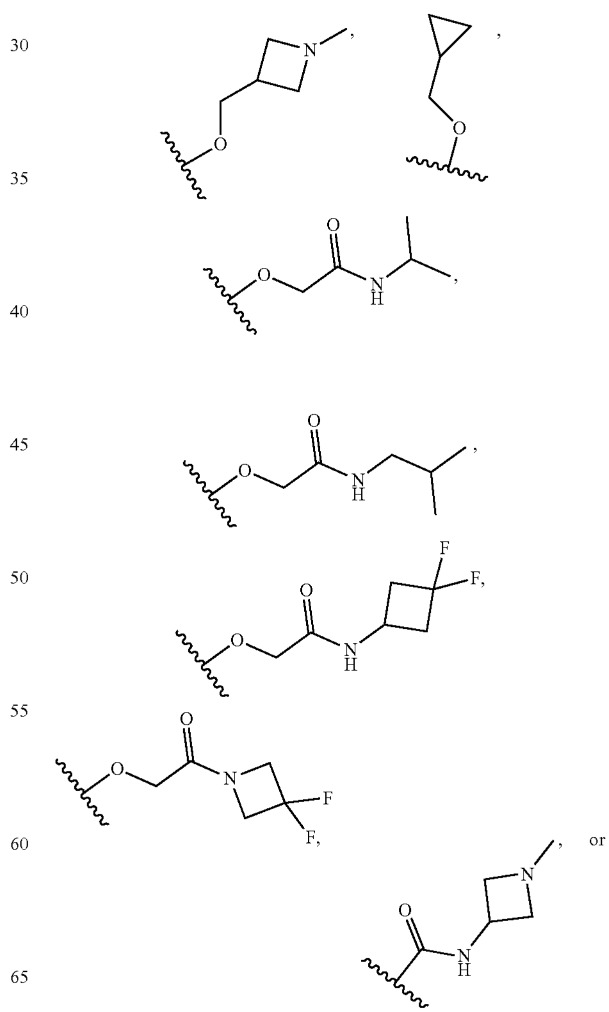

or

-continued

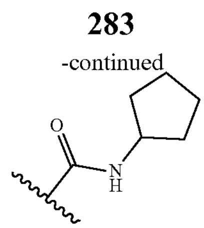

9. A pharmaceutical composition according to claim 5, further comprising a pharmaceutically acceptable auxiliary material selected from a disintegrant, a glidant, a lubricant, a diluent, a filler, an adhesive, and a colorant.

10. A method for treating idiopathic pulmonary fibrosis, comprising administering to a subject in need thereof an effective amount of the compound of formula (I) or the racemate, the stereoisomer, the tautomer, the nitrogen oxide, the isotopically labeled compound, the solvate, the polymorph, the pharmaceutically acceptable salt thereof according to claim 1.

* * * * *